US008288322B2

(12) United States Patent
Ladner et al.

(10) Patent No.: US 8,288,322 B2
(45) Date of Patent: Oct. 16, 2012

(54) METHODS OF CONSTRUCTING LIBRARIES COMPRISING DISPLAYED AND/OR EXPRESSED MEMBERS OF A DIVERSE FAMILY OF PEPTIDES, POLYPEPTIDES OR PROTEINS AND THE NOVEL LIBRARIES

(75) Inventors: Robert C. Ladner, Ijamsville, MD (US); Edward H. Cohen, Belmont, MA (US); Horacio G. Nastri, Newton, MA (US); Kristin L. Rookey, Revere, MA (US); Rene Hoet, Maastricht (NL); Hendricus Renerus Jacobus Mattheus Hoogenboom, Maastricht (NL)

(73) Assignee: Dyax Corp., Burlington, MA (US)

( * ) Notice: Subject to any disclaimer, the term of this patent is extended or adjusted under 35 U.S.C. 154(b) by 664 days.

(21) Appl. No.: 10/045,674

(22) Filed: Oct. 25, 2001

(65) Prior Publication Data
US 2003/0232333 A1 Dec. 18, 2003
US 2009/0162835 A9 Jun. 25, 2009

Related U.S. Application Data

(63) Continuation-in-part of application No. 10/000,516, filed on Oct. 24, 2001, now abandoned, which is a continuation-in-part of application No. 09/837,306, filed on Apr. 17, 2001, now abandoned.

(60) Provisional application No. 60/198,069, filed on Apr. 17, 2000.

(51) Int. Cl.
*C12Q 1/68* (2006.01)
*C12P 19/34* (2006.01)

(52) U.S. Cl. .......... 506/18; 435/6.1; 435/6.18; 435/91.2
(58) Field of Classification Search ................ None
See application file for complete search history.

(56) References Cited

U.S. PATENT DOCUMENTS

| 5,118,605 A | 6/1992 | Urdea |
| 5,223,409 A | 6/1993 | Ladner et al. |
| 5,380,833 A | 1/1995 | Urdea ................. 536/22.1 |
| 5,565,332 A | 10/1996 | Hoogenboom et al. |
| 5,618,920 A | 4/1997 | Robinson et al. |

(Continued)

FOREIGN PATENT DOCUMENTS
DE 19624562 A1 1/1998
(Continued)

OTHER PUBLICATIONS

Heddle, R. J.; Rowley, D. "Dog immunoglobulins. I. Immunochemical characterization of dog serum, parotid saliva, colostrum, milk and small bowel fluid." Immunology, 1975, 29, 1, pp. 185-195.*

(Continued)

*Primary Examiner* — Ardin Marschel
*Assistant Examiner* — Christian Boesen
(74) *Attorney, Agent, or Firm* — Lando & Anastasi, LLP; Shelby J. Walker; Laurie Butler Lawrence

(57) ABSTRACT

A library containing a collection of genetic packages that display a member of a diverse family of peptides, polypeptides or proteins and that collectively display at least a portion of the family, the displayed peptides, polypeptides or proteins being encoded by DNA sequences containing sequences encoding a heavy chain CDR region is described.

18 Claims, 22 Drawing Sheets

| VH-CDR1 |
| 1 Y 1 M 1 |

(SEQ ID NO: 636)

| VH-CDR2 |
| 2 I 2 3 S G G 1 T 1  YADSVKG |

(SEQ ID NO: 637)

U.S. PATENT DOCUMENTS

| | | | |
|---|---|---|---|
| 5,658,727 A | 8/1997 | Barbas et al. | |
| 5,688,666 A | 11/1997 | Bass et al. | 435/69.4 |
| 5,723,323 A | 3/1998 | Kauffman et al. | |
| 5,733,743 A | 3/1998 | Johnson et al. | |
| 5,739,281 A | 4/1998 | Thogersen et al. | |
| 5,750,373 A | 5/1998 | Garrard et al. | |
| 5,780,279 A | 7/1998 | Matthews et al. | |
| 5,798,208 A | 8/1998 | Crea | 435/6 |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,830,663 A | 11/1998 | Embleton et al. | |
| 5,837,242 A | 11/1998 | Holliger et al. | |
| 5,840,479 A | 11/1998 | Little et al. | |
| 5,846,765 A | 12/1998 | Matthews et al. | |
| 5,858,657 A | 1/1999 | Winter et al. | |
| 5,858,671 A | 1/1999 | Jones | |
| 5,871,907 A | 2/1999 | Winter et al. | |
| 5,872,215 A | 2/1999 | Osbourne et al. | |
| 5,885,793 A | 3/1999 | Griffiths et al. | |
| 5,917,018 A | 6/1999 | Thogersen et al. | |
| 5,935,831 A | 8/1999 | Quax et al. | |
| 5,962,255 A | 10/1999 | Griffiths et al. | |
| 5,962,271 A | 10/1999 | Chenchik et al. | |
| 5,962,272 A | 10/1999 | Chenchik et al. | |
| 5,969,108 A | 10/1999 | McCafferty et al. | |
| 5,976,862 A | 11/1999 | Kauffman et al. | |
| 5,994,519 A | 11/1999 | Osbourne et al. | |
| 6,010,884 A | 1/2000 | Griffiths et al. | |
| 6,017,732 A | 1/2000 | Jespers et al. | |
| 6,040,136 A | 3/2000 | Gerrard et al. | |
| 6,057,098 A | 5/2000 | Buechler et al. | |
| 6,140,471 A | 10/2000 | Johnson et al. | |
| 6,172,197 B1 | 1/2001 | McCafferty et al. | |
| 6,180,336 B1 | 1/2001 | Osbourn et al. | |
| 6,225,447 B1 | 5/2001 | Winter et al. | |
| 6,248,516 B1 | 6/2001 | Winter et al. | |
| 6,291,158 B1 | 9/2001 | Winter et al. | |
| 6,291,159 B1 | 9/2001 | Winter et al. | |
| 6,291,160 B1 | 9/2001 | Lerner et al. | |
| 6,291,161 B1 | 9/2001 | Lerner et al. | |
| 6,291,650 B1 | 9/2001 | Winter et al. | |
| 6,300,064 B1 | 10/2001 | Knappik et al. | |
| 6,319,690 B1 | 11/2001 | Little et al. | |
| 6,342,588 B1 | 1/2002 | Osbourn et al. | |
| 6,420,113 B1 | 7/2002 | Buechler et al. | |
| 6,489,123 B2 | 12/2002 | Osbourn et al. | |
| 6,492,107 B1 | 12/2002 | Kauffman et al. | |
| 6,492,123 B1 | 12/2002 | Holliger et al. | |
| 6,492,160 B1 | 12/2002 | Griffiths et al. | |
| 6,521,404 B1 | 2/2003 | Griffiths et al. | |
| 6,531,580 B1 * | 3/2003 | Huse et al. | 530/388.22 |
| 6,544,731 B1 | 4/2003 | Griffiths et al. | |
| 6,545,142 B1 | 4/2003 | Winter et al. | |
| 6,555,313 B1 | 4/2003 | Griffiths et al. | |
| 6,569,641 B1 | 5/2003 | Kauffman et al. | |
| 6,582,915 B1 | 6/2003 | Griffiths et al. | |
| 6,589,527 B1 | 7/2003 | Winter et al. | |
| 6,593,081 B1 | 7/2003 | Griffiths et al. | |
| 6,680,192 B1 | 1/2004 | Lerner et al. | |
| 6,696,245 B2 | 2/2004 | Winter et al. | |
| 6,696,248 B1 | 2/2004 | Knappik et al. | |
| 6,706,484 B1 | 3/2004 | Knappik et al. | |
| 6,753,136 B2 | 6/2004 | Lohning | |
| 6,806,079 B1 | 10/2004 | McCafferty et al. | |
| 6,828,422 B1 | 12/2004 | Achim et al. | |
| 6,846,634 B1 | 1/2005 | Tomilson et al. | |
| 6,916,605 B1 | 7/2005 | McCafferty et al. | |
| 6,969,586 B1 | 11/2005 | Lerner et al. | |
| 7,063,943 B1 | 6/2006 | McCafferty et al. | |
| 7,189,841 B2 | 3/2007 | Lerner et al. | |
| 2002/0004215 A1 | 1/2002 | Osbourn et al. | |
| 2003/0114659 A1 | 6/2003 | Winter et al. | |
| 2003/0130496 A1 | 7/2003 | Winter et al. | |
| 2003/0148372 A1 | 8/2003 | Tomlinson et al. | |
| 2003/0190674 A1 | 10/2003 | Griffiths et al. | |
| 2003/0232333 A1 | 12/2003 | Ladner et al. | |
| 2004/0038921 A1 | 2/2004 | Kreutzer et al. | |
| 2004/0110941 A2 | 6/2004 | Winter et al. | |
| 2004/0157214 A1 | 8/2004 | McCafferty et al. | |
| 2004/0157215 A1 | 8/2004 | McCafferty et al. | |
| 2005/0202512 A1 | 9/2005 | Tomlinson et al. | |
| 2006/0003334 A1 | 1/2006 | Achim et al. | |
| 2006/0019260 A1 | 1/2006 | Lerner et al. | |
| 2006/0166252 A1 | 7/2006 | Ladner | |
| 2006/0257937 A1 | 11/2006 | Ladner | |
| 2007/0031879 A1 | 2/2007 | Ley | |

FOREIGN PATENT DOCUMENTS

| | | | |
|---|---|---|---|
| WO | WO 94/07922 | * | 4/1994 |
| WO | 9708320 | | 3/1997 |
| WO | 97/15690 A1 | | 5/1997 |
| WO | WO 97/20923 | | 6/1997 |
| WO | WO 97/49809 | | 12/1997 |
| WO | 9906834 | | 2/1999 |
| WO | 99/55367 | | 11/1999 |
| WO | 00/18905 | | 4/2000 |
| WO | 0179481 A2 | | 10/2001 |

OTHER PUBLICATIONS

Roitt, I.; Brostoff, J.; Male, D. Immunology Sixth Edition. New York: Mosby 2001, p. 67-70 and 80.*

Hrncir et al. "Anticardiolipin antibodies in diffuse connective tissue diseases in the IgG, IgM and IgA isotypes" Vnitrni Lekarstvi. Nov. 1999, 36(11), 1041-1049, translation pp. 1-13.*

Tomlinson (Oct. 5, 1992) Journal of Molecular Biology vol. 227 pp. 776 to 798.*

Stewart (Feb. 1, 1993) Journal of Experimental Medicine vol. 177 pp. 409 to 418.*

Yang (1995) Journal of Molecular Biology vol. 254 pp. 392 to 403.*

Brezinschek (May 1997) Journal of Clinical Investigation vol. 99 pp. 2488 to 2501.*

Pini (Aug. 21, 1998) Journal of Biological Chemistry vol. 273 pp. 21769 to 21776.*

Alves J. et al., "Accuracy of the EcoRV restriction endonuclease: binding and cleavage studies with oligodeoxynucleotide substrates containing degenerate recognition sequences," *Biochemistry*, 34(35):11191-11197 (1995).

Blakesley R. et al., "Duplex Regions in "Single-Stranded" ØX174 DNA Are Cleaved by a Restriction Endonuclease from *Haemophilus Aegyptius*," *The Journal of Bilogical Chemistry*, 252:7300-7306 (1977).

Grimes E. et al., "Achilles' heel cleavage: creation of rare restriction sites in λ phage genomes and evaluation of additional operators, repressors and restriction/modification systems," *Gene*, 90(1):1-7 (1990).

Hasan N. and Szybalski W., "Control of cloned gene expression by promoter inversion in vivo: construction of improved vectors with a multiple cloning site and the $P_{tac}$ promoter," *Gene*, 56(1):145-151 (1987).

Kaczorowski T. and Szybalski W., "Genomic DNA sequencing by SPEL-6 primer walking using hexamer ligation," *Gene*, 223(1-2):83-91 (1998).

Kim S.C. et al., "Structural requirements for FokI-DNA interaction and oligodeoxyribonucleotide-instructed cleavage," *J. Mol. Biol.*, 258(4):638-649 (1996).

Kim S.C. et al., "Cleaving DNA at any predetermined site with adapter-primers and class-IIS restriction enzymes," *Science*, 240(4851):504-506 (1988).

Koob M. et al., "RecA-AC: single-site cleavage of plasmids and chromosomes at any predetermined restriction site," *Nucleic Acids Res.*, 20(21):5831-5836 (1992).

Koob M. and Szybalski W., "Cleaving yeast and *Escherichia coli* genomes at a single site," *Science*, 250(4978):271-273 (1990).

Koob M. et al., "Conferring operator specificity on restriction endonucleases," *Science*, 241(4869):1084-1086 (1988).

Koob M. et al., "Conferring new specificity upon restriction endonucleases by combining repressor-operator interaction and methylation," *Gene*, 74(1):165-167 (1988).

Kur J. et al., "A novel method for converting common restriction enzymes into rare cutters: integration host factor-mediated Achilles' cleavage (IHF-AC)," *Gene*, 110(1):1-7 (1992).

Nishigaki K. et al., "Type II Restriction Endonucleases Cleave Single-Stranded DNAs in General," *Nucleic Acids Research*, 13:5747-5760 (1985).

Podhajska A.J. and Szybalski W., "Conversion of the Fok-I endonuclease to a universal restriction enzyme: cleavage of phage M13mp7 DNA at predetermined sites," *Gene*, 40(1):175-182 (1985).

Podhajska A.J. et al., Conferring new specificities on restriction enzymes: cleavage at any predetermined site by combining adapter oligodeoxynucleotide and class-IIS enzyme, *Methods Enzymol*, 216(G):303-309 (1992).

Pósfai G. and Szybalski W., "A simple method for locating methylated bases in DNA using class-IIS restriction enzymes," *Gene*, 74(1):179-181 (1988).

Qi G. et al., "Restriction of Single-Stranded M13 DNA Using Synthetic Oligonucleotides: The Structural Requirement of Restriction Enzymes," *Cell Biol.*, 65:50-55 (1986).

Szybalski W., "Reasons and risks to study restriction/modification enzymes form extreme thermophiles: chilly coldrooms, 13th sample, and 13-codon overlap," *Gene*, 112(1):1-2 (1992).

Szybalski W., "Universal restriction endonucleases: designing novel cleavage specificities by combining adapter oligodeoxynucleotide and enzyme moieties," *Gene*, 40(2-3):169-173 (1985).

Szybalski W. and Skalka A., "Nobel prizes and restriction enzymes," *Gene*, 4(3):181-182 (1978).

Szybalski W. et al., "Class-IIS restriction enzymes—a review." *Gene*, 100:13-26 (1991).

Thielking V. et al., "Accuracy of the EcoRI restriction endonuclease: binding and cleavage studies with oligodeoxynucleotide substrates containing degenerate recognition sequences," *Biochemistry*, 29(19):4682-4691 (1990).

Zhu D., "Oligodeoxynucleotide-directed cleavage and repair of a single-stranded vector: a method of site-specific mutagenesis," *Analytical Biochemistry*, 177(1):120-124 (1989).

Arden, "Conserved motifs in T-cell receptor CDR1 and CDR2: implications for ligand and CD8 co-receptor binding" Current Opinion in Immunology, Current Biology LTD., 10(1):74-81, 1998, XP004313624.

Barbas et al., "Human Autoantibody Recognition of DNA" Proc. Natl. Acad. Sci. 92:2529-2533, 1995, XP002927212.

Davies et al., "Affinity improvement of single antibody VH domains: residues in all three hypervariable regions affect antigen binding", Immunotechnology 2(3):169-179, 1996, XP004070292.

de Haard et al., "A Large Non-immunized Human Fab Fragment Phage Library That Permits Rapid Isolation and Kinetic Analysis of High Affinity Antibodies" Journal of Biological Chemistry, 274(26):18218-18230, 1999, XP002128301.

Hoogenboom et al., "By-passing Immunisation Human Antibodies from Synthetic Repertoires of Germline $V_H$ Gene Segments Rearranged in Vitro" Journal of Molecular Biology, 227:381-388, 1992, XP002974448.

Knappik et al., "Fully Synthetic Human Combinatorial Antibody Libraries (HuCAL) Based on Modular Consensus Frameworks and CDRs Randomized with Trinucleotides" J. Mol. Biol., 296:57-86, 2000.

Solderlind et al., "The Immune Diversity in a Test Tube—Non-Immunised Antibody Libraries and Functional Variability in Defined Protein Scaffolds" Combinotorial Chemistry & High Throughput Screening, 4:409-416, 2001.

Tomlinson et al., The Repertoire of Human Germline $V_H$ Sequences Reveals about Fifty Groups of $V_H$ Segments with Different Hypervariable Loops, Journal of Molecular Biology, 227:776-798, 1992, XP000990787.

Lowman, H.B.; Wells, J.A. "Affinity Maturation of Human Growth Hormone by Monovalent Phage Display" J. Mol. Biol. 1993, 234, 564-578.

Seed, B. "Developments in expression cloning" Current Opinion in Biotechnology 1995, 6: 567-573.

Suzuki, M.; Takemura, H.; Sumida, T. "Light Chain Determines the Binding Property of Human Anti-dsDNA IgG Autoantibodies" Biochem. Biophys. Res. Commun. Apr. 29, 2000, 271, 240-243.

Gushiken et al., "Polymorphism of β2-Glycoprotein I at Codons 306 and 316 in Patients with Systemic Lupus Erythematosus and Antiphospholipid Syndrome", Arthritis & Rheumatism, Jun. 1999, 42(6): 1189-1193.

Barbas, C.F., "Assembly of Combinatorial antibody libraries on phage surfaces: The gene III site", Proc. Natl. Acad. Sci., vol. 88, pp. 7978-7982, Sep. 1991.

Clackson, T., "In Vitro Selection from Protein and Peptide Libraries", Elsevier Science Ltd., vol. 12, pp. 173-184, May 1, 1994.

Courtney, B.C., "A phage display vector with improved stability, applicability and ease of manipulation", Gene, vol. 165, No. 1, pp. 139-140, Nov. 7, 1995.

Extended European Search Report dated May 26, 2010 from European Application No. 10156326.0.

Fan, Z-C, "Three-dimensional Structure of an Fv from a Human IgM Immunoglobulin", J. Mol. Biol., vol. 228, No. 1, pp. 188-207, Nov. 5, 1992.

Hoet, R.M., "Generation of high-affinity human antibodies by combining donor-derived and synthetic complementarity-determining-region diversity", Nature Biotechnology, vol. 23, No. 3, pp. 344-348, Mar. 2005.

Hoogenboom, H.R., "Multi-subunit proteins on the surface of filamentous phage: methodologies for displaying antibody (Fab) heavy and light chains", Nucleic Acids Research, vol. 19, No. 15, pp. 4133-4137, Jan. 1, 1991.

Schoonbroodt, S, "Oligonucleotide-assisted cleavage and ligation: a novel directional DNA cloning technology to capture cDNAs. Application in the construction of a human immune antibody phage-display library", Nucleic Acids Research, vol. 33, No. 9, p. E81, 2005.

Smith, G.P., "Phage Display", Chem. Rev., vol. 97, No. 2, pp. 391-410, Mar. 1, 1997.

Hoet et al., "The Importance of the Light Chain for the Epitope Specificity of Human Anti-U1 Small Nuclear RNA Autoantibodies Present in Systemic Lupus Erythematosus Patients" Journal of Immunology 1999, 163(6), 3304-3312.

Aujame et al., "High affinity human antibodies by phage display", Human Antibodies, 8(4):155-168 (1997).

Barbas et al., "Semisynthetic combinatorial antibody libraries: a chemical solution to the diversity problem," Proceedings of the National Academy of Sciences of USA, 89:4457-4461 (1992).

Balint et al., "Antibody engineering by parsimonious mutagenesis," Gene, 1993, vol. 137, pp. 109-118.

Corbett et al., "Sequence of the human immunoglobulin diversity (D) segment locus: a systematic analysis provides no evidence for the use of DIR segments, inverted D segments, "minor" D segments or D-D recombination", J. Mol. Biol. 270(4): 587-597 (1997).

Hoogenboom et al., "Antibody phage display technology and its applications," Immunotechnology, 4(1):1-20 (1998).

Jirholt et al., "Exploiting sequence space: shuffling in vivo formed complementarity determining regions into a master framework," Gene, 1998, vol. 215, No. 2, pp. 471-476.

Knappik et al., "Fully Synthetic Human Combinatorial Antibody Libraries (HuCAL) Based on Modular Consensus Frameworks and CDRs Randomized with Trinucleotides", J. Mol. Biol., 296:57-86 (2000).

Kruif et al., "Selection and application of human single chain Fv antibody fragments from a semi-synthetic phage antibody display library with designed CDR3 regions", J. Mol. Biol., 248(1):97-105 (1995).

Powell et al., "Construction, assembly and selection of combinatorial antibody libraries", pp. 155-172 in Genetic Engineering with PCR (Horton and Tait, Eds. 1998), vol. 5 of the Current Innovations in Molecular Biology series, Horizon Scientific Press.

Ryu et al., "Recent Progress in Biomolecular Engineering", Biotechnology Progress, 2000, vol. 15, No. 1, pp. 2-16.

Saviranta et al., "Engineering the steroid-specificity of an anti-17B-estradiol Fab by random mutagenesis and competitive phage panning," Protein Engineering, 1998, vol. 11, No. 2, pp. 143-152.

Sheets et al., "Efficient construction of a large nonimmune phage antibody library: The production of high-affinity human single-chain antibodies to protein antigens," Proc. Natl. Acad. Sci. USA, 1998, vol. 95, pp. 6157-6162.

Short et al., "Contribution of Antibody Heavy Chain CDR1 to Digoxin Binding Analyzed by Random Mutagenesis of Phage-displayed Fab 26-10", Journal of Biol. Chem., vol. 270 (1):28541-28550 (1995).

Soderlind et al., "Domain libraries: Synthetic diversity for de novo design of antibody V-regions", Gene, 1995, vol. 160, No. 2, pp. 269-272.

Zucconi et al., "Domain repertoires as a tool to derive protein recognition rules", 2000, FEBS Letters, vol. 480, No. 1, pp. 49-54.

Podhajska A J Szybalski W.: "Conversion of the FOK-I Endonuclease to a Universal Restriction Enzyme Cleavage of Phage M-13-MP-7 DNA at Predetermined Sites", Gene (Amsterdam), vol. 40, No. 2-3, pp. 175-182 (1985).

Zhu D: "Oligodeoxynucleotide-Directed Cleavage and Repair of a Single-Stranded Vector a Method of Site-Specific Mutagenesis", Analytical Biochemistry, vol. 177, No. 1, pp. 120-124 (1989).

Extended European Search Report from European Application No. 10179777.7 dated Feb. 2, 2011.

Extended European Search Report dated Mar. 10, 2011 from European Application No. 10179786.8.

Barbas et al., "Human autoantibody recognition of DNA," PNAS USA, 1995, vol. 92, pp. 2529-2533, XP002927212.

* cited by examiner

Gel analysis of PCR product from extender-kappa amplification
Approx. 75ng/5μl → 15ng/μl 1 - 100bp
2 - LDM
3 - 50ng template
4 - 10ng template
5 - ssDNA unligated
6 - negative control
7 - LDM
8 - 100bp

Gel purified PCR product from extender-kappa amplification
Concentration : ± 35ng/μl 1 - LDM
2 - 1μl purif.

Gel-analysis of digested κ-ssDNA

1μl digested ssDNA ≈ 8ng ssDNA
Total volume of 50μl = 400ng ssDNA
➔ 400ng ssDNA available for ligation of the bridge-extenders 1 - 100bp
2 - LDM
3 - 1μl ssDNA pure
4 - 4μl beads after dig.
5 - 8μl beads after dig.
6 - LDM
7 - 100bp

Gel analysis of extender – cleaved kappa ligation

20ng/5μl eluted material → 4ng/μl

1 - 100bp
2 - LDM
3 - Ligationmix, 4μl
4 - Unligated ssDNA
5 - LDM

Cleavage and ligation Kappa light chains

A) BsmA1 cleavage

1. 100 bp marker
2. LDM marker
3. Sup. ssDNA after dig.
4. beads after dig. (uncleaved material)
5. DNA before cleavage

80% cleavage

B) Bridge Ligation

1. 100 bp marker
2. LDM marker
3. Ligationmix
4. Unligated ssDNA

90% ligation

C) PCR

1. 100 bp marker
2. LDM marker
3. 50 ng template (13 cycles)

VH-CDR1
1 Y 1 M 1
(SEQ ID NO: 636)

VH-CDR2
2 I 2 3 S G G 1 T 1 YADSVKG
(SEQ ID NO: 637)

FIG. 10

3. PCR

```
PCRpr.:
        5'-GAC TGG GTG TAG TGA TCT AG-3
                     +70
(FR3)           V    *   *   S   R   D   N   S   ...   Y   Y   C   A   K
Bridge : 5'-G GTG TAG TGA TCT AGT GAC AAC TCT ... TAC TAT TGT GCG AAA-3'
Ext :    3'-C CAC ATC ACT AGA TCT CTG TTG AGA ... ATG ATA-5'
                         --XbaI-
```

1. Annealing

+92

3'-XXX XXX XXX-VH

2. Ligation

FIG. 20

METHODS OF CONSTRUCTING LIBRARIES COMPRISING DISPLAYED AND/OR EXPRESSED MEMBERS OF A DIVERSE FAMILY OF PEPTIDES, POLYPEPTIDES OR PROTEINS AND THE NOVEL LIBRARIES

This application is a continuation-in-part of U.S. patent application Ser. No. 09/837,306, filed on Apr. 17, 2001, which claims the benefit of U.S. provisional application 60/198,069, filed on Apr. 17, 2000. All of the earlier applications are specifically incorporated by reference herein.

The present invention relates to libraries of genetic packages that display and/or express a member of a diverse family of peptides, polypeptides or proteins and collectively display and/or express at least a portion of the diversity of the family. In an alternative embodiment, the invention relates to libraries that include a member of a diverse family of peptides, polypeptides or proteins and collectively comprise at least a portion of the diversity of the family. In a preferred embodiment, the displayed and/or expressed polypeptides are human Fabs.

More specifically, the invention is directed to the methods of cleaving single-stranded nucleic acids at chosen locations, the cleaved nucleic acids encoding, at least in part, the peptides, polypeptides or proteins displayed on the genetic packages of, and/or expressed in, the libraries of the invention. In a preferred embodiment, the genetic packages are filamentous phage or phagemids or yeast.

The present invention further relates to vectors for displaying and/or expressing a diverse family of peptides, polypeptides or proteins.

The present invention further relates to methods of screening the libraries of the invention and to the peptides, polypeptides and proteins identified by such screening.

BACKGROUND OF THE INVENTION

It is now common practice in the art to prepare libraries of genetic packages that display, express or comprise a member of a diverse family of peptides, polypeptides or proteins and collectively display, express or comprise at least a portion of the diversity of the family. In many common libraries, the peptides, polypeptides or proteins are related to antibodies. Often, they are Fabs or single chain antibodies.

In general, the DNAs that encode members of the families to be displayed and/or expressed must be amplified before they are cloned and used to display and/or express the desired member. Such amplification typically makes use of forward and backward primers.

Such primers can be complementary to sequences native to the DNA to be amplified or complementary to oligonucleotides attached at the 5' or 3' ends of that DNA. Primers that are complementary to sequences native to the DNA to be amplified are disadvantaged in that they bias the members of the families to be displayed. Only those members that contain a sequence in the native DNA that is substantially complementary to the primer will be amplified. Those that do not will be absent from the family. For those members that are amplified, any diversity within the primer region will be suppressed.

For example, in European patent 368,684 B1, the primer that is used is at the 5' end of the $V_H$ region of an antibody gene. It anneals to a sequence region in the native DNA that is said to be "sufficiently well conserved" within a single species. Such primer will bias the members amplified to those having this "conserved" region. Any diversity within this region is extinguished.

It is generally accepted that human antibody genes arise through a process that involves a combinatorial selection of V and J or V, D, and J followed by somatic mutations. Although most diversity occurs in the Complementary Determining Regions (CDRs), diversity also occurs in the more conserved Framework Regions (FRs) and at least some of this diversity confers or enhances specific binding to antigens (Ag). As a consequence, libraries should contain as much of the CDR and FR diversity as possible.

To clone the amplified DNAs of the peptides, polypeptides or proteins that they encode for display on a genetic package and/or for expression, the DNAs must be cleaved to produce appropriate ends for ligation to a vector. Such cleavage is generally effected using restriction endonuclease recognition sites carried on the primers. When the primers are at the 5' end of DNA produced from reverse transcription of RNA, such restriction leaves deleterious 5' untranslated regions in the amplified DNA. These regions interfere with expression of the cloned genes and thus the display of the peptides, polypeptides and proteins coded for by them.

SUMMARY OF THE INVENTION

It is an object of this invention to provide novel methods for constructing libraries that display, express or comprise a member of a diverse family of peptides, polypeptides or proteins and collectively display, express or comprise at least a portion of the diversity of the family. These methods are not biased toward DNAs that contain native sequences that are complementary to the primers used for amplification. They also enable any sequences that may be deleterious to expression to be removed from the amplified DNA before cloning and displaying and/or expressing.

It is another object of this invention to provide a method for cleaving single-stranded nucleic acid sequences at a desired location, the method comprising the steps of:
  (i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
  (ii) cleaving the nucleic acid solely at the recognition site formed by the complementation of the nucleic acid and the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

It is a further object of this invention to provide an alternative method for cleaving single-stranded nucleic acid sequences at a desired location, the method comprising the steps of:
  (i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a restriction endonuclease recognition site; and (ii) cleaving the nucleic acid solely at the cleavage site formed by the complementation of the nucleic acid and the single-stranded region of the oligonucleotide;

the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

In an alternative embodiment of this object of the invention, the restriction endonuclease recognition site is not initially located in the double-stranded part of the oligonucleotide. Instead, it is part of an amplification primer, which primer is complementary to the double-stranded region of the oligonucleotide. On amplification of the DNA-partially double-stranded combination, the restriction endonuclease recognition site carried on the primer becomes part of the DNA. It can then be used to cleave the DNA.

Preferably, the restriction endonuclease recognition site is that of a Type II-S restriction endonuclease whose cleavage site is located at a known distance from its recognition site.

It is another object of the present invention to provide a method of capturing DNA molecules that comprise a member of a diverse family of DNAs and collectively comprise at least a portion of the diversity of the family. These DNA molecules in single-stranded form have been cleaved by one of the methods of this invention. This method involves ligating the individual single-stranded DNA members of the family to a partially duplex DNA complex. The method comprises the steps of:
  (i) contacting a single-stranded nucleic acid sequence that has been cleaved with a restriction endonuclease with a partially double-stranded oligonucleotide, the single-stranded region of the oligonucleotide being functionally complementary to the nucleic acid in the region that remains after cleavage, the double-stranded region of the oligonucleotide including any sequences necessary to return the sequences that remain after cleavage into proper reading frame for expression and containing a restriction endonuclease recognition site 5' of those sequences; and
  (ii) cleaving the partially double-stranded oligonucleotide sequence solely at the restriction endonuclease cleavage site contained within the double-stranded region of the partially double-stranded oligonucleotide.

As before, in this object of the invention, the restriction endonuclease recognition site need not be located in the double-stranded portion of the oligonucleotide. Instead, it can be introduced on amplification with an amplification primer that is used to amplify the DNA-partially double-stranded oligonucleotide combination.

It is another object of this invention to prepare libraries, that display, express or comprise a diverse family of peptides, polypeptides or proteins and collectively display, express or comprise at least part of the diversity of the family, using the methods and DNAs described above.

It is an object of this invention to screen those libraries to identify useful peptides, polypeptides and proteins and to use those substances in human therapy.

Additional objects of the invention are reflected in claims 1-116. Each of these claims is specifically incorporated by reference in this specification.

BRIEF DESCRIPTION OF THE DRAWINGS

FIG. 10 is a schematic of the design for CDR1 (SEQ ID NO:636) and CDR2 (SEQ ID NO:637) synthetic diversity.

FIG. 20 is a schematic of a process for incorporating fixed FR1 residues in an antibody heavy chain sequence. The PCRpr oligonucleotide is shown in SEQ ID NO: 612. The Bridge oligonucleotides are shown in SEQ ID NOS 613 & 615, respectively, in order of appearance, while the encoded peptides are shown in SEQ ID NOS 614 & 616, respectively, in order of appearance.

TERMS

Figure 1:
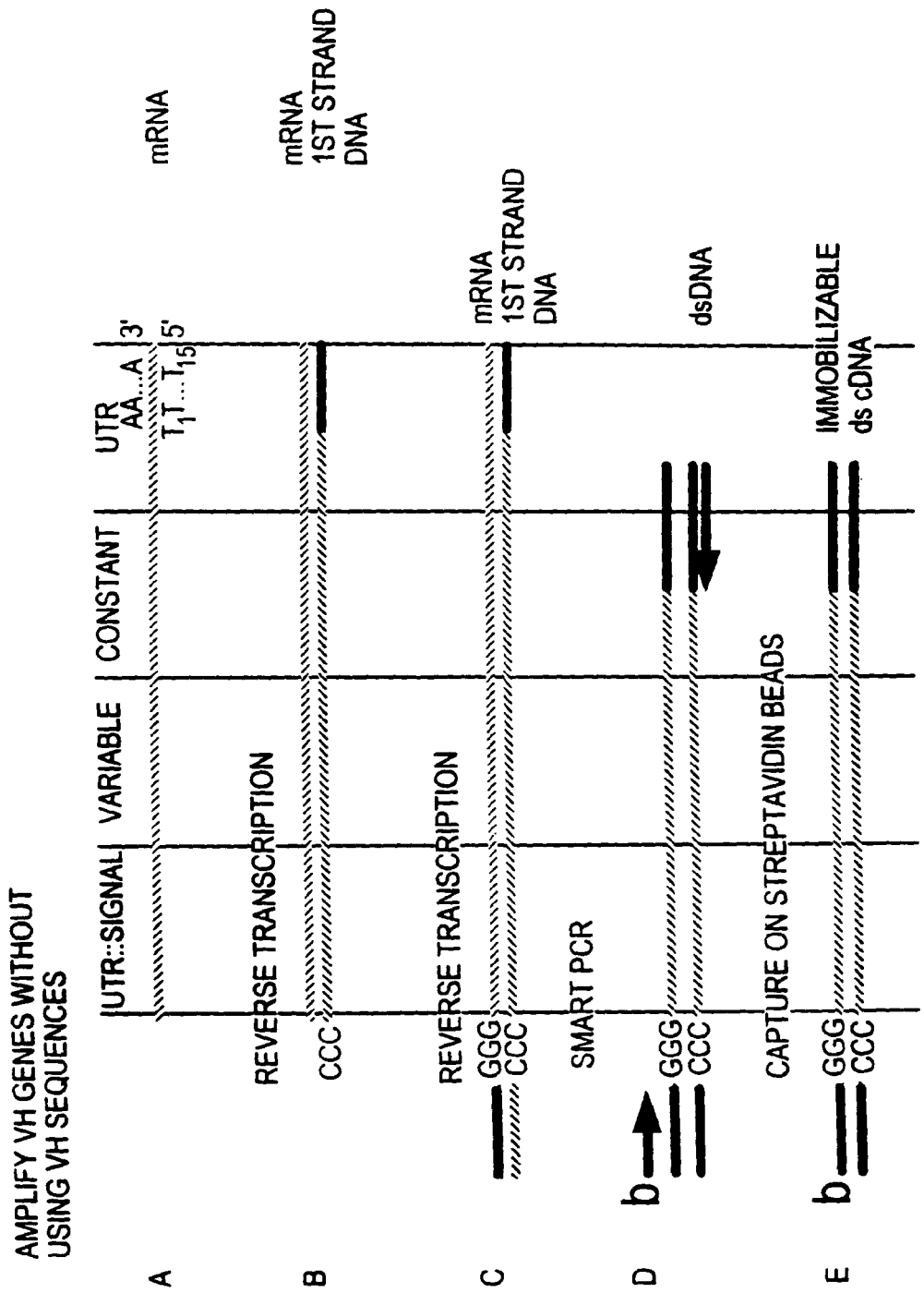
FIG. 1 is a schematic of various methods that may be employed to amplify VH genes without using primers specific for VH sequences. The $T_{15}$ oligonucleotide is shown in SEQ ID NO: 622.

In this application, the following terms and abbreviations are used:

| | |
|---|---|
| Sense strand | The upper strand of ds DNA as usually written. In the sense strand, 5'-ATG-3' codes for Met. |
| Antisense strand | The lower strand of ds DNA as usually written. In the |

| | |
|---|---|
| | antisense strand, 3'-TAC-5' would correspond to a Met codon in the sense strand. |
| Forward primer | A "forward" primer is complementary to a part of the sense strand and primes for synthesis of a new antisense-strand molecule. "Forward primer" and "lower-strand primer" are equivalent. |
| Backward primer | A "backward" primer is complementary to a part of the antisense strand and primes for synthesis of a new sense-strand molecule. "Backward primer" and "top-strand primer" are equivalent. |
| Bases | Bases are specified either by their position in a vector or gene as their position within a gene by codon and base. For example, "89.1" is the first base of codon 89, 89.2 is the second base of codon 89. |
| Sv | Streptavidin |
| Ap | Ampicillin |
| $ap^R$ | A gene conferring ampicillin resistance. |
| RERS | Restriction endonuclease recognition site |
| RE | Restriction endonuclease-cleaves preferentially at RERS |
| URE | Universal restriction endonuclease |
| Functionally complementary | Two sequences are sufficiently complementary so as to anneal under the chosen conditions. |
| AA | Amino acid |
| PCR | Polymerization chain reaction |
| GLGs | Germline genes |
| Ab | Antibody: an immunoglobin. The term also covers any protein having a binding domain which is homologous to an immunoglobin binding domain. A few examples of antibodies within this definition are, inter alia, immunoglobin isotypes and the Fab, $F(ab^1)_2$, scfv, Fv, dAb and Fd fragments. |
| Fab | Two chain molecule comprising an Ab light chain and part of a heavy-chain. |
| scFv | A single-chain Ab comprising either VH::linker::VL or VL::linker::VH. |
| w.t. | Wild type |
| HC | Heavy chain |
| LC | Light chain |
| VK | A variable domain of a Kappa light chain. |
| VH | A variable domain of a heavy chain. |
| VL | A variable domain of a lambda light chain. |

In this application when it is said that nucleic acids are cleaved solely at the cleavage site of a restriction endonuclease, it should be understood that minor cleavage may occur at random, e.g., at non-specific sites other than the specific cleavage site that is characteristic of the restriction endonuclease. The skilled worker will recognize that such non-specific, random cleavage is the usual occurrence. Accordingly, "solely at the cleavage site" of a restriction endonuclease means that cleavage occurs preferentially at the site characteristic of that endonuclease.

As used in this application and claims, the term "cleavage site formed by the complementation of the nucleic acid and the single-stranded region of the oligonucleotide" includes cleavage sites formed by the single-stranded portion of the partially double-stranded oligonucleotide duplexing with the single-stranded DNA, cleavage sites in the double-stranded portion of the partially double-stranded oligonucleotide, and cleavage sites introduced by the amplification primer used to amplify the single-stranded DNA-partially double-stranded oligonucleotide combination.

In the two methods of this invention for preparing single-stranded nucleic acid sequences, the first of those cleavage sites is preferred. In the methods of this invention for capturing diversity and cloning a family of diverse nucleic acid sequences, the latter two cleavage sites are preferred.

In this application, all references referred to are specifically incorporated by reference.

DETAILED DESCRIPTION OF THE PREFERRED EMBODIMENTS

The nucleic acid sequences that are useful in the methods of this invention, i.e., those that encode at least in part the individual peptides, polypeptides and proteins displayed, or expressed in or comprising the libraries of this invention, may be native, synthetic or a combination thereof. They may be mRNA, DNA or cDNA. In the preferred embodiment, the nucleic acids encode antibodies. Most preferably, they encode Fabs.

The nucleic acids useful in this invention may be naturally diverse, synthetic diversity may be introduced into those naturally diverse members, or the diversity may be entirely synthetic. For example, synthetic diversity can be introduced into one or more CDRs of antibody genes. Preferably, it is introduced into CDR1 and CDR2 of immunoglobulins. Preferably, natural diversity is captured in the CDR3 regions of the immunoglobin genes of this invention from B cells. Most preferably, the nucleic acids of this invention comprise a population of immunoglobin genes that comprise synthetic diversity in at least one, and more preferably both of the CDR1 and CDR2 and diversity in CDR3 captured from B cells.

Synthetic diversity may be created, for example, through the use of TRIM technology (U.S. Pat. No. 5,869,644). TRIM technology allows control over exactly which amino-acid types are allowed at variegated positions and in what proportions. In TRIM technology, codons to be diversified are synthesized using mixtures of trinucleotides. This allows any set of amino acid types to be included in any proportion.

Another alternative that may be used to generate diversified DNA is mixed oligonucleotide synthesis. With TRIM technology, one could allow Ala and Trp. With mixed oligonucleotide synthesis, a mixture that included Ala and Trp would also necessarily include Ser and Gly. The amino-acid types allowed at the variegated positions are picked with reference to the structure of antibodies, or other peptides, polypeptides or proteins of the family, the observed diversity in germline genes, the observed somatic mutations frequently observed, and the desired areas and types of variegation.

In a preferred embodiment of this invention, the nucleic acid sequences for at least one CDR or other region of the peptides, polypeptides or proteins of the family are cDNAs produced by reverse transcription from mRNA. More preferably, the mRNAs are obtained from peripheral blood cells, bone marrow cells, spleen cells or lymph node cells (such as B-lymphocytes or plasma cells) that express members of naturally diverse sets of related genes. More preferable, the mRNAs encode a diverse family of antibodies. Most preferably, the mRNAs are obtained from patients suffering from at least one autoimmune disorder or cancer. Preferably, mRNAs containing a high diversity of autoimmune diseases, such as systemic lupus erythematosus, systemic sclerosis, rheumatoid arthritis, antiphospholipid syndrome and vasculitis are used.

In a preferred embodiment of this invention, the cDNAs are produced from the mRNAs using reverse transcription. In this preferred embodiment, the mRNAs are separated from the cell and degraded using standard methods, such that only the full length (i.e., capped) mRNAs remain. The cap is then removed and reverse transcription used to produce the cDNAs.

The reverse transcription of the first (antisense) strand can be done in any manner with any suitable primer. See, e.g., H J de Haard et al., *Journal of Biological Chemistry*, 274(26): 18218-30 (1999). In the preferred embodiment of this invention where the mRNAs encode antibodies, primers that are complementary to the constant regions of antibody genes may be used. Those primers are useful because they do not generate bias toward subclasses of antibodies. In another embodiment, poly-dT primers may be used (and may be preferred for the heavy-chain genes). Alternatively, sequences complementary to the primer may be attached to the termini of the antisense strand.

In one preferred embodiment of this invention, the reverse transcriptase primer may be biotinylated, thus allowing the cDNA product to be immobilized on streptavidin (Sv) beads. Immobilization can also be effected using a primer labeled at the 5' end with one of a) free amine group, b) thiol, c) carboxylic acid, or d) another group not found in DNA that can react to form a strong bond to a known partner on an insoluble medium. If, for example, a free amine (preferably primary amine) is provided at the 5' end of a DNA primer, this amine can be reacted with carboxylic acid groups on a polymer bead using standard amide-forming chemistry. If such preferred immobilization is used during reverse transcription, the top strand RNA is degraded using well-known enzymes, such as a combination of RNAseH and RNAseA, either before or after immobilization.

The nucleic acid sequences useful in the methods of this invention are generally amplified before being used to display and/or express the peptides, polypeptides or proteins that they encode. Prior to amplification, the single-stranded DNAs may be cleaved using either of the methods described before. Alternatively, the single-stranded DNAs may be amplified and then cleaved using one of those methods.

Any of the well known methods for amplifying nucleic acid sequences may be used for such amplification. Methods that maximize, and do not bias, diversity are preferred. In a preferred embodiment of this invention where the nucleic acid sequences are derived from antibody genes, the present invention preferably utilizes primers in the constant regions of the heavy and light chain genes and primers to a synthetic sequence that are attached at the 5' end of the sense strand. Priming at such synthetic sequence avoids the use of sequences within the variable regions of the antibody genes. Those variable region priming sites generate bias against V genes that are either of rare subclasses or that have been mutated at the priming sites. This bias is partly due to suppression of diversity within the primer region and partly due to lack of priming when many mutations are present in the region complementary to the primer. The methods disclosed in this invention have the advantage of not biasing the population of amplified antibody genes for particular V gene types.

The synthetic sequences may be attached to the 5' end of the DNA strand by various methods well known for ligating DNA sequences together. RT CapExtention is one preferred method.

In RT CapExtention (derived from Smart PCR(™)), a short overlap (5'- . . . GGG-3' in the upper-strand primer (USP-GGG) complements 3'-CCC . . . . 5' in the lower strand) and reverse transcriptases are used so that the reverse complement of the upper-strand primer is attached to the lower strand.

Figure 2:
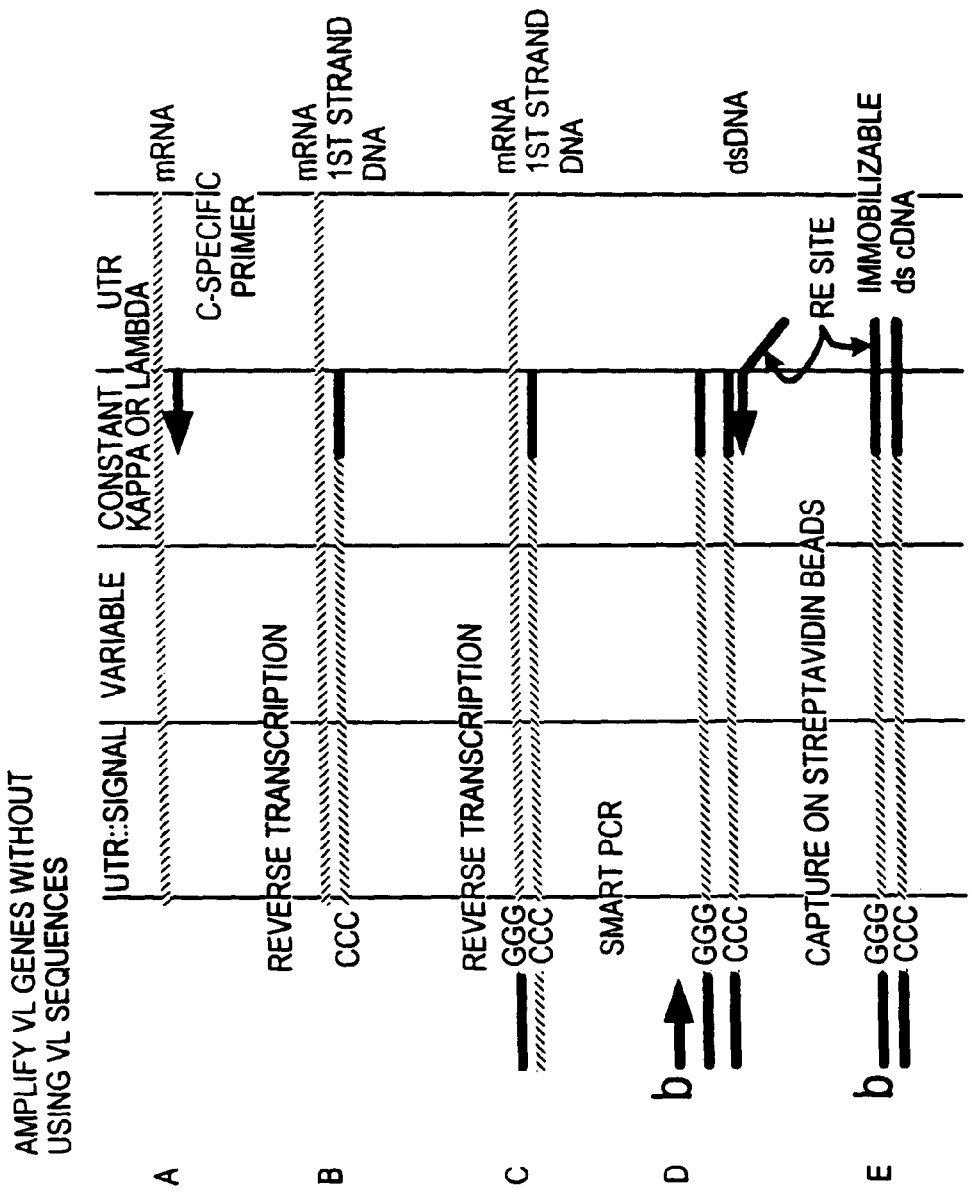
FIG. 2 is a schematic of various methods that may be employed to amplify VL genes without using primers specific for VL sequences.

FIGS. 1 and 2 show schematics to amplify VH and VL genes using RT CapExtention. FIG. 1 shows a schematic of the amplification of VH genes. FIG. 1, Panel A shows a primer specific to the poly-dT region of the 3' UTR priming synthesis of the first, lower strand. Primers that bind in the constant region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. Panel E shows immobilized double-stranded (ds) cDNA obtained by using a 5'-biotinylated top-strand primer.

FIG. 2 shows a similar schematic for amplification of VL genes. FIG. 2, Panel A shows a primer specific to the constant region at or near the 3' end priming synthesis of the first, lower strand. Primers that bind in the poly-dT region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. The bottom-strand primer also contains a useful restriction endonuclease site, such as AscI. Panel E shows immobilized ds cDNA obtained by using a 5'-biotinylated top-strand primer.

In FIGS. 1 and 2, each V gene consists of a 5' untranslated region (UTR) and a secretion signal, followed by the variable region, followed by a constant region, followed by a 3' untranslated region (which typically ends in poly-A). An initial primer for reverse transcription may be complementary to the constant region or to the poly A segment of the 3'-UTR. For human heavy-chain genes, a primer of 15 T is preferred. Reverse transcriptases attach several C residues to the 3' end of the newly synthesized DNA. RT CapExtention exploits this feature. The reverse transcription reaction is first run with only a lower-strand primer. After about 1 hour, a primer ending in GGG (USP-GGG) and more RTase are added. This causes the lower-strand cDNA to be extended by the reverse complement of the USP-GGG up to the final GGG. Using one primer identical to part of the attached synthetic sequence and a second primer complementary to a region of known sequence at the 3' end of the sense strand, all the V genes are amplified irrespective of their V gene subclass.

In another preferred embodiment, synthetic sequences may be added by Rapid Amplification of cDNA Ends (RACE) (see Frohman, M. A., Dush, M. K., & Martin, G. R. (1988) *Proc. Natl. Acad. Sci. USA* (85): 8998-9002).

FIG. 1 shows a schematic of RACE amplification of antibody heavy and light chains. First, mRNA is selected by treating total or poly(A+) RNA with calf intestinal phosphatase (CIP) to remove the 5'-phosphate from all molecules that have them such as ribosomal RNA, fragmented mRNA, tRNA and genomic DNA. Full length mRNA (containing a protective 7-methyl cap structure) is uneffected. The RNA is then treated with tobacco acid pyrophosphatase (TAP) to remove the cap structure from full length mRNAs leaving a 5'-monophosphate group. Next, a synthetic RNA adaptor is ligated to the RNA population, only molecules which have a 5-phosphate (uncapped, full length mRNAs) will accept the adaptor. Reverse trascriptase reactions using an oligodT primer, and nested PCR (using one adaptor primer (located in the 5' synthetic adaptor) and one primer for the gene) are then used to amplify the desired transcript.

In a preferred embodiment of this invention, the upper strand or lower strand primer may be also biotinylated or labeled at the 5' end with one of a) free amino group, b) thiol, c) carboxylic acid and d) another group not found in DNA that can react to form a strong bond to a known partner as an insoluble medium. These can then be used to immobilize the labeled strand after amplification. The immobilized DNA can be either single or double-stranded.

After amplification (using e.g., RT CapExtension or RACE), the DNAs of this invention are rendered single-stranded. For example, the strands can be separated by using a biotinylated primer, capturing the biotinylated product on streptavidin beads, denaturing the DNA, and washing away the complementary strand. Depending on which end of the captured DNA is wanted, one will choose to immobilize either the upper (sense) strand or the lower (antisense) strand.

To prepare the single-stranded amplified DNAs for cloning into genetic packages so as to effect display of, or for expression of, the peptides, polypeptides or proteins encoded, at least in part, by those DNAs, they must be manipulated to provide ends suitable for cloning and display and/or expression. In particular, any 5' untranslated regions and mammalian signal sequences must be removed and replaced, in frame, by a suitable signal sequence that functions in the display or expression host. Additionally, parts of the variable domains (in antibody genes) may be removed and replaced by synthetic segments containing synthetic diversity. The diversity of other gene families may likewise be expanded with synthetic diversity.

According to the methods of this invention, there are two ways to manipulate the single-stranded DNAs for display and/or expression. The first method comprises the steps of:
(i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
(ii) cleaving the nucleic acid solely at the recognition site formed by the complementation of the nucleic acid and the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

In this first method, short oligonucleotides are annealed to the single-stranded DNA so that restriction endonuclease recognition sites formed within the now locally double-stranded regions of the DNA can be cleaved. In particular, a recognition site that occurs at the same position in a substantial fraction of the single-stranded DNAs is identical.

For antibody genes, this can be done using a catalog of germline sequences. For other families, similar comparisons exist and may be used to select appropriate regions for cleavage and to maintain diversity.

For example, Table 1 depicts the DNA sequences of the FR3 regions of the 51 known human VH germline genes. In this region, the genes contain restriction endonuclease recognition sites shown in Table 2. Restriction endonucleases that cleave a large fraction of germline genes at the same site are preferred over endonucleases that cut at a variety of sites. Furthermore, it is preferred that there be only one site for the restriction endonucleases within the region to which the short oligonucleotide binds on the single-stranded DNA, e.g., about 10 bases on either side of the restriction endonuclease recognition site.

An enzyme that cleaves downstream in FR3 is also more preferable because it captures fewer mutations in the framework. This may be advantageous is some cases. However, it is well known that framework mutations exist and confer and enhance antibody binding. The present invention, by choice of appropriate restriction site, allows all or part of FR3 diversity to be captured. Hence, the method also allows extensive diversity to be captured.

Finally, in the methods of this invention restriction endonucleases that are active between about 37° C. and about 75° C. are used. Preferably, restriction endonucleases that are active between about 45° C. and about 75° C. may be used. More preferably, enzymes that are active above 50° C., and most preferably active about 55° C., are used. Such temperatures maintain the nucleic acid sequence to be cleaved in substantially single-stranded form.

Enzymes shown in Table 2 that cut many of the heavy chain FR3 germline genes at a single position include: MaeIII (24@4), Tsp45I(21@4), HphI(44@5), BsaJI(23@65), AluI (23@47), BlpI(21@48), DdeI(29@58), BglII(10@61), MslI (44@72), BsiEI(23@74), EaeI(23@74), EagI(23@74), HaeIII(25@75), Bst4CI(51@86), HpyCH4III(51@86), HinfI(38@2), MlyI(18@2), PleI(18@2), MnlI(31@67), HpyCH4V(21@44), BsmAI(16@11), BpmI(19@12), XmnI (12@30), and SacI(11@51). (The notation used means, for example, that BsmAI cuts 16 of the FR3 germline genes with a restriction endonuclease recognition site beginning at base 11 of FR3.)

For cleavage of human heavy chains in FR3, the preferred restriction endonucleases are: Bst4CI (or TaaI or HpyCH4III), BlpI, HpyCH4V, and MslI. Because ACNGT (the restriction endonuclease recognition site for Bst4CI, TaaI, and HpyCH4III) is found at a consistent site in all the human FR3 germline genes, one of those enzymes is the most preferred for capture of heavy chain CDR3 diversity. BlpI and HpyCH4V are complementary. BlpI cuts most members of the VH1 and VH4 families while HpyCH4V cuts most members of the VH3, VH5, VH6, and VH7 families. Neither enzyme cuts VH2s, but this is a very small family, containing only three members. Thus, these enzymes may also be used in preferred embodiments of the methods of this invention.

The restriction endonucleases HpyCH4III, Bst4CI, and TaaI all recognize 5'-ACnGT-3' and cut upper strand DNA after n and lower strand DNA before the base complementary to n. This is the most preferred restriction endonuclease recognition site for this method on human heavy chains because it is found in all germline genes. Furthermore, the restriction endonuclease recognition region (ACnGT) matches the second and third bases of a tyrosine codon (tay) and the following cysteine codon (tgy) as shown in Table 3. These codons are highly conserved, especially the cysteine in mature antibody genes.

Table 4 E shows the distinct oligonucleotides of length 22 (except the last one which is of length 20) bases. Table 5 C shows the analysis of 1617 actual heavy chain antibody genes. Of these, 1511 have the site and match one of the candidate oligonucleotides to within 4 mismatches. Eight oligonucleotides account for most of the matches and are given in Table 4 F.1. The 8 oligonucleotides are very similar so that it is likely that satisfactory cleavage will be achieved with only one oligonucleotide (such as H43.77.97.1-02#1) by adjusting temperature, pH, salinity, and the like. One or two oligonucleotides may likewise suffice whenever the germline gene sequences differ very little and especially if they differ very little close to the restriction endonuclease recognition region to be cleaved. Table 5 D shows a repeat analysis of 1617 actual heavy chain antibody genes using only the 8 chosen oligonucleotides. This shows that 1463 of the sequences match at least one of the oligonucleotides to within 4 mismatches and have the site as expected. Only 7 sequences have a second HpyCH4III restriction endonuclease recognition region in this region.

Another illustration of choosing an appropriate restriction endonuclease recognition site involves cleavage in FR1 of human heavy chains. Cleavage in FR1 allows capture of the entire CDR diversity of the heavy chain.

The germline genes for human heavy chain FR1 are shown in Table 6. Table 7 shows the restriction endonuclease recognition sites found in human germline genes FR1s. The preferred sites are BsgI(GTGCAG;39@4), BsoFI(GCngc; 43@6,11@9,2@3,1@12), TseI(Gcwgc;43@6,11@9,2@3, 1@12), MspA1I(CMGckg;46@7,2@1), PvuII(CAGctg; 46@7,2@1), AluI(AGct;48@82@2), DdeI(Ctnag;22@52, 9@48), HphI(tcacc;22@80), BssKI(Nccngg;35@39,2@40), BsaJI(Ccnngg;32@40,2@41), BstNI(CCwgg;33@40), ScrFI(CCngg;35@40,2@41), Eco0109I(RGgnccy;22@46, 11@43), Sau96I(Ggncc;23@47,11@44), AvaII(Ggwcc; 23@47,4@44), PpuMI(RGgwccy;22@46,4@43), BsmFI (gtccc;20@48), HinfI(Gantc;34@16,21@56,21@77), TfiI (21@77), MlyI(GAGTC;34@16), MlyI(gactc;21@56), and AlwNI(CAGnnnctg;22@68). The more preferred sites are MspAI and PvuII. MspAI and PvuII have 46 sites at 7-12 and 2 at 1-6. To avoid cleavage at both sites, oligonucleotides are used that do not fully cover the site at 1-6. Thus, the DNA will not be cleaved at that site. We have shown that DNA that extends 3, 4, or 5 bases beyond a PvuII-site can be cleaved efficiently.

Another illustration of choosing an appropriate restriction endonuclease recognition site involves cleavage in FR1 of human kappa light chains. Table 8 shows the human kappa FR1 germline genes and Table 9 shows restriction endonuclease recognition sites that are found in a substantial number of human kappa FR1 germline genes at consistent locations. Of the restriction endonuclease recognition sites listed, BsmAI and PflFI are the most preferred enzymes. BsmAI sites are found at base 18 in 35 of 40 germline genes. PflFI sites are found in 35 of 40 germline genes at base 12.

Another example of choosing an appropriate restriction endonuclease recognition site involves cleavage in FR1 of the human lambda light chain. Table 10 shows the 31 known human lambda FR1 germline gene sequences. Table 11 shows restriction endonuclease recognition sites found in human lambda FR1 germline genes. HinfI and DdeI are the most preferred restriction endonucleases for cutting human lambda chains in FR1.

After the appropriate site or sites for cleavage are chosen, one or more short oligonucleotides are prepared so as to functionally complement, alone or in combination, the chosen recognition site. The oligonucleotides also include sequences that flank the recognition site in the majority of the amplified genes. This flanking region allows the sequence to anneal to the single-stranded DNA sufficiently to allow cleavage by the restriction endonuclease specific for the site chosen.

The actual length and sequence of the oligonucleotide depends on the recognition site and the conditions to be used for contacting and cleavage. The length must be sufficient so that the oligonucleotide is functionally complementary to the single-stranded DNA over a large enough region to allow the two strands to associate such that cleavage may occur at the chosen temperature and at the desired location.

Typically, the oligonucleotides of this preferred method of the invention are about 17 to about 30 nucleotides in length. Below about 17 bases, annealing is too weak and above 30 bases there can be a loss of specificity. A preferred length is 18 to 24 bases.

Oligonucleotides of this length need not be identical complements of the germline genes. Rather, a few mismatches taken may be tolerated. Preferably, however, no more than 1-3 mismatches are allowed. Such mismatches do not adversely affect annealing of the oligonucleotide to the single-stranded DNA. Hence, the two DNAs are said to be functionally complementary.

The second method to manipulate the single-stranded DNAs of this invention for display and/or expression comprises the steps of:
(i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a restriction endonuclease recognition site; and
(ii) cleaving the nucleic acid solely at the cleavage site formed by the complementation of the nucleic acid and the single-stranded region of the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

As explained above, the cleavage site may be formed by the single-stranded portion of the partially double-stranded oligonucleotide duplexing with the single-stranded DNA, the cleavage site may be carried in the double-stranded portion of the partially double-stranded oligonucleotide, or the cleavage site may be introduced by the amplification primer used to amplify the single-stranded DNA-partially double-stranded oligonucleotide combination. In this embodiment, the first is preferred. And, the restriction endonuclease recognition site may be located in either the double-stranded portion of the oligonucleotide or introduced by the amplification primer, which is complementary to that double-stranded region, as used to amplify the combination.

Preferably, the restriction endonuclease site is that of a Type II-S restriction endonuclease, whose cleavage site is located at a known distance from its recognition site.

This second method, preferably, employs Universal Restriction Endonucleases ("URE"). UREs are partially double-stranded oligonucleotides. The single-stranded portion or overlap of the URE consists of a DNA adapter that is functionally complementary to the sequence to be cleaved in the single-stranded DNA. The double-stranded portion consists of a restriction endonuclease recognition site, preferably type II-S.

The URE method of this invention is specific and precise and can tolerate some (e.g., 1-3) mismatches in the complementary regions, i.e., it is functionally complementary to that region. Further, conditions under which the URE is used can be adjusted so that most of the genes that are amplified can be cut, reducing bias in the library produced from those genes.

The sequence of the single-stranded DNA adapter or overlap portion of the URE typically consists of about 14-22 bases. However, longer or shorter adapters may be used. The size depends on the ability of the adapter to associate with its functional complement in the single-stranded DNA and the temperature used for contacting the URE and the single-stranded DNA at the temperature used for cleaving the DNA with the restriction enzyme. The adapter must be functionally complementary to the single-stranded DNA over a large enough region to allow the two strands to associate such that the cleavage may occur at the chosen temperature and at the desired location. We prefer singe-stranded or overlap portions of 14-17 bases in length, and more preferably 18-20 bases in length.

The site chosen for cleavage using the URE is preferably one that is substantially conserved in the family of amplified DNAs. As compared to the first cleavage method of this invention, these sites do not need to be endonuclease recognition sites. However, like the first method, the sites chosen can be synthetic rather than existing in the native DNA. Such sites may be chosen by references to the sequences of known antibodies or other families of genes. For example, one preferred site occurs near the end of FR3—codon 89 through the second base of codon 93. CDR3 begins at codon 95.

The sequences of 79 human heavy chain genes are available at Table 12 B.

Most preferably, one or more sequences are identified using these sites or other available sequence information. These sequences together are present in a substantial fraction of the amplified DNAs. For example, multiple sequences could be used to allow for known diversity in germline genes or for frequent somatic mutations. Synthetic degenerate sequences could also be used. Preferably, a sequence(s) that occurs in at least 65% of genes examined with no more than 2-3 mismatches is chosen.

URE single-stranded adapters or overlaps are then made to be complementary to the chosen regions. Conditions for using the UREs are determined empirically. These conditions should allow cleavage of DNA that contains the functionally complementary sequences with no more than 2 or 3 mismatches but that do not allow cleavage of DNA lacking such sequences.

As described above, the double-stranded portion of the URE includes an endonuclease recognition site, preferably a Type II-S recognition site. Any enzyme that is active at a temperature necessary to maintain the single-stranded DNA substantially in that form and to allow the single-stranded DNA adapter portion of the URE to anneal long enough to the single-stranded DNA to permit cleavage at the desired site may be used.

The preferred Type II-S enzymes for use in the URE methods of this invention provide asymmetrical cleavage of the single-stranded DNA. Among these are the enzymes listed in Table 13. The most preferred Type II-S enzyme is FokI.

When the preferred FokI containing URE is used, several conditions are preferably used to effect cleavage:

1) Excess of the URE over target DNA should be present to activate the enzyme. URE present only in equimolar amounts to the target DNA would yield poor cleavage of ssDNA because the amount of active enzyme available would be limiting.
2) An activator may be used to activate part of the FokI enzyme to dimerize without causing cleavage. Examples of appropriate activators are shown in Table 14.
3) The cleavage reaction is performed at a temperature between 45°-75° C., preferably above 50° C. and most preferably above 55° C.

The UREs used in the prior art contained a 14-base single-stranded segment, a 10-base stem (containing a FokI site), followed by the palindrome of the 10-base stem. While such UREs may be used in the methods of this invention, the preferred UREs of this invention also include a segment of three to eight bases (a loop) between the FokI restriction endonuclease recognition site containing segments. In the preferred embodiment, the stem (containing the FokI site) and its palindrome are also longer than 10 bases. Preferably, they are 10-14 bases in length. Examples of these "lollipop" URE adapters are shown in Table 15.

One example of using a URE to cleave an single-stranded DNA involves the FR3 region of human heavy chain. Table 16 shows an analysis of 840 full-length mature human heavy chains with the URE recognition sequences shown. The vast majority (718/840=0.85) will be recognized with 2 or fewer mismatches using five UREs (VHS881-1.1, VHS881-1.2, VHS881-2.1, VHS881-4.1, and VHS881-9.1). Each has a 20-base adaptor sequence to complement the germline gene, a ten-base stem segment containing a FokI site, a five base loop, and the reverse complement of the first stem segment. Annealing those adapters, alone or in combination, to single-stranded antisense heavy chain DNA and treating with FokI in the presence of, e.g., the activator FOKIact, will lead to cleavage of the antisense strand at the position indicated.

Another example of using a URE(s) to cleave a single-stranded DNA involves the FR1 region of the human Kappa light chains. Table 17 shows an analysis of 182 full-length human kappa chains for matching by the four 19-base probe sequences shown. Ninety-six percent of the sequences match one of the probes with 2 or fewer mismatches. The URE adapters shown in Table 17 are for cleavage of the sense strand of kappa chains. Thus, the adaptor sequences are the reverse complement of the germline gene sequences. The URE consists of a ten-base stem, a five base loop, the reverse complement of the stem and the complementation sequence. The loop shown here is TTGTT, but other sequences could be used. Its function is to interrupt the palindrome of the stems so that formation of a lollypop monomer is favored over dimerization. Table 17 also shows where the sense strand is cleaved.

Another example of using a URE to cleave a single-stranded DNA involves the human lambda light chain. Table 18 shows analysis of 128 human lambda light chains for matching the four 19-base probes shown. With three or fewer mismatches, 88 of 128 (69%) of the chains match one of the probes. Table 18 also shows URE adapters corresponding to these probes. Annealing these adapters to upper-strand ssDNA of lambda chains and treatment with FokI in the presence of FOKIact at a temperature at or above 45° C. will lead to specific and precise cleavage of the chains.

The conditions under which the short oligonucleotide sequences of the first method and the UREs of the second method are contacted with the single-stranded DNAs may be empirically determined. The conditions must be such that the single-stranded DNA remains in substantially single-stranded form. More particularly, the conditions must be such that the single-stranded DNA does not form loops that may interfere with its association with the oligonucleotide sequence or the URE or that may themselves provide sites for cleavage by the chosen restriction endonuclease.

The effectiveness and specificity of short oligonucleotides (first method) and UREs (second method) can be adjusted by controlling the concentrations of the URE adapters/oligonucleotides and substrate DNA, the temperature, the pH, the concentration of metal ions, the ionic strength, the concentration of chaotropes (such as urea and formamide), the concentration of the restriction endonuclease(e.g., FokI), and the time of the digestion. These conditions can be optimized with synthetic oligonucleotides having: 1) target germline gene sequences, 2) mutated target gene sequences, or 3) somewhat related non-target sequences. The goal is to cleave most of the target sequences and minimal amounts of non-targets.

In accordance with this invention, the single-stranded DNA is maintained in substantially that form using a temperature between about 37° C. and about 75° C. Preferably, a temperature between about 45° C. and about 75° C. is used. More preferably, a temperature between 50° C. and 60° C., most preferably between 55° C. and 60° C., is used. These temperatures are employed both when contacting the DNA with the oligonucleotide or URE and when cleaving the DNA using the methods of this invention.

The two cleavage methods of this invention have several advantages. The first method allows the individual members of the family of single-stranded DNAs to be cleaved preferentially at one substantially conserved endonuclease recognition site. The method also does not require an endonuclease recognition site to be built into the reverse transcription or amplification primers. Any native or synthetic site in the family can be used.

The second method has both of these advantages. In addition, the preferred URE method allows the single-stranded DNAs to be cleaved at positions where no endonuclease recognition site naturally occurs or has been synthetically constructed.

Most importantly, both cleavage methods permit the use of 5' and 3' primers so as to maximize diversity and then cleavage to remove unwanted or deleterious sequences before cloning, display and/or expression.

After cleavage of the amplified DNAs using one of the methods of this invention, the DNA is prepared for cloning, display and/or expression. This is done by using a partially duplexed synthetic DNA adapter, whose terminal sequence is based on the specific cleavage site at which the amplified DNA has been cleaved.

The synthetic DNA is designed such that when it is ligated to the cleaved single-stranded DNA in proper reading frame so that the desired peptide, polypeptide or protein can be displayed on the surface of the genetic package and/or expressed. Preferably, the double-stranded portion of the adapter comprises the sequence of several codons that encode the amino acid sequence characteristic of the family of peptides, polypeptides or proteins up to the cleavage site. For human heavy chains, the amino acids of the 3-23 framework are preferably used to provide the sequences required for expression of the cleaved DNA.

Preferably, the double-stranded portion of the adapter is about 12 to 100 bases in length. More preferably, about 20 to 100 bases are used. The double-standard region of the adapter also preferably contains at least one endonuclease recognition site useful for cloning the DNA into a suitable display and/or expression vector (or a recipient vector used to archive the diversity). This endonuclease restriction site may be native to the germline gene sequences used to extend the DNA sequence. It may be also constructed using degenerate sequences to the native germline gene sequences. Or, it may be wholly synthetic.

The single-stranded portion of the adapter is complementary to the region of the cleavage in the single-stranded DNA. The overlap can be from about 2 bases up to about 15 bases. The longer the overlap, the more efficient the ligation is likely to be. A preferred length for the overlap is 7 to 10. This allows some mismatches in the region so that diversity in this region may be captured.

The single-stranded region or overlap of the partially duplexed adapter is advantageous because it allows DNA cleaved at the chosen site, but not other fragments to be captured. Such fragments would contaminate the library with genes encoding sequences that will not fold into proper antibodies and are likely to be non-specifically sticky.

One illustration of the use of a partially duplexed adaptor in the methods of this invention involves ligating such adaptor to a human FR3 region that has been cleaved, as described above, at 5'-ACnGT-3' using HpyCH4III, Bst4CI or TaaI.

Table 4 F.2 shows the bottom strand of the double-stranded portion of the adaptor for ligation to the cleaved bottom-strand DNA. Since the HpyCH4III-Site is so far to the right (as shown in Table 3), a sequence that includes the AflII-site as well as the XbaI site can be added. This bottom strand portion of the partially-duplexed adaptor, H43.XAExt, incorporates both XbaI and AflII-sites. The top strand of the double-stranded portion of the adaptor has neither site (due to planned mismatches in the segments opposite the XbaI and AflII-Sites of H43.XAExt), but will anneal very tightly to H43.XAExt. H43AExt contains only the AflII-site and is to be used with the top strands H43.ABr1 and H43.ABr2 (which have intentional alterations to destroy the AflII-site).

After ligation, the desired, captured DNA can be PCR amplified again, if desired, using in the preferred embodiment a primer to the downstream constant region of the antibody gene and a primer to part of the double-standard region of the adapter. The primers may also carry restriction endonuclease sites for use in cloning the amplified DNA.

After ligation, and perhaps amplification, of the partially double-stranded adapter to the single-stranded amplified DNA, the composite DNA is cleaved at chosen 5' and 3' endonuclease recognition sites.

The cleavage sites useful for cloning depend on the phage or phagemid or other vectors into which the cassette will be inserted and the available sites in the antibody genes. Table 19 provides restriction endonuclease data for 75 human light chains. Table 20 shows corresponding data for 79 human heavy chains. In each Table, the endonucleases are ordered by increasing frequency of cutting. In these Tables, Nch is the number of chains cut by the enzyme and Ns is the number of sites (some chains have more than one site).

From this analysis, SfiI, NotI, AflII, ApaLI, and AscI are very suitable. SfiI and NotI are preferably used in pCES1 to insert the heavy-chain display segment. ApaLI and AscI are preferably used in pCES1 to insert the light-chain display segment.

BstEII-sites occur in 97% of germ-line JH genes. In rearranged V genes, only 54/79 (68%) of heavy-chain genes contain a BstEII-Site and 7/61 of these contain two sites. Thus, 47/79 (59%) contain a single BstEII-Site. An alternative to using BstEII is to cleave via UREs at the end of JH and ligate to a synthetic oligonucleotide that encodes part of CH1.

One example of preparing a family of DNA sequences using the methods of this invention involves capturing human CDR 3 diversity. As described above, mRNAs from various autoimmune patients are reverse transcribed into lower strand cDNA. After the top strand RNA is degraded, the lower strand is immobilized and a short oligonucleotide used to cleave the cDNA upstream of CDR3. A partially duplexed synthetic DNA adapter is then annealed to the DNA and the DNA is amplified using a primer to the adapter and a primer to the constant region (after FR4). The DNA is then cleaved using BstEII (in FR4) and a restriction endonuclease appropriate to the partially double-stranded adapter (e.g., XbaI and AflII (in FR3)). The DNA is then ligated into a synthetic VH skeleton such as 3-23.

One example of preparing a single-stranded DNA that was cleaved using the URE method involves the human Kappa chain. The cleavage site in the sense strand of this chain is depicted in Table 17. The oligonucleotide kapextURE is annealed to the oligonucleotides (kaBR01UR, kaBR02UR, kaBR03UR, and kaBR04UR) to form a partially duplex DNA. This DNA is then ligated to the cleaved soluble kappa chains. The ligation product is then amplified using primers kapextUREPCR and CKForeAsc (which inserts a AscI site after the end of C kappa). This product is then cleaved with ApaLI and AscI and ligated to similarly cut recipient vector.

Another example involves the cleavage of lambda light chains, illustrated in Table 18. After cleavage, an extender (ON_LamEx133) and four bridge oligonucleotides (ON_LamB1-133, ON_LamB2-133, ON_LamB3-133, and ON_LamB4-133) are annealed to form a partially duplex DNA. That DNA is ligated to the cleaved lambda-chain sense strands. After ligation, the DNA is amplified with ON_Lam133PCR and a forward primer specific to the lambda constant domain, such as CL2ForeAsc or CL7ForeAsc (Table 130).

In human heavy chains, one can cleave almost all genes in FR4 (downstream, i.e., toward the 3' end of the sense strand, of CDR3) at a BstEII-Site that occurs at a constant position in a very large fraction of human heavy-chain V genes. One then needs a site in FR3, if only CDR3 diversity is to be captured, in FR2, if CDR2 and CDR3 diversity is wanted, or in FR1, if all the CDR diversity is wanted. These sites are preferably inserted as part of the partially double-stranded adaptor.

The preferred process of this invention is to provide recipient vectors (e.g., for display and/or expression) having sites that allow cloning of either light or heavy chains. Such vectors are well known and widely used in the art. A preferred phage display vector in accordance with this invention is phage MALIA3. This displays in gene III. The sequence of the phage MALIA3 is shown in Table 21A (annotated) and Table 21B (condensed).

The DNA encoding the selected regions of the light or heavy chains can be transferred to the vectors using endonucleases that cut either light or heavy chains only very rarely. For example, light chains may be captured with ApaLI and AscI. Heavy-chain genes are preferably cloned into a recipient vector having SfiI, NcoI, XbaI, AflII, BstEII, ApaI, and NotI sites. The light chains are preferably moved into the library as ApaLI-AscI fragments. The heavy chains are preferably moved into the library as SfiI-NotI fragments.

Most preferably, the display is had on the surface of a derivative of M13 phage. The most preferred vector contains all the genes of M13, an antibiotic resistance gene, and the display cassette. The preferred vector is provided with restriction sites that allow introduction and excision of members of the diverse family of genes, as cassettes. The preferred vector is stable against rearrangement under the growth conditions used to amplify phage.

In another embodiment of this invention, the diversity captured by the methods of the present invention may be displayed and/or expressed in a phagemid vector (e.g., pCES1) that displays and/or expresses the peptide, polypeptide or protein. Such vectors may also be used to store the diversity for subsequent display and/or expression using other vectors or phage.

In another embodiment of this invention, the diversity captured by the methods of the present invention may be displayed and/or expressed in a yeast vector.

In another embodiment, the mode of display may be through a short linker to anchor domains—one possible anchor comprising the final portion of M13 III ("IIIstump") and a second possible anchor being the full length III mature protein.

The IIIstump fragment contains enough of M13 III to assemble into phage but not the domains involved in mediating infectivity. Because the w.t. III proteins are present the phage is unlikely to delete the antibody genes and phage that do delete these segments receive only a very small growth advantage. For each of the anchor domains, the DNA encodes the w.t. AA sequence, but differs from the w.t. DNA sequence to a very high extent. This will greatly reduce the potential for homologous recombination between the anchor and the w.t. gene that is also present (see Example 6).

Most preferably, the present invention uses a complete phage carrying an antibiotic-resistance gene (such as an ampicillin-resistance gene) and the display cassette. Because the w.t. iii and possibly viii genes are present, the w.t. proteins are also present. The display cassette is transcribed from a regulatable promoter (e.g., $P_{LacZ}$). Use of a regulatable promoter allows control of the ratio of the fusion display gene to the corresponding w.t. coat protein. This ratio determines the average number of copies of the display fusion per phage (or phagemid) particle.

Another aspect of the invention is a method of displaying peptides, polypeptides or proteins (and particularly Fabs) on filamentous phage. In the most preferred embodiment this method displays FABs and comprises:

a) obtaining a cassette capturing a diversity of segments of DNA encoding the elements:

$P_{reg}$::RBS1::SS1::VL::CL::stop::RBS2::SS2::VH::CH1::linker::anchor::stop::, where $P_{reg}$ is a regulatable promoter, RBS1 is a first ribosome binding site, SS1 is a signal sequence operable in the host strain, VL is a member of a diverse set of light-chain variable regions, CL is a light-chain constant region, stop is one or more stop codons, RBS2 is a second ribosome binding site, SS2 is a second signal sequence operable in the host strain, VH is a member of a diverse set of heavy-chain variable regions, CH1 is an antibody heavy-chain first constant domain, linker is a sequence of amino acids of one to about 50 residues, anchor is a protein that will assemble into the filamentous phage particle and stop is a second example of one or more stop codons; and b) positioning that cassette within the phage genome to maximize the viability of the phage and to minimize the potential for deletion of the cassette or parts thereof.

The DNA encoding the anchor protein in the above preferred cassette should be designed to encode the same (or a closely related) amino acid sequence as is found in one of the coat proteins of the phage, but with a distinct DNA sequence.

This is to prevent unwanted homologous recombination with the w.t. gene. In addition, the cassette should be placed in the intergenic region. The positioning and orientation of the display cassette can influence the behavior of the phage.

In one embodiment of the invention, a transcription terminator may be placed after the second stop of the display cassette above (e.g., Trp). This will reduce interaction between the display cassette and other genes in the phage antibody display vector.

In another embodiment of the methods of this invention, the phage or phagemid can display and/or express proteins other than Fab, by replacing the Fab portions indicated above, with other protein genes.

Various hosts can be used the display and/or expression aspect of this invention. Such hosts are well known in the art. In the preferred embodiment, where Fabs are being displayed and/or expressed, the preferred host should grow at 30° C. and be RecA$^-$ (to reduce unwanted genetic recombination) and EndA$^-$ (to make recovery of RF DNA easier). It is also preferred that the host strain be easily transformed by electroporation.

XL1-Blue MRF' satisfies most of these preferences, but does not grow well at 30° C. XL1-Blue MRF' does grow slowly at 38° C. and thus is an acceptable host. TG-1 is also an acceptable host although it is RecA$^+$ and EndA$^+$. XL1-Blue MRF' is more preferred for the intermediate host used to accumulate diversity prior to final construction of the library.

After display and/or expression, the libraries of this invention may be screened using well known and conventionally used techniques. The selected peptides, polypeptides or proteins may then be used to treat disease. Generally, the peptides, polypeptides or proteins for use in therapy or in pharmaceutical compositions are produced by isolating the DNA encoding the desired peptide, polypeptide or protein from the member of the library selected. That DNA is then used in conventional methods to produce the peptide, polypeptides or protein it encodes in appropriate host cells, preferably mammalian host cells, e.g., CHO cells. After isolation, the peptide, polypeptide or protein is used alone or with pharmaceutically acceptable compositions in therapy to treat disease.

EXAMPLES

Example 1

RACE Amplification of Heavy and Light Chain Antibody Repertoires from Autoimmune Patients Total RNA was isolated from individual blood samples (50 ml) of 11 patients using a RNAzol™ kit (CINNA/Biotecx), as described by the manufacturer. The patients were diagnosed as follows:
1. SLE and phospholipid syndrome
2. limited systemic sclerosis
3. SLE and Sjogren syndrome
4. Limited Systemic sclerosis
5. Reumatoid Arthritis with active vasculitis
6. Limited systemic sclerosis and Sjogren Syndrome
7. Reumatoid Arthritis and (not active) vasculitis
8. SLE and Sjogren syndrome
9. SLE
10. SLE and (active) glomerulonephritis
11. Polyarthritis/Raynauds Phenomen
From these 11 samples of total RNA, Poly-A+ RNA was isolated using Promega PolyATtract® mRNA Isolation kit (Promega).

Figure 3:
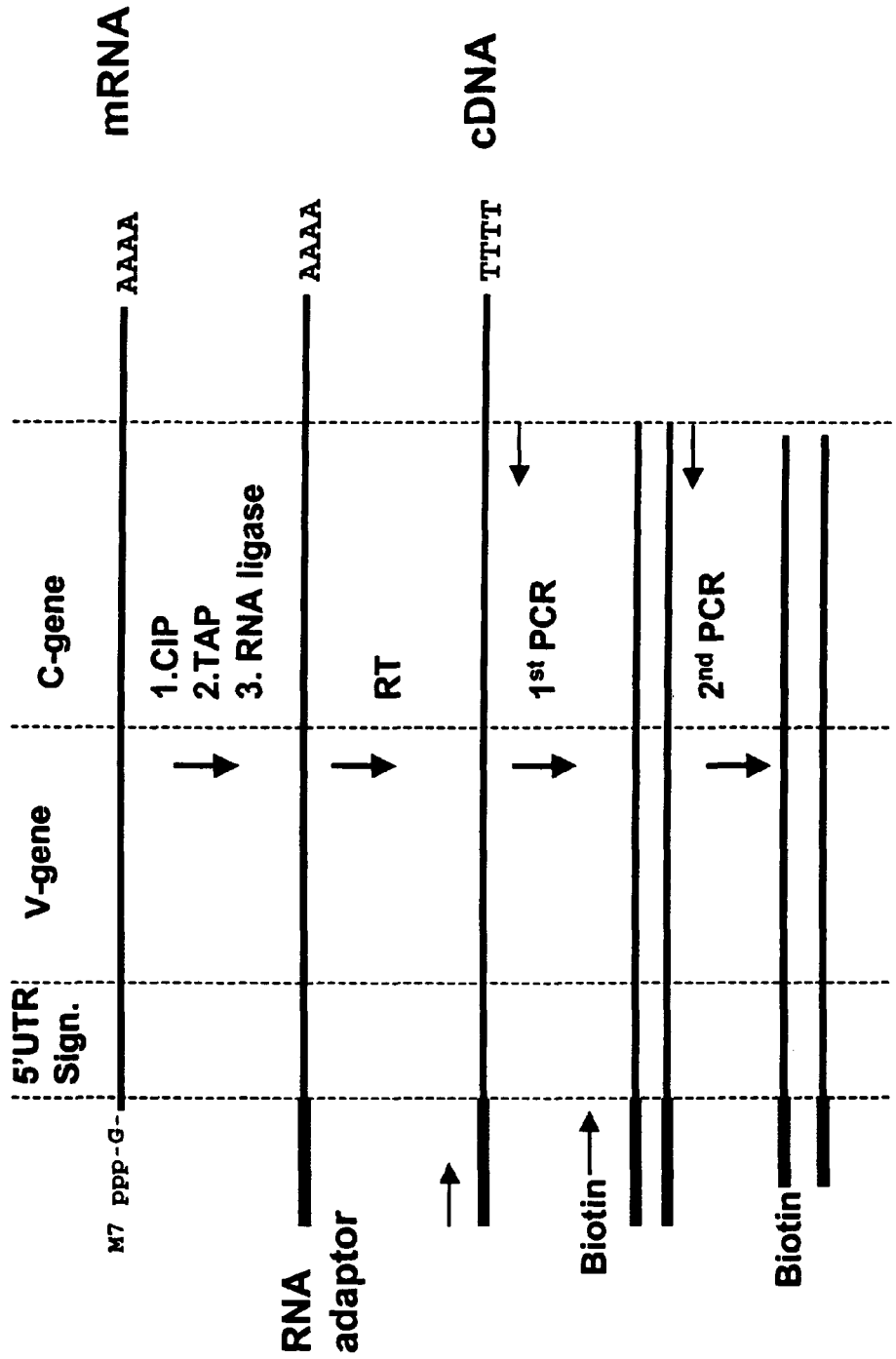
FIG. 3 is a schematic of RACE amplification of antibody heavy and light chains.

250 ng of each poly-A+ RNA sample was used to amplify antibody heavy and light chains with the GeneRAacer™ kit (Invitrogen cat no. L1500-01). A schematic overview of the RACE procedure is shown in FIG. 3.

Using the general protocol of the GeneRAacer™ kit, an RNA adaptor was ligated to the 5' end of all mRNAs. Next, a reverse transcriptase reaction was performed in the presence of oligo(dT15) specific primer under conditions described by the manufacturer in the GeneRAacer™ kit.

$\frac{1}{5}$ of the cDNA from the reverse transcriptase reaction was used in a 20 ul PCR reaction. For amplification of the heavy chain IgM repertoire, a forward primer based on the CH1 chain of IgM [HuCmFOR] and a backward primer based on the ligated synthetic adaptor sequence [5'A] were used. (See Table 22).

For amplification of the kappa and lambda light chains, a forward primer that contains the 3' coding-end of the cDNA [HuCkFor and HuCLFor2+HuCLfor7] and a backward primer based on the ligated synthetic adapter sequence [5'A] was used (See Table 22). Specific amplification products after 30 cycles of primary PCR were obtained.

Figure 4:
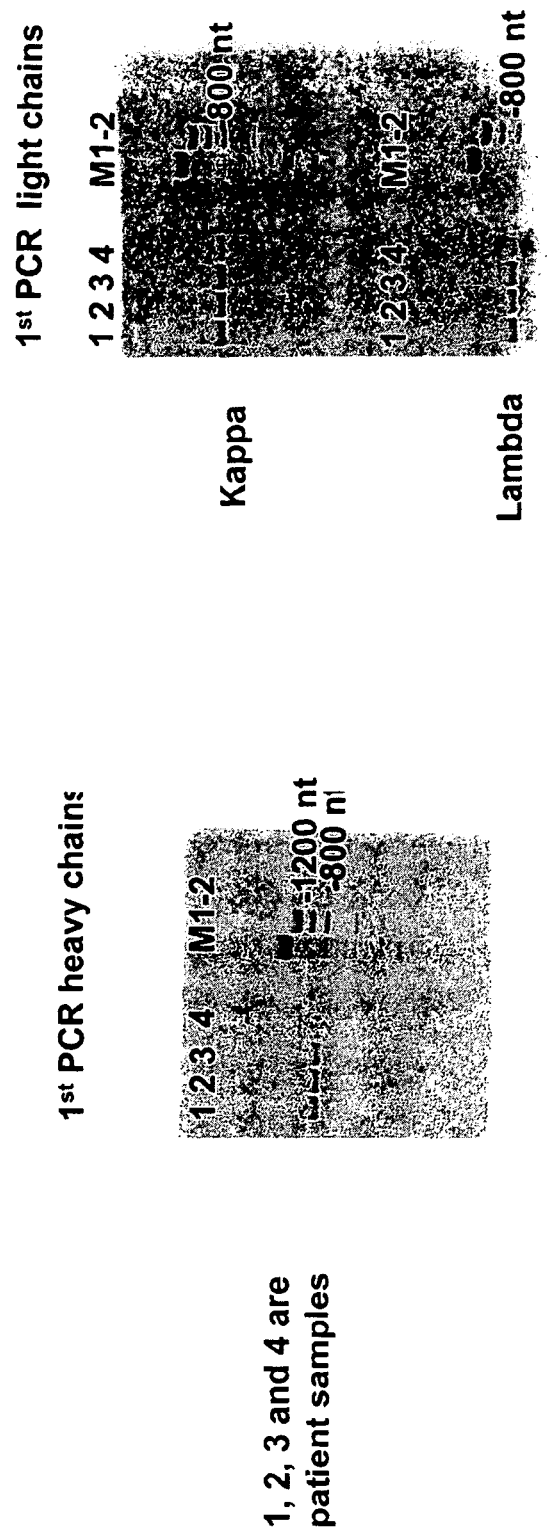
FIG. 4 depicts gel analysis of amplification products obtained after the primary PCR reaction from 4 different patient samples.

FIG. 4 shows the amplification products obtained after the primary PCR reaction from 4 different patient samples. 8 ul primary PCR product from 4 different patients was analyzed on a agarose gel [labeled 1, 2, 3 and 4]. For the heavy chain, a product of approximately 950 nt is obtained while for the kappa and lambda light chains the product is approximately 850 nt. M1-2 are molecular weight markers.

PCR products were also analyzed by DNA sequencing [10 clones from the lambda, kappa or heavy chain repertoires]. All sequenced antibody genes recovered contained the full coding sequence as well as the 5' leader sequence and the V gene diversity was the expected diversity (compared to literature data).

50 ng of all samples from all 11 individual amplified samples were mixed for heavy, lambda light or kappa light chains and used in secondary PCR reactions.

In all secondary PCRs approximately 1 ng template DNA from the primary PCR mixture was used in multiple 50 ul PCR reactions [25 cycles].

For the heavy chain, a nested biotinylated forward primer [HuCm-Nested] was used, and a nested 5'end backward primer located in the synthetic adapter-sequence [5'NA] was used. The 5'end lower-strand of the heavy chain was biotinylated.

For the light chains, a 5'end biotinylated nested primer in the synthetic adapter was used [5'NA] in combination with a 3'end primer in the constant region of Ckappa and Clambda, extended with a sequence coding for the AscI restriction site [kappa: HuCkForAscI, Lambda: HuCL2-FOR-ASC+HuCL7-FOR-ASC]. [5'end Top strand DNA was biotinylated]. After gel-analysis the secondary PCR products were pooled and purified with Promega Wizzard PCR cleanup. Approximately 25 ug biotinylated heavy chain, lambda and kappa light chain DNA was isolated from the 11 patients.

Example 2

Capturing Kappa Chains with BsmAI

A repertoire of human-kappa chain mRNAs was prepared using the RACE method of Example 1 from a collection of patients having various autoimmune diseases.

This Example followed the protocol of Example 1. Approximately 2 micrograms (ug) of human kappa-chain (Igkappa) gene PACE material with biotin attached to 5'-end of upper strand was immobilized as in Example 1 on 200 microliters (µL) of Seradyn magnetic beads. The lower strand was removed by washing the DNA with 2 aliquots 200 µL of 0.1 M NaOH (pH 13) for 3 minutes for the first aliquot followed by 30 seconds for the second aliquot. The beads were neutralized with 200 µL of 10 mM Tris (pH 7.5) 100 mM NaCl. The short oligonucleotides shown in Table 23 were added in 40 fold molar excess in 100 µL of NEB buffer 2 (50 mM NaCl, 10 mM Tris-HCl, 10 mM MgCl$_2$, 1 mM dithiothreitol pH 7.9) to the dry beads. The mixture was incubated at 95° C. for 5 minutes then cooled down to 55° C. over 30 minutes. Excess oligonucleotide was washed away with 2 washes of NEB buffer 3 (100 mM NaCl, 50 mM Tris-HCl, 10 mM MgCl$_2$, 1 mM dithiothreitol pH 7.9). Ten units of BsmAI (NEB) were added in NEB buffer 3 and incubated for 1 h at 55° C. The cleaved downstream DNA was collected and purified over a Qiagen PCR purification column (FIGS. 5 and 6).

Figure 5:
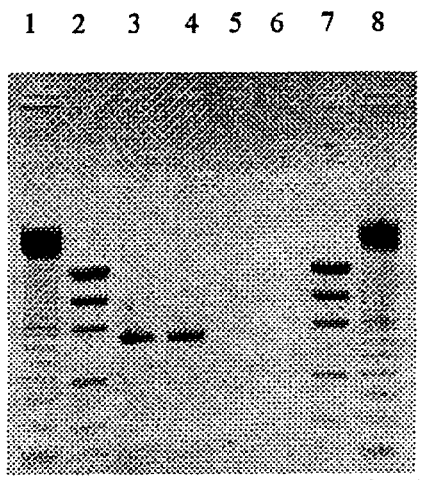
FIG. 5 depicts gel analysis of cleaved kappa DNA from Example 2.

FIG. 5 shows an analysis of digested kappa single-stranded DNA. Approximately 151.5 pmol of adapter was annealed to 3.79 pmol of immobilized kappa single-stranded DNA followed by digestion with 15 U of BsmAI. The supernatant containing the desired DNA was removed and analyzed by 5% polyacrylamide gel along with the remaining beads which contained uncleaved full length kappa DNA. 189 pmol of cleaved single-stranded DNA was purified for further analysis. Five percent of the original full length ssDNA remained on the beads.

Figure 6:
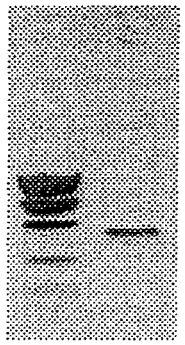
FIG. 6 depicts gel analysis of extender-cleaved kappa DNA from Example 2.

FIG. 6 shows an analysis of the extender—cleaved kappa ligation. 180 pmol of pre-annealed bridge/extender was ligated to 1.8 pmol of BsmAI digested single-stranded DNA. The ligated DNA was purified by Qiagen PCR purification column and analyzed on a 5% polyacrylamide gel. Results indicated that the ligation of extender to single-stranded DNA was 95% efficient.

A partially double-stranded adaptor was prepared using the oligonucleotide shown in Table 23. The adaptor was added to the single-stranded DNA in 100 fold molar excess along with 1000 units of T4 DNA ligase and incubated overnight at 16° C. The excess oligonucleotide was removed with a Qiagen PCR purification column. The ligated material was amplified by PCR using the primers kapPCRt1 and kapfor shown in Table 23 for 10 cycles with the program shown in Table 24.

Figure 7:
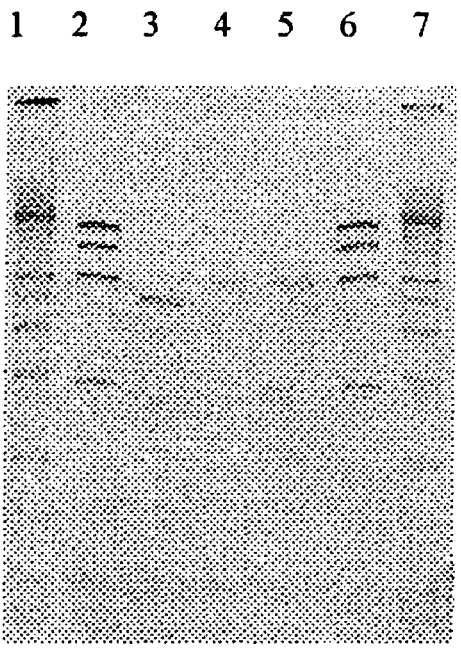
FIG. 7 depicts gel analysis of the PCR product from the extender-kappa amplification from Example 2.
Figure 8:
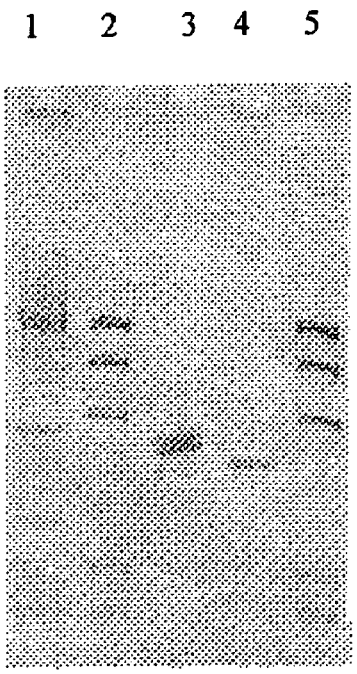
FIG. 8 depicts gel analysis of purified PCR product from the extender-kappa amplification from Example 2.

The soluble PCR product was run on a gel and showed a band of approximately 700 n, as expected (FIGS. 7 and 8). The DNA was cleaved with enzymes ApaLI and AscI, gel purified, and ligated to similarly cleaved vector pCES1.

FIG. 7 shows an analysis of the PCR product from the extender-kappa amplification. Ligated extender-kappa single-stranded DNA was amplified with primers specific to the extender and to the constant region of the light chain. Two different template concentrations, 10 ng versus 50 ng, were used as template and 13 cycles were used to generate approximately 1.5 ug of dsDNA as shown by 0.8% agarose gel analysis.

FIG. 8 shows an analysis of the purified PCR product from the extender-kappa amplification. Approximately 5 ug of PCR amplified extender-kappa double-stranded DNA was run out on a 0.8% agarose gel, cut out, and extracted with a GFX gel purification column. By gel analysis, 3.5 ug of double-stranded DNA was prepared.

Figure 9:
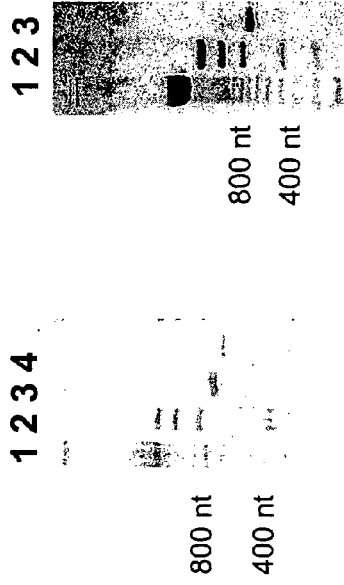
FIG. 9 depicts gel analysis of cleaved and ligated kappa light chains from Example 2.
Figure 9:
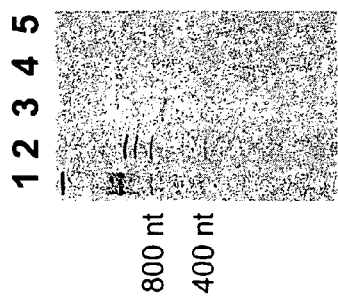
Figure 9:

The assay for capturing kappa chains with BsmA1 was repeated and produced similar results. FIG. 9A shows the DNA after it was cleaved and collected and purified over a Qiagen PCR purification column. FIG. 9B shows the partially double-stranded adaptor ligated to the single-stranded DNA. This ligated material was then amplified (FIG. 9C). The gel showed a band of approximately 700 n.

Table 25 shows the DNA sequence of a kappa light chain captured by this procedure. Table 26 shows a second sequence captured by this procedure. The closest bridge sequence was complementary to the sequence 5'-agccacc-3', but the sequence captured reads 5'-Tgccacc-3', showing that some mismatch in the overlapped region is tolerated.

Example 3

Construction of Synthetic CDR1 and CDR2 Diversity in V-3-23 VH Framework

Synthetic diversity in Complementary Determinant Region (CDR) 1 and 2 was created in the 3-23 VH framework in a two step process: first, a vector containing the 3-23 VH framework was constructed; and then, a synthetic CDR 1 and 2 was assembled and cloned into this vector.

For construction of the 3-23 VH framework, 8 oligonucleotides and two PCR primers (long oligonucleotides—TOPFR1A, BOTFR1B, BOTFR2, BOTFR3, F06, BoTFR4, ON-vgC1, and ON-vgC2 and primers—SFPRMET and BOTPCRPRIM, shown in Table 27) that overlap were designed based on the Genebank sequence of 3-23 VH framework region. The design incorporated at least one useful restriction site in each framework region, as shown in Table 27. In Table 27, the segments that were synthesized are shown as bold, the overlapping regions are underscored, and the PCR priming regions at each end are underscored.

A mixture of these 8 oligos was combined at a final concentration of 2.5 uM in a 20 ul PCR reaction. The PCR mixture contained 200 uM dNTPs, 2.5 mM MgCl$_2$, 0.02 U Pfu Turbo™ DNA Polymerase, 1 U Qiagen HotStart Taq DNA Polymerase, and 1× Qiagen PCR buffer. The PCR program consisted of 10 cycles of 94° C. for 30 s, 55° C. for 30 s, and 72° C. for 30 s.

The assembled 3-23 VH DNA sequence was then amplified, using 2.5 ul of a 10-fold dilution from the initial PCR in 100 ul PCR reaction. The PCR reaction contained 200 uM dNTPs, 2.5 mM MgCl$_2$, 0.02 U Pfu Turbo™ DNA Polymerase, 1 U Qiagen HotStart Taq DNA Polymerase, 1× Qiagen PCR Buffer and 2 outside primers (SFPRMET and BOTPCRPRIM) at a concentration of 1 uM. The PCR program consisted of 23 cycles at 94° C. for 30 s, 55° C. for 30 s, and 72° C. for 60 s. The 3-23 VH DNA sequence was digested and cloned into pCES1 (phagemid vector) using the SfiI and BstEII restriction endonuclease sites. All restriction enzymes mentioned herein were supplied by New England BioLabs, Beverly, Mass. and used as per the manufacturer's instructions.

Stuffer sequences (shown in Table 28 and Table 29) were introduced into pCES1 to replace CDR1/CDR2 sequences (900 bases between BspEI and XbaI RE sites) and CDR3 sequences (358 bases between AflII and BstEII) prior to cloning the CDR1/CDR2 diversity. This new vector was termed pCES5 and its sequence is given in Table 29.

Having stuffers in place of the CDRs avoids the risk that a parental sequence would be over-represented in the library. The stuffer sequences are fragments from the penicillase gene of *E. coli*. The CDR1-2 stuffer contains restriction sites for BglII, Bsu36I, BclI, XcmI, MluI, PvuII, HpaI, and HincII, the underscored sites being unique within the vector pCES5. The stuffer that replaces CDR3 contains the unique restriction endonuclease site RsrII.

A schematic representation of the design for CDR1 and CDR2 synthetic diversity is shown FIG. 10. The design was based on the presence of mutations in DP47/3-23 and related germline genes. Diversity was designed to be introduced at the positions within CDR1 and CDR2 indicated by the numbers in FIG. 10. The diversity at each position was chosen to be one of the three following schemes: 1=ADEFGHIKLM-NPQRSTVWY; 2=YRWVGS; 3=PS, in which letters encode equimolar mixes of the indicated amino acids.

For the construction of the CDR1 and CDR2 diversity, 4 overlapping oligonucleotides (ON-vgC1, ON_Br12, ON_CD2Xba, and ON-vgC2, shown in Table 27 and Table 30) encoding CDR1/2, plus flanking regions, were designed. A mixture of these 4 oligos was combined at a final concentration of 2.5 uM in a 40 ul PCR reaction. Two of the 4 oligos contained variegated sequences positioned at the CDR1 and the CDR2. The PCR mixture contained 200 uM dNTPs, 2.5 U Pwo DNA Polymerase (Roche), and 1×Pwo PCR buffer with 2 mM MgSO$_4$. The PCR program consisted of 10 cycles at 94° C. for 30 s, 60° C. for 30 s, and 72° C. for 60 s. This assembled CDR1/2 DNA sequence was amplified, using 2.5 ul of the mixture in 100 ul PCR reaction. The PCR reaction contained 200 uM dNTPs, 2.5 U Pwo DNA Polymerase, 1×Pwo PCR Buffer with 2 mM MgSO$_4$ and 2 outside primers at a concentration of 1 uM. The PCR program consisted of 10 cycles at 94° C. for 30 s, 60° C. for 30 s, and 72° C. for 60 s. These variegated sequences were digested and cloned into the 3-23 VH framework in place of the CDR1/2 stuffer.

We obtained approximately 7×10$^7$ independent transformants. CDR3 diversity either from donor populations or from synthetic DNA can be cloned into the vector containing synthetic CDR1 and CDR 2 diversity.

Figure 11:
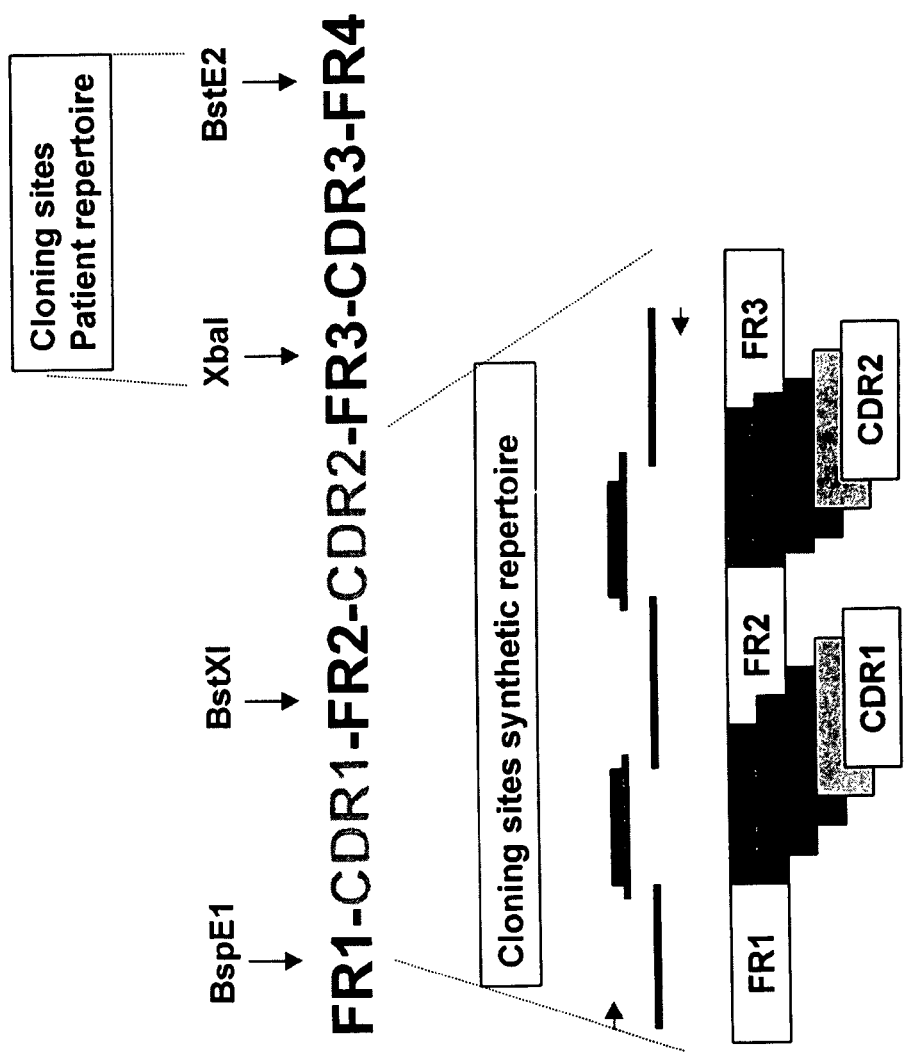
FIG. 11 is a schematic of the cloning schedule for construction of the heavy chain repertoire.

A schematic representation of this procedure is shown in FIG. 11. A sequence encoding the FR-regions of the human V3-23 gene segment and CDR regions with synthetic diversity was made by oligonucleotide assembly and cloning via BspE1 and XbaI sites into a vector that complements the FR1 and FR3 regions. Into this library of synthetic VH segments, the complementary VH-CDR3 sequence (top right) was cloned via XbaI an BstEll sites. The resulting cloned CH genes contain a combination of designed synthetic diversity and natural diversity (see FIG. 11).

Example 4

Cleavage and Ligation of the Lambda Light Chains with HinfI

Figure 12A:
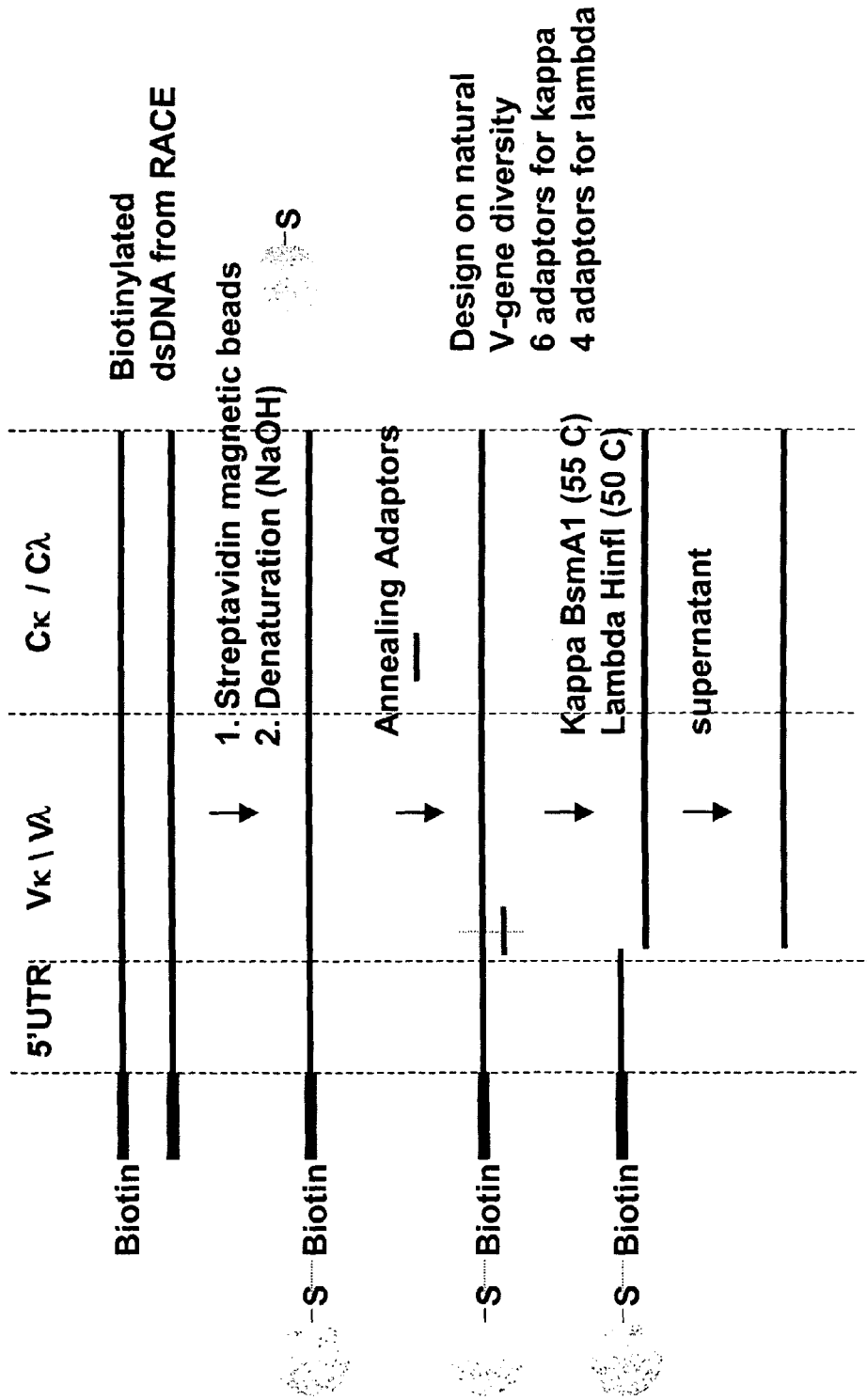
FIG. 12 is a schematic of the cleavage and ligation of the antibody light chain.
Figure 12B:
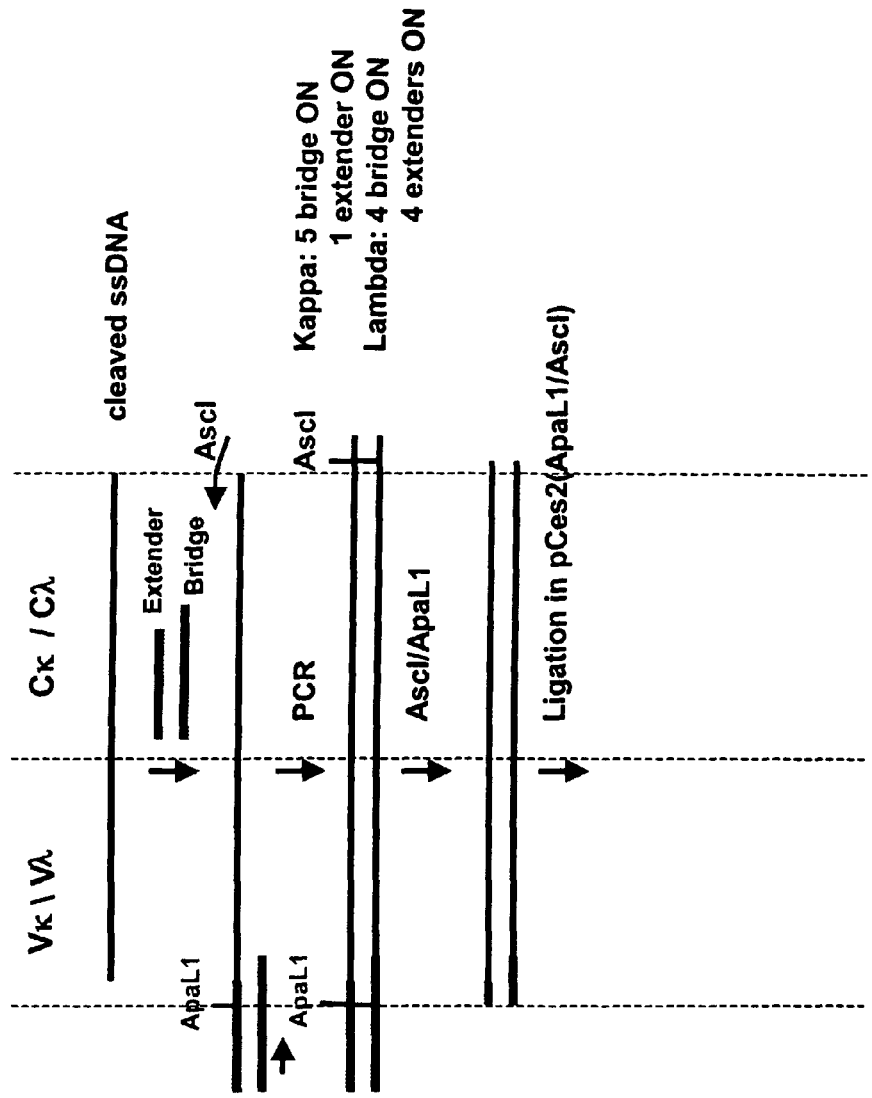

A schematic of the cleavage and ligation of antibody light chains is shown in FIGS. 12A and 12B. Approximately 2 ug of biotinylated human Lambda DNA prepared as described in Example 1 was immobilized on 200 ul Seradyn magnetic beads. The lower strand was removed by incubation of the DNA with 200 ul of 0.1 M NaOH (pH=13) for 3 minutes, the supernatant was removed and an additional washing of 30 seconds with 200 ul of 0.1 M NaOH was performed. Supernatant was removed and the beads were neutralized with 200 ul of 10 mM Tris (pH=7.5), 100 mM NaCl. 2 additional washes with 200 ul NEB2 buffer 2, containing 10 mM Tris (pH=7.9), 50 mM NaCl, 10 mM MgCl2 and 1 mM dithiothreitol, were performed. After immobilization, the amount of ssDNA was estimated on a 5% PAGE-UREA gel.

About 0.8 ug ssDNA was recovered and incubated in 100 ul NEB2 buffer 2 containing 80 molar fold excess of an equimolar mix of ON_Lam1aB7, ON_Lam2aB7, ON_Lam31B7 and ON_Lam3rB7 [each oligo in 20 fold molar excess] (see Table 31).

The mixture was incubated at 95° C. for 5 minutes and then slowly cooled down to 50° C. over a period of 30 minutes. Excess of oligonucleotide was washed away with 2 washes of 200 ul of NEB buffer 2. 4 U/ug of Hinf I was added and incubated for 1 hour at 50° C. Beads were mixed every 10 minutes.

Figure 13:
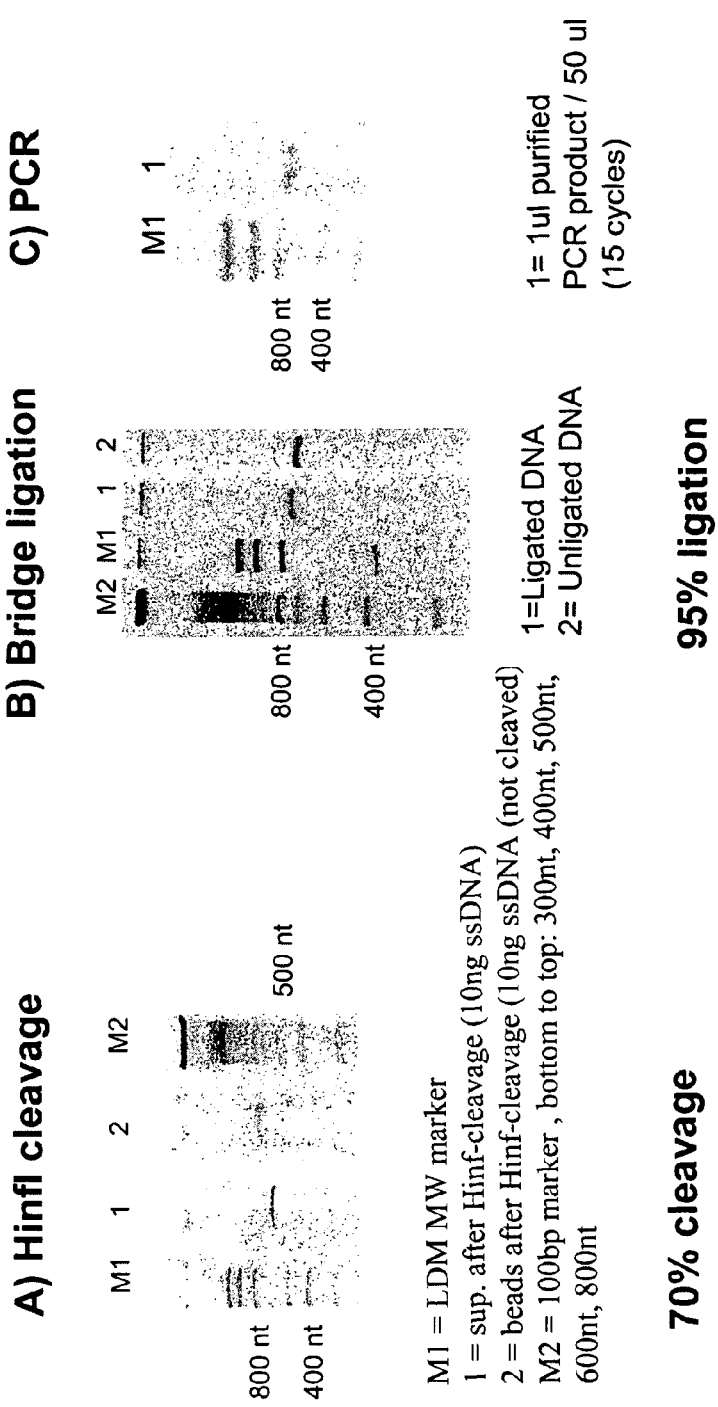
FIG. 13 depicts gel analysis of cleaved and ligated lambda light chains from Example 4.

After incubation the sample was purified over a Qiagen PCR purification column and was subsequently analysed on a 5% PAGE-urea gel (see FIG. 13A, cleavage was more than 70% efficient).

A schematic of the ligation of the cleaved light chains is shown in FIG. 12B. A mix of bridge/extender pairs was prepared from the Brg/Ext oligo's listed in Table 31 (total molar excess 100 fold) in 1000 U of T4 DNA Ligase (NEB) and incubated overnight at 16° C. After ligation of the DNA, the excess oligonucleotide was removed with a Qiagen PCR purification column and ligation was checked on a Urea-PAGE gel (see FIG. 13B; ligation was more than 95% efficient).

Multiple PCRs were performed containing 10 ng of the ligated material in an 50 ul PCR reaction using 25 pMol ON lamPlePCR and 25 pmol of an equimolar mix of Hu-CL2AscI/HuCL7AscI primer (see Example 1).

PCR was performed at 60° C. for 15 cycles using Pfu polymerase. About 1 ug of dsDNA was recovered per PCR (see FIG. 13C) and cleaved with ApaL1 and AscI for cloning the lambda light chains in pCES2.

Example 5

Capture of Human Heavy-chain CDR3 Population

Figure 14A:
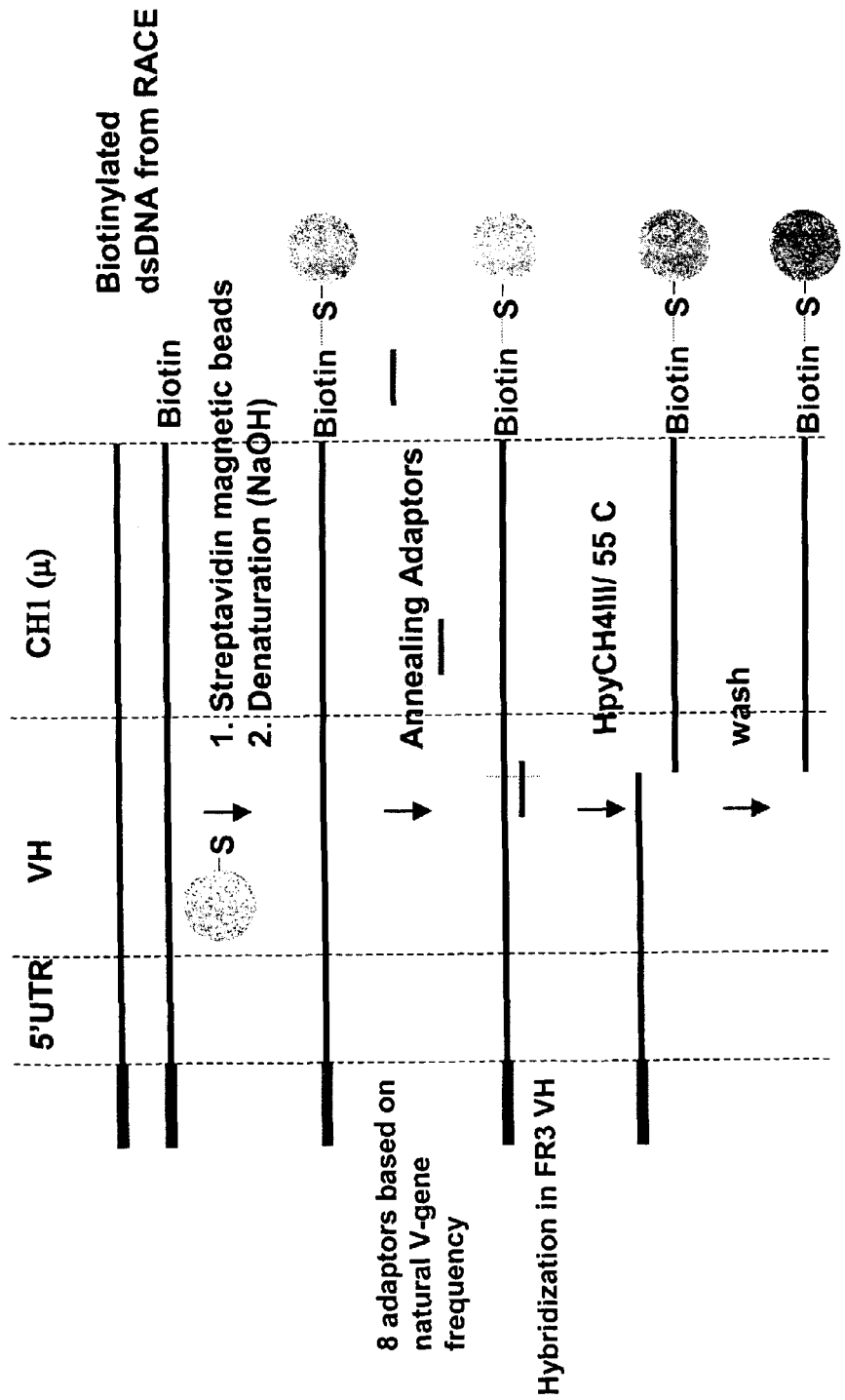
FIG. 14 is a schematic of the cleavage and ligation of the antibody heavy chain.
Figure 14B:
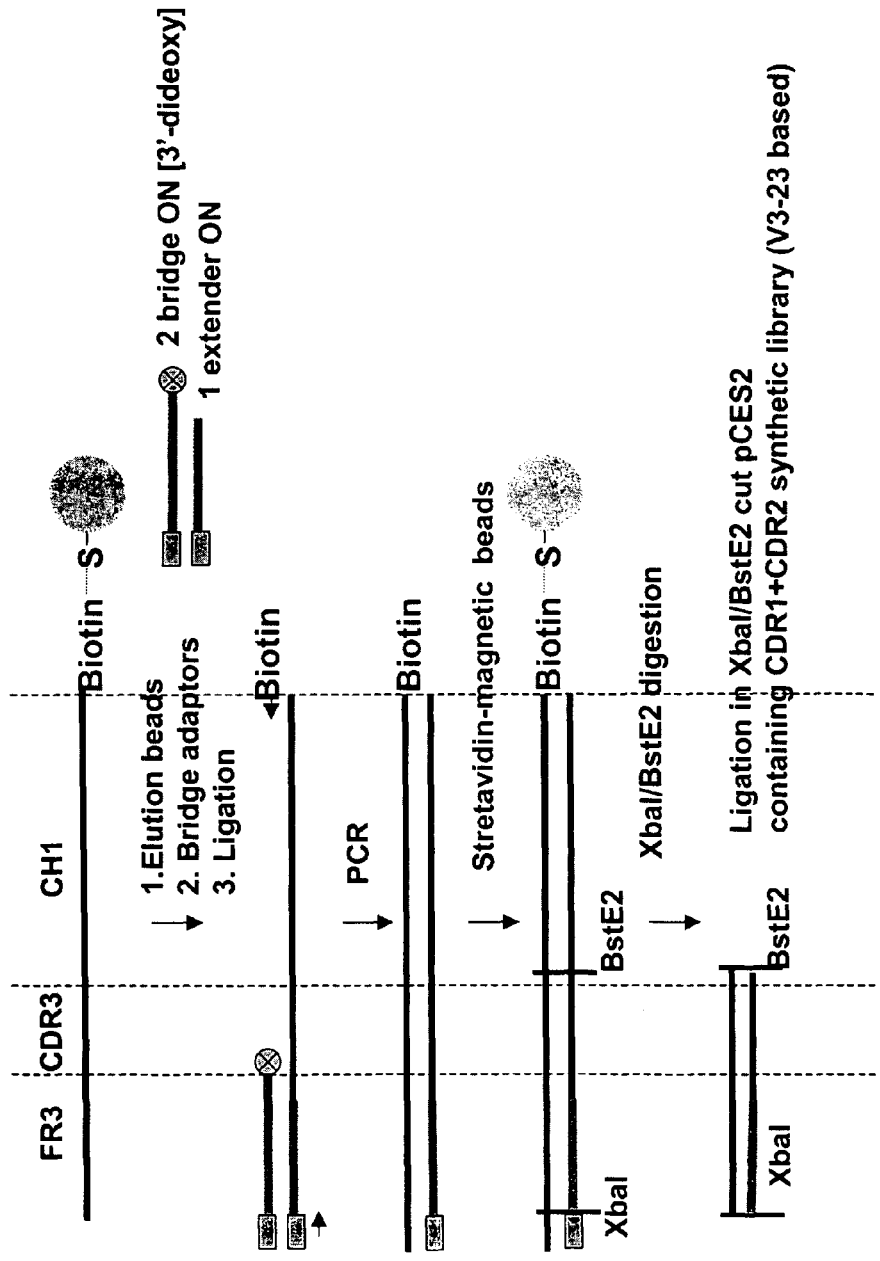

A schematic of the cleavage and ligation of antibody light chains is shown in FIGS. 14A and 14B.

Figure 15:
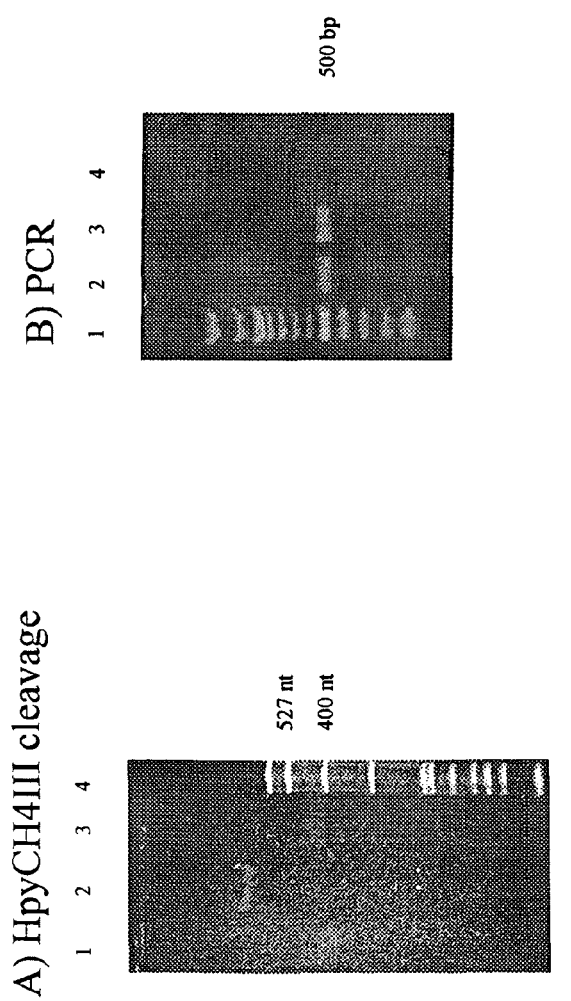
FIG. 15 depicts gel analysis of cleaved and ligated lambda light chains from Example 5.

Approximately 3 ug of human heavy-chain (IgM) gene RACE material with biotin attached to 5'-end of lower strand was immobilized on 300 uL of Seradyn magnetic beads. The upper strand was removed by washing the DNA with 2 aliquots 300 uL of 0.1 M NaOH (pH 13) for 3 minutes for the first aliquot followed by 30 seconds for the second aliquot. The beads were neutralized with 300 uL of 10 mM Tris (pH 7.5) 100 mM NaCl. The REdaptors (oligonucleotides used to make single-stranded DNA locally double-stranded) shown in Table 32 were added in 30 fold molar excess in 200 uL of NEB buffer 4 (50 mM Potassium Acetate, 20 mM Tris-Acetate, 10 mM Magnesium Acetate, 1 mM dithiothreitol pH 7.9) to the dry beads. The REadaptors were incubated with the single-stranded DNA at 80° C. for 5 minutes then cooled down to 55° C. over 30 minutes. Excess REdaptors were washed away with 2 washes of NEB buffer 4. Fifteen units of HpyCH4III (NEB) were added in NEB buffer 4 and incubated for 1 hour at 55° C. The cleaved downstream DNA remaining on the beads was removed from the beads using a Qiagen Nucleotide removal column (see FIG. 15).

The Bridge/Extender pairs shown in Table 33 were added in 25 molar excess along with 1200 units of T4 DNA ligase and incubated overnight at 16° C. Excess Bridge/Extender was removed with a Qiagen PCR purification column. The ligated material was amplified by PCR using primers H43.XAExtPCR2 and Hucumnest shown in Table 34 for 10 cycles with the program shown in Table 35.

The soluble PCR product was run on a gel and showed a band of approximately 500 n, as expected (see FIG. 15B). The DNA was cleaved with enzymes SfiI and NotI, gel purified, and ligated to similarly cleaved vector PCES1.

Example 6

Description of Phage Display Vector CJRA05, a Member of the Library Built in Vector DY3F7

Figure 16:
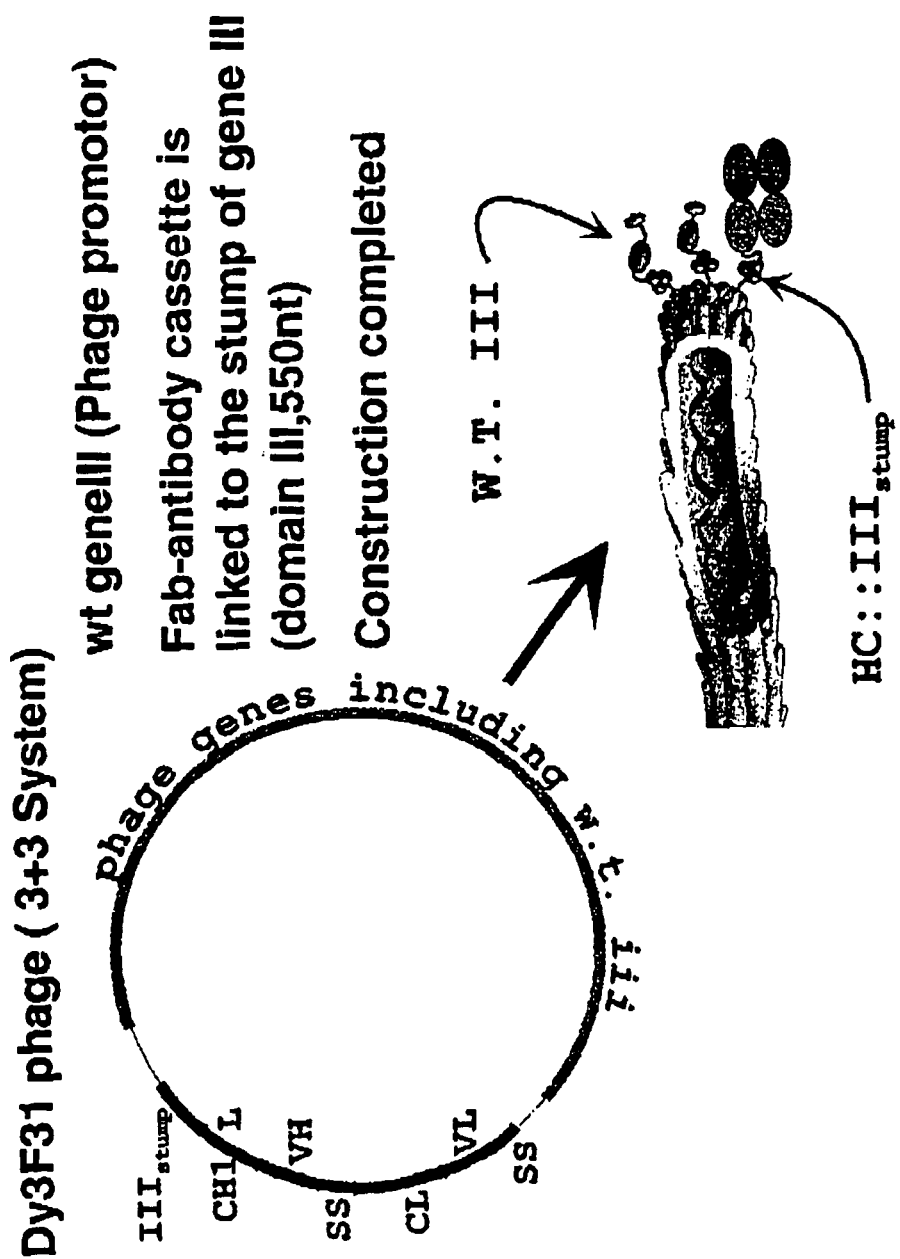
FIG. 16 is a schematic of a phage display vector.

Table 36 contains an annotated DNA sequence of a member of the library, CJRA05, see FIG. 16. Table 36 is to be read as follows: on each line everything that follows an exclamation mark "!" is a comment. All occurrences of A, C, G, and T before "!" are the DNA sequence. Case is used only to show that certain bases constitute special features, such as restriction sites, ribosome binding sites, and the like, which are labeled below the DNA. CJRA05 is a derivative of phage DY3F7, obtained by cloning an ApaLI to NotI fragment into these sites in DY3F31. DY3F31 is like DY3F7 except that the light chain and heavy chain genes have been replaced by "stuffer" DNA that does not code for any antibody. DY3F7 contains an antibody that binds streptavidin, but did not come from the present library.

The phage genes start with gene ii and continue with genes x, v, vii, ix, viii, iii, vi, i, and iv. Gene iii has been slightly modified in that eight codons have been inserted between the signal sequence and the mature protein and the final amino acids of the signal sequence have been altered. This allows restriction enzyme recognition sites EagI and XbaI to be present. Following gene iv is the phage origin of replication (ori). After ori is bla which confers resistance to ampicillin (ApR). The phage genes and bla are transcribed in the same sense.

Figure 17:
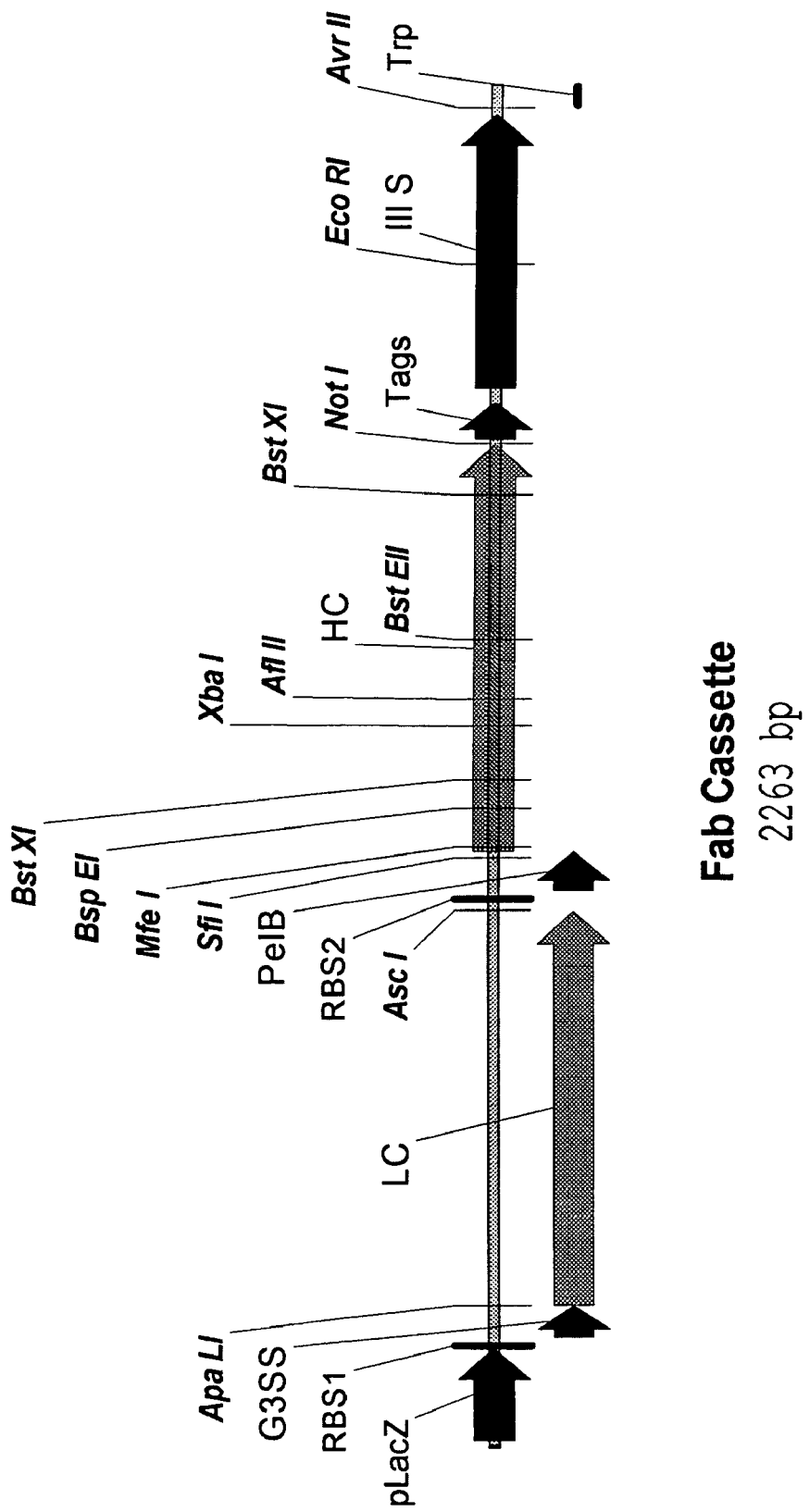
FIG. 17 is a schematic of a Fab cassette.

After bla, is the Fab cassette (illustrated in FIG. 17) comprising:
a) PlacZ promoter,
b) A first Ribosome Binding Site (RBS1),
c) The signal sequence form M13 iii,
d) An ApaLI RERS,
e) A light chain (a kappa L20::JK1 shortened by one codon at the V-J boundary in this case),
f) An AscI RERS,
g) A second Ribosome Binding Site (RBS2),
h) A signal sequence, preferably PelB, which contains,
i) An SfiI RERS,
j) A synthetic 3-23 V region with diversity in CDR1 and CDR2,
k) A captured CDR3,
l) A partially synthetic J region (FR4 after BstEII),
m) CH1,
n) A NotI RERS,
o) A His6 tag (SEQ ID NO: 12),
p) A cMyc tag,
q) An amber codon,
r) An anchor DNA that encodes the same amino-acid sequence as codons 273 to 424 of M13 iii (as shown in Table 37).
s) Two stop codons,
t) An AvrII RERS, and
u) A trp terminator.

The anchor (item r) encodes the same amino-acid sequence as do codons 273 to 424 of M13 iii but the DNA is approximately as different as possible from the wild-type DNA sequence. In Table 36, the III' stump runs from base 8997 to base 9455. Below the DNA, as comments, are the differences with wild-type iii for the comparable codons with "!W.T" at the ends of these lines. Note that Met and Trp have only a single codon and must be left as is. These AA types are rare. Ser codons can be changed at all three base, while Leu and Arg codons can be changed at two.

In most cases, one base change can be introduced per codon. This has three advantages: 1) recombination with the wild-type gene carried elsewhere on the phage is less likely, 2) new restriction sites can be introduced, facilitating construction; and 3) sequencing primers that bind in only one of the two regions can be designed.

The fragment of M13 III shown in CJRA05 is the preferred length for the anchor segment. Alternative longer or shorter anchor segments defined by reference to whole mature III protein may also be utilized.

The sequence of M13 III consists of the following elements: Signal Sequence::Domain 1 (D1)::Linker 1 (L1)::Domain 2 (D2)::Linker 2 (L2)::Domain 3 (D3)::Transmembrane Segment (TM)::Intracellular anchor (IC) (see Table 38).

The pIII anchor (also known as trpIII) preferably consists of D2::L2::D3::TM::IC. Another embodiment for the pIII anchor consists of D2'::L2::D3::TM::IC (where D2' comprises the last 21 residues of D2 with the first 109 residues deleted). A further embodiment of the pIII anchor consists of D2' (C>S)::L2::D3::TM::IC (where D2' (C>S) is D2' with the single C converted to S), and d) D3::TM::IC.

Table 38 shows a gene fragment comprising the NotI site, His6 tag (SEQ ID NO: 12), cMyc tag, an amber codon, a recombinant enterokinase cleavage site, and the whole of mature M13 III protein. The DNA used to encode this sequence is intentionally very different from the DNA of wild-type gene iii as shown by the lines denoted "W.T." containing the w.t. bases where these differ from this gene. III is divided into domains denoted "domain 1", "linker 1", "domain 2", "linker 2", "domain 3", "transmembrane segment", and "intracellular anchor".

Alternative preferred anchor segments (defined by reference to the sequence of Table 38) include:
codons 1-29 joined to codons 104-435, deleting domain 1 and retaining linker 1 to the end;
codons 1-38 joined to codons 104-435, deleting domain 1 and retaining the rEK cleavage site plus linker 1 to the end from III;
codons 1-29 joined to codons 236-435, deleting domain 1, linker 1, and most of domain 2 and retaining linker 2 to the end;
codons 1-38 joined to codons 236-435, deleting domain 1, linker 1, and most of domain 2 and retaining linker 2 to the end and the rEK cleavage site;
codons 1-29 joined to codons 236-435 and changing codon 240 to Ser(e.g., agc), deleting domain 1, linker 1, and most of domain 2 and retaining linker 2 to the end; and
codons 1-38 joined to codons 236-435 and changing codon 240 to Ser(e.g., agc), deleting domain 1, linker 1, and most of domain 2 and retaining linker 2 to the end and the rEK cleavage site.

The constructs would most readily be made by methods similar to those of Wang and Wilkinson (*Biotechniques* 2001: 31(4)722-724) in which PCR is used to copy the vector except the part to be deleted and matching restriction sites are introduced or retained at either end of the part to be kept. Table 39 shows the oligonucleotides to be used in deleting parts of the III anchor segment. The DNA shown in Table 38 has an NheI site before the DINDDRMA (residues 29-36 of SEQ ID NO: 594) recombinant enterokinase cleavage site (rEKCS). If NheI is used in the deletion process with this DNA, the rEKCS site would be lost. This site could be quite useful in cleaving Fabs from the phage and might facilitate capture of very high-affinity antibodies. One could mutagenize this sequence so that the NheI site would follow the rEKCS site, an Ala Ser amino-acid sequence is already present. Alternatively, one could use SphI for the deletions. This would involve a slight change in amino acid sequence but would be of no consequence.

Example 7

Selection of Antigen Binders from an Enriched Library of Human Antibodies Using Phage Vector DY3F31

In this example the human antibody library used is described in de Haard et al., (*Journal of Biological Chemistry*, 274 (26): 18218-30 (1999). This library, consisting of a large non-immune human Fab phagemid library, was first enriched on antigen, either on streptavidin or on phenyl-oxazolone (phOx). The methods for this are well known in the art. Two preselected Fab libraries, the first one selected once on immobilized phOx-BSA (R1-ox) and the second one selected twice on streptavidin (R2-strep), were chosen for recloning.

These enriched repertoires of phage antibodies, in which only a very low percentage have binding activity to the antigen used in selection, were confirmed by screening clones in an ELISA for antigen binding. The selected Fab genes were transferred from the phagemid vector of this library to the DY3F31 vector via ApaL1-Not1 restriction sites.

DNA from the DY3F31 phage vector was pretreated with ATP dependent DNAse to remove chromosomal DNA and then digested with ApaL1 and Not1. An extra digestion with AscI was performed in between to prevent self-ligation of the vector. The ApaL1/NotI Fab fragment from the preselected libraries was subsequently ligated to the vector DNA and transformed into competent XL1-blue MRF' cells.

Libraries were made using vector:insert ratios of 1:2 for phOx-library and 1:3 for STREP library, and using 100 ng ligated DNA per 50 µl of electroporation-competent cells (electroporation conditions: one shock of 1700 V, 1 hour recovery of cells in rich SOC medium, plating on ampicillin-containing agar plates).

This transformation resulted in a library size of $1.6 \times 10^6$ for R1-ox in DY3F31 and $2.1 \times 10^6$ for R2-strep in DY3F31. Sixteen colonies from each library were screened for insert, and all showed the correct size insert (±1400 bp) (for both libraries).

Phage was prepared from these Fab libraries as follows. A representative sample of the library was inoculated in medium with ampicillin and glucose, and at OD 0.5, the medium exchanged for ampicillin and 1 mM IPTG. After overnight growth at 37° C., phage was harvested from the supernatant by PEG-NaCl precipitation. Phage was used for selection on antigen. R1-ox was selected on phOx-BSA coated by passive adsorption onto immunotubes and R2-strep on streptavidin coated paramagnetic beads (Dynal, Norway), in procedures described in de Haard et. al. and Marks et. al., *Journal of Molecular Biology*, 222(3): 581-97 (1991). Phage titers and enrichments are given in Table 40.

Clones from these selected libraries, dubbed R2-ox and R3-strep respectively, were screened for binding to their antigens in ELISA. 44 clones from each selection were picked randomly and screened as phage or soluble Fab for binding in ELISA. For the libraries in DY3F31, clones were first grown in 2TY-2% glucose-50 µg/ml AMP to an OD600 of approximately 0.5, and then grown overnight in 2TY-50 µg/ml AMP+/−1 mM IPTG. Induction with IPTG may result in the production of both phage-Fab and soluble Fab. Therefore the (same) clones were also grown without IPTG. Table 41 shows the results of an ELISA screening of the resulting supernatant, either for the detection of phage particles with antigen binding (Anti-M13 HRP=anti-phage antibody), or for the detection of human Fabs, be it on phage or as soluble fragments, either with using the anti-myc antibody 9E10 which detects the myc-tag that every Fab carries at the C-terminal end of the heavy chain followed by a HRP-labeled rabbit-anti-Mouse serum (column 9E10/RAM-HRP), or with anti-light chain reagent followed by a HRP-labeled goat-anti-rabbit antiserum(anti-CK/CL Gar-HRP).

The results shows that in both cases antigen-binders are identified in the library, with as Fabs on phage or with the anti-Fab reagents (Table 41). IPTG induction yields an increase in the number of positives. Also it can be seen that for the phOx-clones, the phage ELISA yields more positives than the soluble Fab ELISA, most likely due to the avid binding of phage. Twenty four of the ELISA-positive clones were screened using PCR of the Fab-insert from the vector, followed by digestion with BstNI. This yielded 17 different patterns for the phOx-binding Fab's in 23 samples that were correctly analyzed, and 6 out of 24 for the streptavidin binding clones. Thus, the data from the selection and screening from this pre-enriched non-immune Fab library show that the DY3F31 vector is suitable for display and selection of Fab fragments, and provides both soluble Fab and Fab on phage for screening experiments after selection.

Example 8

Selection of Phage-antibody Libraries on Streptavidin Magnetic Beads

The following example describes a selection in which one first depletes a sample of the library of binders to streptavidin and optionally of binders to a non-target (i.e., a molecule other than the target that one does not want the selected Fab to bind). It is hypothesized that one has a molecule, termed a "competitive ligand", which binds the target and that an antibody which binds at the same site would be especially useful.

For this procedure Streptavidin Magnetic Beads (Dynal) were blocked once with blocking solution (2% Marvel Milk, PBS (pH 7.4), 0.01% Tween-20 ("2% MPBST")) for 60 minutes at room temperature and then washed five times with 2% MPBST. 450 µL of beads were blocked for each depletion and subsequent selection set.

Per selection, 6.25 µL of biotinylated depletion target (1 mg/mL stock in PBST) was added to 0.250 mL of washed, blocked beads (from step 1). The target was allowed to bind overnight, with tumbling, at 4° C. The next day, the beads are washed 5 times with PBST.

Per selection, 0.010 mL of biotinylated target antigen (1 mg/mL stock in PBST) was added to 0.100 mL of blocked and washed beads (from step 1). The antigen was allowed to bind overnight, with tumbling, at 4° C. The next day, the beads were washed 5 times with PBST.

In round 1, $2 \times 10^{12}$ up to $10^{13}$ plaque forming units (pfu) per selection were blocked against non-specific binding by adding to 0.500 mL of 2% MPBS (=2% MPBST without Tween) for 1 hr at RT (tumble). In later rounds, 1011 pfu per selection were blocked as done in round 1.

Each phage pool was incubated with 50 µL of depletion target beads (final wash supernatant removed just before use) on a Labquake rotator for 10 min at room temperature. After incubation, the phage supernatant was removed and incubated with another 50 µL of depletion target beads. This was repeated 3 more times using depletion target beads and twice using blocked streptavidin beads for a total of 7 rounds of depletion, so each phage pool required 350 µL of depletion beads.

A small sample of each depleted library pool was taken for tittering. Each library pool was added to 0.100 mL of target beads (final wash supernatant was removed just before use) and allowed to incubate for 2 hours at room temperature (tumble).

Beads were then washed as rapidly as possible (e.g., 3 minutes total) with 5×0.500 mL PBST and then 2× with PBS. Phage still bound to beads after the washing were eluted once with 0.250 mL of competitive ligand (~1 μμM) in PBST for 1 hour at room temperature on a Labquake rotator. The eluate was removed, mixed with 0.500 mL Minimal A salts solution and saved. For a second selection, 0.500 mL 100 mM TEA was used for elution for 10 min at RT, then neutralized in a mix of 0.250 mL of 1 M Tris, pH 7.4+0.500 mL Min A salts.

After the first selection elution, the beads can be eluted again with 0.300 mL of non-biotinylated target (1 mg/mL) for 1 hr at RT on a Labquake rotator. Eluted phage are added to 0.450 mL Minimal A salts.

Three eluates (competitor from 1st selection, target from 1st selection and neutralized TEA elution from 2nd selection) were kept separate and a small aliquot taken from each for tittering. 0.500 mL Minimal A salts were added to the remaining bead aliquots after competitor and target elution and after TEA elution. Take a small aliquot from each was taken for tittering.

Each elution and each set of eluted beads was mixed with 2×YT and an aliquot (e.g., 1 mL with 1. E 10/mL) of XL1-Blue MRF' E. coli cells (or other F' cell line) which had been chilled on ice after having been grown to mid-logarithmic phase, starved and concentrated (see procedure below— "Mid-Log prep of XL-1 blue MRF' cells for infection").

After approximately 30 minutes at room temperature, the phage/cell mixtures were spread onto Bio-Assay Dishes (243×243×18 mm, Nalge Nunc) containing 2×YT, 1 mM IPTG agar. The plates were incubated overnight at 30° C. The next day, each amplified phage culture was harvested from its respective plate. The plate was flooded with 35 mL TBS or LB, and cells were scraped from the plate. The resuspended cells were transferred to a centrifuge bottle. An additional 20 mL TBS or LB was used to remove any cells from the plate and pooled with the cells in the centrifuge bottle. The cells were centrifuged out, and phage in the supernatant was recovered by PEG precipitation. Over the next day, the amplified phage preps were titered.

In the first round, two selections yielded five amplified eluates. These amplified eluates were panned for 2-3 more additional rounds of selection using ~1. E 12 input phage/round. For each additional round, the depletion and target beads were prepared the night before the round was initiated.

For the elution steps in subsequent rounds, all elutions up to the elution step from which the amplified elution came from were done, and the previous elutions were treated as washes. For the bead infection amplified phage, for example, the competitive ligand and target elutions were done and then tossed as washes (see below). Then the beads were used to infect E. coli. Two pools, therefore, yielded a total of 5 final elutions at the end of the selection.

1st selection set
   A. Ligand amplified elution: elute w/ligand for 1 hr, keep as elution
   B. Target amplified elution: elute w/ligand for 1 hr, toss as wash elute w/target for 1 hr, keep as elution
   C. Bead infect. amp. elution: elute w/ligand for 1 hr, toss as wash elute w/target for 1 hr, toss as wash elute w/cell infection, keep as elution 2nd selection set
   A. TEA amplified elution; elute w/TEA 10 min, keep as elution
   B. Bead infect. amp. elution; elute w/TEA 10 min, toss as wash elute w/cell infection, keep as elution Mid-log Prep of XL1 Blue MRF' Cells for Infection (Based on Barbas et al. Phage Display Manual Procedure)

Culture XL1 blue MRF' in NZCYM (12.5 mg/mL tet) at 37° C. and 250 rpm overnight. Started a 500 mL culture in 2 liter flask by diluting cells 1/50 in NZCYM/tet (10 mL overnight culture added) and incubated at 37° C. at 250 rpm until OD600 of 0.45 (1.5-2 hrs) was reached. Shaking was reduced to 100 rpm for 10 min. When OD600 reached between 0.55-0.65, cells were transferred to 2×250 mL centrifuge bottles, centrifuged at 600 g for 15 min at 4° C. Supernatant was poured off. Residual liquid was removed with a pipette.

The pellets were gently resuspended (not pipetting up and down) in the original volume of 1× Minimal A salts at room temp. The resuspended cells were transferred back into 2-liter flask, shaken at 100 rpm for 45 min at 37° C. This process was performed in order to starve the cells and restore pili. The cells were transferred to 2×250 mL centrifuge bottles, and centrifuged as earlier.

The cells were gently resuspended in ice cold Minimal A salts (5 mL per 500 mL original culture). The cells were put on ice for use in infections as soon as possible.

The phage eluates were brought up to 7.5 mL with 2×YT medium and 2.5 mL of cells were added. Beads were brought up to 3 mL with 2×YT and 1 mL of cells were added. Incubated at 37° C. for 30 min. The cells were plated on 2×YT, 1 mM IPTG agar large NUNC plates and incubated for 18 hr at 30° C.

Example 9

Incorporation of Synthetic Region in FR1/3 Region

Described below are examples for incorporating of fixed residues in antibody sequences for light chain kappa and lambda genes, and for heavy chains. The experimental conditions and oligonucleotides used for the examples below have been described in previous examples (e.g., Examples 3 & 4).

Figure 18:
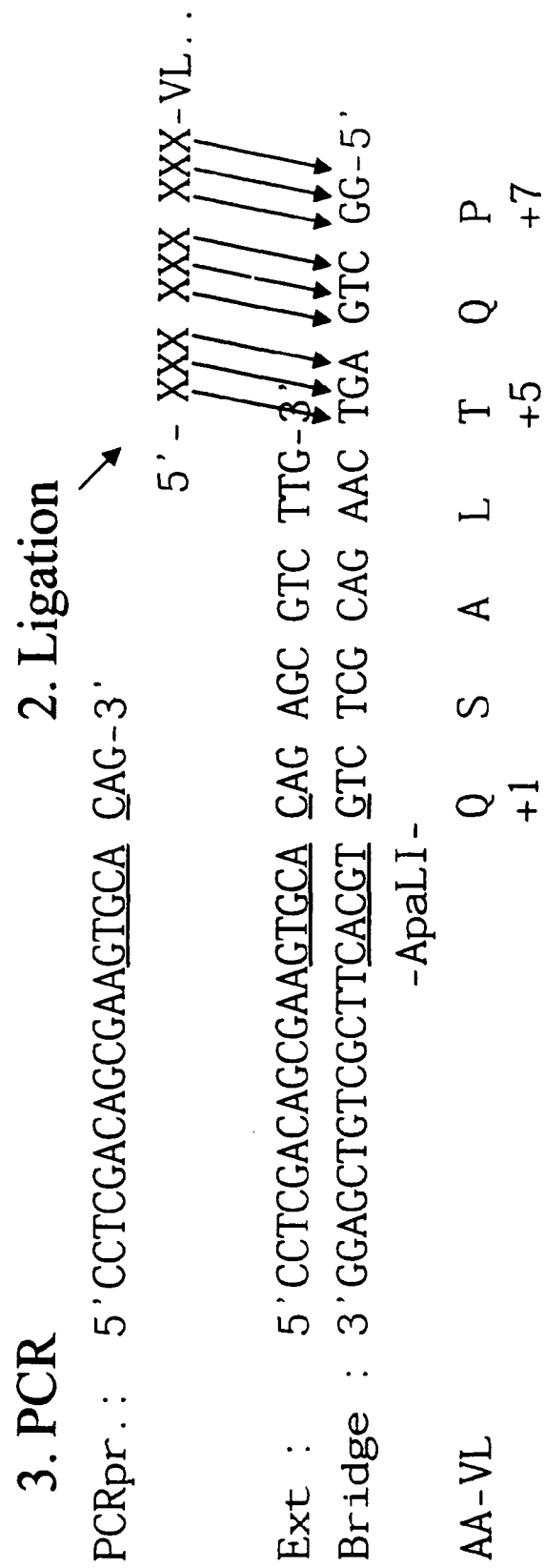
FIG. 18 is a schematic of a process for incorporating fixed FR1 residues in an antibody lambda sequence. The PCRpr oligonucleotide is shown in SEQ ID NO: 605 while the Bridge oligonucleotide and encoded peptide are shown in SEQ ID NOS 606-607, respectively.

The process for incorporating fixed FR1 residues in an antibody lambda sequence consists of 3 steps (see FIG. 18): (1) annealing of single-stranded DNA material encoding VL genes to a partially complementary oligonucleotide mix (indicated with Ext and Bridge), to anneal in this example to the region encoding residues 5-7 of the FR1 of the lambda genes (indicated with X . . . X; within the lambda genes the overlap may sometimes not be perfect); (2) ligation of this complex; (3) PCR of the ligated material with the indicated primer ('PCRpr') and for example one primer based within the VL gene. In this process the first few residues of all lambda genes will be encoded by the sequences present in the oligonucleotides (Ext., Bridge or PCRpr). After the PCR, the lambda genes can be cloned using the indicated restriction site for ApaLI.

Figure 19:
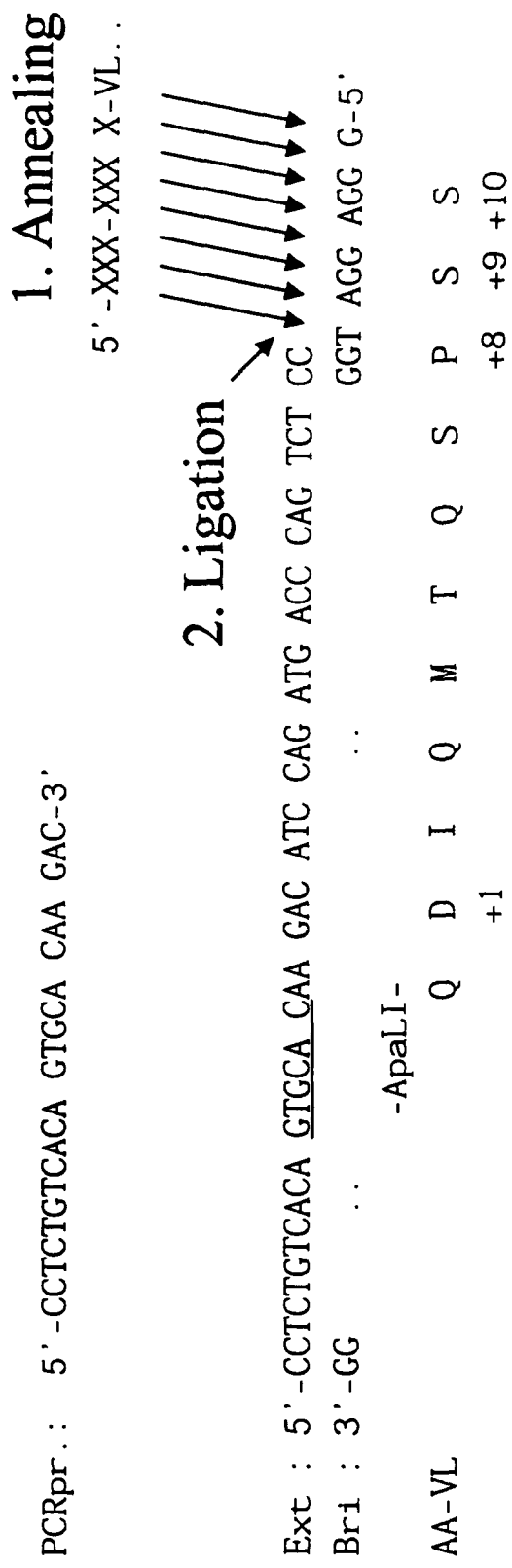
FIG. 19 is a schematic of a process for incorporating fixed FR1 residues in an antibody kappa sequence (see SEQ ID NOS 608-611, respectively, in order of appearance).

The process for incorporating fixed FR1 residues in an antibody kappa sequence (FIG. 19) consists of 3 steps: (1) annealing of single-stranded DNA material encoding VK genes to a partially complementary oligonucleotide mix (indicated with Ext and Bri), to anneal in this example to the region encoding residues 8-10 of the FR1 of the kappa genes (indicated with X . . . X; within the kappa genes the overlap may sometimes not be perfect); (2) ligation of this complex; (3) PCR of the ligated material with the indicated primer ('PCRpr') and for example one primer based within the VK gene. In this process the first few (8) residues of all kappa genes will be encode by the sequences present in the oligonucleotides (Ext., Bridge or PCRpr). After the PCR, the kappa genes can be cloned using the indicated restriction site for ApaLI.

The process of incorporating fixed FR3 residues in a antibody heavy chain sequence (FIG. 20) consists of 3 steps: (1) annealing of single-stranded DNA material encoding part of the VH genes (for example encoding FR3, CDR3 and FR4 regions) to a partially complementary oligonucleotide mix (indicated with Ext and Bridge), to anneal in this example to the region encoding residues 92-94 (within the FR3 region) of VH genes (indicated with X . . . X; within the VH genes the overlap may sometimes not be perfect); (2) ligation of this complex; (3) PCR of the ligated material with the indicated primer ('PCRpr') and for example one primer based within the VH gene (such as in the FR4 region). In this process certain residues of all VH genes will be encoded by the sequences present in the oligonucleotides used here, in particular from PCRpr (for residues 70-73), or from Ext/Bridge oligonucleotides (residues 74-91). After the PCR, the partial VH genes can be cloned using the indicated restriction site for XbaI.

It will be understood that the foregoing is only illustrative of the principles of this invention and that various modifications can be made by those skilled in the art without departing from the scope of and sprit of the invention.

TABLE 1

Human GLG FR3 sequences

```
! VH1
!  66  67  68  69  70  71  72  73  74  75  76  77  78  79  80
   agg gtc acc atg acc agg gac acg tcc atc agc aca gcc tac atg !  81  82  82a 82b 82c 83  84  85  86  87  88  89  90  91  92
   gag ctg agc agg ctg aga tct gac gac acg gcc gtg tat tac tgt !  93  94  95
   gcg aga ga  ! 1-02# 1 (SEQ ID NO: 34)

aga gtc acc att acc agg gac aca tcc gcg agc aca gcc tac atg gag ctg agc agc ctg aga tct gaa gac acg gct gtg tat tac tgt gcg aga ga  ! 1-03# 2 (SEQ ID NO: 35)

aga gtc acc atg acc agg aac acc tcc ata agc aca gcc tac atg gag ctg agc agc ctg aga tct gag gac acg gcc gtg tat tac tgt gcg aga gg  ! 1-08# 3 (SEQ ID NO: 36)

aga gtc acc atg acc aca gac aca tcc acg agc aca gcc tac atg gag ctg agg agc ctg aga tct gac gac acg gcc gtg tat tac tgt gcg aga ga  ! 1-18# 4 (SEQ ID NO: 37)

aga gtc acc atg acc gag gac aca tct aca gac aca gcc tac atg gag ctg agc agc ctg aga tct gag gac acg gcc gtg tat tac tgt gcg aca ga  ! 1-24# 5 (SEQ ID NO: 38)

aga gtc acc att acc agg gac agg tct atg agc aca gcc tac atg gag ctg agc agc ctg aga tct gag gac aca gcc atg tat tac tgt gca aga ta  ! 1-45# 6 (SEQ ID NO: 39)

aga gtc acc atg acc agg gac acg tcc acg agc aca gtc tac atg gag ctg agc agc ctg aga tct gag gac acg gcc gtg tat tac tgt gcg aga ga  ! 1-46# 7 (SEQ ID NO: 40)

aga gtc acc att acc agg gac atg tcc aca agc aca gcc tac atg gag ctg agc agc ctg aga tcc gag gac acg gcc gtg tat tac tgt gcg gca ga  ! 1-58# 8 (SEQ ID NO: 41)

aga gtc acg att acc gcg gac gaa tcc acg agc aca gcc tac atg gag ctg agc agc ctg aga tct gag gac acg gcc gtg tat tac tgt gcg aga ga  ! 1-69# 9 (SEQ ID NO: 42)
```

TABLE 1-continued

| Human GLG FR3 sequences |
|---| aga gtc acg att acc gcg gac aaa tcc acg agc aca gcc tac atg gag ctg agc agc ctg aga tct gag gac acg gcc gtg tat tac tgt gcg aga ga ! 1-e# 10 (SEQ ID NO: 43)

aga gtc acc ata acc gcg gac acg tct aca gac aca gcc tac atg gag ctg agc agc ctg aga tct gag gac acg gcc gtg tat tac tgt gcg aca ga ! 1-f# 11 (SEQ ID NO: 44)

! VH2
agg ctc acc atc acc aag gac acc tcc aaa aac cag gtg gtc ctt aca atg acc aac atg gac cct gtg gac aca gcc aca tat tac tgt gca cac aga c! 2-05# 12 (SEQ ID NO: 45)

agg ctc acc atc tcc aag gac acc tcc aaa agc cag gtg gtc ctt acc atg acc aac atg gac cct gtg gac aca gcc aca tat tac tgt gca cgg ata c! 2-26# 13 (SEQ ID NO: 46)

agg ctc acc atc tcc aag gac acc tcc aaa aac cag gtg gtc ctt aca atg acc aac atg gac cct gtg gac aca gcc acg tat tac tgt gca cgg ata c! 2-70# 14 (SEQ ID NO: 47)

! VH3
cga ttc acc atc tcc aga gac aac gcc aag aac tca ctg tat ctg caa atg aac agc ctg aga gcc gag gac acg gct gtg tat tac tgt gcg aga ga ! 3-07# 15 (SEQ ID NO: 48)

cga ttc acc atc tcc aga gac aac gcc aag aac tcc ctg tat ctg caa atg aac agt ctg aga gct gag gac acg gcc ttg tat tac tgt gca aaa gat a! 3-09# 16 (SEQ ID NO: 49)

cga ttc acc atc tcc agg gac aac gcc aag aac tca ctg tat ctg caa atg aac agc ctg aga gcc gag gac acg gcc gtg tat tac tgt gcg aga ga ! 3-11# 17 (SEQ ID NO: 50)

cga ttc acc atc tcc aga gaa aat gcc aag aac tcc ttg tat ctt caa atg aac agc ctg aga gcc ggg gac acg gct gtg tat tac tgt gca aga ga ! 3-13# 18 (SEQ ID NO: 51)

aga ttc acc atc tca aga gat gat tca aaa aac acg ctg tat ctg caa atg aac agc ctg aaa acc gag gac aca gcc gtg tat tac tgt acc aca ga ! 3-15# 19 (SEQ ID NO: 52)

cga ttc acc atc tcc aga gac aac gcc aag aac tcc ctg tat ctg caa atg aac agt ctg aga gcc gag gac acg gcc ttg tat cac tgt gcg aga ga ! 3-20# 20 (SEQ ID NO: 53)

cga ttc acc atc tcc aga gac aac gcc aag aac tca ctg tat ctg caa atg aac agc ctg aga gcc gag gac acg gct gtg tat tac tgt gcg aga ga ! 3-21# 21 (SEQ ID NO: 54)

TABLE 1-continued

| Human GLG FR3 sequences |
|---| cgg ttc acc atc tcc aga gac aat tcc aag aac acg ctg tat ctg
caa atg aac agc ctg aga gcc gag gac acg gcc gta tat tac tgt
gcg aaa ga ! 3-23# 22 (SEQ ID NO: 55)

cga ttc acc atc tcc aga gac aat tcc aag aac acg ctg tat ctg
caa atg aac agc ctg aga gct gag gac acg gct gtg tat tac tgt
gcg aaa ga ! 3-30# 23 (SEQ ID NO: 56)

cga ttc acc atc tcc aga gac aat tcc aag aac acg ctg tat ctg
caa atg aac agc ctg aga gct gag gac acg gct gtg tat tac tgt
gcg aga ga ! 3303# 24 (SEQ ID NO: 57)

cga ttc acc atc tcc aga gac aat tcc aag aac acg ctg tat ctg
caa atg aac agc ctg aga gct gag gac acg gct gtg tat tac tgt
gcg aaa ga ! 3305# 25 (SEQ ID NO: 58)

cga ttc acc atc tcc aga gac aat tcc aag aac acg ctg tat ctg
caa atg aac agc ctg aga gcc gag gac acg gct gtg tat tac tgt
gcg aga ga ! 3-33# 26 (SEQ ID NO: 59)

cga ttc acc atc tcc aga gac aac agc aaa aac tcc ctg tat ctg
caa atg aac agt ctg aga act gag gac acc gcc ttg tat tac tgt
gca aaa gat a! 3-43# 27 (SEQ ID NO: 60)

cga ttc acc atc tcc aga gac aat gcc aag aac tca ctg tat ctg
caa atg aac agc ctg aga gac gag gac acg gct gtg tat tac tgt
gcg aga ga ! 3-48# 28 (SEQ ID NO: 61)

aga ttc acc atc tca aga gat ggt tcc aaa agc atc gcc tat ctg
caa atg aac agc ctg aaa acc gag gac aca gcc gtg tat tac tgt
act aga ga ! 3-49# 29 (SEQ ID NO: 62)

cga ttc acc atc tcc aga gac aat tcc aag aac acg ctg tat ctt
caa atg aac agc ctg aga gcc gag gac acg gcc gtg tat tac tgt
gcg aga ga ! 3-53# 30 (SEQ ID NO: 63)

aga ttc acc atc tcc aga gac aat tcc aag aac acg ctg tat ctt
caa atg ggc agc ctg aga gct gag gac atg gct gtg tat tac tgt
gcg aga ga ! 3-64# 31 (SEQ ID NO: 64)

aga ttc acc atc tcc aga gac aat tcc aag aac acg ctg tat ctt
caa atg aac agc ctg aga gct gag gac acg gct gtg tat tac tgt
gcg aga ga ! 3-66# 32 (SEQ ID NO: 65)

aga ttc acc atc tca aga gat gat tca aag aac tca ctg tat ctg
caa atg aac agc ctg aaa acc gag gac acg gcc gtg tat tac tgt
gct aga ga ! 3-72# 33 (SEQ ID NO: 66)

agg ttc acc atc tcc aga gat gat tca aag aac acg gcg tat ctg
caa atg aac agc ctg aaa acc gag gac acg gcc gtg tat tac tgt
act aga ca ! 3-73# 34 (SEQ ID NO: 67)

TABLE 1-continued

| Human GLG FR3 sequences |
|---| cga ttc acc atc tcc aga gac aac gcc aag aac acg ctg tat ctg
caa atg aac agt ctg aga gcc gag gac acg gct gtg tat tac tgt
gca aga ga ! 3-74# 35 (SEQ ID NO: 68)

aga ttc acc atc tcc aga gac aat tcc aag aac acg ctg cat ctt
caa atg aac agc ctg aga gct gag gac acg gct gtg tat tac tgt
aag aaa ga ! 3-d# 36 (SEQ ID NO: 69)

! VH4
cga gtc acc ata tca gta gac aag tcc aag aac cag ttc tcc ctg
aag ctg agc tct gtg acc gcc gcg gac acg gcc gtg tat tac tgt
gcg aga ga ! 4-04# 37 (SEQ ID NO: 70)

cga gtc acc atg tca gta gac acg tcc aag aac cag ttc tcc ctg
aag ctg agc tct gtg acc gcc gtg gac acg gcc gtg tat tac tgt
gcg aga aa ! 4-28# 38 (SEQ ID NO: 71)

cga gtt acc ata tca gta gac acg tct aag aac cag ttc tcc ctg
aag ctg agc tct gtg act gcc gcg gac acg gcc gtg tat tac tgt
gcg aga ga ! 4301# 39 (SEQ ID NO: 72)

cga gtc acc ata tca gta gac agg tcc aag aac cag ttc tcc ctg
aag ctg agc tct gtg acc gcc gcg gac acg gcc gtg tat tac tgt
gcc aga ga ! 4302# 40 (SEQ ID NO: 73)

cga gtt acc ata tca gta gac acg tcc aag aac cag ttc tcc ctg
aag ctg agc tct gtg act gcc gca gac acg gcc gtg tat tac tgt
gcc aga ga ! 4304# 41 (SEQ ID NO: 74)

cga gtt acc ata tca gta gac acg tct aag aac cag ttc tcc ctg
aag ctg agc tct gtg act gcc gcg gac acg gcc gtg tat tac tgt
gcg aga ga ! 4-31# 42 (SEQ ID NO: 75)

cga gtc acc ata tca gta gac acg tcc aag aac cag ttc tcc ctg
aag ctg agc tct gtg acc gcc gcg gac acg gct gtg tat tac tgt
gcg aga ga ! 4-34# 43 (SEQ ID NO: 76)

cga gtc acc ata tcc gta gac acg tcc aag aac cag ttc tcc ctg
aag ctg agc tct gtg acc gcc gca gac acg gct gtg tat tac tgt
gcg aga ca ! 4-39# 44 (SEQ ID NO: 77)

cga gtc acc ata tca gta gac acg tcc aag aac cag ttc tcc ctg
aag ctg agc tct gtg acc gct gcg gac acg gcc gtg tat tac tgt
gcg aga ga ! 4-59# 45 (SEQ ID NO: 78)

cga gtc acc ata tca gta gac acg tcc aag aac cag ttc tcc ctg
aag ctg agc tct gtg acc gct gcg gac acg gcc gtg tat tac tgt
gcg aga ga ! 4-61# 46 (SEQ ID NO: 79)

cga gtc acc ata tca gta gac acg tcc aag aac cag ttc tcc ctg
aag ctg agc tct gtg acc gcc gca gac acg gcc gtg tat tac tgt
gcg aga ga ! 4-b# 47 (SEQ ID NO: 80)

TABLE 1-continued

Human GLG FR3 sequences

! VH5
cag gtc acc atc tca gcc gac aag tcc atc agc acc gcc tac ctg cag tgg agc agc ctg aag gcc tcg gac acc gcc atg tat tac tgt gcg aga ca ! 5-51# 48 (SEQ ID NO: 81)

cac gtc acc atc tca gct gac aag tcc atc agc act gcc tac ctg cag tgg agc agc ctg aag gcc tcg gac acc gcc atg tat tac tgt gcg aga ! 5-a# 49 (SEQ ID NO: 82)

! VH6
cga ata acc atc aac cca gac aca tcc aag aac cag ttc tcc ctg cag ctg aac tct gtg act ccc gag gac acg gct gtg tat tac tgt gca aga ga ! 6-1# 50 (SEQ ID NO: 83)

! VH7
cgg ttt gtc ttc tcc ttg gac acc tct gtc agc acg gca tat ctg cag atc tgc agc cta aag gct gag gac act gcc gtg tat tac tgt gcg aga ga ! 74.1# 51 (SEQ ID NO: 84)

TABLE 2

Enzymes that either cut 15 or more human GLGs or have 5+-base recognition in FR3

Typical entry:
REname Recognition                          #sites
GLGid#: base# GLGid#: base# GLGid#: base# . . .

```
BstEII Ggtnacc                              2
  1:  3  48:  3
There are 2 hits at base# 3
MaeIII gtnac                                36
  1:  4   2:  4   3:  4   4:  4   5:  4   6:  4
  7:  4   8:  4   9:  4  10:  4  11:  4  37:  4
 37: 58  38:  4  38: 58  39:  4  39: 58  40:  4
 40: 58  41:  4  41: 58  42:  4  42: 58  43:  4
 43: 58  44:  4  44: 58  45:  4  45: 58  46:  4
 46: 58  47:  4  47: 58  48:  4  49:  4  50: 58
There are 24 hits at base# 4
Tsp45I gtsac                                33
  1:  4   2:  4   3:  4   4:  4   5:  4   6:  4
  7:  4   8:  4   9:  4  10:  4  11:  4  37:  4
 37: 58  38:  4  38: 58  39:  4  40:  4  40: 58
 41: 58  42: 58  43:  4  43: 58  44:  4  44: 58
 45:  4  45: 58  46:  4  46: 58  47:  4  47: 58
 48:  4  49:  4  50: 58
There are 21 hits at base# 4
HphI tcacc                                  45
  1:  5   2:  5   3:  5   4:  5   5:  5   6:  5
  7:  5   8:  5  11:  5  12:  5  12: 11  13:  5
 14:  5  15:  5  16:  5  17:  5  18:  5  19:  5
 20:  5  21:  5  22:  5  23:  5  24:  5  25:  5
 26:  5  27:  5  28:  5  29:  5  30:  5  31:  5
 32:  5  33:  5  34:  5  35:  5  36:  5  37:  5
 38:  5  39:  5  40:  5  43:  5  44:  5  45:  5  46:  5
 47:  5  48:  5  49:  5
There are 44 hits at base# 5
NlaIII CATG                                 26
  1:  9   1: 42   2: 42   3:  9   3: 42   4:  9
  4: 42   5:  9   5: 42   6: 42   6: 78   7:  9
  7: 42   8:  9   8: 42   9: 42  10: 42  11: 42
 12: 57  13: 48  13: 57  14: 57  31: 72  38:  9
 48: 78  49: 78
There are 11 hits at base# 42
There are 1 hits at base# 48
Could cause raggedness.
```

```
BsaJI Ccnngg                                37
  1: 14   2: 14   5: 14   6: 14   7: 14   8: 14
  8: 65   9: 14  10: 14  11: 14  12: 14  13: 14
 14: 14  15: 65  17: 14  17: 65  18: 65  19: 65
 20: 65  21: 65  22: 65  26: 65  29: 65  30: 65
 33: 65  34: 65  35: 65  37: 65  38: 65  39: 65
 40: 65  42: 65  43: 65  48: 65  49: 65  50: 65
 51: 14
There are 23 hits at base# 65
There are 14 hits at base# 14
AluI AGct                                   42
  1: 47   2: 47   3: 47   4: 47   5: 47   6: 47
  7: 47   8: 47   9: 47  10: 47  11: 47  16: 63
 23: 47  24: 47  25: 63  31: 63  32: 63  36: 63
 37: 47  37: 52  38: 47  38: 52  39: 47  39: 52
 40: 47  40: 52  41: 47  41: 52  42: 47  42: 52
 43: 47  43: 52  44: 47  44: 52  45: 47  45: 52
 46: 47  46: 52  47: 47  47: 52  49: 15  50: 47
There are 23 hits at base# 47
There are 11 hits at base# 52
Only 5 bases from 47
BlpI GCtnagc                                21
  1: 48   2: 48   3: 48   5: 48   6: 48   7: 48
  8: 48   9: 48  10: 48  11: 48  37: 48  38: 48
 39: 48  40: 48  41: 48  42: 48  43: 48  44: 48
 45: 48  46: 48  47: 48
There are 21 hits at base# 48
MwoI GCNNNNNnngc(SEQ ID NO: 85)             19
  1: 48   2: 28  19: 36  22: 36  23: 36  24: 36
 25: 36  26: 36  35: 36  37: 67  39: 67  40: 67
 41: 67  42: 67  43: 67  44: 67  45: 67  46: 67
 47: 67
There are 10 hits at base# 67
There are 7 hits at base# 36
DdeI Ctnag                                  71
  1: 49   1: 58   2: 49   2: 58   3: 49   3: 58
  3: 65   4: 49   4: 58   5: 49   5: 58   5: 65
  6: 49   6: 58   6: 65   7: 49   7: 58   7: 65
```

TABLE 2-continued

Enzymes that either cut 15 or more human GLGs
or have 5+-base recognition in FR3

Typical entry:
REname Recognition                    #sites
GLGid#: base# GLGid#: base# GLGid#: base# . . .

```
  8: 49    8: 58    9: 49    9: 58    9: 65   10: 49
 10: 58   10: 65   11: 49   11: 58   11: 65   15: 58
 16: 58   16: 65   17: 58   18: 58   20: 58   21: 58
 22: 58   23: 58   23: 65   24: 58   24: 65   25: 58
 25: 65   26: 58   27: 58   27: 65   28: 58   30: 58
 31: 58   31: 65   32: 58   32: 65   35: 58   36: 58
 36: 65   37: 49   38: 49   39: 26   39: 49   40: 49
 41: 49   42: 26   42: 49   43: 49   44: 49   45: 49
 46: 49   47: 49   48: 12   49: 12   51: 65
There are 29 hits at base# 58
There are 22 hits at base# 49
Only nine base from 58
There are 16 hits at base# 65
Only seven bases from 58
BglII  Agatct                               11
  1: 61    2: 61    3: 61    4: 61    5: 61    6: 61
  7: 61    9: 61   10: 61   11: 61   51: 47
There are 10 hits at base# 61
BstYI  Rgatcy                               12
  1: 61    2: 61    3: 61    4: 61    5: 61    6: 61
  7: 61    8: 61    9: 61   10: 61   11: 61   51: 47
There are 11 hits at base# 61
Hpy188I  TCNga                              17
  1: 64    2: 64    3: 64    4: 64    5: 64    6: 64
  7: 64    8: 64    9: 64   10: 64   11: 64   16: 57
 20: 57   27: 57   35: 57   48: 67   49: 67
There are 11 hits at base# 64
There are 4 hits at base# 57
There are 2 hits at base# 67  Could be ragged.
MslI  CAYNNnnRTG (SEQ ID NO: 86)            44
  1: 72    2: 72    3: 72    4: 72    5: 72    6: 72
  7: 72    8: 72    9: 72   10: 72   11: 72   15: 72
 17: 72   18: 72   19: 72   21: 72   23: 72   24: 72
 25: 72   26: 72   28: 72   29: 72   30: 72   31: 72
 32: 72   33: 72   34: 72   35: 72   36: 72   37: 72
 38: 72   39: 72   40: 72   41: 72   42: 72   43: 72
 44: 72   45: 72   46: 72   47: 72   48: 72   49: 72
 50: 72   51: 72
There are 44 hits at base# 72
BsiEI  CGRYcg                               23
  1: 74    3: 74    4: 74    5: 74    7: 74    8: 74
  9: 74   10: 74   11: 74   17: 74   22: 74   30: 74
 33: 74   34: 74   37: 74   38: 74   39: 74   40: 74
 41: 74   42: 74   45: 74   46: 74   47: 74
There are 23 hits at base#74
EaeI  Yggccr                                23
  1: 74    3: 74    4: 74    5: 74    7: 74    8: 74
  9: 74   10: 74   11: 74   17: 74   22: 74   30: 74
 33: 74   34: 74   37: 74   38: 74   39: 74   40: 74
 41: 74   42: 74   45: 74   46: 74   47: 74
There are 23 hits at base# 74
EagI  Cggccg                                23
  1: 74    3: 74    4: 74    5: 74    7: 74    8: 74
  9: 74   10: 74   11: 74   17: 74   22: 74   30: 74
 33: 74   34: 74   37: 74   38: 74   39: 74   40: 74
 41: 74   42: 74   45: 74   46: 74   47: 74
There are 23 hits at base# 74
HaeIII  GGcc                                27
  1: 75    3: 75    4: 75    5: 75    7: 75    8: 75
  9: 75   10: 75   11: 75   16: 75   17: 75   20: 75
 22: 75   30: 75   33: 75   34: 75   37: 75   38: 75
 39: 75   40: 75   41: 75   42: 75   45: 75   46: 75
 47: 75   48: 63   49: 63
There are 25 hits at base# 75
Bst4CI  ACNgt 65° C.                 63 Sites
                                 There is a third
                                 isoschismer
  1: 86    2: 86    3: 86    4: 86    5: 86    6: 86
  7: 34    7: 86    8: 86    9: 86   10: 86   11: 86
 12: 86   13: 86   14: 86   15: 36   15: 86   16: 53
 16: 86   17: 36   17: 86   18: 86   19: 86   20: 53
 20: 86   21: 36   21: 86   22:  0   22: 86   23: 86
 24: 86   25: 86   26: 86   27: 53   27: 86   28: 36
 28: 86   29: 86   30: 86   31: 86   32: 86   33: 86
 33: 86   34: 86   35: 53   35: 86   36: 86   37: 86
 38: 86   39: 86   40: 86   41: 86   42: 86   43: 86
 44: 86   45: 86   46: 86   47: 86   48: 86   49: 86
 50: 86   51:  0   51: 86
There are 51 hits at base# 86
All the other sites are well away
HpyCH4III  ACNgt                            63
  1: 86    2: 86    3: 86    4: 86    5: 86    6: 86
  7: 34    7: 86    8: 86    9: 86   10: 86   11: 86
 12: 86   13: 86   14: 86   15: 36   15: 86   16: 53
 16: 86   17: 36   17: 86   18: 86   19: 86   20: 53
 20: 86   21: 36   21: 86   22:  0   22: 86   23: 86
 24: 86   25: 86   26: 86   27: 53   27: 86   28: 86
 28: 86   29: 86   30: 86   31: 86   32: 86   33: 86
 33: 86   34: 86   35: 53   35: 86   36: 86   37: 86
 38: 86   39: 86   40: 86   41: 86   42: 86   43: 86
 44: 86   45: 86   46: 86   47: 86   48: 86   49: 86
 50: 86   51:  0   51: 86
There are 51 hits at base# 86
HinfI  Gantc                                43
  2:  2    3:  2    4:  2    5:  2    6:  2    7:  2
  8:  2    9:  2    9: 22   10:  2   11:  2   15:  2
 16:  2   17:  2   18:  2   19:  2   19: 22   20:  2
 21:  2   23:  2   24:  2   25:  2   26:  2   27:  2
 28:  2   29:  2   30:  2   31:  2   32:  2   33:  2
 33: 22   34: 22   35:  2   36:  2   37:  2   38:  2
 40:  2   43:  2   44:  2   45:  2   46:  2   47:  2
 50: 60
There are 38 hits at base# 2
MlyI  GAGTCNNNNNn (SEQ ID NO: 87)            18
  2:  2    3:  2    4:  2    5:  2    6:  2    7:  2
  8:  2    9:  2   10:  2   11:  2   37:  2   38:  2
 40:  2   43:  2   44:  2   45:  2   46:  2   47:  2
There are 18 hits at base# 2
PleI  gagtc                                 18
  2:  2    3:  2    4:  2    5:  2    6:  2    7:  2
  8:  2    9:  2   10:  2   11:  2   37:  2   38:  2
 40:  2   43:  2   44:  2   45:  2   46:  2   47:  2
There are 18 hits at base# 2
AciI  Ccgc                                  24
  2: 26    9: 14   10: 14   11: 14   27: 74   37: 62
 37: 65   38: 62   39: 65   40: 62   40: 65   41: 65
 42: 65   43: 62   43: 65   44: 62   44: 65   45: 65
 46: 62   47: 62   47: 65   48: 35   48: 74   49: 74
There are 8 hits at base# 62
There are 8 hits at base# 65
There are 3 hits at base# 14
There are 3 hits at base# 74
There are 1 hits at base# 26
There are 1 hits at base# 35
-"-  Gcgg                                   11
  8: 91    9: 16   10: 16   11: 16   37: 67   39: 67
 40: 67   42: 67   43: 67   45: 67   46: 67
There are 7 hits at base# 67
There are 3 hits at base# 16
There are 1 hits at base# 91
BsiHKAI  GWGCWc                             20
  2: 30    4: 30    6: 30    7: 30    9: 30   10: 30
 12: 89   13: 89   14: 89   37: 51   38: 51   39: 51
 40: 51   41: 51   42: 51   43: 51   44: 51   45: 51
 46: 51   47: 51
There are 11 hits at base# 51
Bsp1286I  GDGCHc                            20
  2: 30    4: 30    6: 30    7: 30    9: 30   10: 30
 12: 89   13: 89   14: 89   37: 51   38: 51   39: 51
 40: 51   41: 51   42: 51   43: 51   44: 51   45: 51
 46: 51   47: 51
There are 11 hits at base# 51
HgiAI  GWGCWc                               20
  2: 30    4: 30    6: 30    7: 30    9: 30   10: 30
 12: 89   13: 89   14: 89   37: 51   38: 51   39: 51
 40: 51   41: 51   42: 51   43: 51   44: 51   45: 51
```

TABLE 2-continued

Enzymes that either cut 15 or more human GLGs or have 5+-base recognition in FR3

Typical entry:
REname  Recognition                              #sites
GLGid#: base# GLGid#: base# GLGid#: base# . . .

```
 46: 51    47: 51
There are 11 hits at base# 51
BsoFI  GCngc                                       26
  2: 53     3: 53     5: 53     6: 53     7: 53     8: 53
  8: 91     9: 53    10: 53    11: 53    31: 53    36: 36
 37: 64    39: 64    40: 64    41: 64    42: 64    43: 64
 44: 64    45: 64    46: 64    47: 64    48: 53    49: 53
 50: 45    51: 53
There are 13 hits at base# 53
There are 10 hits at base# 64
TseI   Gcwgc                                       17
  2: 53     3: 53     5: 53     6: 53     7: 53     8: 53
  9: 53    10: 53    11: 53    31: 53    36: 36    45: 64
 46: 64    48: 53    49: 53    50: 45    51: 53
There are 13 hits at base# 53
MnlI   gagg                                        34
  3: 67     3: 95     4: 51     5: 16     5: 67     6: 67
  7: 67     8: 67     9: 67    10: 67    11: 67    15: 67
 16: 67    17: 67    19: 67    20: 67    21: 67    22: 67
 23: 67    24: 67    25: 67    26: 67    27: 67    28: 67
 29: 67    30: 67    31: 67    32: 67    33: 67    34: 67
 35: 67    36: 67    50: 67    51: 67
There are 31 hits at base# 67
HpyCH4V TGca                                       34
  5: 90     6: 90    11: 90    12: 90    13: 90    14: 90
 15: 44    16: 44    16: 90    17: 44    18: 90    19: 44
 20: 44    21: 44    22: 44    23: 44    24: 44    25: 44
 26: 44    27: 44    27: 90    28: 44    29: 44    33: 44
 34: 44    35: 44    35: 90    36: 38    48: 44    49: 44
 50: 44    50: 90    51: 44    51: 52
There are 21 hits at base# 44
There are 1 hits at base# 52
AccI   GTmkac                                      13  5-base
                                                      recognition
  7: 37    11: 24    37: 16    38: 16    39: 16    40: 16
 41: 16    42: 16    43: 16    44: 16    45: 16    46: 16
 47: 16
There are 11 hits at base# 16
SacII  CCGCgg                                       8  6-base
                                                      recognition
  9: 14    10: 14    11: 14    37: 65    39: 65    40: 65
 42: 65    43: 65
There are 5 hits at base# 65
There are 3 hits at base# 14
TfiI   Gawtc                                       24
  9: 22    15:  2    16:  2    17:  2    18:  2    19:  2
 19: 22    20:  2    21:  2    23:  2    24:  2    25:  2
 26:  2    27:  2    28:  2    29:  2    30:  2    31:  2
 32:  2    33:  2    33: 22    34: 22    35:  2    36:  2
There are 20 hits at base# 2
BsmAI  Nnnnnngagac (SEQ ID NO: 88)                 19
 15: 11    16: 11    20: 11    21: 11    22: 11    23: 11
 24: 11    25: 11    26: 11    27: 11    28: 11    28: 56
 30: 11    31: 11    32: 11    35: 11    36: 11    44: 87
 48: 87
There are 16 hits at base# 11
BpmI   ctccag                                      19
 15: 12    16: 12    17: 12    18: 12    20: 12    21: 12
 22: 12    23: 12    24: 12    25: 12    26: 12    27: 12
 28: 12    30: 12    31: 12    32: 12    34: 12    35: 12
 36: 12
There are 19 hits at base# 12
XmnI   GAANNnnttc (SEQ ID NO: 89)                  12
 37: 30    38: 30    39: 30    40: 30    41: 30    42: 30
 43: 30    44: 30    45: 30    46: 30    47: 30    50: 30
There are 12 hits at base# 30
BsrI   NCcagt                                      12
 37: 32    38: 32    39: 32    40: 32    41: 32    42: 32
 43: 32    44: 32    45: 32    46: 32    47: 32    50: 32
There are 12 hits at base# 32
BanII  GRGCYc                                      11
 37: 51    38: 51    39: 51    40: 51    41: 51    42: 51
 43: 51    44: 51    45: 51    46: 51    47: 51
There are 11 hits at base# 51
Ecl136I GAGctc                                     11
 37: 51    38: 51    39: 51    40: 51    41: 51    42: 51
 43: 51    44: 51    45: 51    46: 51    47: 51
There are 11 hits at base# 51
SacI   GAGCTc                                      11
 37: 51    38: 51    39: 51    40: 51    41: 51    42: 51
 43: 51    44: 51    45: 51    46: 51    47: 51
There are 11 hits at base# 51
```

TABLE 3

Synthetic 3-23 FR3 of human heavy chains showning positions of possible cleavage sites ! Sites engineered into the synthetic gene are shown in upper case DNA
! with the RE name between vertical bars (as in |  XbaI   |).
! RERSs frequently found in GLGs are shown below the synthetic sequence
! with the name to the right (as in gtn ac = MaeIII(24), indicating that
! 24 of the 51 GLGs contain the site).

```
!                                                  |---FR3---
!                                                  89   90        (codon # in
!                                                   R    F        synthetic 3-23)
!                                                  |cgc|ttc|   6
! Allowed DNA                                      |cgn|tty|
!                                                  |agr|
!                                                    ga ntc = HinfI(38)
!                                                    ga gtc = PleI(18)
!                                                    ga wtc = TfiI(20)
!                                                       gtn ac = MaeIII(24)
!                                                       gts ac = Tsp45I(21)
!                                                       tc acc = HphI(44)
!
!         --------FR3-----------------------------------------
!         91  92  93  94  95  96  97  98  99 100 101 102 103 104 105
!          T   I   S   R   D   N   S   K   N   T   L   Y   L   Q   M
(SEQ ID NO: 91)
```

TABLE 3-continued

Synthetic 3-23 FR3 of human heavy chains showning positions of possible cleavage sites

```
         |act|atc|TCT|AGA|gac|aac|tct|aag|aat|act|ctc|tac|ttg|cag|atg|   51
!allowed|acn|ath|tcn|cgn|gay|aay|tcn|aar|aay|acn|ttr|tay|ttr|car|atg|
(SEQ ID NO: 90)
!                |agy|agr|       |agy|            |ctn|    |ctn|
!                |   ga|gac = BsmAI(16)                      ag ct = AluI(23)
!              c|tcc ag = BpmI(19)                      g ctn agc = BlpI(21)
!                |   |                g aan nnn ttc = XmnI(12)
!                | XbaI |                                tg ca = HpyCH4V (21)
!
!
!        ---FR3---------------------------------------------->|
!         106 107 108 109 110 111 112 113 114 115 116 117 118 119 120
!          N   S   L   R   A   E   D   T   A   V   Y   Y   C   A   K
         |aac|agC|TTA|AGg|gct|gag|gac|aCT|GCA|Gtc|tac|tat|tgc|gct|aaa|   96
!allowed|aay|tcn|ttr|cgn|gcn|gar|gay|acn|gcn|gtn|tay|tay|tgy|gcn|aar|
!           |agy|ctn|agr|           |            |
!               |   |   cc nng g = BsaJI(23)          ac ngt - Bst4CI(51)
!               |   aga tct = BglII(10)               ac ngt = HpyCH4III(51)
!               | Rga tcY = BstYI(II)       |         ac ngt = TaaI(51)
!               |          c ayn nnn rtc = MslI(44)
!               |                     cg ryc g = BsiEI(23)
!               |                     yg gcc r = EaeI(23)
!               |                     cg gcc g = EagI(23)
!               |                     |g gcc = HaeIII(25)
!               |                gag g = MnlI(31)|
!               |AflII |                   | PstI |
```

TABLE 4

REdaptors, Extenders, and Bridges used for Cleavage and Capture of Human Heavy Chains in FR3.

```
A: HpyCH4V Probes of actual human HC genes (SEQ ID NOS 92-100,
respectively, in order of appearance)
 !HpyCH4V in FR3 of human HC, bases 35-56; only those with TGca site
 TGca;10,
 RE recognition:tgca                          of length 4 is expected at 10
   1                                              6-1 agttctccctgcagctgaactc
   2                      3-11, 3-07, 3-21, 3-72, 3-48 cactgtatctgcaaatgaacag
   3                                  3-09, 3-43, 3-20 ccctgtatctgcaaatgaacag
   4                                             5-51 ccgcctacctgcagtggagcag
   5  3-15, 3-30, 3-30.5, 3-30.3, 3-74, 3-23 , 3-33 cgctgtatctgcaaatgaacag
   6                                            7-4.1 cggcatatctgcagatctgcag
   7                                             3-73 cggcgtatctgcaaatgaacag
   8                                              5-a ctgcctacctgcagtggagcag
   9                                             3-49 tcgcctatctgcaaatgaacag
B: HpyCH4V REdaptors, Extenders, and Bridges
  B.1 REdaptors
! Cutting HC lower strand:
! TmKeller for 100 mM NaCl, zero formamide                          SEQ
! Edapters for cleavage                         Tm^w    Tm^K        ID NO:
```

| | | | | |
|---|---|---|---|---|
| (ON_HCFR36-1) | 5'-agttctcccTGCAgctgaactc-3' | 68.0 | 64.5 | 92 |
| (ON_HCFR36-1A) | 5'-ttctcccTGCAgctgaactc-3' | 62.0 | 62.5 | residues 3-22 of 92 |
| (ON_HCFR36-1B) | 5'-ttctcccTGCAgctgaac-3' | 56.0 | 59.9 | residues 3-20 of 92 |
| (ON_HCFR33-15) | 5'-cgctgtatcTGCAaatgaacag-3' | 64.0 | 60.8 | 96 |
| (ON_HCFR33-15A) | 5'-ctgtatcTGCAaatgaacag-3' | 56.0 | 56.3 | residues 3-22 of 96 |
| (ON_HCFR33-15B) | 5'-ctgtatcTGCAaatgaac-3' | 50.0 | 53.1 | residues 3-20 of 96 |
| (ON_HCFR33-11) | 5'-cactgtatcTGCAaatgaacag-3' | 62.0 | 58.9 | 93 |
| (ON_HCFR35-51) | 5'-ccgcctaccTGCAgtggagcag-3' | 74.0 | 70.1 | 95 |

```
!
  B.2 Segment of synthetic 3-23 gene into which captured CDR3 is to be cloned
!              XbaI...                        (SEQ ID NO: 101)
!D323*   cgCttcacTaag tcT aga gac aaC tcT aag aaT acT ctC taC
!        scab........ designed gene 3-23 gene................
!
!       HpyCH4V
!       ..  ..          AflII...
!       Ttg caG atg aac agc TtA agG . . .
!       ..........................  . . .
!
```

TABLE 4-continued

REdaptors, Extenders, and Bridges used for Cleavage and Capture of Human Heavy Chains in FR3.

```
   B.3 Extender and Bridges
! Extender (bottom strand):
!                                                       (SEQ ID NO: 102)
(ON_HCHpyEx01) 5'-cAAgTAgAgAgTATTcTTAgAgTTgTcTcTAgAcTTAgTgAAgcg-3'
! ON_HCHpyEx01 is the reverse complement of
! 5'-cgCttcacTaag tcT aga gac aaC tcT aag aaT acT ctC taC Ttg -3'
!
! Bridges (top strand, 9-base overlap):
!                                                       (SEQ ID NO: 103)
(ON_HCHpyBr016-1)    5'-cgCttcacTaag tcT aga gac aaC tcT aag-
                        aaT acT ctC taC Ttg CAgctgaac-3' {3'-term C is blocked}
!
! 3-15 et al. + 3-11                              (SEQ ID NO: 104)
(ON_HCHpyBr023-15)   5'-cgCttcacTaag tcT aga gac aaC tcT aag-
                        aaT acT ctC taC Ttg CAaatgaac-3' {3'-term C is blocked}
!
! 5-51                                            (SEQ ID NO: 105)
(ON_HCHpyBr045-51)   5'-cgCttcacTaag tcT aga gac aaC tcT aag-
                        aaT acT ctC taC Ttg CAgtggagc-3' {3'-term C is blocked}
!
! PCR primer (top strand)
!
(ON_HCHpyPCR)        5'-cgCttcacTaag tcT aga gac-3' (SEQ ID NO: 106)
!
C: BlpI Probes from human HC GLGs
    1          1-58, 1-03, 1-08, 1-69, 1-24, 1-45, 1-46, 1-f, 1-e acatggaGCTGAGCagcctgag
(SEQ ID NO: 107)
    2                                                              1-02 acatggaGCTGAGCaggctgag
(SEQ ID NO: 108)
    3                                                             1-18 acatggagctgaggagcctgag
(SEQ ID NO: 109)
    4                                                      5-51, 5-a acctgcagtggagcagcctgaa
(SEQ ID NO: 110)
    5                                              3-15, 3-73, 3-49, 3-72 atctgcaaatgaacagcctgaa
(SEQ ID NO: 111)
    6      3303, 3-33, 3-07, 3-11, 3-30, 3-21, 3-23, 3305, 3-48 atctgcaaatgaacagcctgag
(SEQ ID NO: 112)
    7                                              3-20, 3-74, 3-09, 3-43 atctgcaaatgaacagtctgag
(SEQ ID NO: 113)
    8                                                          74.1 atctgcagatctgcagcctaaa
(SEQ ID NO: 114)
    9                                         3-66, 3-13, 3-53, 3-d atcttcaaatgaacagcctgag
(SEQ ID NO: 115)
   10                                                         3-64 atcttcaaatgggcagcctgag
(SEQ ID NO: 116)
   11 4301, 4-28, 4302, 4-04, 4304, 4-31, 4-34, 4-39, 4-59, 4-61, 4-b ccctgaaGCTGAGCtctgtgac
(SEQ ID NO: 117)
   12                                                          6-1 ccctgcagctgaactctgtgac
(SEQ ID NO: 118)
   13                                                    2-70, 2-05 tccttacaatgaccaacatgga
(SEQ ID NO: 119)
   14                                                         2-26 tccttaccatgaccaacatgga
(SEQ ID NO: 120)
D: BlpI REdaptors, Extenders, and Bridges
   D.1 REdaptors
                                                         Tm^w    Tm^K (SEQ ID NO: 121)
(BlpF3HC1-58)   5'-ac atg gaG CTG AGC agc ctg ag-3'        70     66.4
                     (SEQ ID NO: 122)
(BlpF3HC6-1)    5'-cc ctg aag ctg agc tct gtg ac-3'        70     66.4
! BlpF3HC6-1 matches 4-30.1, not 6-1.
   D.2 Segment of synthetic 3-23 gene into which captured CDR3 is to be cloned
!
BlpI
!           XbaI...                                      . ...
...
!D323* cgCttcacTaag TCT AGA gac aaC tcT aag aaT acT ctC taC Ttg caG atg
aac
(SEQ ID NO: 123)!
!              AflII...
!          agC TTA AGG
```

TABLE 4-continued

REdaptors, Extenders, and Bridges used for Cleavage and Capture of Human Heavy Chains in FR3.

```
    D.3 Extender and Bridges
! Bridges (BlpF3Br1)  5'-cgCttcacTcag tcT aga gaT aaC AGT aaA aaT acT TtG-
            taC Ttg caG Ctg a|GC agc ctg-3' (SEQ ID NO: 124)

(BlpF3Br2)  5'-cgCttcacTcag tcT aga gaT aaC AGT aaA aaT acT TtG-
!           taC Ttg caG Ctg a|gc tct gtg-3' (SEQ ID NO: 125)
                              | lower strand is cut here ! Extender
(BlpF3Ext) 5'-TcAgcTgcAAgTAcAAAgTATTTTTAcTgTTATcTcTAgAcTgAgTgAAgcg-3' (SEQ
ID NO: 126)
! BlpF3Ext is the reverse complement of:
! 5'-cgCttcacTcag tcT aga gaT aaC AGT aaA aaT acT TtG taC Ttg caG Ctg a-3'
!
(BlpF3PCR) 5'-cgCttcacTcag tcT aga gaT aaC-3' (SEQ ID NO: 127)
E: HpyCH4III Distinct GLG sequences surrounding site, bases 77-98
    1           102#1, 118#4, 146#7, 169#9, 1e#10, 311#17, 353#30, 404#37,  4301 ccgtgtattac
                                                                                tgtgcgagaga
(SEQ ID NO: 128)
    2           103#2, 307#15, 321#21, 3303#24, 333#26, 348#28, 364#31,   366#32 ctgtgtattac
                                                                                tgtgcgagaga
(SEQ ID NO: 129)
    3                                                               108#3 ccgtgtattac
                                                                         tgtgcgagagg
(SEQ ID NO: 130)
    4                                                        124#5, 1f#11 ccgtgtattac
                                                                          tgtgcaacaga
(SEQ ID NO: 131)
    5                                                               145#6 ccatgtattac
                                                                         tgtgcaagata
(SEQ ID NO: 132)
    6                                                               158#8 ccgtgtattac
                                                                         tgtgcggcaga
(SEQ ID NO: 133)
    7                                                              205#12 ccacatattac
                                                                         tgtgcacacag
(SEQ ID NO: 134)
    8                                                              226#13 ccacatattac
                                                                         tgtgcacggat
(SEQ ID NO: 135)
    9                                                              270#14 ccacgtattac
                                                                         tgtgcacggat
(SEQ ID NO: 136)
   10                                                     309#16, 343#27 ccttgtattac
                                                                         tgtgcaaaaga
(SEQ ID NO: 137)
   11                                             313#18, 374#35, 61#50 ctgtgtattac
                                                                         tgtgcaagaga
(SEQ ID NO: 138)
   12                                                              315#19 ccgtgtattac
                                                                         tgtaccacaga
(SEQ ID NO: 139)
   13                                                              320#20 ccttgtatcac
                                                                         tgtgcgagaga
(SEQ ID NO: 140)
   14                                                              323#22 ccgtatattac
                                                                         tgtgcgaaaga
(SEQ ID NO: 141)
   15                                                     330#23, 3305#25 ctgtgtattac
                                                                          tgtgcgaaaga
(SEQ ID NO: 142)
   16                                                              349#29 ccgtgtattac
                                                                         tgtactagaga
(SEQ ID NO: 143)
   17                                                              372#33 ccgtgtattac
                                                                         tgtgctagaga
(SEQ ID NO: 144)
   18                                                              373#34 ccgtgtattac
                                                                         tgtactagaca
(SEQ ID NO: 145)
   19                                                               3d#36 ctgtgtattac
                                                                         tgtaagaaaga
```

TABLE 4-continued

REdaptors, Extenders, and Bridges used for Cleavage and Capture of
Human Heavy Chains in FR3.

```
(SEQ ID NO: 146)
  20                                              428#38     ccgtgtattac
                                                             tgtgcgagaaa
(SEQ ID NO: 147)
  21                                    4302#40, 4304#41     ccgtgtattac
                                                             tgtgccagaga
(SEQ ID NO: 148)
  22                                              439#44     ctgtgtattac
                                                             tgtgcgagaca
(SEQ ID NO: 149)
  23                                              551#48     ccatgtattac
                                                             tgtgcgagaca
(SEQ ID NO: 150)
  24                                               5a#49     ccatgtattac
                                                             tgtgcgaga
(SEQ ID NO: 151)
F: HpyCH4III REdaptors, Extenders, and Bridges
  F.1 REdaptors
(SEQ ID NOS 152-159, respectively, in order of appearance)
! ONs for cleavage of HC(lower) in FR3(bases 77-97)
! For cleavage with HpyCH4III, Bst4CI, or TaaI
! cleavage is in lower chain before base 88.
!                77  788 888 888 889 999 999 9
!                                                         T_m^W   T_m^K
                 78  901 234 567 890 123 456 7

(H43.77.97.1-02#1)   5'-cc gtg tat tAC TGT gcg aga  g-3'   6462.6
(H43.77.97.1-03#2)   5'-ct gtg tat tAC TGT gcg aga  g-3'   6260.6
(H43.77.97.108#3)    5'-cc gtg tat tAC TGT gcg aga  g-3'   6462.6
(H43.77.97.323#22)   5'-cc gta tat tac tgt gcg aaa  g-3'   6058.7
(H43.77.97.330#23)   5'-ct gtg tat tac tgt gcg aaa  g-3'   6058.7
(H43.77.97.439#44)   5'-ct gtg tat tac tgt gcg aga  c-3'   6260.6
(H43.77.97.551#48)   5'-cc atg tat tac tgt gcg aga  c-3'   6260.6
(H43.77.97.5a#49)    5'-cc atg tat tAC TGT gcg aga   -3'   5858.3
  F.2 Extender and Bridges
! XbaI and AflII sites in bridges are bunged
(H43.XABr1) 5'-ggtgtagtga-

|TCT|AGt|gac|aac|tct|aag|aat|act|ctc|tac|ttg|cag|atg|-
|aac|agC|TTt|AGg|gct|gag|gac|aCT|GCA|Gtc|tac|tat tgt gct aga-3'

(SEQ ID NO: 160)
(H43.XABr2) 5'-ggtgtagtga-

|TCT|AGt|gac|aac|tct|aag|aat|act|ctc|tac|ttg|cag|atg|-
|aac|agC|TTt|AGg|gct|gag|gac|aCT|GCA|Gtc|tac|tat tgt gct aaa-3'

(SEQ ID NO: 161)

(H43.XAExt) 5'-ATAgTAgAcT gcAgTgTccT cAgcccTTAA gcTgTTcATc TgcAAgTAgA-
             gAgTATTcTT AgAgTTgTcT cTAgATcAcT AcAcc-3'  (SEQ ID NO: 162)
!H43.XAExt is the reverse complement of
! 5'-ggtgtagtga- !  |TCT|AGA|gac|aac|tct|aag|aat|act|ctc|tac|ttg|cag|atg|-
!  |aac|agC|TTA|AGg|gct|gag|gac|aCT|GCA|Gtc|tac|tat -3'

(H43.XAPCR)   5'-ggtgtagtga |TCT|AGA|gac|aac-3'  (SEQ ID NO: 163)
! XbaI and AflII sites in bridges are bunged
(H43.ABr1) 5'-ggtgtagtga-

|aac|agC|TTt|AGg|gct|gag|gac|aCT|GCA|Gtc|tac|tat tgt gcg aga-3'

(SEQ ID NO: 164)
(H43.ABr2) 5'-ggtgtagtga-

|aac|agC|TTt|AGg|gct|gag|gac|aCT|GCA|Gtc|tac|tat tgt gcg aaa-3'

(SEQ ID NO: 165)
(H43.AExt) 5'-ATAgTAgAcTgcAgTgTccTcAgcccTTAAgcTgTTTcAcTAcAcc-3'
(SEQ ID NO: 166)
! (H43.AExt) is the reverse complement of 5'-ggtgtagtga-
```

TABLE 4-continued

REdaptors, Extenders, and Bridges used for Cleavage and Capture of
Human Heavy Chains in FR3.

```
!          |aac|agC|TTA|AGg|gct|gag|gac|aCT|GCA|Gtc|tac|tat -3' (SEQ ID NO: 167)
(H43.APCR)     5'-ggtgtagtga |aac|agC|TTA|AGg|gct|g-3' (SEQ ID NO: 168)
```

TABLE 5

Analysis of frequency of matching REdaptors in actual V genes

A: HpyCH4V in HC at bases 35-36

| Id | Ntot | Number of mismatches | | | | | | | | | | | Cut | ID | Probe |
| | | 0 | 1 | 2 | 3 | 4 | 5 | 6 | 7 | 8 | 9 | 10 | Number | | |
|---|---|---|---|---|---|---|---|---|---|---|---|---|---|---|---|
| 1 | 510 | 5 | 11 | 274 | 92 | 61 | 25 | 22 | 11 | 1 | 3 | 5 | 443 | 6-1 | agttctcccTGCAgctgaactc |
| 2 | 192 | 54 | 42 | 32 | 24 | 15 | 2 | 3 | 10 | 3 | 1 | 6 | 167 | 3-11 | cactgtatcTGCAaatgaacag |
| 3 | 58 | 19 | 7 | 17 | 6 | 5 | 1 | 0 | 1 | 0 | 2 | 0 | 54 | 3-09 | ccctgtatcTGCAaatgaacag |
| 4 | 267 | 42 | 33 | 9 | 8 | 8 | 82 | 43 | 22 | 8 | 11 | 1 | 100 | 5-51 | ccgcctaccTGCAgtggagcag |
| 5 | 250 | 111 | 59 | 41 | 24 | 7 | 5 | 1 | 0 | 0 | 2 | 0 | 242 | 3-15 | cgctgtatcTGCAaatgaacag |
| 6 | 7 | 0 | 2 | 0 | 1 | 0 | 0 | 0 | 0 | 0 | 4 | 0 | 3 | 7-4.1 | cggcatatcTGCAgatctgcag |
| 7 | 7 | 0 | 2 | 2 | 0 | 0 | 2 | 1 | 0 | 0 | 0 | 0 | 4 | 3-73 | cggcgtatcTGCAaatgaacag |
| 8 | 26 | 10 | 4 | 1 | 3 | 1 | 2 | 1 | 3 | 1 | 0 | 0 | 19 | 5-a | ctgcctaccTGCAgtggagcag |
| 9 | 21 | 8 | 2 | 3 | 1 | 6 | 1 | 0 | 0 | 0 | 0 | 0 | 20 | 3-49 | tcgcctatcTGCAaatgaacag |
| | 1338 | 249 | 162 | 379 | 149 | 103 | 120 | 71 | 47 | 13 | 23 | 12 | 1052 | | (SEQ ID NOS 169-177, repetively in order of appearance) |
| | | | 249 | 411 | 790 | 939 | 1042 | 1162 | 1233 | 1280 | 1293 | 1316 | 1338 | | | |

| Id | Probe | dotted probe |
|---|---|---|
| 6-1 | agttctcccTGCAgctgaactc | agttctcccTGCAgctgaactc |
| 3-11 | cactgtatcTGCAaatgaacag | cac.g.at.....aa.....ag |
| 3-09 | ccctgtatcTGCAaatgaacag | ccc.g.at.....aa.....ag |
| 5-51 | ccgcctaccTGCAgtggagcag | ccgc..a.......tg..g.ag |
| 3-15 | cgctgtatcTGCAaatgaacag | c.c.g.at.....aa.....ag |
| 7-4.1 | cggcatatcTGCAgatctgcag | c.gca.at......a.ctg.ag |
| 3-73 | cggcgtatcTGCAaatgaacag | c.gcg.at.....aa.....ag |
| 5-a | ctgcctaccTGCAgtggagcag | ctgc..a.......tg..g.ag |
| 3-49 | tcgcctatcTGCAaatgaacag | tcgc..at.....aa.....ag |

(SEQ ID NOS 169-177, respectively in order of appearance)

Seqs with the expected RE site only.......1004

(Counts only cases with 4 or fewer mismatches)

Seqs with only an unexpected site.........   0

Seqs with both expected and unexpected....  48

(Counts only cases with 4 or fewer mismatches)

Seqs with no sites........................   0

TABLE 5-continued

Analysis of frequency of matching REdaptors in actual V genes

B: BlpI in HC

| Id | Ntot | 0 | 1 | 2 | 3 | 4 | 5 | 6 | 7 | 8 | Ncut | Name | |
|----|------|---|---|---|---|---|---|---|---|---|------|------|---|
| 1  | 133  | 73  | 16 | 11 | 13 | 6  | 9  | 1 | 4 | 0 | 119  | 1-58 | acatggaGCTGAGCagcctgag |
| 2  | 14   | 11  | 1  | 0  | 0  | 0  | 0  | 1 | 0 | 1 | 12   | 1-02 | acatggagctgagcaggctgag |
| 3  | 34   | 17  | 8  | 2  | 6  | 1  | 0  | 0 | 0 | 0 | 0    | 1-18 | acatggagctgaggagcctgag |
| 4  | 120  | 50  | 32 | 16 | 10 | 9  | 1  | 1 | 1 | 0 | 2    | 5-51 | acctgcagtggagcagcctgaa |
| 5  | 55   | 13  | 11 | 10 | 17 | 3  | 1  | 0 | 0 | 0 | 0    | 3-15 | atctgcaaatgaacagcctgaa |
| 6  | 340  | 186 | 88 | 41 | 15 | 6  | 3  | 0 | 1 | 0 | 0    | 3303 | atctgcaatgaacagcctgag |
| 7  | 82   | 25  | 16 | 25 | 12 | 1  | 3  | 0 | 0 | 0 | 0    | 3-20 | atctgcaaatgaacagtctgag |
| 8  | 3    | 0   | 2  | 0  | 1  | 0  | 0  | 0 | 0 | 0 | 0    | 74.1 | atctgcagatctgcagcctaaa |
| 9  | 23   | 18  | 2  | 2  | 1  | 0  | 0  | 0 | 0 | 0 | 0    | 3-66 | atcttcaaatgaacagcctgag |
| 10 | 2    | 1   | 0  | 1  | 0  | 0  | 0  | 0 | 0 | 0 | 0    | 3-64 | atcttcaaatgggcagcctgag |
| 11 | 486  | 249 | 78 | 81 | 38 | 21 | 10 | 4 | 4 | 1 | 467  | 4301 | ccctgaagctgagctctgtgac |
| 12 | 16   | 6   | 3  | 1  | 0  | 1  | 1  | 3 | 1 | 0 | 1    | 6-1  | ccctgcagctgaactctgtgac |
| 13 | 28   | 15  | 8  | 2  | 2  | 1  | 0  | 0 | 0 | 0 | 0    | 2-70 | tccttacaatgaccaacatgga |
| 14 | 2    | 0   | 2  | 0  | 0  | 0  | 0  | 0 | 0 | 0 | 0    | 2-26 | tccttaccatgaccaacatgga |
|    |      |     |    |    |    |    |    |   |   |   | 601  |      | (SEQ ID NOS 178-191), respectively in order of appearance) |

| Name | Full sequence | Dot mode |
|------|---------------|----------|
| 1-58   | acatggaGCTGAGCagcctgag | acatggaGCTGAGCagcctgag |
| 1-02   | acatggagctgagcaggctgag | ................g..... |
| 1-18   | acatggagctgaggagcctgag | .............g........ |
| 5-51   | acctgcagtggagcagcctgaa | ..c..c..tg...........a |
| 3-15   | atctgcaaatgaacagcctgaa | .tc..c.aa...a........a |
| 3-30.3 | atctgcaaatgaacagcctgag | .tc..c.aa...a......... |
| 3-20   | atctgcaaatgaacagtctgag | .tc..c.aa...a...t..... |
| 7-4.1  | atctgcagatctgcagcctaaa | .tc..c...a.ct.......a.a |
| 3-66   | atcttcaaatgaacagcctgag | .tc.tc.aa...a......... |
| 3-64   | atcttcaaatgggcagcctgag | .tc.tc.aa...g......... |
| 4-30.1 | ccctgaagctgagctctgtgac | c.c..a........tctg...c |
| 6-1    | ccctgcagctgaactctgtgac | c.c..c......a.tctg...c |
| 2-70   | tccttacaatgaccaacatgga | t.c.tacaa...c..a.a...ga |
| 2-26   | tccttaccatgaccaacatgga | t.c.tacca...c..a.a...ga |

(SEQ ID NOS 178-191, respectively in order of appearance)

Seqs with the expected RE site only....... 597 (counting sequences with 4 or fewer mismatches)

Seqs with only an unexpected site......... 2

Seqs with both expected and unexpected.... 2

Seqs with no sites........................ 686

TABLE 5-continued

Analysis of frequency of matching REdaptors in actual V genes

C: HpyCH4III, Bst4CI, or TaaI in HC
In scoring whether the RE site of interest is present,
only ONs that have 4 or fewer mismatches are counted.
Number of sequences.......... 1617

| Id | Ntot | 0 | 1 | 2 | 3 | 4 | 5 | 6 | 7 | 8 | Ncut | | acngt |
|---|---|---|---|---|---|---|---|---|---|---|---|---|---|
| 1 | 244 | 78 | 92 | 43 | 18 | 10 | 1 | 2 | 0 | 0 | 241 | 102#1,1 | ccgtgtattACTGTgcgagaga |
| 2 | 457 | 69 | 150 | 115 | 66 | 34 | 11 | 8 | 3 | 1 | 434 | 103#2,3 | ctgtgtattactgtgcgagaga |
| 3 | 173 | 52 | 45 | 36 | 22 | 14 | 3 | 0 | 0 | 1 | 169 | 108#3 | ccgtgtattactgtgcgagagg |
| 4 | 16 | 0 | 3 | 2 | 2 | 1 | 6 | 0 | 1 | 1 | 8 | 124#5,1 | ccgtgtattactgtgcaacaga |
| 5 | 4 | 0 | 0 | 1 | 0 | 1 | 1 | 0 | 1 | 0 | 2 | 145#6 | ccatgtattactgtgcaagata |
| 6 | 15 | 1 | 0 | 1 | 0 | 6 | 4 | 1 | 1 | 1 | 8 | 158#8 | ccgtgtattactgtgcggcaga |
| 7 | 23 | 4 | 8 | 5 | 2 | 2 | 1 | 1 | 0 | 0 | 21 | 205#12 | ccacatattactgtgcacacag |
| 8 | 9 | 1 | 1 | 1 | 0 | 3 | 2 | 1 | 0 | 0 | 6 | 226#13 | ccacatattactgtgcacggat |
| 9 | 7 | 1 | 3 | 1 | 1 | 0 | 0 | 1 | 0 | 0 | 6 | 270#14 | ccacgtattactgtgcacggat |
| 10 | 23 | 7 | 3 | 5 | 5 | 2 | 1 | 0 | 0 | 0 | 22 | 309#16, | ccttgtattactgtgcaaaaga |
| 11 | 35 | 5 | 10 | 7 | 6 | 3 | 3 | 0 | 1 | 0 | 31 | 313#18, | ctgtgtattactgtgcaagaga |
| 12 | 18 | 2 | 3 | 2 | 2 | 6 | 1 | 0 | 2 | 0 | 15 | 315#19 | ccgtgtattactgtaccacaga |
| 13 | 3 | 1 | 2 | 0 | 0 | 0 | 0 | 0 | 0 | 0 | 3 | 320#20 | ccttgtatcactgtgcgagaga |
| 14 | 117 | 29 | 23 | 28 | 22 | 8 | 4 | 2 | 1 | 0 | 110 | 323#22 | ccgtatattactgtgcgaaaga |
| 15 | 75 | 21 | 25 | 13 | 9 | 1 | 4 | 2 | 0 | 0 | 69 | 330#23, | ctgtgtattactgtgcgaaaga |
| 16 | 14 | 2 | 2 | 2 | 3 | 0 | 3 | 1 | 1 | 0 | 9 | 349#29 | ccgtgtattactgtactagaga |
| 17 | 2 | 0 | 0 | 1 | 0 | 0 | 1 | 0 | 0 | 0 | 1 | 372#33 | ccgtgtattactgtgctagaga |
| 18 | 1 | 0 | 0 | 1 | 0 | 0 | 0 | 0 | 0 | 0 | 1 | 373#34 | ccgtgtattactgtactagaca |
| 19 | 2 | 0 | 0 | 0 | 0 | 0 | 0 | 0 | 0 | 2 | 0 | 3d#36 | ctgtgtattactgtaagaaaga |
| 20 | 34 | 4 | 9 | 9 | 4 | 5 | 3 | 0 | 0 | 0 | 31 | 428#38 | ccgtgtattactgtgcgagaaa |
| 21 | 17 | 5 | 4 | 2 | 2 | 3 | 1 | 0 | 0 | 0 | 16 | 4302#40 | ccgtgtattactgtgccagaga |
| 22 | 75 | 15 | 17 | 24 | 7 | 10 | 1 | 1 | 0 | 0 | 73 | 439#44 | ctgtgtattactgtgcgagaca |
| 23 | 40 | 14 | 15 | 4 | 5 | 1 | 0 | 1 | 0 | 0 | 39 | 551#48 | ccatgtattactgtgcgagaca |
| 24 | 213 | 26 | 56 | 60 | 42 | 20 | 7 | 2 | 0 | 0 | 204 | 5a#49 | ccatgtattactgtgcgagaAA |

| Group | | 337 | 471 | 363 | 218 | 130 | 58 | 23 | 11 | 6 | | (SEQ ID NOS 192-215, respectively |
| Cumulative | | 337 | 808 | 1171 | 1389 | 1519 | 1577 | 1600 | 1611 | 1617 | | in order of appearance) |

| | acngt | acngt |
|---|---|---|
| 102#1,1 | ccgtgtattACTGTgcgagaga | ccgtgtattactgtgcgagaga |
| 103#2,3 | ctgtgtattactgtgcgagaga | .t.................... |
| 108#3 | ccgtgtattactgtgcgagagg | .....................g |
| 124#5,1 | ccgtgtattactgtgcaacaga | ................a.c... |
| 145#6 | ccatgtattactgtgcaagata | ...a...........a...t. |
| 158#8 | ccgtgtattactgtgcggcaga | .................gc... |
| 205#12 | ccacatattactgtgcacacag | ...aca..........acacag |
| 226#13 | ccacatattactgtgcacggat | ...aca..........ac.gat |
| 270#14 | ccacgtattactgtgcacggat | ...ac...........ac.gat |

TABLE 5-continued

Analysis of frequency of matching REdaptors in actual V genes

```
309#16,   ccttgtattactgtgcaaaaga    ..t............a.a...
313#18,   ctgtgtattactgtgcaagaga    .t.............a.....
315#19    ccgtgtattactgtaccacaga    .............a.c.c...
320#20    ccttgtatcactgtgcgagaga    ..t.....c............
323#22    ccgtatattactgtgcgaaaga    ....a..............a.
330#23,   ctgtgtattactgtgcgaaaga    .t.................a.
349#29    ccgtgtattactgtactagaga    ...............a.t...
372#33    ccgtgtattactgtgctagaga    .................t...
373#34    ccgtgtattactgtactagaca    ...............a.t...c.
3d#36     ctgtgtattactgtaagaaaga    .t...........aa..a...
428#38    ccgtgtattactgtgcgagaaa    ...................a.
4302#40   ccgtgtattactgtgccagaga    .................c...
439#44    ctgtgtattactgtgcgagaca    .t.................c.
551#48    ccatgtattactgtgcgagaca    ...a...............c.
5a#49     ccatgtattactgtgcgagaAA    ...a...............AA
```

Seqs with the expected RE site only.......1511
Seqs with only an unexpected site.........   0
Seqs with both expected and unexpected....   8
Seqs with no sites........................   0

TABLE 5D

Analysis repeated using only 8 best REdaptors

| Id | Ntot | 0 | 1 | 2 | 3 | 4 | 5 | 6 | 7 | 8+ | | | | |
|---|---|---|---|---|---|---|---|---|---|---|---|---|---|---|
| 1 | 301 | 78 | 101 | 54 | 32 | 16 | 9 | 10 | 1 | 0 | 281 | 102#1 | ccgtgtattactgtgcgagaga | (SEQ ID NO: 267) |
| 2 | 493 | 69 | 155 | 125 | 73 | 37 | 14 | 11 | 3 | 6 | 459 | 103#2 | ctgtgtattactgtgcgagaga | (SEQ ID NO: 268) |
| 3 | 189 | 52 | 45 | 38 | 23 | 18 | 5 | 4 | 1 | 3 | 176 | 108#3 | ccgtgtattactgtgcgagagg | (SEQ ID NO: 269) |
| 4 | 127 | 29 | 23 | 28 | 24 | 10 | 6 | 5 | 2 | 0 | 114 | 323#22 | ccgtatattactgtgcgaaaga | (SEQ ID NO: 270) |
| 5 | 78 | 21 | 25 | 14 | 11 | 1 | 4 | 2 | 0 | 0 | 72 | 330#23 | ctgtgtattactgtgcgaaaga | |
| 6 | 79 | 15 | 17 | 25 | 8 | 11 | 1 | 2 | 0 | 0 | 76 | 439#44 | ctgtgtattactgtgcgagaca | (SEQ ID NO: 272) |
| 7 | 43 | 14 | 15 | 5 | 5 | 3 | 0 | 1 | 0 | 0 | 42 | 551#48 | ccatgtattactgtgcgagaca | (SEQ ID NO: 273) |
| 8 | 307 | 26 | 63 | 72 | 51 | 38 | 24 | 14 | 13 | 6 | 250 | 5a#49 | ccatgtattactgtgcgaga | (residues 1-20 of SEQ ID NO: 274) |

```
1  102#1   ccgtgtattactgtgcgagaga    ccgtgtattactgtgcgagaga
2  103#2   ctgtgtattactgtgcgagaga    .t....................
3  108#3   ccgtgtattactgtgcgagagg    .....................g
4  323#22  ccgtatattactgtgcgaaaga    ....a..............a..
5  330#23  ctgtgtattactgtgcgaaaga    .t.................a..
6  439#44  ctgtgtattactgtgcgagaca    .t.................c..
```

TABLE 5D-continued

Analysis repeated using only 8 best REdaptors

| | | | | |
|---|---|---|---|---|
| 7 | 551#48 | ccatgtattactgtgcgagaca | ..a................c. | |
| 8 | 5a#49 | ccatgtattactgtgcgagaAA | ..a................AA | |

(SEQ ID NOS 267-274, respectively in order of appearance)

Seqs with the expected RE site only.......1463/1617

Seqs with only an unexpected site.........    0

Seqs with both expected and unexpected....    7

Seqs with no sites........................    0

TABLE 6

Human HC GLG FR1 Sequences
VH Exon - Nucleotide sequence alignment

VH1

1-02  CAG GTG CAG CTG GTG CAG TCT GGG GCT GAG GTG AAG AAG CCT GGG GCC TCA GTG AAG
      GTC TCC TGC AAG GCT TCT GGA TAC ACC TTC ACC (SEQ ID NO: 216)

1-03  cag gtC cag ctT gtg cag tct ggg gct gag gtg aag aag cct ggg gcc tca gtg aag
      gtT tcc tgc aag gct tct gga tac acc ttc acT (SEQ ID NO: 217)

1-08  cag gtg cag ctg gtg cag tct ggg gct gag gtg aag aag cct ggg gcc tca gtg aag
      gtc tcc tgc aag gct tct gga tac acc ttc acc (SEQ ID NO: 218)

1-18  cag gtT cag ctg gtg cag tct ggA gct gag gtg aag aag cct ggg gcc tca gtg aag
      gtc tcc tgc aag gct tct ggT tac acc ttT acc (SEQ ID NO: 219)

1-24  cag gtC cag ctg gtA cag tct ggg gct gag gtg aag aag cct ggg gcc tca gtg aag
      gtc tcc tgc aag gTt tcC gga tac acc Ctc acT (SEQ ID NO: 220)

1-45  cag Atg cag ctg gtg cag tct ggg gct gag gtg aag aag Act ggg Tcc tca gtg aag
      gtT tcc tgc aag gct tcC gga tac acc ttc acc (SEQ ID NO: 221)

1-46  cag gtg cag ctg gtg cag tct ggg gct gag gtg aag aag cct ggg gcc tca gtg aag
      gtT tcc tgc aag gcA tct gga tac acc ttc acc (SEQ ID NO: 222)

1-58  caA Atg cag ctg gtg cag tct ggg Cct gag gtg aag aag cct ggg Acc tca gtg aag
      gtc tcc tgc aag gct tct gga tTc acc ttT acT (SEQ ID NO: 223)

1-69  cag gtg cag ctg gtg cag tct ggg gct gag gtg aag aag cct ggg Tcc tcG gtg aag
      gtc tcc tgc aag gct tct gga GGc acc ttc aGc (SEQ ID NO: 224)

1-e   cag gtg cag ctg gtg cag tct ggg gct gag gtg aag aag cct ggg Tcc tcG gtg aag
      gtc tcc tgc aag gct tct gga GGc acc ttc aGc (SEQ ID NO: 225)

1-f   Gag gtC cag ctg gtA cag tct ggg gct gag gtg aag aag cct ggg gcT Aca gtg aaA
      Atc tcc tgc aag gTt tct gga tac acc ttc acc (SEQ ID NO: 226)

VH2

2-05  CAG ATC ACC TTG AAG GAG TCT GGT CCT ACG CTG GTG AAA CCC ACA CAG ACC CTC ACG
      CTG ACC TGC ACC TTC TCT GGG TTC TCA CTC AGC (SEQ ID NO: 227)

2-26  cag Gtc acc ttg aag gag tct ggt cct GTg ctg gtg aaa ccc aca Gag acc ctc acg
      ctg acc tgc acc Gtc tct ggg ttc tca ctc agc (SEQ ID NO: 228)

2-70  cag Gtc acc ttg aag gag tct ggt cct Gcg ctg gtg aaa ccc aca cag acc ctc acA
      ctg acc tgc acc ttc tct ggg ttc tca ctc agc (SEQ ID NO: 229)

VH3

3-07  GAG GTG CAG CTG GTG GAG TCT GGG GGA GGC TTG GTC CAG CCT GGG GGG TCC CTG AGA
      CTC TCC TGT GCA GCC TCT GGA TTC ACC TTT AGT (SEQ ID NO: 230)

3-09  gaA gtg cag ctg gtg gag tct ggg gga ggc ttg gtA cag cct ggC Agg tcc ctg aga
      ctc tcc tgt gca gcc tct gga ttc acc ttt Gat (SEQ ID NO: 231)

3-11  Cag gtg cag ctg gtg gag tct ggg gga ggc ttg gtc Aag cct ggA ggg tcc ctg aga
      ctc tcc tgt gca gcc tct gga ttc acc ttC agt (SEQ ID NO: 232)

TABLE 6-continued

Human HC GLG FR1 Sequences
VH Exon - Nucleotide sequence alignment 3-13    gag gtg cag ctg gtg gag tct ggg gga ggc ttg gtA cag cct ggg ggg tcc ctg aga
        ctc tcc tgt gca gcc tct gga ttc acc ttC agt (SEQ ID NO: 233)

3-15    gag gtg cag ctg gtg gag tct ggg gga ggc ttg gtA Aag cct ggg ggg tcc ctT aga
        ctc tcc tgt gca gcc tct gga ttc acT ttC agt (SEQ ID NO: 234)

3-20    gag gtg cag ctg gtg gag tct ggg gga ggT Gtg gtA cGg cct ggg ggg tcc ctg aga
        ctc tcc tgt gca gcc tct gga ttc acc ttt Gat (SEQ ID NO: 235)

3-21    gag gtg cag ctg gtg gag tct ggg gga ggc Ctg gtc Aag cct ggg ggg tcc ctg aga
        ctc tcc tgt gca gcc tct gga ttc acc ttC agt (SEQ ID NO: 236)

3-23    gag gtg cag ctg Ttg gag tct ggg gga ggc ttg gtA cag cct ggg ggg tcc ctg aga
        ctc tcc tgt gca gcc tct gga ttc acc ttt agC (SEQ ID NO: 237)

3-30    Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 238)

3-30.3  Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 239)

3-30.5  Cag gtg cag ctg gtg gag tct ggg gga ggc Gtg gtc cag cct ggg Agg tcc ctg aga
        ctc tcc tgt gca gcc tct gga ttc acc ttC agt (SEQ ID NO: 240)

3-33    Cag gtg cag ctg gtg gag tct ggg gga ggc Gtg gtc cag cct ggg Agg tcc ctg aga
        ctc tcc tgt gca gcG tct gga ttc acc ttC agt (SEQ ID NO: 241)

3-43    gaA gtg cag ctg gtg gag tct ggg gga gTc Gtg gtA cag cct ggg ggg tcc ctg aga
        ctc tcc tgt gca gcc tct gga ttc acc ttt Gat (SEQ ID NO: 242)

3-48    gag gtg cag ctg gtg gag tct ggg gga ggc ttg gtA cag cct ggg ggg tcc ctg aga
        ctc tcc tgt gca gcc tct gga ttc acc ttC agt (SEQ ID NO: 243)

3-49    gag gtg cag ctg gtg gag tct ggg gga ggc ttg gtA cag ccA ggg Cgg tcc ctg aga
        ctc tcc tgt Aca gcT tct gga ttc acc ttt Ggt (SEQ ID NO: 244)

3-53    gag gtg cag ctg gtg gag Act ggA gga ggc ttg Atc cag cct ggg ggg tcc ctg aga
        ctc tcc tgt gca gcc tct ggG ttc acc GtC agt (SEQ ID NO: 245)

3-64    gag gtg cag ctg gtg gag tct ggg gga ggc ttg gtc cag cct ggg ggg tcc ctg aga
        ctc tcc tgt gca gcc tct gga ttc acc ttC agt (SEQ ID NO: 246)

3-66    gag gtg cag ctg gtg gag tct ggg gga ggc ttg gtc cag cct ggg ggg tcc ctg aga
        ctc tcc tgt gca gcc tct gga ttc acc GtC agt (SEQ ID NO: 247)

3-72    gag gtg cag ctg gtg gag tct ggg gga ggc ttg gtc cag cct ggA ggg tcc ctg aga
        ctc tcc tgt gca gcc tct gga ttc acc ttC agt (SEQ ID NO: 248)

3-73    gag gtg cag ctg gtg gag tct ggg gga ggc ttg gtc cag cct ggg ggg tcc ctg aAa
        ctc tcc tgt gca gcc tct ggG ttc acc ttC agt (SEQ ID NO: 249)

3-74    gag gtg cag ctg gtg gag tcC ggg gga ggc ttA gtT cag cct ggg ggg tcc ctg aga
        ctc tcc tgt gca gcc tct gga ttc acc ttC agt (SEQ ID NO: 250)

3-d     gag gtg cag ctg gtg gag tct Cgg gga gTc ttg gtA cag cct ggg ggg tcc ctg aga
        ctc tcc tgt gca gcc tct gga ttc acc GtC agt (SEQ ID NO: 251)

VH4

4-04    CAG GTG CAG CTG CAG GAG TCG GGC CCA GGA CTG GTG AAG CCT TCG GGG ACC CTG TCC
        CTC ACC TGC GCT GTC TCT GGT GGC TCC ATC AGC (SEQ ID NO: 252)

4-28    cag gtg cag ctg cag gag tcg ggc cca gga ctg gtg aag cct tcg gAC acc ctg tcc
        ctc acc tgc gct gtc tct ggt TAc tcc atc agc (SEQ ID NO: 253)

4-30.1  cag gtg cag ctg cag gag tcg ggc cca gga ctg gtg aag cct tcA CAg acc ctg tcc
        ctc acc tgc Act gtc tct ggt ggc tcc atc agc (SEQ ID NO: 254)

4-30.2  cag Ctg cag ctg cag gag tcC ggc Tca gga ctg gtg aag cct tcA CAg acc ctg tcc
        ctc acc tgc gct gtc tct ggt ggc tcc atc agc (SEQ ID NO: 255)

4-30.4  cag gtg cag ctg cag gag tcg ggc cca gga ctg gtg aag cct tcA CAg acc ctg tcc
        ctc acc tgc Act gtc tct ggt ggc tcc atc agc (SEQ ID NO: 256)

4-31    cag gtg cag ctg cag gag tcg ggc cca gga ctg gtg aag cct tcA CAg acc ctg tcc
        ctc acc tgc Act gtc tct ggt ggc tcc atc agc (SEQ ID NO: 257)

TABLE 6-continued

Human HC GLG FR1 Sequences
VH Exon - Nucleotide sequence alignment

```
4-34    cag gtg cag ctA cag Cag tGg ggc Gca gga ctg Ttg aag cct tcg gAg acc ctg tcc
        ctc acc tgc gct gtc tAt ggt ggG tcc Ttc agT (SEQ ID NO: 258)

4-39    cag Ctg cag ctg cag gag tcg ggc cca gga ctg gtg aag cct tcg gAg acc ctg tcc
        ctc acc tgc Act gtc tct ggt ggc tcc atc agc (SEQ ID NO: 259)

4-59    cag gtg cag ctg cag gag tcg ggc cca gga ctg gtg aag cct tcg gAg acc ctg tcc
        ctc acc tgc Act gtc tct ggt ggc tcc atc agT (SEQ ID NO: 260)

4-61    cag gtg cag ctg cag gag tcg ggc cca gga ctg gtg aag cct tcg gAg acc ctg tcc
        ctc acc tgc Act gtc tct ggt ggc tcc Gtc agc (SEQ ID NO: 261)

4-b     cag gtg cag ctg cag gag tcg ggc cca gga ctg gtg aag cct tcg gAg acc ctg tcc
        ctc acc tgc gct gtc tct ggt TAC tcc atc agc (SEQ ID NO: 262)
```

VH5

```
5-51    GAG GTG CAG CTG GTG CAG TCT GGA GCA GAG GTG AAA AAG CCC GGG GAG TCT CTG AAG
        ATC TCC TGT AAG GGT TCT GGA TAC AGC TTT ACC (SEQ ID NO: 263)

5-a     gaA gtg cag ctg gtg cag tct gga gca gag gtg aaa aag ccc ggg gag tct ctg aGg
        atc tcc tgt aag ggt tct gga tac agc ttt acc (SEQ ID NO: 264)
```

VH6

```
6-1     CAG GTA CAG CTG CAG CAG TCA GGT CCA GGA CTG GTG AAG CCC TCG CAG ACC CTC TCA
        CTC ACC TGT GCC ATC TCC GGG GAC AGT GTC TCT (SEQ ID NO: 265)
```

VH7

```
7-4.1   CAG GTG CAG CTG GTG CAA TCT GGG TCT GAG TTG AAG AAG CCT GGG GCC TCA GTG AAG
        GTT TCC TGC AAG GCT TCT GGA TAC ACC TTC ACT (SEQ ID NO: 266)
```

TABLE 7

RERS sites in Human HC GLG FR1s where there are at least 20 GLGs cut

```
BsgI  GTGCAG                        71
                                    (cuts 16/14 bases to right)
 1:  4    1: 13    2: 13    3:  4    3: 13    4: 13
 6: 13    7:  4    7: 13    8: 13    9:  4    9: 13
10:  4   10: 13   15:  4   15: 65   16:  4   16: 65
17:  4   17: 65   18:  4   18: 65   19:  4   19: 65
20:  4   20: 65   21:  4   21: 65   22:  4   22: 65
23:  4   23: 65   24:  4   24: 65   25:  4   25: 65
26:  4   26: 65   27:  4   27: 65   28:  4   28: 65
29:  4   30:  4   30: 65   31:  4   31: 65   32:  4
32: 65   33:  4   33: 65   34:  4   34: 65   35:  4
35: 65   36:  4   36: 65   37:  4   38:  4   39:  4
41:  4   42:  4   43:  4   45:  4   46:  4   47:  4
48:  4   48: 13   49:  4   49: 13   51:  4
There are 39 hits at base# 4
There are 21 hits at base# 65
-"-   ctgcac                         9
12: 63   13: 63   14: 63   39: 63   41: 63   42: 63
44: 63   45: 63   46: 63
BbvI  GCAGC                         65
 1:  6    3:  6    6:  6    7:  6    8:  6    9:  6
10:  6   15:  6   15: 67   16:  6   16: 67   17:  6
17: 67   18:  6   18: 67   19:  6   19: 67   20:  6
20: 67   21:  6   21: 67   22:  6   22: 67   23:  6
23: 67   24:  6   24: 67   25:  6   25: 67   26:  6
26: 67   27:  6   27: 67   28:  6   28: 67   29:  6
30:  6   30: 67   31:  6   31: 67   32:  6   32: 67
33:  6   33: 67   34:  6   34: 67   35:  6   35: 67
36:  6   36: 67   37:  6   38:  6   39:  6   40:  6
41:  6   42:  6   43:  6   44:  6   45:  6   46:  6
47:  6   48:  6   49:  6   50: 12   51:  6
There are 43 hits at base# 6
Bolded sites very near sit s
listed below
There are 21 hits at base# 67
```

TABLE 7-continued

RERS sites in Human HC GLG FR1s where there are at least 20 GLGs cut

```
-"- gctgc                       13
 37:  9   38:  9   39:  9   40:  3   40:  9   41:  9
 42:  9   44:  3   44:  9   45:  9   46:  9   47:  9
 50:  9
There are 11 hits at base# 9
BsoFI GCngc                     78
  1:  6    3:  6    6:  6    7:  6    8:  6    9:  6
 10:  6   15:  6   15: 67   16:  6   16: 67   17:  6
 17: 67   18:  6   18: 67   19:  6   19: 67   20:  6
 20: 67   21:  6   21: 67   22:  6   22: 67   23:  6
 23: 67   24:  6   24: 67   25:  6   25: 67   26:  6
 26: 67   27:  6   27: 67   28:  6   28: 67   29:  6
 30:  6   30: 67   31:  6   31: 67   32:  6   32: 67
 33:  6   33: 67   34: 67   34:  6   35:  6   35: 67
 36:  6   36: 67   37:  6   37:  9   38:  6   38:  9
 39:  6   39:  9   40:  3   40:  6   40:  9   41:  6
 41:  9   42:  6   42:  9   43:  6   44:  3   44:  6
 44:  9   45:  6   45:  9   46:  6   46:  9   47:  6
 47:  9   48:  6   49:  6   50:  9   50: 12   51:  6
There are 43 hits at base# 6
These often occur together.
There are 11 hits at base# 9
There are 2 hits at base# 3
There are 21 hits at base# 67
TseI Gcwgc                      78
  1:  6    3:  6    6:  6    7:  6    8:  6    9:  6
 10:  6   15:  6   15: 67   16:  6   16: 67   17:  6
 17: 67   18:  6   18: 67   19:  6   19: 67   20:  6
 20: 67   21:  6   21: 67   22:  6   22: 67   23:  6
 23: 67   24:  6   24: 67   25:  6   25: 67   26:  6
 26: 67   27:  6   27: 67   28:  6   28: 67   29:  6
 30:  6   30: 67   31:  6   31: 67   32:  6   32: 67
 33:  6   33: 67   34:  6   34: 67   35:  6   35: 67
 36:  6   36: 67   37:  6   37:  9   38:  6   38:  9
 39:  6   39:  9   40:  3   40:  6   40:  9   41:  6
 41:  9   42:  6   42:  9   43:  6   44:  3   44:  6
 44:  9   45:  6   45:  9   46:  6   46:  9   47:  6
 47:  9   48:  6   49:  6   50:  9   50: 12   51:  6
There are 43 hits at base# 6 Often together.
There are 11 hits at base# 9
There are 2 hits at base# 3
There are 1 hits at base# 12
There are 21 hits at base# 67
MspA1I CMGckg                   48
  1:  7    3:  7    4:  7    5:  7    6:  7    7:  7
  8:  7    9:  7   10:  7   11:  7   15:  7   16:  7
 17:  7   18:  7   19:  7   20:  7   21:  7   22:  7
 23:  7   24:  7   25:  7   26:  7   27:  7   28:  7
 29:  7   30:  7   31:  7   32:  7   33:  7   34:  7
 35:  7   36:  7   37:  7   38:  7   39:  7   40:  1
 40:  7   41:  7   42:  7   44:  1   44:  7   45:  7
 46:  7   47:  7   48:  7   49:  7   50:  7   51:  7
There are 46 hits at base# 7
PvuII CAGctg                    48
  1:  7    3:  7    4:  7    5:  7    6:  7    7:  7
  8:  7    9:  7   10:  7   11:  7   15:  7   16:  7
 17:  7   18:  7   19:  7   20:  7   21:  7   22:  7
 23:  7   24:  7   25:  7   26:  7   27:  7   28:  7
 29:  7   30:  7   31:  7   32:  7   33:  7   34:  7
 35:  7   36:  7   37:  7   38:  7   39:  7   40:  1
 40:  7   41:  7   42:  7   44:  1   44:  7   45:  7
 46:  7   47:  7   48:  7   49:  7   50:  7   51:  7
There are 46 hits at base# 7
There are 2 hits at base# 1
AluI AGct                       54
  1:  8    2:  8    3:  8    4:  8    4: 24    5:  8
  6:  8    7:  8    8:  8    9:  8   10:  8   11:  8
 15:  8   16:  8   17:  8   18:  8   19:  8   20:  8
 21:  8   22:  8   23:  8   24:  8   25:  8   26:  8
 27:  8   28:  8   29:  8   29: 69   30:  8   31:  8
 32:  8   33:  8   34:  8   35:  8   36:  8   37:  8
 38:  8   39:  8   40:  2   40:  8   41:  8   42:  8
 43:  8   44:  2   44:  8   45:  8   46:  8   47:  8
 48:  8   48: 82   49:  8   49: 82   50:  8   51:  8
```

TABLE 7-continued

RERS sites in Human HC GLG FR1s
where there are at least 20 GLGs cut

There are 48 hits at base# 8
There are 2 hits at base# 2
DdeI Ctnag                          48
  1: 26    1: 48    2: 26    2: 48    3: 26    3: 48
  4: 26    4: 48    5: 26    5: 48    6: 26    6: 48
  7: 26    7: 48    8: 26    8: 48    9: 26   10: 26
 11: 26   12: 85   13: 85   14: 85   15: 52   16: 52
 17: 52   18: 52   19: 52   20: 52   21: 52   22: 52
 23: 52   24: 52   25: 52   26: 52   27: 52   28: 52
 29: 52   30: 52   31: 52   32: 52   33: 52   35: 30
 35: 52   36: 52   40: 24   49: 52   51: 26   51: 48
There are 22 hits at base# 52
52 and 48 never together.
There are 9 hits at base# 48
There are 12 hits at base# 26
26 and 24 never together.
HphI tcacc                          42
  1: 86    3: 86    6: 86    7: 86    8: 80   11: 86
 12:  5   13:  5   14:  5   15: 80   16: 80   17: 80
 18: 80   20: 80   21: 80   22: 80   23: 80   24: 80
 25: 80   26: 80   27: 80   28: 80   29: 80   30: 80
 31: 80   32: 80   33: 80   34: 80   35: 80   36: 80
 37: 59   38: 59   39: 59   40: 59   41: 59   42: 59
 43: 59   44: 59   45: 59   46: 59   47: 59   50: 59
There are 22 hits at base# 80
80 and 86 never together
There are 5 hits at base# 86
There are 12 hits at base# 59
BssKI Nccngg                        50
  1: 39    2: 39    3: 39    4: 39    5: 39    7: 39
  8: 39    9: 39   10: 39   11: 39   15: 39   16: 39
 17: 39   18: 39   19: 39   20: 39   21: 29   21: 39
 22: 39   23: 39   24: 39   25: 39   26: 39   27: 39
 28: 39   29: 39   30: 39   31: 39   32: 39   33: 39
 34: 39   35: 19   35: 39   36: 39   37: 24   38: 24
 39: 24   41: 24   42: 24   44: 24   45: 24   46: 24
 47: 24   <u>48: 39   48: 40</u>   <u>49: 39   49: 40</u>   50: 24
 50: 73   51: 39
There are 35 hits at base# 39
39 and 40 together twice.
There are 2 hits at base# 40
BsaJI Ccnngg                        47
  1: 40    2: 40    3: 40    4: 40    5: 40    7: 40
  8: 40    9: 40    9: 47   10: 40   10: 47   11: 40
 15: 40   18: 40   19: 40   20: 40   21: 40   22: 40
 23: 40   24: 40   25: 40   26: 40   27: 40   28: 40
 29: 40   30: 40   31: 40   32: 40   34: 40   35: 20
 35: 40   36: 40   37: 24   38: 24   39: 24   41: 24
 42: 24   44: 24   45: 24   46: 24   47: 24   <u>48: 40</u>
 <u>48: 41</u>   <u>49: 40   49: 41</u>   50: 74   51: 40
There are 32 hits at base#40
40 and 41 together twice
There are 2 hits at base# 41
There are 9 hits at base# 24
There are 2 hits at base# 47
BstNI CCwgg                         44
PspGI ccwgg
ScrFI($M.HpaII) CCwgg
  1: 40    2: 40    3: 40    4: 40    5: 40    7: 40
  8: 40    9: 40   10: 40   11: 40   15: 40   16: 40
 17: 40   18: 40   19: 40   20: 40   21: 30   21: 40
 22: 40   23: 40   24: 40   25: 40   26: 40   27: 40
 28: 40   29: 40   30: 40   31: 40   32: 40   33: 40
 34: 40   35: 40   36: 40   37: 40   38: 25   39: 25
 41: 25   42: 25   44: 25   45: 25   46: 25   47: 25
 50: 25   51: 40
There are 33 hits at base# 40
ScrFI CCngg                         50
  1: 40    2: 40    3: 40    4: 40    5: 40    7: 40
  8: 40    9: 40   10: 40   11: 40   15: 40   16: 40
 17: 40   18: 40   19: 40   20: 40   21: 30   21: 40
 22: 40   23: 40   24: 40   25: 40   26: 40   27: 40
 28: 40   29: 40   30: 40   31: 40   32: 40   33: 40
 34: 40   35: 20   35: 40   36: 40   37: 25   38: 25
 39: 25   41: 25   42: 25   44: 25   45: 25   46: 25
 47: 25   48: 40   48: 41   49: 40   49: 41   50: 25
 50: 74   51: 40

TABLE 7-continued

RERS sites in Human HC GLG FR1s
where there are at least 20 GLGs cut

```
There are 35 hits at base# 40
There are 2 hits at base# 41
EcoO109I RGgnccy              34
  1: 43    2: 43    3: 43    4: 43    5: 43    6: 43
  7: 43    8: 43    9: 43   10: 43   15: 46   16: 46
 17: 46   18: 46   19: 46   20: 46   21: 46   22: 46
 23: 46   24: 46   25: 46   26: 46   27: 46   28: 46
 30: 46   31: 46   32: 46   33: 46   34: 46   35: 46
 36: 46   37: 46   43: 79   51: 43
There are 22 hits at base# 46
46 and 43 never together
There are 11 hits at base# 43
NlaIV GGNncc                  71
  1: 43    2: 43    3: 43    4: 43    5: 43    6: 43
  7: 43    8: 43    9: 43    9: 79   10: 43   10: 79
 15: 46   15: 47   16: 47   17: 46   17: 47   18: 46
 18: 47   19: 46   19: 47   20: 46   20: 47   21: 46
 21: 47   22: 46   22: 47   23: 47   24: 47   25: 47
 26: 47   27: 46   27: 47   28: 46   28: 47   29: 47
 30: 46   30: 47   31: 46   31: 47   32: 46   32: 47
 33: 46   33: 47   34: 46   34: 47   35: 46   35: 47
 36: 46   36: 47   37: 21   37: 46   37: 47   37: 79
 38: 21   39: 21   39: 79   40: 79   41: 21   41: 79
 42: 21   42: 79   43: 79   44: 21   44: 79   45: 21
 45: 79   46: 21   46: 79   47: 21   51: 43
There are 23 hits at base# 47
46 & 47 often together
There are 17 hits at base# 46
There are 11 hits at base# 43
Sau96I Ggncc                  70
  1: 44    2:  3    2: 44    3: 44    4: 44    5:  3    5: 44    6: 44
  7: 44    8: 22    8: 44    9: 44   10: 44   11:  3   12: 22   13: 22
 14: 22   15: 33   15: 47   16: 47   17: 47   18: 47   19: 47   20: 47
 21: 47   22: 47   23: 33   23: 47   24: 33   24: 47   25: 33   25: 47
 26: 33   26: 47   27: 47   28: 47   29: 47   30: 47   31: 33   31: 47
 32: 33   32: 47   33: 33   33: 47   34: 33   34: 47   35: 47   36: 47
 37: 21   37: 22   37: 47   38: 21   38: 22   39: 21   39: 22   41: 21
 41: 22   42: 21   42: 22   43: 80   44: 21   44: 22   45: 21   45: 22
 46: 21   46: 22   47: 21   47: 22   50: 22   51: 44
There are 23 hits at base# 47 These do not occur together.
There are 11 hits at base# 44
There are 14 hits at base# 22 These do occur together.
There are 9 hits at base# 21
(SEQ ID NO: 13)
BsmAI GTCTCNnnnn              22
  1: 58    3: 58    4: 58    5: 58    8: 58    9: 58
 10: 58   13: 70   36: 18   37: 70   38: 70   39: 70
 40: 70   41: 70   42: 70   44: 70   45: 70   46: 70
 47: 70   48: 48   49: 48   50: 85
There are 11 hits at base# 70
(SEQ ID NO: 14)
-"- Nnnnnngagac               27
 13: 40   15: 48   16: 48   17: 48   18: 48   20: 48
 21: 48   22: 48   23: 48   24: 48   25: 48   26: 48
 27: 48   28: 48   29: 48   30: 10   30: 48   31: 48
 32: 48   33: 48   35: 48   36: 48   43: 40   44: 40
 45: 40   46: 40   47: 40
There are 20 hits at base# 48
AvaII Ggwcc                   44
Sau96I($M.HaeIII) Ggwcc       44
  2:  3    5:  3    6: 44    8: 44    9: 44   10: 44
 11:  3   12: 22   13: 22   14: 22   15: 33   15: 47
 16: 47   17: 47   18: 47   19: 47   20: 47   21: 47
 22: 47   23: 33   23: 47   24: 33   24: 47   25: 33
 25: 47   26: 33   26: 47   27: 47   28: 47   29: 47
 30: 47   31: 33   31: 47   32: 33   32: 47   33: 33
 33: 47   34: 33   34: 47   35: 47   36: 47   37: 47
 43: 80   50: 22
There are 23 hits at base# 47
44 & 47 never together
There are 4 hits at base# 44
PpuMI RGgwccy                 27
  6: 43    8: 43    9: 43   10: 43   15: 46   16: 46
 17: 46   18: 46   19: 46   20: 46   21: 46   22: 46
 23: 46   24: 46   25: 46   26: 46   27: 46   28: 46
 30: 46   31: 46   32: 46   33: 46   34: 46   35: 46
 36: 46   37: 46   43: 79
```

TABLE 7-continued

RERS sites in Human HC GLG FR1s where there are at least 20 GLGs cut

```
There are 22 hits at base# 46
43 and 46 never occur together.
There are 4 hits at base# 43
BsmFI GGGAC                          3
 8:  43   37:  46   50:  77
 -"- gtccc                          33
15:  48   16:  48   17:  48   1:   0   1:   0   20:  48
21:  48   22:  48   23:  48   24:  48   25:  48   26:  48
27:  48   28:  48   29:  48   30:  48   31:  48   32:  48
33:  48   34:  48   35:  48   36:  48   37:  54   38:  54
39:  54   40:  54   41:  54   42:  54   43:  54   44:  54
45:  54   46:  54   47:  54
There are 20 hits at base# 48
There are 11 hits at base# 54
HinfI Gantc                         80
 8:  77   12:  16   13:  16   14:  16   15:  16   15:  56
15:  77   16:  16   16:  56   16:  77   17:  16   17:  56
17:  77   18:  16   18:  56   18:  77   19:  16   19:  56
19:  77   20:  16   20:  56   20:  77   21:  16   21:  56
21:  77   22:  16   22:  56   22:  77   23:  16   23:  56
23:  77   24:  16   24:  56   24:  77   25:  16   25:  56
25:  77   26:  16   26:  56   26:  77   27:  16   27:  26
27:  56   27:  77   28:  16   28:  56   28:  77   29:  16
29:  56   29:  77   30:  56   31:  16   31:  56   31:  77
32:  16   32:  56   32:  77   33:  16   33:  56   33:  77
34:  16   35:  16   35:  56   35:  77   36:  16   36:  26
36:  56   36:  77   37:  16   38:  16   39:  16   40:  16
41:  16   42:  16   44:  16   45:  16   46:  16   47:  16
48:  46   49:  46
There are 34 hits at base# 16
TfiI Gawtc                          21
 8:  77   15:  77   16:  77   17:  77   18:  77   19:  77
20:  77   21:  77   22:  77   23:  77   24:  77   25:  77
26:  77   27:  77   28:  77   29:  77   31:  77   32:  77
33:  77   35:  77   36:  77
There are 21 hits at base# 77
MlyI GAGTC                          38
12:  16   13:  16   14:  16   15:  16   16:  16   17:  16
18:  16   19:  16   20:  16   21:  16   22:  16   23:  16
24:  16   25:  16   26:  16   27:  16   27:  26   28:  16
29:  16   31:  16   32:  16   33:  16   34:  16   35:  16
36:  16   36:  26   37:  16   38:  16   39:  16   40:  16
41:  16   42:  16   44:  16   45:  16   46:  16   47:  16
48:  46   49:  46
There are 34 hits at base# 16
 -"- GACTC                          21
15:  56   16:  56   17:  56   18:  56   19:  56   20:  56
21:  56   22:  56   23:  56   24:  56   25:  56   26:  56
27:  56   28:  56   29:  56   30:  56   31:  56   32:  56
33:  56   35:  56   36:  56
There are 21 hits at base# 56
PleI gagtc                          38
12:  16   13:  16   14:  16   15:  16   16:  16   17:  16
18:  16   19:  16   20:  16   21:  16   22:  16   23:  16
24:  16   25:  16   26:  16   27:  16   27:  26   28:  16
29:  16   31:  16   32:  16   33:  16   34:  16   35:  16
36:  16   36:  26   37:  16   38:  16   39:  16   40:  16
41:  16   42:  16   44:  16   45:  16   46:  16   47:  16
48:  46   49:  46
There are 34 hits at base# 16
 -"- gactc                          21
15:  56   16:  56   17:  56   18:  56   19:  56   20:  56
21:  56   22:  56   23:  56   24:  56   25:  56   26:  56
27:  56   28:  56   29:  56   30:  56   31:  56   32:  56
33:  56   35:  56   36:  56
There are 21 hits at base# 56
AlwNI CAGNNNctg                     26
15:  68   16:  68   17:  68   18:  68   19:  68   20:  68
21:  68   22:  68   23:  68   24:  68   25:  68   26:  68
27:  68   28:  68   29:  68   30:  68   31:  68   32:  68
33:  68   34:  68   35:  68   36:  68   39:  46   40:  46
41:  46   42:  46
There are 22 hits at base# 68
```

TABLE 8

Kappa FR1 GLGs

```
! 1   2   3   4   5   6   7   8   9   10  11  12
  GAC ATC CAG ATG ACC CAG TCT CCA TCC TCC CTG TCT    O12   (SEQ ID NO: 275)
! 13  14  15  16  17  18  19  20  21  22  23
  GCA TCT GTA GGA GAC AGA GTC ACC ATC ACT TGC !

GAC ATC CAG ATG ACC CAG TCT CCA TCC TCC CTG TCT    O2    (SEQ ID NO: 276)
  GCA TCT GTA GGA GAC AGA GTC ACC ATC ACT TGC !

GAC ATC CAG ATG ACC CAG TCT CCA TCC TCC CTG TCT    O18   (SEQ ID NO: 277)
  GCA TCT GTA GGA GAC AGA GTC ACC ATC ACT TGC !

GAC ATC CAG ATG ACC CAG TCT CCA TCC TCC CTG TCT    O8    (SEQ ID NO: 278)
  GCA TCT GTA GGA GAC AGA GTC ACC ATC ACT TGC !

GAC ATC CAG ATG ACC CAG TCT CCA TCC TCC CTG TCT    A20   (SEQ ID NO: 279)
  GCA TCT GTA GGA GAC AGA GTC ACC ATC ACT TGC !

GAC ATC CAG ATG ACC CAG TCT CCA TCC TCC CTG TCT    A30   (SEQ ID NO: 280)
  GCA TCT GTA GGA GAC AGA GTC ACC ATC ACT TGC !

AAC ATC CAG ATG ACC CAG TCT CCA TCT GCC ATG TCT    L14   (SEQ ID NO: 281)
  GCA TCT GTA GGA GAC AGA GTC ACC ATC ACT TGT !

GAC ATC CAG ATG ACC CAG TCT CCA TCC TCA CTG TCT    L1    (SEQ ID NO: 282)
  GCA TCT GTA GGA GAC AGA GTC ACC ATC ACT TGT !

GAC ATC CAG ATG ACC CAG TCT CCA TCC TCA CTG TCT    L15   (SEQ ID NO: 283)
  GCA TCT GTA GGA GAC AGA GTC ACC ATC ACT TGT !

GCC ATC CAG TTG ACC CAG TCT CCA TCC TCC CTG TCT    L4    (SEQ ID NO: 284)
  GCA TCT GTA GGA GAC AGA GTC ACC ATC ACT TGC !

GCC ATC CAG TTG ACC CAG TCT CCA TCC TCC CTG TCT    L18   (SEQ ID NO: 285)
  GCA TCT GTA GGA GAC AGA GTC ACC ATC ACT TGC !

GAC ATC CAG ATG ACC CAG TCT CCA TCT TCC GTG TCT    L5    (SEQ ID NO: 286)
  GCA TCT GTA GGA GAC AGA GTC ACC ATC ACT TGT !

GAC ATC CAG ATG ACC CAG TCT CCA TCT TCT GTG TCT    L19   (SEQ ID NO: 287)
  GCA TCT GTA GGA GAC AGA GTC ACC ATC ACT TGT !

GAC ATC CAG TTG ACC CAG TCT CCA TCC TTC CTG TCT    L8    (SEQ ID NO: 288)
  GCA TCT GTA GGA GAC AGA GTC ACC ATC ACT TGC !

GCC ATC CGG ATG ACC CAG TCT CCA TTC TCC CTG TCT    L23   (SEQ ID NO: 289)
  GCA TCT GTA GGA GAC AGA GTC ACC ATC ACT TGC !

GCC ATC CGG ATG ACC CAG TCT CCA TCC TCA TTC TCT    L9    (SEQ ID NO: 290)
  GCA TCT ACA GGA GAC AGA GTC ACC ATC ACT TGT !

GTC ATC TGG ATG ACC CAG TCT CCA TCC TTA CTC TCT    L24   (SEQ ID NO: 291)
  GCA TCT ACA GGA GAC AGA GTC ACC ATC AGT TGT !

GCC ATC CAG ATG ACC CAG TCT CCA TCC TCC CTG TCT    L11   (SEQ ID NO: 292)
  GCA TCT GTA GGA GAC AGA GTC ACC ATC ACT TGC !

GAC ATC CAG ATG ACC CAG TCT CCT TCC ACC CTG TCT    L12   (SEQ ID NO: 293)
  GCA TCT GTA GGA GAC AGA GTC ACC ATC ACT TGC !
```

TABLE 8-continued

| Kappa FR1 GLGs | | |
|---|---|---|
| GAT ATT GTG ATG ACC CAG ACT CCA CTC TCC CTG CCC GTC ACC CCT GGA GAG CCG GCC TCC ATC TCC TGC ! | O11 | (SEQ ID NO: 294) |
| GAT ATT GTG ATG ACC CAG ACT CCA CTC TCC CTG CCC GTC ACC CCT GGA GAG CCG GCC TCC ATC TCC TGC ! | O1 | (SEQ ID NO: 295) |
| GAT GTT GTG ATG ACT CAG TCT CCA CTC TCC CTG CCC GTC ACC CTT GGA CAG CCG GCC TCC ATC TCC TGC ! | A17 | (SEQ ID NO: 296) |
| GAT GTT GTG ATG ACT CAG TCT CCA CTC TCC CTG CCC GTC ACC CTT GGA CAG CCG GCC TCC ATC TCC TGC ! | A1 | (SEQ ID NO: 297) |
| GAT ATT GTG ATG ACC CAG ACT CCA CTC TCT CTG TCC GTC ACC CCT GGA CAG CCG GCC TCC ATC TCC TGC ! | A18 | (SEQ ID NO: 298) |
| GAT ATT GTG ATG ACC CAG ACT CCA CTC TCT CTG TCC GTC ACC CCT GGA CAG CCG GCC TCC ATC TCC TGC ! | A2 | (SEQ ID NO: 299) |
| GAT ATT GTG ATG ACT CAG TCT CCA CTC TCC CTG CCC GTC ACC CCT GGA GAG CCG GCC TCC ATC TCC TGC ! | A19 | (SEQ ID NO: 300) |
| GAT ATT GTG ATG ACT CAG TCT CCA CTC TCC CTG CCC GTC ACC CCT GGA GAG CCG GCC TCC ATC TCC TGC ! | A3 | (SEQ ID NO: 301) |
| GAT ATT GTG ATG ACC CAG ACT CCA CTC TCC TCA CCT GTC ACC CTT GGA CAG CCG GCC TCC ATC TCC TGC ! | A23 | (SEQ ID NO: 302) |
| GAA ATT GTG TTG ACG CAG TCT CCA GGC ACC CTG TCT TTG TCT CCA GGG GAA AGA GCC ACC CTC TCC TGC ! | A27 | (SEQ ID NO: 303) |
| GAA ATT GTG TTG ACG CAG TCT CCA GCC ACC CTG TCT TTG TCT CCA GGG GAA AGA GCC ACC CTC TCC TGC ! | A11 | (SEQ ID NO: 304) |
| GAA ATA GTG ATG ACG CAG TCT CCA GCC ACC CTG TCT GTG TCT CCA GGG GAA AGA GCC ACC CTC TCC TGC ! | L2 | (SEQ ID NO: 305) |
| GAA ATA GTG ATG ACG CAG TCT CCA GCC ACC CTG TCT GTG TCT CCA GGG GAA AGA GCC ACC CTC TCC TGC ! | L16 | (SEQ ID NO: 306) |
| GAA ATT GTG TTG ACA CAG TCT CCA GCC ACC CTG TCT TTG TCT CCA GGG GAA AGA GCC ACC CTC TCC TGC ! | L6 | (SEQ ID NO: 307) |
| GAA ATT GTG TTG ACA CAG TCT CCA GCC ACC CTG TCT TTG TCT CCA GGG GAA AGA GCC ACC CTC TCC TGC ! | L20 | (SEQ ID NO: 308) |
| GAA ATT GTA ATG ACA CAG TCT CCA GCC ACC CTG TCT TTG TCT CCA GGG GAA AGA GCC ACC CTC TCC TGC ! | L25 | (SEQ ID NO: 309) |
| GAC ATC GTG ATG ACC CAG TCT CCA GAC TCC CTG GCT GTG TCT CTG GGC GAG AGG GCC ACC ATC AAC TGC ! | B3 | (SEQ ID NO: 310) |
| GAA ACG ACA CTC ACG CAG TCT CCA GCA TTC ATG TCA GCG ACT CCA GGA GAC AAA GTC AAC ATC TCC TGC ! | B2 | (SEQ ID NO: 311) |
| GAA ATT GTG CTG ACT CAG TCT CCA GAC TTT CAG TCT GTG ACT CCA AAG GAG AAA GTC ACC ATC ACC TGC ! | A26 | (SEQ ID NO: 312) |
| GAA ATT GTG CTG ACT CAG TCT CCA GAC TTT CAG TCT | A10 | (SEQ ID NO: 313) |

TABLE 8-continued

| Kappa FR1 GLGs |
|---|
| GTG ACT CCA AAG GAG AAA GTC ACC ATC ACC TGC  ! |
| GAT GTT GTG ATG ACA CAG TCT CCA GCT TTC CTC TCT  A14  (SEQ ID NO: 314) |
| GTG ACT CCA GGG GAG AAA GTC ACC ATC ACC TGC  ! |

TABLE 9

RERS sites found in Human Kappa FR1 GLGs

|  |  | MslI | FokI --><-- --> | PflFI | BsrI | BsmAI | MnlI | HpyCH4V |
|---|---|---|---|---|---|---|---|---|
| VKI |  |  |  |  |  |  |  |  |
| O12 | 1-69 | 3 | 3   23 | 12   49 | 15 | 18   47 | 26 | 36 |
| O2 | 101-169 | 103 | 103   123 | 112   149 | 115 | 118   147 | 126 | 136 |
| O18 | 201-269 | 203 | 203   223 | 212   249 | 215 | 218   247 | 226 | 236 |
| O8 | 301-369 | 303 | 303   323 | 312   349 | 315 | 318   347 | 326 | 336 |
| A20 | 401-469 | 403 | 403   423 | 412   449 | 415 | 418   447 | 426 | 436 |
| A30 | 501-569 | 503 | 503   523 | 512   549 | 515 | 518   547 | 526 | 536 |
| L14 | 601-669 | 603 | 603 | 612   649 | 615 | 618   647 | — | 636 |
| L1 | 701-769 | 703 | 703   723 | 712   749 | 715 | 718   747 | 726 | 736 |
| L15 | 801-869 | 803 | 803   823 | 812   849 | 815 | 818   847 | 826 | 836 |
| L4 | 901-969 | — | 903   923 | 912   949 | 906  915 | 918   947 | 926 | 936 |
| L18 | 1001-1069 | — | 1003 | 1012 1049 | 1006 1015 | 1018 1047 | 1026 | 1036 |
| L5 | 1101-1169 | 1103 | — | 1112 1149 | 1115 | 1118 1147 | — | 1136 |
| L19 | 1201-1269 | 1203 | 1203 | 1212 1249 | 1215 | 1218 1247 | — | 1236 |
| L8 | 1301-1369 | — | 1303 1323 | 1312 1349 | 1306 1315 | 1318 1347 | — | 1336 |
| L23 | 1401-1469 | 1403 | 1403 1408 | 1412 1449 | 1415 | 1418 1447 | — | 1436 |
| L9 | 1501-1569 | 1503 | 1503 1508 1523 | 1512 1549 | 1515 | 1518 1547 | 1526 | 1536 |
| L24 | 1601-1669 | 1603 | 1608 1623 | 1612 1649 | 1615 | 1618 1647 | — | 1636 |
| L11 | 1701-1769 | 1703 | 1703 1723 | 1712 1749 | 1715 | 1718 1747 | 1726 | 1736 |
| L12 | 1801-1869 | 1803 | 1803 | 1812 1849 | 1815 | 1818 1847 | — | 1836 |
| VKII |  |  |  |  |  |  |  |  |
| O11 | 1901-1969 | — | — | — | — | — | 1956 | — |
| O1 | 2001-2069 | — | — | — | — | — | 2056 | — |
| A17 | 2101-2169 | — | — | 2112 | — | 2118 | 2156 | — |
| A1 | 2201-2269 | — | — | 2212 | — | 2218 | 2256 | — |
| A18 | 2301-2369 | — | — | — | — | — | 2356 | — |
| A2 | 2401-2469 | — | — | — | — | — | 2456 | — |
| A19 | 2501-2569 | — | — | 2512 | — | 2518 | 2556 | — |
| A3 | 2601-2669 | — | — | 2612 | — | 2618 | 2656 | — |
| A23 | 2701-2769 | — | — | — | — | — | 2729 2756 | — |
| VKIII |  |  |  |  |  |  |  |  |
| A27 | 2801-2869 | — | — | 2812 | — | 2818 2839 | 2860 | — |
| A11 | 2901-2969 | — | — | 2912 | — | 2918 2939 | 2960 | — |
| L2 | 3001-3069 | — | — | 3012 | — | 3018 3039 | 3060 | — |
| L16 | 3101-3169 | — | — | 3112 | — | 3118 3139 | 3160 | — |
| L6 | 3201-3269 | — | — | 3212 | — | 3218 3239 | 3260 | — |
| L20 | 3301-3369 | — | — | 3312 | — | 3318 3339 | 3360 | — |
| L25 | 3401-3469 | — | — | 3412 | — | 3418 3439 | 3460 | — |
| VKIV |  |  |  |  |  |  |  |  |
| B3 | 3501-3569 | 3503 | — | 3512 | 3515 | 3518 3539 | 3551< | — |
| VKV |  |  |  |  |  |  |  |  |
| B2 | 3601-3669 | — | — | 3649 | — | 3618 3647 | — | — |
| VKVI |  |  |  |  |  |  |  |  |
| A26 | 3701-3769 | — | — | 3712 | — | 3718 | — | — |
| A10 | 3801-3869 | — | — | 3812 | — | 3818 | — | — |
| A14 | 3901-3969 | — | — | 3912 | — | 3918 | 3930> | — |

|  |  | SfaNI | SfcI | HinfI | MlyI --> --><-- | MaeIII Tsp45I same sites | HphI xx38 xx56 xx62 | HpaII MspI xx06 xx52 |
|---|---|---|---|---|---|---|---|---|
| VKI |  |  |  |  |  |  |  |  |
| O12 | 1-69 | 37 | 41 | 53 | 53 | 55 | 56 | — |
| O2 | 101-169 | 137 | 141 | 153 | 153 | 155 | 156 | — |
| O18 | 201-269 | 237 | 241 | 253 | 253 | 255 | 256 | — |

TABLE 9-continued

RERS sites found in Human Kappa FR1 GLGs

| | | | | | | | | |
|---|---|---|---|---|---|---|---|---|
| O8 | 301-369 | 337 | 341 | 353 | 353 | 355 | 356 | — |
| A20 | 401-469 | 437 | 441 | 453 | 453 | 455 | 456 | — |
| A30 | 501-569 | 537 | 541 | 553 | 553 | 555 | 556 | — |
| L14 | 601-669 | 637 | 641 | 653 | 653 | 655 | 656 | — |
| L1 | 701-769 | 737 | 741 | 753 | 753 | 755 | 756 | — |
| L15 | 801-869 | 837 | 841 | 853 | 853 | 855 | 856 | — |
| L4 | 901-969 | 937 | 941 | 953 | 953 | 955 | 956 | — |
| L18 | 1001-1069 | 1037 | 1041 | 1053 | 1053 | 1055 | 1056 | — |
| L5 | 1101-1169 | 1137 | 1141 | 1153 | 1153 | 1155 | 1156 | — |
| L19 | 1201-1269 | 1237 | 1241 | 1253 | 1253 | 1255 | 1256 | — |
| L8 | 1301-1369 | 1337 | 1341 | 1353 | 1353 | 1355 | 1356 | — |
| L23 | 1401-1469 | 1437 | 1441 | 1453 | 1453 | 1455 | 1456 | 1406 |
| L9 | 1501-1569 | 1537 | 1541 | 1553 | 1553 | 1555 | 1556 | 1506 |
| L24 | 1601-1669 | 1637 | 1641 | 1653 | 1653 | 1655 | 1656 | |
| L11 | 1701-1769 | 1737 | 1741 | 1753 | 1753 | 1755 | 1756 | |
| L12 | 1801-1869 | 1837 | 1841 | 1853 | 1853 | 1855 | 1856 | |
| VKII | | | | | | | | |
| O11 | 1901-1969 | — | — | 1918 | 1918 | 1937 | 1938 | 1952 |
| O1 | 2001-2069 | — | — | 2018 | 2018 | 2037 | 2038 | 2052 |
| A17 | 2101-2169 | — | — | 2112 | 2112 | 2137 | 2138 | 2152 |
| A1 | 2201-2169 | — | — | 2212 | 2212 | 2237 | 2238 | 2252 |
| A18 | 2301-2369 | — | — | 2318 | 2318 | 2337 | 2338 | 2352 |
| A2 | 2401-2469 | — | — | 2418 | 2418 | 2437 | 2438 | 2452 |
| A19 | 2501-2569 | — | — | 2512 | 2512 | 2537 | 2538 | 2552 |
| A3 | 2601-2669 | — | — | 2612 | 2612 | 2637 | 2638 | 2652 |
| A23 | 2701-2769 | — | — | 2718 | 2718 | 2737 | 2731* 2738* | — |
| VKIII | | | | | | | | |
| A27 | 2801-2869 | — | — | — | — | | | — |
| A11 | 2901-2969 | — | — | — | — | | | — |
| L2 | 3001-3069 | — | — | — | — | | | — |
| L16 | 3101-3169 | — | — | — | — | | | — |
| L6 | 3201-3269 | — | — | — | — | | | — |
| L20 | 3301-3369 | — | — | — | — | | | — |
| L25 | 3401-3469 | — | — | — | — | | | — |
| VKIV | | | | | | | | |
| B3 | 3501-3569 | — | — | 3525 | 3525 | | | |
| VKV | | | | | | | | |
| B2 | 3601-3669 | — | — | 3639 | 3639 | | | |
| VKVI | | | | | | | | |
| A26 | 3701-3769 | — | — | 3712 3739 | 3712 3739 | 3737 3755 | 3756 3762 | — |
| A10 | 3801-3869 | — | — | 3812 3839 | 3812 3839 | 3837 3855 | 3856 3862 | — |
| A14 | 3901-3969 | — | — | 3939 | 3939 | 3937 3955 | 3956 3962 | — |

| | | BsaJI<br>xx29 xx42 xx43 | BssKI (NstNI)<br>xx22 xx30 xx43 | BpmI<br>xx20 xx41 xx44<br>--> --> <-- | BsrFI<br>Cac8I<br>NaeI<br>NgoMIV | HaeIII | Tsp509I |
|---|---|---|---|---|---|---|---|
| VKI | | | | | | | |
| O12 | 1-69 | — | — | — | — | — | — |
| O2 | 101-169 | — | — | — | — | — | — |
| O18 | 201-269 | — | — | — | — | — | — |
| O8 | 301-369 | — | — | — | — | — | — |
| A20 | 401-469 | — | — | — | — | — | — |
| A30 | 501-569 | — | — | — | — | — | — |
| L14 | 601-669 | — | — | — | — | — | — |
| L1 | 701-769 | — | — | — | — | — | — |
| L15 | 801-869 | — | — | — | — | — | — |
| L4 | 901-969 | — | — | — | — | — | — |
| L18 | 1001-1069 | — | — | — | — | — | — |
| L5 | 1101-1169 | — | — | — | — | — | — |
| L19 | 1201-1269 | — | — | — | — | — | — |
| L8 | 1301-1369 | — | — | — | — | — | — |
| L23 | 1401-1469 | — | — | — | — | — | — |
| L9 | 1501-1569 | — | — | — | — | — | — |
| L24 | 1601-1669 | — | — | — | — | — | — |
| L11 | 1701-1769 | — | — | — | — | — | — |
| L12 | 1801-1869 | — | — | — | — | — | — |
| VKII | | | | | | | |
| O11 | 1901-1969 | 1942 | 1943 | 1944 | 1951 | 1954 | — |
| O1 | 2001-2069 | 2042 | 2043 | 2044 | 2051 | 2054 | |

TABLE 9-continued

RERS sites found in Human Kappa FR1 GLGs

| A17 | 2101-2169 | 2142 | — | — | 2151 | 2154 | — |
|---|---|---|---|---|---|---|---|
| A1 | 2201-2269 | 2242 | — | — | 2251 | 2254 | — |
| A18 | 2301-2369 | 2342 | 2343 | — | 2351 | 2354 | — |
| A2 | 2401-2469 | 2442 | 2443 | — | 2451 | 2454 | — |
| A19 | 2501-2569 | 2542 | 2543 | 2544 | 2551 | 2554 | — |
| A3 | 2601-2669 | 2642 | 2643 | 2644 | 2651 | 2654 | — |
| A23 | 2701-2769 | 2742 | — | — | 2751 | 2754 | — |
| VKIII | | | | | | | |
| A27 | 2801-2869 | 2843 | 2822 2843 | 2820 2841 | — | — | 2803 |
| A11 | 2901-2969 | 2943 | 2943 | 2920 2941 | — | — | 2903 |
| L2 | 3001-3069 | 3043 | 3043 | 3041 | — | — | — |
| L16 | 3101-3169 | 3143 | 3143 | 3120 3141 | — | — | — |
| L6 | 3201-3269 | 3243 | 3243 | 3220 3241 | — | — | 3203 |
| L20 | 3301-3369 | 3343 | 3343 | 3320 3341 | — | — | 3303 |
| L25 | 3401-3469 | 3443 | 3443 | 3420 3441 | — | — | 3403 |
| VKIV | | | | | | | |
| B3 | 3501-3569 | 3529 | 3530 | 3520 | — | 3554 | |
| VKV | | | | | | | |
| B2 | 3601-3669 | | 3643 | 3620 3641 | — | — | |
| VKVI | | | | | | | |
| A26 | 3701-3769 | | — | 3720 | — | — | 3703 |
| A10 | 3801-3869 | | — | 3820 | — | — | 3803 |
| A14 | 3901-3969 | 3943 | 3943 | 3920 3941 | — | — | — |

TABLE 10

Lambda FR1 GLG sequences

```
! VL1  CAG TCT GTG CTG ACT CAG CCA CCC TCG GTG TCT GAA   1a    (SEQ ID NO: 315)
       GCC CCC AGG CAG AGG GTC ACC ATC TCC TGT !

cag tct gtg ctg acG cag ccG ccc tcA gtg tct gGG   1e    (SEQ ID NO: 316)
       gcc ccA Ggg cag agg gtc acc atc tcc tgC !

cag tct gtg ctg act cag cca ccc tcA gCg tct gGG   1c    (SEQ ID NO: 317)
       Acc ccc Ggg cag agg gtc acc atc tcT tgt !

cag tct gtg ctg act cag cca ccc tcA gCg tct gGG   1g    (SEQ ID NO: 318)
       Acc ccc Ggg cag agg gtc acc atc tcT tgt !

cag tct gtg Ttg acG cag ccG ccc tcA gtg tct gCG   1b    (SEQ ID NO: 319)
       gcc ccA GgA cag aAg gtc acc atc tcc tgC !

! VL2  CAG TCT GCC CTG ACT CAG CCT CCC TCC GCG TCC GGG   2c    (SEQ ID NO: 320)
       TCT CCT GGA CAG TCA GTC ACC ATC TCC TGC !

cag tct gcc ctg act cag cct cGc tcA gTg tcc ggg   2e    (SEQ ID NO: 321)
       tct cct gga cag tca gtc acc atc tcc tgc !

cag tct gcc ctg act cag cct Gcc tcc gTg tcT ggg   2a2   (SEQ ID NO: 322)
       tct cct gga cag tcG Atc acc atc tcc tgc !

cag tct gcc ctg act cag cct ccc tcc gTg tcc ggg   2d    (SEQ ID NO: 323)
       tct cct gga cag tca gtc acc atc tcc tgc !

cag tct gcc ctg act cag cct Gcc tcc gTg tcT ggg   2b2   (SEQ ID NO: 324)
       tct cct gga cag tcG Atc acc atc tcc tgc !

! VL3  TCC TAT GAG CTG ACT CAG CCA CCC TCA GTG TCC GTG   3r    (SEQ ID NO: 325)
       TCC CCA GGA CAG ACA GCC AGC ATC ACC TGC !

tcc tat gag ctg act cag cca cTc tca gtg tcA gtg   3j    (SEQ ID NO: 326)
       Gcc cTG gga cag acG gcc agG atT acc tgT !

tcc tat gag ctg acA cag cca ccc tcG gtg tcA gtg   3p    (SEQ ID NO: 327)
       tcc cca gga caA acG gcc agG atc acc tgc !

tcc tat gag ctg acA cag cca ccc tcG gtg tcA gtg   3a    (SEQ ID NO: 328)
       tcc cTa gga cag aTG gcc agG atc acc tgc !
```

TABLE 10-continued

Lambda FR1 GLG sequences

```
         tcT tCt gag ctg act cag GAC ccT GcT gtg tcT gtg    3l      (SEQ ID NO: 329)
         Gcc TTG gga cag aca gTc agG atc acA tgc !

tcc tat gTg ctg act cag cca ccc tca gtg tcA gtg    3h      (SEQ ID NO: 330)
         Gcc cca gga Aag acG gcc agG atT acc tgT !

tcc tat gag ctg acA cag cTa ccc tcG gtg tcA gtg    3e      (SEQ ID NO: 331)
         tcc cca gga cag aca gcc agG atc acc tgc !

tcc tat gag ctg aTG cag cca ccc tcG gtg tcA gtg    3m      (SEQ ID NO: 332)
         tcc cca gga cag acG gcc agG atc acc tgc !

tcc tat gag ctg acA cag cca Tcc tca gtg tcA gtg    V2-19   (SEQ ID NO: 333)
         tcT ccG gga cag aca gcc agG atc acc tgc !

! VL4    CTG CCT GTG CTG ACT CAG CCC CCG TCT GCA TCT GCC    4c      (SEQ ID NO: 334)
         TTG CTG GGA GCC TCG ATC AAG CTC ACC TGC !

cAg cct gtg ctg act caA TcA TcC tct gcC tct gcT    4a      (SEQ ID NO: 335)
         tCC ctg gga Tcc tcg Gtc aag ctc acc tgc !

cAg cTt gtg ctg act caA TcG ccC tct gcC tct gcc    4b      (SEQ ID NO: 336)
         tCC ctg gga gcc tcg Gtc aag ctc acc tgc !

! VL5    CAG CCT GTG CTG ACT CAG CCA CCT TCC TCC TCC GCA    5e      (SEQ ID NO: 337)
         TCT CCT GGA GAA TCC GCC AGA CTC ACC TGC !

cag Gct gtg ctg act cag ccG Gct tcc CTc tcT gca    5c      (SEQ ID NO: 338)
         tct cct gga gCa tcA gcc agT ctc acc tgc !

cag cct gtg ctg act cag cca Tct tcc CAT tcT gca    5b      (SEQ ID NO: 339)
         tct Tct gga gCa tcA gtc aga ctc acc tgc !

! VL6    AAT TTT ATG CTG ACT CAG CCC CAC TCT GTG TCG GAG    6a      (SEQ ID NO: 340)
         TCT CCG GGG AAG ACG GTA ACC ATC TCC TGC !

! VL7    CAG ACT GTG GTG ACT CAG GAG CCC TCA CTG ACT GTG    7a      (SEQ ID NO: 341)
         TCC CCA GGA GGG ACA GTC ACT CTC ACC TGT !

cag Gct gtg gtg act cag gag ccc tca ctg act gtg    7b      (SEQ ID NO: 342)
         tcc cca gga ggg aca gtc act ctc acc tgt !

! VL8    CAG ACT GTG GTG ACC CAG GAG CCA TCG TTC TCA GTG    8a      (SEQ ID NO: 343)
         TCC CCT GGA GGG ACA GTC ACA CTC ACT TGT !

! VL9    CAG CCT GTG CTG ACT CAG CCA CCT TCT GCA TCA GCC    9a      (SEQ ID NO: 344)
         TCC CTG GGA GCC TCG GTC ACA CTC ACC TGC !

! VL10   CAG GCA GGG CTG ACT CAG CCA CCC TCG GTG TCC AAG    10a     (SEQ ID NO: 345)
         GGC TTG AGA CAG ACC GCC ACA CTC ACC TGC !
```

TABLE 11

RERSs found in human lambda FR1 GLGs
! There are 31 lambda GLGs

```
MlyI NnnnnnGACTC (SEQ ID NO: 346)                      25
  1: 6    3: 6    4: 6    6: 6    7: 6    8: 6
  9: 6   10: 6   11: 6   12: 6   15: 6   16: 6
 20: 6   21: 6   22: 6   23: 6   23: 50  24: 6
 25: 6   25: 50  26: 6   27: 6   28: 6   30: 6
 31: 6
There are 23 hits at base# 6
-"- GAGTCNNNNNn (SEQ ID NO: 347)                        1
 26: 34
MwoI GCNNNNNnngc (SEQ ID NO: 348)                      20
  1: 9    2: 9    3: 9    4: 9   11: 9   11: 56
 12: 9   13: 9   14: 9   16: 9   17: 9   18: 9
 19: 9   20: 9   23: 9   24: 9   25: 9   26: 9
 30: 9   31: 9
There are 19 hits at base# 9
HinfI Gantc                                            27
  1: 12   3: 12   4: 12   6: 12   7: 12   8: 12
  9: 12  10: 12  11: 12  12: 12  15: 12  16: 12
 20: 12  21: 12  22: 12  23: 12  23: 46  23: 56
 24: 12  25: 12  25: 56  26: 12  26: 34  27: 12
 28: 12  30: 12  31: 12
There are 23 hits at base# 12
PleI gactc                                             25
  1: 12   3: 12   4: 12   6: 12   7: 12   8: 12
  9: 12  10: 12  11: 12  12: 12  15: 12  16: 12
 20: 12  21: 12  22: 12  23: 12  23: 56  24: 12
 25: 12  25: 56  26: 12  27: 12  28: 12  30: 12
 31: 12
There are 23 hits at base# 12
-"- gagtc                                               1
 26: 34
DdeI Ctnag                                             32
  1: 14   2: 24   3: 14   3: 24   4: 14   4: 24
  5: 24   6: 14   7: 14   7: 24   8: 14   9: 14
 10: 14  11: 14  11: 24  12: 14  12: 24  15:  5
 15: 14  16: 14  16: 24  19: 24  20: 14  23: 14
 24: 14  25: 14  26: 14  27: 14  28: 14  29: 30
 30: 14  31: 14
```

TABLE 11 -continued

RERSs found in human lambda FR1 GLGs
! There are 31 lambda GLGs

```
There are 21 hits at base# 14
BsaJI Ccnngg                                     38
 1: 23   1: 40   2: 39   2: 40   3: 39   3: 40
 4: 39   4: 40   5: 39  11: 39  12: 38  12: 39
13: 23  13: 39  14: 23  14: 39  15: 38  16: 39
17: 23  17: 39  18: 23  18: 39  21: 38  21: 39
21: 47  22: 38  22: 39  22: 47  26: 40  27: 39
28: 39  29: 14  29: 39  30: 38  30: 39  30: 47
31: 23  31: 32
There are 17 hits at base# 39
There are 5 hits at base# 38
There are 5 hits at base# 40
Makes cleavage ragged.
MnlI cctc                                        35
 1: 23   2: 23   3: 23   4: 23   5: 23   6: 19
 6: 23   7: 19   8: 23   9: 19   9: 23  10: 23
11: 23  13: 23  14: 23  16: 23  17: 23  18: 23
19: 23  20: 47  21: 23  21: 29  21: 47  22: 23
22: 29  22: 35  22: 47  23: 26  23: 29  24: 27
27: 23  28: 23  30: 35  30: 47  31: 23
There are 21 hits at base# 23
There are 3 hits at base# 19
There are 3 hits at base# 29
There are 1 hits at base# 26
There are 1 hits at base# 27
These could make cleavage ragged.
-"- gagg                                          7
 1: 48   2: 48   3: 48   4: 48  27: 44  28: 44
29: 44
BssKI Nccngg                                     39
 1: 40   2: 39   3: 39   3: 40   4: 39   4: 40
 5: 39   6: 31   6: 39   7: 31   7: 39   8: 39
 9: 31   9: 39  10: 39  11: 39  12: 38  12: 52
13: 39  13: 52  14: 52  16: 39  16: 52  17: 39
17: 52  18: 39  18: 52  19: 39  19: 52  21: 38
22: 38  23: 39  24: 39  26: 39  27: 39  28: 39
29: 14  29: 39  30: 38
There are 21 hits at base# 39
There are 4 hits at base# 38
There are 3 hits at base# 31
There are 3 hits at base# 40 Ragged
BstNI CCwgg                                      30
 1: 41   2: 40   5: 40   6: 40   7: 40   8: 40
 9: 40  10: 40  11: 40  12: 39  12: 53  13: 40
13: 53  14: 53  16: 40  16: 53  17: 40  17: 53
18: 40  18: 53  19: 53  21: 39  22: 39  23: 40
24: 40  27: 40  28: 40  29: 15  29: 40  30: 39
There are 17 hits at base# 40
There are 7 hits at base# 53
There are 4 hits at base# 39
There are 1 hits at base# 41 Ragged
PspGI ccwgg                                      30
 1: 41   2: 40   5: 40   6: 40   7: 40   8: 40
 9: 40  10: 40  11: 40  12: 39  12: 53  13: 40
13: 53  14: 53  16: 40  16: 53  17: 40  17: 53
18: 40  18: 53  19: 53  21: 39  22: 39  23: 40
24: 40  27: 40  28: 40  29: 15  29: 40  30: 39
There are 17 hits at base# 40
There are 7 hits at base# 53
There are 4 hits at base# 39
There are 1 hits at base# 41
ScrFI CCngg                                      39
 1: 41   2: 40   3: 40   3: 41   4: 40   4: 41
 5: 40   6: 32   6: 40   7: 32   7: 40   8: 40
 9: 32   9: 40  10: 40  11: 40  12: 39  12: 53
13: 40  13: 53  14: 53  16: 40  16: 53  17: 40
17: 53  18: 40  18: 53  19: 40  19: 53  21: 39
22: 39  23: 40  24: 40  26: 40  27: 40  28: 40
29: 15  29: 40  30: 39
There are 21 hits at base# 40
There are 4 hits at base# 39
There are 3 hits at base# 41
MaeIII gtnac                                     16
 1: 52   2: 52   3: 52   4: 52   5: 52   6: 52
 7: 52   9: 52  26: 52  27: 10  27: 52  28: 10
28: 52  29: 10  29: 52  30: 52
There are 13 hits at base# 52
Tsp45I gtsac                                     15
 1: 52   2: 52   3: 52   4: 52   5: 52   6: 52
 7: 52   9: 52  27: 10  27: 52  28: 10  28: 52
29: 10  29: 52  30: 52
There are 12 hits at base# 52
HphI tcacc                                       26
 1: 53   2: 53   3: 53   4: 53   5: 53   6: 53
 7: 53   8: 53   9: 53  10: 53  11: 59  13: 59
14: 59  17: 59  18: 59  19: 59  20: 59  21: 59
22: 59  23: 59  24: 59  25: 59  27: 59  28: 59
30: 59  31: 59
There are 16 hits at base# 59
There are 10 hits at base# 53
BspMI ACCTGCNNNNn (SEQ ID NO: 349)                14
11: 61  13: 61  14: 61  17: 61  18: 61  19: 61
20: 61  21: 61  22: 61  23: 61  24: 61  25: 61
30: 61  31: 61
There are 14 hits at base# 61 Goes into CDR1
```

TABLE 12

Matches to URE FR3 adapters in 79 human HC.

A. List of Heavy-chains genes sampled

| | | | | |
|---|---|---|---|---|
| AF008566 | AF103367 | HSA235674 | HSU94417 | S83240 |
| AF035043 | AF103368 | HSA235673 | HSU94418 | SABVH369 |
| AF103026 | AF103369 | HSA240559 | HSU96389 | SADEIGVH |
| af103033 | AF103370 | HSCB201 | HSU96391 | SAH2IGVH |
| AF103061 | af103371 | HSIGGVHC | HSU96392 | SDA3IGVH |
| Af103072 | AF103372 | HSU44791 | HSU96395 | SIGVHTTD |
| af103078 | AF158381 | HSU44793 | HSZ93849 | SUK4IGVH |
| AF103099 | E05213 | HSU82771 | HSZ93850 | |
| AF103102 | E05886 | HSU82949 | HSZ93851 | |
| AF103103 | E05887 | HSU82950 | HSZ93853 | |

TABLE 12-continued

Matches to URE FR3 adapters in 79 human HC.

| | | | |
|---|---|---|---|
| AF103174 | HSA235661 | HSU82952 | HSZ93855 |
| AF103186 | HSA235664 | HSU82961 | HSZ93857 |
| af103187 | HSA235660 | HSU86522 | HSZ93860 |
| AF103195 | HSA235659 | HSU86523 | HSZ93863 |
| af103277 | HSA235678 | HSU92452 | MCOMFRAA |
| af103286 | HSA235677 | HSU94412 | MCOMFRVA |
| AF103309 | HSA235676 | HSU94415 | S82745 |
| af103343 | HSA235675 | HSU94416 | S82764 |

Table 12B. Testing all distinct GLGs from bases 89.1 to 93.2 of the heavy variable domain

| Id | Nb | 0 | 1 | 2 | 3 | 4 | | | SEQ ID NO: |
|---|---|---|---|---|---|---|---|---|---|
| 1 | 38 | 15 | 11 | 10 | 0 | 2 | Seq1 | gtgtattactgtgc | 25 |
| 2 | 19 | 7 | 6 | 4 | 2 | 0 | Seq2 | atAtattactgtgc | 26 |
| 3 | 1 | 0 | 0 | 1 | 0 | 0 | Seq3 | gtgtattactgtAA | 27 |
| 4 | 7 | 1 | 5 | 1 | 0 | 0 | Seq4 | gtgtattactgtAc | 28 |
| 5 | 0 | 0 | 0 | 0 | 0 | 0 | Seq5 | Ttgtattactgtgc | 29 |
| 6 | 0 | 0 | 0 | 0 | 0 | 0 | Seq6 | TtgtatCactgtgc | 30 |
| 7 | 3 | 1 | 0 | 1 | 1 | 0 | Seq7 | ACAtattactgtgc | 31 |
| 8 | 2 | 0 | 2 | 0 | 0 | 0 | Seq8 | ACgtattactgtgc | 32 |
| 9 | 9 | 2 | 2 | 4 | 1 | 0 | Seq9 | ATgtattactgtgc | 33 |
| Group | | 26 | 26 | 21 | 4 | 2 | | | |
| Cumulative | | 26 | 52 | 73 | 77 | 79 | | | |

Table 12C Most important URE recognition seqs in FR3 Heavy

| | | | | |
|---|---|---|---|---|
| 1 | VHSzy1 | GTGtattactgtgc | (ON_SHC103) | (SEQ ID NO: 25) |
| 2 | VHSzy2 | GTAtattactgtgc | (ON_SHC323) | (SEQ ID NO: 26) |
| 3 | VHSzy4 | GTGtattactgtac | (ON_SHC349) | (SEQ ID NO: 28) |
| 4 | VHSzy9 | ATGtattactgtgc | (ON_SHC5a)  | (SEQ ID NO: 33) |

Table 12D, testing 79 human HC V genes with four probes

Number of sequences.......... 79
Number of bases.............. 29143

Number of mismatches

| Id | Best | 0 | 1 | 2 | 3 | 4 | 5 | | |
|---|---|---|---|---|---|---|---|---|---|
| 1 | 39 | 15 | 11 | 10 | 1 | 2 | 0 | Seq1 gtgtattactgtgc (SEQ ID NO: 25) |
| 2 | 22 | 7 | 6 | 5 | 3 | 0 | 1 | Seq2 gtAtattactgtgc (SEQ ID NO: 26) |

TABLE 12-continued

Matches to URE FR3 adapters in 79 human HC.

| | | | | | | | | |
|---|---|---|---|---|---|---|---|---|
| 3 | 7 | 1 | 5 | 1 | 0 | 0 | 0 | Seq4 gtgtattactgtAc (SEQ ID NO: 28) |
| 4 | 11 | 2 | 4 | 4 | 1 | 0 | 0 | Seq9 ATgtattactgtgc (SEQ ID NO: 33) |
| Group | | 25 | 26 | 20 | 5 | 2 | | |
| Cumulative | | 25 | 51 | 71 | 76 | 78 | | |

One sequence has five mismatches with sequences 2, 4, and 9; it is scored as best for 2.
Id is the number of the adapter.
Best is the number of sequence for which the identified adapter was the best available.
The rest of the table shows how well the sequences match the adapters.
For example, there are 10 sequences that match VHSzy1 (ID = 1) with 2 mismatches and are worse for all other adapters. In this sample, 90% come within 2 bases of one of the four adapters.

TABLE 13

The following list of enzymes was taken from http://rebase.neb.com/cgi-bin/asymmlist.
I have removed the enzymes that a) cut within the recognition, b) cut on both sides of the recognition, or c) have fewer than 2 bases between recognition and closest cut site.
REBASE Enzymes
04/13/2001
Type II restriction enzymes with asymmetric recognition sequences:

| Enzymes | Recognition Sequence | Isoschizomers | Suppliers |
|---|---|---|---|
| AarI | CACCTGCNNNN^NNNN_ | – | y |
| AceIII | CAGCTCNNNNNNN^NNNN_ | – | – |
| Bbr7I | GAAGACNNNNNNN^NNNN_ | – | – |
| BbvI | GCAGCNNNNNNNN^NNNN_ | | y |
| BbvII | GAAGACNN^NNNN_ | | |
| Bce83I | CTTGAGNNNNNNNNNNNNNNNN_NN^ | – | – |
| BceAI | ACGGCNNNNNNNNNNNN^NN_ | – | y |
| BcefI | ACGGCNNNNNNNNNNNN^N_ | – | – |
| BciVI | GTATCCNNNNN_N^ | BfuI | y |
| BfiI | ACTGGGNNNN_N^ | BmrI | y |
| BinI | GGATCNNNN^N_ | | |
| BscAI | GCATCNNNN^NN_ | – | – |
| BseRI | GAGGAGNNNNNNNN_NN^ | – | y |
| BsmFI | GGGACNNNNNNNNNN^NNNN_ | BspLU11III | y |
| BspMI | ACCTGCNNNN^NNNN_ | Acc36I | y |
| EciI | GGCGGANNNNNNNNN_NN^ | – | y |
| Eco57I | CTGAAGNNNNNNNNNNNNNN_NN^ | BspKT5I | y |
| FauI | CCCGCNNNN^NN_ | BstFZ438I | y |
| FokI | GGATGNNNNNNNNN^NNNN_ | BstPZ418I | y |
| GsuI | CTGGAGNNNNNNNNNNNNNN_NN^ | – | y |
| HgaI | GACGCNNNNN^NNNNN_ | – | y |
| HphI | GGTGANNNNNNN_N^ | AsuHPI | y |
| MboII | GAAGANNNNNNN_N^ | – | y |
| MlyI | GAGTCNNNNN^ | SchI | y |
| MmeI | TCCRACNNNNNNNNNNNNNNNNNNNN_NN^ | – | – |

TABLE 13-continued

The following list of enzymes was taken from
http://rebase.neb.com/cgi-bin/asymmlist.
I have removed the enzymes that a) cut within the recognition, b)
cut on both sides of the recognition, or c) have fewer than 2
bases between recognition and closest cut site.
REBASE Enzymes
04/13/2001
Type II restriction enzymes with asymmetric recognition sequences:

| Enzymes | Recognition Sequence | Isoschizomers | Suppliers |
| --- | --- | --- | --- |
| MnlI | CCTCNNNNNN_N^ | — | y |
| PleI | GAGTCNNNN^N_ | PpsI | y |
| RleAI | CCCACANNNNNNNNN_NNN^ | — | — |
| SfaNI | GCATCNNNNN^NNNN_ | BspST5I | y |
| SspD5I | GGTGANNNNNNNN^ | — | — |
| Sth132I | CCCGNNNN^NNNN_ | — | — |
| StsI | GGATGNNNNNNNNNNNN^NNNN_ | — | — |
| TaqII | GACCGANNNNNNNNN_NN^, | — | — |
|  | CACCCANNNNNNNNN_NN^ |  |  |
| Tth111II | CAARCANNNNNNNNN_NN^ | — | — |
| UbaPI | CGAACG | — | — |

(SEQ ID NOS 356-390, respectively in order of appearance)

The notation is ^ means cut the upper strand and _ means cut the lower strand. If
the upper and lower strand are cut at the same place, then only ^ appears.

TABLE 14

```
(FOKIact)     5'-cAcATccgTg TTgTT cAcggATgTg-3' (SEQ ID NO: 350)
(VHEx881) 5'-AATAgTAgAc TgcAgTgTcc TcAgcccTTA AgcTgTTcAT cTgcAAgTAg-
              AgAgTATTcT TAgAgTTgTc TcTAgAcTTA gTgAAgcg-3' (SEQ ID NO: 351)
! note that VHEx881 is the reverse complement of the ON below
! note that VHEx881 is the reverse complement of the ON below
!         [RC} 5'-cgCttcacTaag-
!         Scab........
!         Synthetic 3-23 as in Table 206
!         |TCT|AGA|gac|aac|tct|aag|aat|act|ctc|tac|ttg|cag|atg|-
!         XbaI...
!         |aac|agC|TTA|AGg|gct|gag}gac}aCT|GCA|Gtc|tac|tat}t-3' (SEQ ID NO: 352)
!            AflII...

(VHBA881)
              5'-cgCttcacTaag-
                 |TCT|AGA|gac|aac|tct|aag|aat|act|ctc|tac|ttg|cag|atg|-
                 |aac|agC|TTA|AGg|gct|gag|gac|aCT|GCA|Gtc|tac|tat|tgt gcg ag-3' (SEQ ID NO: 353)

(VHBB881)
              5'-cgCttcacTaag-
                 |TCT|AGA|gac|aac|tct|aag|aat|act|ctc|tac|ttg|cag|atg|-
                 |aac|agC|TTA|AGg|gct|gag|gac|aCT|GCA|Gtc|tac|tat|tgt Acg ag-3' (SEQ ID NO: 354)

(VH881PCR)    5'-cgCttcacTaag-|TCT|AGA|gac|aac-3' (SEQ ID NO: 353)
```

TABLE 15

Use of FokI as "Universal Restriction Enzyme"

FokI - for dsDNA, ‖ represents sites of cleavage

```
                                   sites of cleavage
           5'-cacGGATGtg--nnnnnnn|nnnnnnnn-3' (SEQ ID NO:15)
           3'-gtgCCTACac--nnnnnnnnnnnn|nnn-5' (SEQ ID NO:16)
              RECOG
              NITion of FokI
```

Case I

```
5'-...gtg|tatt-actgtgc..Substrate....-3' (SEQ ID NO:17)
   3'-cad-ataa|tgacacg┐
                       gtGTAGGcac\
               5'-caCATCCgtg/(SEQ ID NO:18)
```

Case II

```
            5'-...gtgtatt|agac-tgc..Substrate....-3'  (SEQ ID NO:19)
                ┌cacataa-tctg|acg-5'
      /gtCCTACac
      \cacGGATGtg-3'(SEQ ID NO:20)
```

Case III (Case I rotated 180 degrees)

```
       /gtgCCTACac-5'
       \cacGGATGtg┐
                   gtgtctt|acag-tcc-3' Adapter (SEQ ID NO:21)
            3'-...cacagaa-tgtc|agg..substrate....-5' (SEQ ID NO:22)
```

Case IV (Case II rotated 180 degrees)

```
                          3'- gtGTAGGcac\ (SEQ ID NO:23)
                              ┌caCATCCgtg/
              5'-gag|tctc-actgagc
 Substrate 3'-...ctc-agag|tgactcg...-5' (SEQ ID NO:24)
```

Improved FokI adapters
FokI - for dsDNA, ‖ represents sites of cleavage
Case I
Stem 11, loop 5, stem 11, recognition 17

```
         5'-...catgtg|tatt-actgtgc..Substrate.....-3'  (SEQ ID NO: 1)
         3'-gtacac-ataa|tgacacg┐          ┌T┐
                                gtGTAGGcacG  T
                           5'- caCATCCgtgc  C   (SEQ ID NO: 2)
                                          └TT┘
```

Case II
Stem 10, loop 5, stem 10, recognition 18

```
                                                 (SEQ ID NO: 3)
              5'-...gtgtatt|agac-tgctgcc..Substrate....-3'
    ┌T┐          ┌cacataa-tctg|acgacgg-5'
    T  gtgCCTACac
    C  cacGGATGtg-3'                             (SEQ ID NO: 4)
    └TT┘
```

Case III (Case I rotated 180 degrees)
Stem 11, loop 5, stem 11, recognition 20

```
         ┌T┐
         T  TgtgCCTACac-5'                       (SEQ ID NO: 5)
         G  AcacGGATGtg┐
         └TT┘           gtgtctt|acag-tccattctg-3' Adapter
                  3'-...cacagaa-tgtc|aggtaagac..substrate....-5'
                                                 (SEQ ID NO: 6)
```

US 8,288,322 B2

TABLE 15-continued

Use of FokI as "Universal Restriction Enzyme"

Case IV (Case II rotated 180 degrees)
Stem 11, loop 4, stem 11, recognition 17

```
                                          ┌T┐
                          3'- gtGTAGGcacc  T
  (SEQ ID NO: 7)                ┌caCATCCgtgg T
            5'-atcgag|tctc-actgagc        └T┘
 Substrate 3'-...tagctc-agag|tgactcg...-5'  (SEQ ID NO: 8)
```

BseRI

```
              (SEQ ID NO: 9)        | sites of cleavage
          5'-cacGAGGAGnnnnnnnnnn|nnnnn-3'
          3'-gtgctcctcnnnnnnnn|nnnnnnn-5'
              RECOG
              NITion of BseRI
```

Stem 11, loop 5, stem 11, recognition 19

```
           3'-.......gaacat|cg-ttaagccagta.....5'  (SEQ ID NO: 10)
    ┌T-T┐           cttgta-gc|aattcggtcat-3'
    C   GCTGAGGAGTC-┘
    T   cgactcctcag-5'  An adapter for BseRI to claim the substrate
above.
    └T─┘        (SEQ ID NO: 11)
```

TABLE 16

Human heavy chains bases 88.1 to 94.2

Number of sequences . . . . . . . . . . . 840
            Number of Mismatchers . . . . . . . . . .

| Id | Ntot | 0 | 1 | 2 | 3 | 4 | 5 | 6 | 7 | Name | Probe Sequence............ | Dot form............ |
|---|---|---|---|---|---|---|---|---|---|---|---|---|
| 1 | 364 | 152 | 97 | 76 | 26 | 7 | 4 | 2 | 0 | VHS881-1.1 | gctgtgtattactgtgcgag | gctgtgtattactgtgcgag |
| 2 | 265 | 150 | 60 | 33 | 13 | 5 | 4 | 0 | 0 | VHS881-1.2 | gccgtgtattactgtgcgag | ...c................ |
| 3 | 96 | 14 | 34 | 16 | 10 | 5 | 7 | 9 | 1 | VHS881-2.1 | gccgtatattactgtgcgag | ...c...a............ |
| 4 | 20 | 0 | 3 | 4 | 9 | 2 | 2 | 0 | 0 | VHS881-4.1 | gccgtgtattactgtacgag | ...c............a... |
| 5 | 95 | 25 | 36 | 18 | 11 | 2 | 2 | 0 | 1 | VHS881-9.1 | gccatgtattactgtgcgag | ...ca............... |
|  | 840 | 341 | 230 | 147 | 69 | 21 | 19 | 11 | 2 | (SEQ ID NOS 391-395, respectively in order of |  |  |
|  |  | 341 | 571 | 718 | 787 | 808 | 827 | 838 | 840 | appearance) |  |  |

```
                88 89 90 91 92 93 94 95 Codon number as in Table 195
             Recognition........... Stem...... Loop. Stem......
(VHS881-1.1) 5'-gctgtgtat|tact-gtgcgag cAcATccgTg TTgTT cAcggATgTg-3'
(VHS881-1.2) 5'-gccgtgtat|tact-gtgcgag cAcATccgTg TTgTT cAcggATgTg-3'
(VHS881-2.1) 5'-gccgtatat|tact-gtgcgag cAcATccgTg TTgTT cAcggATgTg-3'
(VHS881-4.1) 5'-gccgtgtat|tact-gtacgag cAcATccgTg TTgTT cAcggATgTg-3'
(VHS881-9.1) 5'-gccatgtat|tact-gtgcgag cAcATccgTg TTgTT cAcggATgTg-3'
                          | site of substrate cleavage
```

(Sequences in the left column above are SEQ ID NOS 391-395, respectively in order of
appearance; sequences in the right column are all SEQ ID NO: 396)
(FOKIact) 5'-cAcATccgTg TTgTT cAcggagTg-3' (SEQ ID NO: 396)
(VHEx881) 5'-AATAgTAgAc TgcAgTgTcc TcAgcccTTA AgcTgTTcAT cTgcAAgTAg-
    AgAgTATTcT TAgAgTTgTc TcTAgAcTTA gTgAAgcg-3' (SEQ ID NO: 397)
! note that VHEx881 is the reverse complement of the ON below ! note that VHEx881 is the reverse complement of the ON below
!     [RC]5'-cgCttcacTaag-
!     Scab......
!     Synthetic 3-23 as in Table 206
!     |TCT|AGA|gac|aac|tct|aag|aat|act|ctc|tac|ttg|cag|atg|-

TABLE 16-continued

Human heavy chains bases 88.1 to 94.2

```
!       XbaI....
!       |aac|agC|TTA|AGg|gct|gag|gac|aCT|GCA|Gtc|tac|tat|t-3'
!       AflII...
(VHBA881)      5'-cgCttcacTaag-
               |TCT|AGA|gac|aac|tct|aag|aat|act|ctc|tac|ttg|cag|atg|-
               |aac|agC|TTA|AGg|gct|gag|gac|aCT|GCA|Gtc|tac|tat|tgt gcg ag-3' (SEQ ID NO: 398)

(VHBB881)      5'-cgCttcacTaag-
               |TCT|AGA|gac|aac|tct|aag|aat|act|ctc|tac|ttg|cag|atg|-
               |aac|agC|TTA|AGg|gct|gag|gac|aCT|GCA|Gtc|tac|tat|tgt Acg ag-3' (SEQ ID NO: 618)

(VH881PCR)     5'-cgCttcacTaag|TCT|AGA|gac|aac-3'  (SEQ ID NO: 399)
```

TABLE 17

Kappa, bases 12-30

| ID | Ntot | 0 | 1 | 2 | 3 | 4 | 5 | 6 | Name | Sequence | Dot Form | |
|---|---|---|---|---|---|---|---|---|---|---|---|---|
| 1 | 84 | 40 | 21 | 20 | 1 | 2 | 0 | 0 | SK12O12 | gacccagtctccatcctcc | gacccagtctccatcctcc | (residues 26-44 of SEQ ID NO: 400) |
| 2 | 32 | 19 | 3 | 6 | 2 | 1 | 0 | 1 | SK12A17 | gactcagtctccactctcc | ...t.........ct.... | (residues 26-44 of SEQ ID NO: 401) |
| 3 | 26 | 17 | 8 | 1 | 0 | 0 | 0 | 0 | SK12A27 | gacgcagtctccaggcacc | ...g.........gg.a.. | (residues 26-44 of SEQ ID NO: 402) |
| 4 | 40 | 21 | 18 | 1 | 0 | 0 | 0 | 0 | SK12A11 | gacgcagtctccagccacc | ...g.........g..a.. | (residues 26-44 of SEQ ID NO: 403) |
|  | 182 | 97 | 50 | 28 | 3 | 3 | 0 | 1 | | | | |
|  |  | 97 | 147 | 175 | 178 | 181 | 181 | 182 | | | | |

```
URE adapters:
!                 Stem...... Loop. Stem...... Recognition.......
(SzKB1230-O12)               5'-cAcATccgTg TTgTT cAcggATgTg ggAggATggAgAcTgggTc-3' (SEQ ID NO: 400)
!       [RC] 5'-gacccagtctccatcctcc cAcATccgTg AAcAA cAcggATgTg-3'
!                Recognition........ Stem...... loop. Stem......
!                                  FokI.            FokI.
!
!                 Stem...... Loop. Stem...... Recognition.......
(SzKB1230-A17)               5'-cAcATccgTg TTgTT cAcggATgTg ggAgAgTggAgAcTgAgTc-3' (SEQ ID NO: 401)
!       [RC] 5'-gactcagtctccactctcc cAcATccgTg AAcAA cAcggATgTg-3'
!                Recognition........ Stem...... loop. Stem......
!                                  FokI.            FokI.
!
!                 Stem...... Loop. Stem...... Recognition.......
(SzKB1230-A27)               5'-cAcATccgTg TTgTT cAcggATgTg ggTgccTggAgAcTgcgTc-3' (SEQ ID NO: 402)
!       [RC] 5'-gacgcagtctccaggcacc cAcATccgTg AAcAA cAcggATgTg-3'
!                Recognition........ Stem...... loop. Stem......
!                                  FokI.            FokI.
!
!                 Stem...... Loop. Stem....... Recognition.......
(SzKB1230-A11)               5'-cAcATccgTg TTgTT cAcggATgTg ggTggcTggAgAcTgcgTc-3' (SEQ ID NO: 403)
!       [RC] 5'-gacgcagtctccagccacc cAcATccgTg AAcAA cAcggATgTg-3'
!                Recognition........ Stem...... loop. Stem......
!                                  FokI.            FokI.

What happens in the upper strand:

(SzKB1230-O12*)   5'-gac cca gtc | tcc a-tc ctc c-3'   (residues 26-44 of SEQ ID NO: 400)
!                              | Site of cleavage in substrate
!
(SzKB1230-A17*)   5'-gac tca gtc | tcc a-ct ctc c-3'   (residues 26-44 of SEQ ID NO: 401)
!
(SzKB1230-A27*)   5'-gac gca gtc | tcc a-gg cac c-3'   (residues 26-44 of SEQ ID NO: 402)
!
```

TABLE 17-continued

Kappa, bases 12-30

```
(SzKB1230-A11*)    5'-gac gca gtc | tcc a-gc cac c-3'  (residues 26-44 of SEQ ID NO: 403)

(kapextURE)       5'-ccTctactctTgTcAcAgTgcAcAA gAc ATc cAg-3' !sense strand (SEQ ID NO: 404)
                     Scab............ApaLI.

(kapextUREPCR)    5'-ccTctactctTgTcAcAgTg-3' (SEQ ID NO: 405)
                     Scab.............

(kaBR01UR)    5'-ggAggATggA cTggATgTcT TgTgcAcTgT gAcAAgAgTA gAgg-3'    (SEQ ID NO: 406)
!      [RC] 5'-ccTctactctTgTcAcAgTgcAcAA gAc ATc cAg tcc a-tc ctc c-3'  ON above is R.C. of this one (kaBR02UR)    5'-ggAgAgTggA cTggATgTcT TgTgcAcTgT gAcAAgAgTA gAgg-3'    (SEQ ID NO: 407)
!      [RC] 5'-ccTctactctTgTcAcAgTgcAcAA gAc ATc cAg tcc a-ct ctc c-3'  ON above is R.C. of this one (kaBR03UR)    5'-ggTgccTggA cTggATgTcT TgTgcAcTgT gAcAAgAgTA gAgg-3'    (SEQ ID NO: 408)
!      [RC] 5'-ccTctactctTgTcAcAgTgcAcAA gAc ATc cAg tcc a-gg cac c-3'  ON above is R.C. of this one (kaBR04UR)    5'-ggTggcTggA cTggATgTcT TgTgcAcTgT gAcAAgAgTA gAgg-3'    (SEQ ID NO: 409)
!      [RC] 5'-ccTctactctTgTcAcAgTgcAcAA gAc ATc cAg tcc a-gc cac c-3'  ON above is R.C. of this one
             Scab............ApaLI.
```

TABLE 18

Lambda URE adapters bases 13.3 to 19.3

! Number of sequences.......... 128
!
!                    Number of mismatches..............

| ! Id | Ntot | 0 | 1 | 2 | 3 | 4 | 5 | 6 | 7 | 8 | Name | Sequence........... | Dot form........... |
|---|---|---|---|---|---|---|---|---|---|---|---|---|---|
| ! 1 | 58 | 45 | 7 | 1 | 0 | 0 | 0 | 2 | 2 | 1 | VL133-2a2 | gtctcctggacagtcgatc | gtctcctggacagtcgatc (residues 632-635 of SEQ ID NO: 410) |
| ! 2 | 16 | 10 | 1 | 0 | 1 | 0 | 1 | 1 | 0 | 2 | VL133-31 | ggccttgggacagacagtc | .g.cttg......a.ag.. (residues 632-635 of SEQ ID NO: 411) |
| ! 3 | 17 | 6 | 0 | 0 | 0 | 4 | 1 | 1 | 5 | 0 | VL133-2c | gtctcctggacagtcagtc | ..............ag.. (residues 632-635 of SEQ ID NO: 412) |
| ! 4 | 37 | 3 | 0 | 10 | 4 | 4 | 3 | 7 | 4 | 2 | VL133-1c | ggcccagggcagagggtc | .g.c..a..g...ag.g.. (residues 632-635 of SEQ ID NO: 413) |
| ! | 128 | 64 | 8 | 11 | 5 | 8 | 5 | 11 | 11 | 5 | | | |
| ! | | 64 | 72 | 83 | 88 | 96 | 101 | 112 | 123 | 128 | | | |

```
!             Stem...... loop. Stem...... Recognition........
(VL133-2a2)    5'-cAcATccgTg TTgTT cAcggATgTg gATcgAcTgTccAggAgAc-3' (SEQ ID NO: 410)
!      [RC] 5'-gtctcctggacagtcgatc cAcATccgTg AAcAA cAcggATgTg-3'
!             Recognition........ Stem...... Loop. Stem......
!             Stem...... loop. Stem...... Recognition........
(VL133-31)     5'-cAcATccgTg TTgTT cAcggATgTg gAcTgTcTgTcccAAggcc-3' (SEQ ID NO: 411)
!      [RC] 5'-ggccttgggacagacagtc cAcATccgTg AAcAA cAcggATgTg-3'
!             Recognition........ Stem...... Loop. Stem......
!
!             Stem...... loop. Stem...... Recognition........
(VL133-2c)     5'-cAcATccgTg TTgTT cAcggATgTg gAcTgAcTgTccAggAgAc-3' (SEQ ID NO: 412)
!      [RC] 5'-gtctcctggacagtcagtc cAcATccgTg AAcAA cAcggATgTg-3'
!             Recognition........ Stem...... Loop. Stem......
!
!             Stem...... loop. Stem...... Recognition........
(VL133-1c)     5'-cAcATccgTg TTgTT cAcggATgTg gAcccTcTgcccTggggcc-3' (SEQ ID NO: 413)
!      [RC] 5'-ggcccagggcagagggtc cAcATccgTg AAcAA cAcggATgTg-3'
What happens in the top strand:

!                   | site of cleavage in the upper strand
(VL133-2a2*)    5'-g tct cct g|ga cag tcg atc (residues 632-635 of SEQ ID NO: 410)
```

TABLE 18 -continued

Lambda URE adapters bases 13.3 to 19.3

```
!   (VL133-31*)     5'-g gcc ttg g|ga cag aca gtc (residues 632-635 of SEQ ID NO: 411)

!   (VL133-2c*)     5'-g tct cct g|ga cag tca gtc (residues 632-635 of SEQ ID NO: 412)

!   (VL133-1c*)     5'-g gcc cca g|gg cag agg gtc (residues 632-635 of SEQ ID NO: 413)

!
! The following Extenders and Bridges all encode the AA sequence of 2a2 for codons 1-15
!                1
(ON_LamEx133) 5'-ccTcTgAcTgAgT gcA cAg -
!
!     2 3   4 5   6 7   8 9  10 11 12
      AGt gcT TtA acC caA ccG gcT AGT gtT AGC ggT-
!
!    13 14 15
     tcC ccG g ! 2a2 (SEQ ID NO: 414)
!                1
(ON_LamB1-133) [RC] 5'-ccTcTgAcTgAgT gcA cAg -
!
!     2 3   4 5   6 7   8 9  10 11 12
      AGt gcT TtA acC caA ccG gcT AGT gtT AGC ggT-
!
!    13 14 15
     tcC ccG g ga cag tcg at-3' !(SEQ ID NO: 415) 2a2 N.B. the actual seq is the
!                                   reverse complement of the
!                                   one shown.
!
(ON_LamB2-133) [RC] 5'-ccTcTgAcTgAgT gcA cAg -
!
!     2 3   4 5   6 7   8 9  10 11 12
      AGt gcT TtA acC caA ccG gcT AGT gtT AGC ggT-
!
!    13 14 15
     tcC ccG g ga cag aca gt-3' ! 31 (SEQ ID NO: 416) N.B. the actual seq is the
!                                   reverse complement of the
!                                   one shown.
!
!
(ON_LamB3-133) [RC] 5'-ccTcTgAcTgAgT gcA cAg -
!
!     2 3   4 5   6 7    8 9  10 11 12
      AGt gcT TtA acC caA ccG gcT AGT gtT AGC ggT-
!
!    13 14 15
     tcC ccG g ga cag tca gt -3'! 2c (SEQ ID NO: 417) N.B. the actual seq is the
!                                   reverse complement of the
!                                   one shown.
!(ON_LamB4-133) [RC] 5'-ccTcTgAcTgAgT gcA cAg -
!
!   2  3   4  5   6  7   8  9  10 11 12
    AGt gcT TtA acC caA ccG gcT AGT gtT AGC ggT-s
!
!    13 14 15
     tcC ccG g gg cag agg gt-3' ! 1c (SEQ ID NO: 418) N.B. the actual seq is the
!                                   reverse complement of the
!                                   one shown.
!
(ON_Lam133PCR) 5'-ccTcTgAcTgAgT gcA cAg AGt gc-3' (SEQ ID NO: 419)
```

TABLE 19

Cleavage of 75 human light chains.

| Enzyme | Recognition* | Nch | Ns | Planned location of site | Enzyme | Recognition* | Nch | Ns | Planned location of site |
|---|---|---|---|---|---|---|---|---|---|
| AfeI | AGCgct | 0 | 0 | | BssHII | Gcgcgc | 0 | 0 | |
| AflII | Cttaag | 0 | 0 | HC FR3 | BstBI | TTcgaa | 0 | 0 | |
| AgeI | Accggt | 0 | 0 | | DraIII | CACNNNgtg | 0 | 0 | |
| AscI | GGcgcgcc | 0 | 0 | After LC | EagI | Cggccg | 0 | 0 | |
| BglII | Agatct | 0 | 0 | | FseI | GGCCGGcc | 0 | 0 | |
| BsiWI | Cgtacg | 0 | 0 | | FspI | TGCgca | 0 | 0 | |
| BspDI | ATcgat | 0 | 0 | | HpaI | GTTaac | 0 | 0 | |

TABLE 19-continued

Cleavage of 75 human light chains.

| Enzyme | Recognition* | Nch | Ns | Planned location of site |
|---|---|---|---|---|
| MfeI | Caattg | 0 | 0 | HC FR1 |
| MluI | Acgcgt | 0 | 0 | |
| NcoI | Ccatgg | 0 | 0 | Heavy chain signal |
| NheI | Gctagc | 0 | 0 | HC/anchor linker |
| NotI | GCggccgc | 0 | 0 | In linker after HC |
| NruI | TCGcga | 0 | 0 | |
| PacI | TTAATtaa | 0 | 0 | |
| PmeI | GTTTaaac | 0 | 0 | |
| PmlI | CACgtg | 0 | 0 | |
| PvuI | CGATcg | 0 | 0 | |
| SacII | CCGCgg | 0 | 0 | |
| SalI | Gtcgac | 0 | 0 | |
| SfiI | GGCCNNNNnggcc | 0 | 0 | Heavy Chain signal (SEQ ID NO: 436) |
| SgfI | GCGATcgc | 0 | 0 | |
| SnaBI | TACgta | 0 | 0 | |
| StuI | AGGcct | 0 | 0 | |
| XbaI | Tctaga | 0 | 0 | HC FR3 |
| AatII | GACGTc | 1 | 1 | |
| AclI | AAcgtt | 1 | 1 | |
| AseI | ATtaat | 1 | 1 | |
| BsmI | GAATGCN | 1 | 1 | |
| BspEI | Tccgga | 1 | 1 | HC FR1 (SEQ ID NO: 437) |
| BstXI | CCANNNNNNntgg | 1 | 1 | HC FR2 (SEQ ID NO: 438) |
| DrdI | GACNNNNnngtc | 1 | 1 | |
| HindIII | Aagctt | 1 | 1 | |
| PciI | Acatgt | 1 | 1 | |
| SapI | gaagagc | 1 | 1 | |
| ScaI | AGTact | 1 | 1 | |
| SexAI | Accwggt | 1 | 1 | |
| SpeI | Actagt | 1 | 1 | |
| TliI | Ctcgag | 1 | 1 | |
| XhoI | Ctcgag | 1 | 1 | |
| BcgI | cgannnnnntgc | 2 | 2 | (SEQ ID NO: 439) |
| BlpI | GCtnagc | 2 | 2 | |
| BssSI | Ctcgtg | 2 | 2 | |
| BstAPI | GCANNNNntgc | 2 | 2 | (SEQ ID NO: 440) |
| EspI | GCtnagc | 2 | 2 | |
| KasI | Ggcgcc | 2 | 2 | |
| PflMI | CCANNNNntgg | 2 | 2 | (SEQ ID NO: 441) |
| XmnI | GAANNnnttc | 2 | 2 | (SEQ ID NO: 442) |
| ApaLI | Gtgcac | 3 | 3 | LC signal seq |
| NaeI | GCCggc | 3 | 3 | |
| NgoMI | Gccggc | 3 | 3 | |
| PvuII | CAGctg | 3 | 3 | |
| RsrII | CGgwccg | 3 | 3 | |
| BsrBI | GAGcgg | 4 | 4 | |
| BsrDI | GCAATGNNn | 4 | 4 | |
| BstZ17I | GTAtac | 4 | 4 | |
| EcoRI | Gaattc | 4 | 4 | |
| SphI | GCATGc | 4 | 4 | |
| SspI | AATatt | 4 | 4 | |
| AccI | GTmkac | 5 | 5 | |
| BclI | Tgatca | 5 | 5 | |
| BsmBI | Nnnnnngagacg | 5 | 5 | (SEQ ID NO: 443) |
| BsrGI | Tgtaca | 5 | 5 | |
| DraI | TTTaaa | 6 | 6 | |
| NdeI | CAtatg | 6 | 6 | HC FR4 |
| SwaI | ATTTaaat | 6 | 6 | |
| BamHI | Ggatcc | 7 | 7 | |
| SacI | GAGCTc | 7 | 7 | |
| BciVI | GTATCCNNNNNN | 8 | 8 | (SEQ ID NO: 444) |
| BsaBI | GATNNnnatc | 8 | 8 | (SEQ ID NO: 619) |
| NsiI | ATGCAt | 8 | 8 | |
| Bsp120I | Gggccc | 9 | 9 | CH1 |
| ApaI | GGGCCc | 9 | 9 | CH1 |
| PspOMI | Gggccc | 9 | 9 | |
| BspHI | Tcatga | 9 | 11 | |
| EcoRV | GATatc | 9 | 9 | |
| AhdI | GACNNNnngtc | 11 | 11 | (SEQ ID NO: 445) |
| BbsI | GAAGAC | 11 | 14 | |
| PsiI | TTAtaa | 12 | 12 | |
| BsaI | GGTCTCNnnnn | 13 | 15 | (SEQ ID NO: 446) |

| Enzyme | Recognition* | Nch | Ns | Planned location of site |
|---|---|---|---|---|
| XmaI | Cccggg | 13 | 14 | |
| AvaI | Cycgrg | 14 | 16 | |
| BglI | GCCNNNNnggc | 14 | 17 | (SEQ ID NO: 447) |
| AlwNI | CAGNNNctg | 16 | 16 | |
| BspMI | ACCTGC | 17 | 19 | |
| XcmI | CCANNNNNnnnntgg | 17 | 26 | (SEQ ID NO: 448) |
| BstEII | Ggtnacc | 19 | 22 | HC FR4 |
| Sse8387I | CCTGCAgg | 20 | 20 | |
| AvrII | Cctagg | 22 | 22 | |
| HincII | GTYrac | 22 | 22 | |
| BsgI | GTGCAG | 27 | 29 | |
| MscI | TGGcca | 30 | 34 | |
| BseRI | NNnnnnnnnnctcctc | 32 | 35 | (SEQ ID NO: 449) |
| Bsu36I | CCtnagg | 35 | 37 | |
| PstI | CTGCAg | 35 | 40 | |
| EciI | nnnnnnnnntccgcc | 38 | 40 | (SEQ ID NO: 450) |
| PpuMI | RGgwccy | 41 | 50 | |
| StyI | Ccwwgg | 44 | 73 | |
| Eco0109I | RGgnccy | 46 | 70 | |
| Acc65I | Ggtacc | 50 | 51 | |
| KpnI | GGTACc | 50 | 51 | |
| BpmI | ctccag | 53 | 82 | |
| AvaII | Ggwcc | 71 | 124 | |

*cleavage occurs in the top strand after the last upper-case base.
For REs that cut palindromic sequences, the lower strand is cut at the symmetrical site.

TABLE 20

Cleavage of 79 human heavy chains

| Enzyme | Recognition | Nch | Ns | Planned location of site |
|---|---|---|---|---|
| AfeI | AGCgct | 0 | 0 | |
| AflII | Cttaag | 0 | 0 | HC FR3 |
| AscI | GGcgcgcc | 0 | 0 | After LC |
| BsiWI | Cgtacg | 0 | 0 | |
| BspDI | ATcgat | 0 | 0 | |
| BssHII | Gcgcgc | 0 | 0 | |
| FseI | GGCCGGcc | 0 | 0 | |
| HpaI | GTTaac | 0 | 0 | |
| NheI | Gctagc | 0 | 0 | HC Linker |
| NotI | GCggccgc | 0 | 0 | In linker, HC/anchor |
| NruI | TCGcga | 0 | 0 | |
| NsiI | ATGCAt | 0 | 0 | |
| PacI | TTAATtaa | 0 | 0 | |
| PciI | Acatgt | 0 | 0 | |
| PmeI | GTTTaaac | 0 | 0 | |
| PvuI | CGATcg | 0 | 0 | |
| RsrII | CGgwccg | 0 | 0 | |
| SapI | gaagagc | 0 | 0 | |
| SfiI | GGCCNNNNnggcc | 0 | 0 | HC signal seq (SEQ ID NO: 420) |
| SgfI | GCGATcgc | 0 | 0 | |
| SwaI | ATTTaaat | 0 | 0 | |
| AclI | AAcgtt | 1 | 1 | |
| AgeI | Accggt | 1 | 1 | |
| AseI | ATtaat | 1 | 1 | |
| AvrII | Cctagg | 1 | 1 | |
| BsmI | GAATGCN | 1 | 1 | |
| BsrBI | GAGcgg | 1 | 1 | |
| BsrDI | GCAATGNNn | 1 | 1 | |
| DraI | TTTaaa | 1 | 1 | |
| FspI | TGCgca | 1 | 1 | |
| HindIII | Aagctt | 1 | 1 | |
| MfeI | Caattg | 1 | 1 | HC FR1 |
| NaeI | GCCggc | 1 | 1 | |
| NgoMI | Gccggc | 1 | 1 | |
| SpeI | Actagt | 1 | 1 | |
| Acc65I | Ggtacc | 2 | 2 | |
| BstBI | TTcgaa | 2 | 2 | |

TABLE 20-continued

Cleavage of 79 human heavy chains

| Enzyme | Recognition | Nch | Ns | Planned location of site |
|---|---|---|---|---|
| KpnI | GGTACc | 2 | 2 | |
| MluI | Acgcgt | 2 | 2 | |
| NcoI | Ccatgg | 2 | 2 | In HC signal seq |
| NdeI | CAtatg | 2 | 2 | HC FR4 |
| PmlI | CACgtg | 2 | 2 | |
| XcmI | CCANNNNNnnnntgg | 2 | 2 | (SEQ ID NO: 421) |
| BcgI | cgannnnnntgc | 3 | 3 | (SEQ ID NO: 422) |
| BclI | Tgatca | 3 | 3 | |
| BglI | GCCNNNNnggc | 3 | 3 | (SEQ ID NO: 423) |
| BsaBI | GATNNnnatc | 3 | 3 | (SEQ ID NO: 424) |
| BsrGI | Tgtaca | 3 | 3 | |
| SnaBI | TACgta | 3 | 3 | |
| Sse8387I | CCTGCAgg | 3 | 3 | |
| ApaLI | Gtgcac | 4 | 4 | LC Signal/FR1 |
| BspHI | Tcatga | 4 | 4 | |
| BssSI | Ctcgtg | 4 | 4 | |
| PsiI | TTAtaa | 4 | 5 | |
| SphI | GCATGc | 4 | 4 | |
| AhdI | GACNNNnngtc | 5 | 5 | (SEQ ID NO: 425) |
| BspEI | Tccgga | 5 | 5 | HC FR1 |
| MscI | TGGcca | 5 | 5 | |
| SacI | GAGCTc | 5 | 5 | |
| ScaI | AGTact | 5 | 5 | |
| SexAI | Accwggt | 5 | 6 | |
| SspI | AATatt | 5 | 5 | |
| TliI | Ctcgag | 5 | 5 | |
| XhoI | Ctcgag | 5 | 5 | |
| BbsI | GAAGAC | 7 | 8 | |
| BstAPI | GCANNNNntgc | 7 | 8 | (SEQ ID NO: 426) |
| BstZ17I | GTatac | 7 | 7 | |
| EcoRV | GATatc | 7 | 7 | |
| EcoRI | Gaattc | 8 | 8 | |
| BlpI | GCtnagc | 9 | 9 | |
| Bsu36I | CCtnagg | 9 | 9 | |
| DraIII | CACNNNgtg | 9 | 9 | |
| EspI | GCtnagc | 9 | 9 | |
| StuI | AGGcct | 9 | 13 | |
| XbaI | Tctaga | 9 | 9 | HC FR3 |
| Bsp120I | Gggccc | 10 | 11 | CH1 |
| ApaI | GGGCCc | 10 | 11 | CH1 |
| PspOMI | Gggccc | 10 | 11 | |
| BciVI | GTATCCNNNNNN | 11 | 11 | (SEQ ID NO: 427) |
| SalI | Gtcgac | 11 | 12 | |
| DrdI | GACNNNNnngtc | 12 | 12 | (SEQ ID NO: 428) |
| KasI | Ggcgcc | 12 | 12 | |
| XmaI | Cccggg | 12 | 14 | |
| BglII | Agatct | 14 | 14 | |
| HincII | GTYrac | 16 | 18 | |
| BamHI | Ggatcc | 17 | 17 | |
| Pf1MI | CCANNNNntgg | 17 | 18 | (SEQ ID NO: 429) |
| BsmBI | Nnnnnngagacg | 18 | 21 | (SEQ ID NO: 430) |
| BstXI | CCANNNNNNntgg | 18 | 19 | HC FR2 (SEQ ID NO: 431) |
| XmnI | GAANNnnttc | 18 | 18 | (SEQ ID NO: 432) |
| SacII | CCGCgg | 19 | 19 | |
| PstI | CTGCAg | 20 | 24 | |
| PvuII | CAGctg | 20 | 22 | |
| AvaI | Cycgrg | 21 | 24 | |
| EagI | Cggccg | 21 | 22 | |
| AatII | GACGTc | 22 | 22 | |
| BspMI | ACCTGC | 27 | 33 | |
| AccI | GTmkac | 30 | 43 | |
| StyI | Ccwwgg | 36 | 49 | |
| AlwNI | CAGNNNctg | 38 | 44 | |
| BsaI | GGTCTCNnnnn | 38 | 44 | (SEQ ID NO: 433) |
| PpuMI | RGgwccy | 43 | 46 | |
| BsgI | GTGCAG | 44 | 54 | |
| BseRI | NNnnnnnnnnctctc | 48 | 60 | (SEQ ID NO: 434) |
| EciI | nnnnnnnnntccgcc | 52 | 57 | (SEQ ID NO: 435) |
| BstEII | Ggtnacc | 54 | 61 | HC Fr4, 47/79 have one |
| Eco0109I | RGgnccy | 54 | 86 | |
| BpmI | ctccag | 60 | 121 | |
| AvaII | Ggwcc | 71 | 140 | |

TABLE 21

MALIA3, annotated

```
! MALIA3 9532 bases
!-----------------------------------------------------------
   (SEQ ID NO: 451)
    1 aat gct act act att agt aga att gat gcc acc ttt tca gct cgc gcc
!   gene ii continued
   49 cca aat gaa aat ata gct aaa cag gtt att gac cat ttg cga aat gta
   97 tct aat ggt caa act aaa tct act cgt tcg cag aat tgg gaa tca act
  145 gtt aca tgg aat gaa act tcc aga cac cgt act tta gtt gca tat tta
  193 aaa cat gtt gag cta cag cac cag att cag caa tta agc tct aag cca
  241 tcc gca aaa atg acc tct tat caa aag gag caa tta aag gta ctc tct
  289 aat cct gac ctg ttg gag ttt gct tcc gat ctg gtt cgc ttt gaa gct
  337 cga att aaa acg cga tat ttg aag tct ttc ggg ctt cct ctt aat ctt
  385 ttt gat gca atc cgc ttt gct tct gac tat aat agt cag ggt aaa gac
  433 ctg att ttt gat tta tgg tca ttc tcg ttt tct gaa ctg ttt aaa gca
  481 ttt gag ggg gat tca ATG aat att tat gac gat tcc gca gta ttg gac
!              RBS?......  Start gene x, ii continues
  529 gct atc cag tct aaa cat ttt act att acc ccc tct ggc aaa act tct
  577 ttt gca aaa gcc tct cgc tat ttt ggt ttt tat cgt cgt ctg gta aac
  625 gag ggt tat gat agt gtt gct ctt act atg cct cgt aat tcc ttt tgg
  673 cgt tat gta tct gca tta gtt gaa tgt ggt att cct aaa tct caa ctg
  721 atg aat ctt tct acc tgt aat aat gtt gtt ccg tta gtt cgt ttt att
  769 aac gta gat ttt tct tcc caa cgt cct gac tgg tat aat gag cca gtt
  817 ctt aaa atc gca TAA
!                    End X & II
!
  832 ggtaattca ca
!
   (SEQ ID NO: 623)
!        M1                 E5              Q10              T15
  843 ATG att aaa gtt gaa att aaa cca tct caa gcc caa ttt act act cgt
!   Start gene V
```

TABLE 21-continued

MALIA3, annotated

```
!         S17         S20             P25             E30
  891 tct ggt gtt tct cgt cag ggc aag cct tat tca ctg aat gag cag ctt
!
!             V35             E40             V45
  939 tgt tac gtt gat ttg ggt aat gaa tat ccg gtt ctt gtc aag att act
!
!         D50         A55             L60
  987 ctt gat gaa ggt cag cca gcc tat gcg cct ggt cTG TAC Acc gtt cat
!                                                    BsrGI...
!        L65             V70             S75             R80
 1035 ctg tcc tct ttc aaa gtt ggt cag ttc ggt tcc ttg atg att gac cgt
!                     P85     K87 end of V
 1083 ctg cgc ctc gtt ccg gct aag TAA C
!
 1108 ATG gag cag gtc gcg gat ttc gac aca att tat cag gcg atg
      Start gene VII
!
 1150 ata caa atc tcc gtt gta ctt tgt ttc gcg ctt ggt ata atc
!
!                   VII and IX overlap.
!                   ..... S2 V3 L4 V5 (SEQ ID NO: 624)        S10
 1192 gct ggg ggt caa agA TGA gt gtt tta gtg tat tct ttc gcc tct ttc gtt
!
!                     End VII
!                     |start IX
!        L13     W15                 G20             T25
E29
 1242 tta ggt tgg tgc ctt cgt agt ggc att acg tat ttt acc cgt tta agt
gaa
!
 1293 act tcc tc !        .... stop of IX, IX and VIII overlap by four bases
 1301 ATG aaa aag tct tta gtc ctc aaa gcc tct gta gcc gtt gct acc ctc
!     Start signal sequence of viii.
!
 1349 gtt ccg atg ctg tct ttc gct gct gag ggt gac gat ccc gca aaa gcg
!                               mature VIII --->
 1397 gcc ttt aac tcc ctg caa tca gcg acc gaa tat atc ggt tat gcg
 1445 tgg gcg atg gtt gtt gtc att
 1466 gtc ggc gca act atc ggt atc aag ctg ttt aag
 1499 aaa ttc acc tcg aaa gca ! 1515
!      .......... -35 ..
!
 1517     agc tga taaaccgat acaattaaag gctcctttg
!                    ..... -10  ...
!
 1552 gagcctttt ttttGGAGAt ttt ! S.D. underlined
!
!        <------ III signal sequence ------------------------>
!         M   K   K   L   L   F   A   I   P   L   V  (SEQ ID NO: 452)
 1575 caac GTG aaa aaa tta tta ttc gca att cct tta gtt ! 1611
!
!      V   P   F   Y   S   H   S   A   Q
 1612 gtt cct ttc tat tct cac aGT gcA Cag tCT
!                                 ApaLI...
!
 1642 GTC GTG ACG CAG CCG CCC TCA GTG TCT GGG GCC CCA GGG CAG
      AGG GTC ACC ATC TCC TGC ACT GGG AGC AGC TCC AAC ATC GGG GCA
!         BstEII...
 1729 GGT TAT GAT GTA CAC TGG TAC CAG CAG CTT CCA GGA ACA GCC CCC AAA
 1777 CTC CTC ATC TAT GGT AAC AGC AAT CGG CCC TCA GGG GTC CCT GAC CGA
 1825 TTC TCT GGC TCC AAG TCT GGC ACC TCA GCC TCC CTG GCC ATC ACT
 1870 GGG CTC CAG GCT GAG GAT GAG GCT GAT TAT
 1900 TAC TGC CAG TCC TAT GAC AGC AGC CTG AGT
 1930 GGC CTT TAT GTC TTC GGA ACT GGG ACC AAG GTC ACC GTC
!                                            BstEII...
 1969 CTA GGT CAG CCC AAG GCC AAC CCC ACT GTC ACT
 2002 CTG TTC CCG CCC TCC TCT GAG GAG CTC CAA GCC AAC AAG GCC ACA CTA
 2050 GTG TGT CTG ATC AGT GAC TTC TAC CCG GGA GCT GTG ACA GTG GCC TGG
 2098 AAG GCA GAT AGC AGC CCC GTC AAG GCG GGA GTG GAG ACC ACC ACA CCC
 2146 TCC AAA CAA AGC AAC AAC AAG TAC GCG GCC AGC AGC TAT CTG AGC CTG
 2194 ACG CCT GAG CAG TGG AAG TCC CAC AGA AGC TAC AGC TGC CAG GTC ACG
 2242 CAT GAA GGG AGC ACC GTG GAG AAG ACA GTG GCC CCT ACA GAA TGT TCA
 2290 TAA TAA ACCG CCTCCACCGG GCGCGCCAAT TCTATTTCAA GGAGACAGTC ATA
!                             AscI.....
```

TABLE 21-continued

| MALIA3, annotated |

```
!     (SEQ ID NO: 453)
!     PelB signal ------------------------------------------------->
!         M   K   Y   L   L   P   T   A   A   A   G   L   L   L
  2343  ATG AAA TAC CTA TTG CCT ACG GCA GCC GCT GGA TTG TTA TTA CTC
!
!        16  17  18  19  20      21  22
!         A   A   Q   P   A       M   A
  2388  gcG GCC cag ccG GCC     atg gcc
!         SfiI.............
!                 NgoMI...(1/2)
!                   NcoI........
!
!
!                                    FR1(DP47/V3-23)---------------
!                              23  24  25  26  27  28  29  30
!                               E   V   Q   L   L   E   S   G
  2409                         gga|gtt|CAA|TTG|tta|gag|tct|ggt|
!                                      |MfeI|
!     ---------------FR1-----------------------------------------
!        31  32  33  34  35  36  37  38  39  40  41  42  43  44  45
!         G   G   L   V   Q   P   G   G   S   L   R   L   S   C   A
  2433  |ggc|ggt|ctt|gtt|cag|cct|ggt|ggt|tct|tta|cgt|ctt|tct|tgc|gct|
!       ----FR1---------------->|...CDR1................|---FR2------
!        46  47  48  49  50  51  52  53  54  55  56  57  58  59  60
!         A   S   G   F   T   F   S   S   Y   A   M   S   W   V   R
  2478  |gct|TCC|GGA|ttc|act|ttc|tct|tCG|TAC|Gct|atg|tct|tgg|gtt|cgC|
!           | BspEI |                 | BsiWI|
!BstXI.
!       --------FR2-------------------------->|...CDR2.........
!        61  62  63  64  65  66  67  68  69  70  71  72  73  74  75
!         Q   A   P   G   K   G   L   E   W   V   S   A   I   S   G
  2523  |CAa|gct|ccT|GGt|aaa|ggt|ttg|gag|tgg|gtt|tct|gct|atc|tct|ggt|
!     ...BstXI       |
!       ....CDR2.........................................|---FR3---
!        76  77  78  79  80  81  82  83  84  85  86  87  88  89  90
!         S   G   G   S   T   Y   Y   A   D   S   V   K   G   R   F
  2568  |tct|ggt|ggc|agt|act|tac|tat|gct|gac|tcc|gtt|aaa|ggt|cgc|ttc|
!       --------FR3-----------------------------------------------
!        91  92  93  94  95  96  97  98  99 100 101 102 103 104 105
!         T   I   S   R   D   N   S   K   N   T   L   Y   L   Q   M
  2613  |act|atc|TCT|AGA|gac|aac|tct|aag|aat|act|ctc|tac|ttg|cag|atg|
!              | XbaI |
!       ---FR3-------------------------------------------------->|
!       106 107 108 109 110 111 112 113 114 115 116 117 118 119 120
!         N   S   L   R   A   E   D   T   A   V   Y   Y   C   A   K
  2658  |aac|agC|TTA|AGg|gct|gag|gac|acT|GCA|Gtc|tac|tat|tgc|gct|aaa|
!           |AflII  |             | PstI  |
!       .......CDR3..................|----FR4-----------------------
!       121 122 123 124 125 126 127 128 129 130 131 132 133 134 135
!         D   Y   E   G   T   G   Y   A   F   D   I   W   G   Q   G
  2703  |gac|tat|gaa|ggt|act|ggt|tat|gct|ttc|gaC|ATA|TCg|ggt|caa|ggt|
!                                          | NdeI |(1/4)
!       -------------FR4---------->|
!       136 137 138 139 140 141 142
!         T   M   V   T   V   S   S
  2748  |act|atG|GTC|ACC|gtc|tct|agt|
!             | BstEII |
! From BstEII onwards, pV323 is same as pCES1, except as noted.
! BstEII sites may occur in light chains; not likely to be unique in final
! vector.
!                       143 144 145 146 147 148 149 150 151 152
!                         A   S   T   K   G   P   S   V   F   P
  2769                   gcc tcc acc aaG GGC CCa tcg GTC TTC ccc
!                                         Bsp120I.    BbsI...(2/2)
!                                         ApaI....
!       153 154 155 156 157 158 159 160 161 162 163 164 165 166 167
!         L   A   P   S   S   K   S   T   S   G   G   T   A   A   L
  2799  ctg gca ccC TCC TCc aag agc acc tct ggg ggc aca gcg gcc ctg
!                          BseRI...(2/2)
!       168 169 170 171 172 173 174 175 176 177 178 179 180 181 182
!         G   C   L   V   K   D   Y   F   P   E   P   V   T   V   S
  2844  ggc tgc ctg GTC AAG GAC TAC TTC CCc gaA CCG GTg acg gtg tcg
!                                              AgeI....
!       183 184 185 186 187 188 189 190 191 192 193 194 195 196 197
!         W   N   S   G   A   L   T   S   G   V   H   T   F   P   A
  2889  tgg aac tca GGC GCC ctg acc agc ggc gtc cac acc ttc ccg gct
!                   KasI...(1/4)
```

TABLE 21-continued

MALIA3, annotated

```
!         198 199 200 201 202 203 204 205 206 207 208 209 210 211 212
!          V   L   Q   S   S   G   L   Y   S   L   S   S   V   V   T
   2934   gtc cta cag tCt agc GGa ctc tac tcc ctc agc agc gta gtg acc
                        (Bsu36I...)(knocked out)
!         213 214 215 216 217 218 219 220 221 222 223 224 225 226 227
!          V   P   S   S   S   L   G   T   Q   T   Y   I   C   N   V
   2979   gtg ccC tCt tct agc tTG Ggc acc cag acc tac atc tgc aac gtg
                        (BstXI..........)N.B. destruction of BstXI & BpmI sites.
!
!         228 229 230 231 232 233 234 235 236 237 238 239 240 241 242
!          N   H   K   P   S   N   T   K   V   D   K   K   V   E   P
   3024   aat cac aag ccc agc aac acc aag gtg gac aag aaa gtt gag ccc
!
!         243 244 245
!          K   S   C   A   A   A   H   H   H   H   H   S   A
   3069   aaa tct tgt GCG GCC GCt cat cac cac cat cat cac tct gct
                        NotI......
!          E   Q   K   L   I   S   E   E   D   L   N   G   A   A
   3111   gaa caa aaa ctc atc tca gaa gag gat ctg aat ggt gcc gca
!
!
!          D   I   N   D   D   R   M       A   S   G   A
   3153   GAT ATC aac gat gat cgt atg     gct AGC ggc gcc
          rEK cleavage site..........     NheI... KasI...
          EcoRV..
! Domain 1 ----------------------------------------------------------
!             A   E   T   V   E   S   C   L   A
   3183      gct gaa act gtt gaa agt tgt tta gca
!
!
!          K   P   H   T   E   N   S   F
   3210   aaa ccc cat aca gaa aat tca ttt
!
!          T   N   V   W   K   D   D   K   T
   3234   aCT AAC GTC TGG AAA GAC GAC AAA Act
!
!          L   D   R   Y   A   N   Y   E   G   C   L   W   N   A   T   G   V
   3261   tta gat cgt tac gct aac tat gag ggt tgt ctg tgG AAT GCt aca ggc gtt
                                                          BsmI____
!
!          V   V   C   T   G   D   E   T   Q   C   Y   G   T   W   V   P   I
   3312   gta gtt tgt act ggt GAC GAA ACT CAG TGT TAC GGT ACA TGG GTT cct att
!
!          G   L   A   I   P   E   N
   3363   ggg ctt gct atc cct gaa aat
!
! L1 linker -----------------------------------
!          E   G   G   G   S   E   G   G   G   S
   3384   gag ggt ggt ggc tct gag ggt ggc ggt tct
!
!          E   G   G   G   S   E   G   G   G   T
   3414   gag ggt ggc ggt tct gag ggt ggc ggt act
!
! Domain 2 ----------------------------------
   3444   aaa cct cct gag tac ggt gat aca cct att ccg ggc tat act tat atc aac
   3495   cct ctc gac ggc act tat ccg cct ggt act gag caa aac ccc gct aat cct
   3546   aat cct tct ctt GAG GAG tct cag cct ctt aat act ttc atg ttt cag aat
                             BseRI__
   3597   aat agg ttc cga aat agg cag ggg gca tta act gtt tat acg ggc act
   3645   gtt act caa ggc act gac ccc gtt aaa act tat tac cag tac act cct
   3693   gta tca tca aaa gcc atg tat gac gct tac tgg aac ggt aaa ttC AGA
                                                                      AlwNI
   3741   GAC TGc gct ttc cat tct ggc ttt aat gaa gat cca ttc gtt tgt gaa
          AlwNI
   3789   tat caa ggc caa tcg tct gac ctg cct caa cct cct gtc aat gct
!
   3834   ggc ggc ggc tct
! start L2
-----------------------------------------------------------
   3846   ggt ggt ggt tct
   3858   ggt ggc ggc tct
   3870   gag ggt ggt ggc tct gag ggt ggc ggt tct
   3900   gag ggt ggc ggc tct gag gga ggc ggt tcc
   3930   ggt ggt ggc tct ggt       ! end L2
!
```

TABLE 21-continued

| MALIA3, annotated |
| --- |

```
! Domain 3
  (SEQ ID NO: 454)
--------------------------------------------------------------
!        S   G   D   F   D   Y   E   K   M   A   N   A   N   K   G   A
  3945 tcc ggt gat ttt gat tat gaa aag atg gca aac gct aat aag ggg gct
!
!        M   T   E   N   A   D   E   N   A   L   Q   S   D   A   K   G
  3993 atg acc gaa aat gcc gat gaa aac gcg cta cag tct gac gct aaa ggc
!
!        K   L   D   S   V   A   T   D   Y   G   A   A   I   D   G   F
  4041 aaa ctt gat tct gtc gct act gat tac ggt gct gct atc gat ggt ttc
!
!        I   G   D   V   S   G   L   A   N   G   N   G   A   T   G   D
  4089 att ggt gac gtt tcc ggc ctt gct aat ggt aat ggt gct act ggt gat
!
!        F   A   G   S   N   S   Q   M   A   Q   V   G   D   G   D   N
  4137 ttt gct ggc tct aat tcc caa atg gct caa gtc ggt gac ggt gat aat
!
!        S   P   L   M   N   N   F   R   Q   Y   L   P   S   L   P   Q
  4185 tca cct tta atg aat aat ttc cgt caa tat tta cct tcc ctc cct caa
!
!        S   V   E   C   R   P   F   V   F   S   A   G   K   P   Y   E
  4233 tcg gtt gaa tgt cgc cct ttt gtc ttt agc gct ggt aaa cca tat gaa
!
!        F   S   I   D   C   D   K   I   N   L   F   R
  4281 ttt tct att gat tgt gac aaa ata aac tta ttc cgt
!                                                             End Domain 3
!
!        G   V   F   A   F   L   L   Y   V   A   T   F   M   Y   V   F140
  4317 ggt gtc ttt gcg ttt ctt tta tat gtt gcc acc ttt atg tat gta ttt
!        start transmembrane segment
!
!        S   T   F   A   N   I   L
  4365 tct acg ttt gct aac ata ctg
!
!        R   N   K   E   S
  4386 cgt aat aag gag tct TAA ! stop of iii
!     Intracellular anchor.
!
!            (SEQ ID NO: 455)
!            M1  P2   V   L   L5  G   I   P   L   L10 L   R   FL   G15
  4404   tc ATG cca gtt ctt ttg ggt att ccg tta tta ttg cgt ttc ctc ggt
!            Start VI
!
  4451 ttc ctt ctg gta act ttg ttc ggc tat ctg ctt act ttt ctt aaa aag
  4499 ggc ttc ggt aag ata gct att gct att tca ttg ttt ctt gct ctt att
  4547 att ggg ctt aac tca att ctt gtg ggt tat ctc tct gat att agc gct
  4595 caa tta ccc tct gac ttt gtt cag ggt gtt cag tta att ctc ccg tct
  4643 aat gcg ctt ccc tgt ttt tat gtt att ctc tct gta aag gct gct att
  4691 ttc att ttt gac gtt aaa caa aaa atc gtt tct tat ttg gat tgg gat
!
!                  (SEQ ID NO: 456)
!                  M1   A2  V3      F5                  L10           G13
  4739 aaa TAA t ATG gct gtt tat ttt gta act ggc aaa tta ggc tct gga
!        end VI Start gene I
!        14  15  16  17  18  19  20  21  22  23  24  25  26  27  28
!         K   T   L   V   S   V   G   K   I   Q   D   K   I   V   A
  4785 aag acg ctc gtt agc gtt ggt aag att cag gat aaa att gta gct
!
!        29  30  31  32  33  34  35  36  37  38  39  40  41  42  43
!         G   C   K   I   A   T   N   L   D   L   R   L   Q   N   L
  4830 ggg tgc aaa ata gca act aat ctt gat tta agg ctt caa aac ctc
!
!        44  45  46  47  48  49  50  51  52  53  54  55  56  57  58
!         P   Q   V   G   R   F   A   K   T   P   R   V   L   R   I
  4875 ccg caa gtc ggg agg ttc gct aaa acg cct cgc gtt ctt aga ata
!
!        59  60  61  62  63  64  65  66  67  68  69  70  71  72  73
!         P   D   K   P   S   I   S   D   L   L   A   I   G   R   G
  4920 ccg gat aag cct tct ata tct gat ttg ctt gct att ggg cgc ggt
!
!        74  75  76  77  78  79  80  81  82  83  84  85  86  87  88
!         N   D   S   Y   D   E   N   K   N   G   L   L   V   L   D
  4965 aat gat tcc tac gat gaa aat aaa aac ggc ttg ctt gtt ctc gat
!
!        89  90  91  92  93  94  95  96  97  98  99 100 101 102 103
!         E   C   G   T   W   F   N   T   R   S   W   N   D   K   E
  5010 gag tgc ggt act tgg ttt aat acc cgt tct tgg aat gat aag gaa
```

TABLE 21-continued

MALIA3, annotated

```
        104 105 106 107 108 109 110 111 112 113 114 115 116 117 118
         R   Q   P   I   I   D   W   F   L   H   A   R   K   L   G
5055    aga cag ccg att att gat tgg ttt cta cat gct cgt aaa tta gga 119 120 121 122 123 124 125 126 127 128 129 130 131 132 133
         W   D   I   I   F   L   V   Q   D   L   S   I   V   D   K
5100    tgg gat att att ttt ctt gtt cag gac tta tct att gtt gat aaa 134 135 136 137 138 139 140 141 142 143 144 145 146 147 148
         Q   A   R   S   A   L   A   E   H   V   V   Y   C   R   R
5145    cag gcg cgt tct gca tta gct gaa cat gtt gtt tat tgt cgt cgt 149 150 151 152 153 154 155 156 157 158 159 160 161 162 163
         L   D   R   I   T   L   P   F   V   G   T   L   Y   S   L
5190    ctg gac aga att act tta cct ttt gtc ggt act tta tat tct ctt 164 165 166 167 168 169 170 171 172 173 174 175 176 177 178
         I   T   G   S   K   M   P   L   P   K   L   H   V   G   V
5235    att act ggc tcg aaa atg cct ctg cct aaa tta cat gtt ggc gtt 179 180 181 182 183 184 185 186 187 188 189 190 191 192 193
         V   K   Y   G   D   S   Q   L   S   P   T   V   E   R   W
5280    gtt aaa tat ggc gat tct caa tta agc cct act gtt gag cgt tgg 194 195 196 197 198 199 200 201 202 203 204 205 206 207 208
         L   Y   T   G   K   N   L   Y   N   A   Y   D   T   K   Q
5325    ctt tat act ggt aag aat ttg tat aac gca tat gat act aaa cag 209 210 211 212 213 214 215 216 217 218 219 220 221 222 223
         A   F   S   S   N   Y   D   S   G   V   Y   S   Y   L   T
5370    gct ttt tct agt aat tat gat tcc ggt gtt tat tct tat tta acg 224 225 226 227 228 229 230 231 232 233 234 235 236 237 238
         P   Y   L   S   H   G   R   Y   F   K   P   L   N   L   G
5415    cct tat tta tca cac ggt cgg tat ttc aaa cca tta aat tta ggt 239 240 241 242 243 244 245 246 247 248 249 250 251 252 253
         Q   K   M   K   L   T   K   I   Y   L   K   K   F   S   R
5460    cag aag atg aaa tta act aaa ata tat ttg aaa aag ttt tct cgc 254 255 256 257 258 259 260 261 262 263 264 265 266 267 268
         V   L   C   L   A   I   G   F   A   S   A   F   T   Y   S
5505    gtt ctt tgt ctt gcg att gga ttt gca tca gca ttt aca tat agt 269 270 271 272 273 274 275 276 277 278 279 280 281 282 283
         Y   I   T   Q   P   K   P   E   V   K   K   V   V   S   Q
5550    tat ata acc caa cct aag ccg gag gtt aaa aag gta gtc tct cag 284 285 286 287 288 289 290 291 292 293 294 295 296 297 298
         T   Y   D   F   D   K   F   T   I   D   S   S   Q   R   L
5595    acc tat gat ttt gat aaa ttc act att gac tct tct cag cgt ctt 299 300 301 302 303 304 305 306 307 308 309 310 311 312 313
         N   L   S   Y   R   Y   V   F   K   D   S   K   G   K   L
5640    aat cta agc tat cgc tat gtt ttc aag gat tct aag gga aaa TTA
                                                                PacI 314 315 316 317 318 319 320 321 322 323 324 325 326 327 328
         I   N   S   D   D   L   Q   K   Q   G   Y   S   L   T   Y
5685    ATT AAt agc gac gat tta cag aag caa ggt tat tca ctc aca tat
        PacI 329 330 331 332 333 334 335 336 337 338 339 340 341 342 343
         i   I   D   L   C   T   V   S   I   K   K   G   N   S   N   E
                                                             (SEQ ID NO: 620)
        iv                                                          M1  K
5730    att gat tta tgt act gtt tcc att aaa aaa ggt aat tca aAT Gaa
                                                                Start IV 344 345 346 347 348 349
        i    I   V   K   C   N  .End of I
        iv  L3   L  N5   V  I7   N   F  V10
5775        att gtt aaa tgt aat TAA T TTT GTT
        IV continued.....
5800    ttc ttg atg ttt gtt tca tca tct tct ttt gct cag gta att gaa atg
5848    aat aat tcg cct ctg cgc gat ttt gta act tgg tat tca aag caa tca
5896    ggc gaa tcc gtt att gtt tct ccc gat gta aaa ggt act gtt act gta
5944    tat tca tct gac gtt aaa cct gaa aat cta cgc aat ttc ttt att tct
```

TABLE 21-continued

MALIA3, annotated

```
5992 gtt tta cgt gct aat aat ttt gat atg gtt ggt tca att cct tcc ata
6040 att cag aag tat aat cca aac aat cag gat tat att gat gaa ttg cca
6088 tca tct gat aat cag gaa tat gat gat aat tcc gct cct tct ggt ggt
6136 ttc ttt gtt ccg caa aat gat aat gtt act caa act ttt aaa att aat
6184 aac gtt cgg gca aag gat tta ata cga gtt gtc gaa ttg ttt gta aag
6232 tct aat act tct aaa tcc tca aat gta tta tct att gac ggc tct aat
6280 cta tta gtt gtt TCT gca cct aaa gat att tta gat aac ctt cct caa
!                   ApaLI removed
6328 ttc ctt tct act gtt gat ttg cca act gac cag ata ttg att gag ggt
6376 ttg ata ttt gag gtt cag caa ggt gat gct tta gat ttt tca ttt gct
6424 gct ggc tct cag cgt ggc act gtt gca ggc ggt gtt aat act gac cgc
6472 ctc acc tct gtt tta tct tct gct ggt ggt tcg ttc ggt att ttt aat
6520 ggc gat gtt tta ggg cta tca gtt cgc gca tta aag act aat agc cat
6568 tca aaa ata ttg tct gtg cca cgt att ctt acg ctt tca ggt cag aag
6616 ggt tct atc tct gtT GGC CAg aat gtc cct ttt att act ggt cgt gtg
!                        MscI____
6664 act ggt gaa tct gcc aat gta aat aat cca ttt cag acg att gag cgt
6712 caa aat gta ggt att tcc atg agc gtt ttt cct gtt gca atg gct ggc
6760 ggt aat att gtt ctg gat att acc agc aag gcc gat ttg agt tct
6808 tct act cag gca agt gat gtt att act aat caa aga agt att gct aca
6856 acg gtt aat ttg cgt gat gga cag act ctt tta ctc ggt ggc ctc act
6904 gat tat aaa aac act tct caa gat tct ggc gta ccg ttc ctg tct aaa
6952 atc cct tta atc ggc ctc ctg ttt agc tcc cgc tct gat tcc aac gag
7000 gaa agc acg tta tac gtg ctc gtc aaa gca acc ata gta cgc gcc ctg
7048 TAG cggcgcatt
!    End IV
7060 aagcgcggcg ggtgtggtgg ttacgcgcag cgtgaccgct acacttgcca gcgccctagc
7120 gcccgctcct ttcgctttct tcccttcctt tctcgccacg ttcGCCGGCt ttccccgtca
!                                                      NgoMI_
7180 agctctaaat cgggggctcc ctttagggtt ccgatttagt gctttacggc acctcgaccc
7240 caaaaaactt gatttgggtg atggttCACG TAGTGggcca tcgccctgat agacggtttt
!                                  DraIII_____
7300 tcgcccttG ACGTTGGAGT Ccacgttctt taatagtgga ctcttgttcc aaactggaac
!              DrdI_____
7360 aacactcaac cctatctcgg gctattcttt tgatttataa gggattttgc cgatttcgga
7420 accaccatca aacaggattt tcgcctgctg gggcaaacca gcgtggaccg cttgctgcaa
7480 ctctctcagg gccaggcggt gaagggcaat CAGCTGttgc cCGTCTCact ggtgaaaaga
!                                  PvuII.      BsmBI.
7540 aaaaccaccc tGGATCC AAGCTT
!             BamHI HindIII (½)
!             Insert carrying bla gene
7563     gcaggtg gcacttttcg gggaaatgtg cgcggaaccc
7600 ctatttgttt atttttctaa atacattcaa atatGTATCC gctcatgaga caataaccct
!                                          BciVI
7660 gataaatgct tcaataatat tgaaaaAGGA AGAgt
!                          RBS.?...
!        Start bla gene
7695 ATG agt att caa cat ttc cgt gtc gcc ctt att ccc ttt ttt gcg gca ttt
7746 tgc ctt cct gtt ttt gct cac cca gaa acg ctg gtg aaa gta aaa gat gct
7797 gaa gat cag ttg ggC gCA CGA Gtg ggt tac atc gaa ctg gat ctc aac agc
!                       BssSI...
!                   ApaLI removed
7848 ggt aag atc ctt gag agt ttt cgc ccc gaa gaa cgt ttt cca atg atg agc
7899 act ttt aaa gtt ctg cta tgt cat aca cta tta tcc cgt att gac gcc ggg
7950 caa gaG CAA CTC GGT CGc cgg gcg cgg tat tct cag aat gac ttg gtt gAG
!         BcgI_____
ScaI
8001 TAC Tca cca gtc aca gaa aag cat ctt acg gat ggc atg aca gta aga gaa
!    ScaI_
8052 tta tgc agt gct gcc ata acc atg agt gat aac act gcg gcc aac tta ctt
8103 ctg aca aCG ATC Gga gga ccg aag gag cta acc gct ttt ttg cac aac atg
!             PvuI____
8154 ggg gat cat gta act cgc ctt gat cgt tgg gaa ccg gag ctg aat gaa gcc
8205 ata cca aac gac gag cgt gac acc acg atg cct gta gca atg cca aca acg
8256 tTG CGC Aaa cta tta act ggc gaa cta ctt act cta gct tcc cgg caa caa
!    FspI....
!
8307 tta ata gac tgg atg gag gcg gat aaa gtt gca gga cca ctt ctg cgc tcg
8358 GCC ctt ccG GCt ggc tgg ttt att gct gat aaa tct gga gcc ggt gag cgt
!    BglI_____
8409 gGG TCT Cgc ggt atc att gca gca ctg ggg cca gat ggt aag ccc tcc cgt
!    BsaI____
8460 atc gta gtt atc tac acG ACg ggg aGT Cag gca act atg gat gaa cga aat
!                           AhdI_____
8511 aga cag atc gct gag ata ggt gcc tca ctg att aag cat tgg TAA ctgt
!                                                         stop
8560 cagaccaagt ttactcatat actttagat tgatttaaa acttcatttt taatttaaaa
8620 ggatctaggt gaagatcctt tttgataatc tcatgaccaa atcccttaa cgtgagtttt
```

TABLE 21-continued

| MALIA3, annotated |
|---|

```
 8680 cgttccactg tacgtaagac cccc
 8704 AAGCTT    GTCGAC tgaa tggcgaatgg cgctttgcct
!      HindIII  SalI..
!      (2/2)    HincII
 8740 ggtttccggc accagaagcg gtgccggaaa gctggctgga gtgcgatctt
!
 8790 CCTGAGG
!      Bsu36I_
 8797        ccgat actgtcgtcg tcccctcaaa ctggcagatg
 8832 cacggttacg atgcgcccat ctacaccaac gtaacctatc ccattacggt caatccgccg
 8892 tttgttccca cggagaatcc gacgggttgt tactcgctca catttaatgt tgatgaaagc
 8952 tggctacagg aaggccagac gcgaattatt tttgatggcg ttcctattgg ttaaaaaatg
 9012 agctgattta acaaaaattt aacgcgaatt ttaacaaaat attaacgttt acaATTTAAA
!                                                                 SwaI...
 9072 Tatttgctta tacaatcttc ctgttttggg ggcttttctg attatcaacc GGGGTAcat
!                                                                   RBS?
 9131 ATG att gac atg cta gtt tta cga tta ccg ttc atc gat tct ctt gtt tgc
!     Start gene II
 9182 tcc aga ctc tca ggc aat gac ctg ata gcc ttt gtA GAT CTc tca aaa ata
!                                                     BglII...
 9233 gct acc ctc tcc ggc atg aat tta tca gct aga acg gtt gaa tat cat att
 9284 gat ggt gat ttg act gtc tcc ggc ctt tct cac cct ttt gaa tct tta cct
 9335 aca cat tac tca ggc att gca ttt aaa ata tat gag ggt tct aaa aat ttt
 9386 tat cct tgc gtt gaa ata aag gct tct ccc gca aaa gta tta cag ggt cat
 9437 aat gtt ttt ggt aca acc gat tta gct tta tgc tct gag gct tta ttg ctt
 9488 aat ttt gct aat tct ttg cct tgc ctg tat gat tta ttg gat gtt !
 9532
! gene II continues
```

TABLE 21B

| Sequence of MALIA3, condensed LOCUS MALIA3 9532<br>CIRCULAR ORIGIN (SEQ ID NO: 451) |
|---|

```
   1 AATGCTACTA CTATTAGTAG AATTGATGCC ACCTTTTCAG CTCGCGCCCC AAATGAAAAT
  61 ATAGCTAAAC AGGTTATTGA CCATTTGCGA AATGTATCTA ATGGTCAAAC TAAATCTACT
 121 CGTTCGCAGA ATTGGGAATC AACTGTTACA TGGAATGAAA CTTCCAGACA CCGTACTTTA
 181 GTTGCATATT TAAAACATGT TGAGCTACAG CACCAGATTC AGCAATTAAG CTCTAAGCCA
 241 TCCGCAAAAA TGACCTCTTA TCAAAAGGAG CAATTAAAGG TACTCTCTAA TCCTGACCTG
 301 TTGGAGTTTG CTTCCGGTCT GGTTCGCTTT GAAGCTCGAA TTAAAACGCG ATATTTGAAG
 361 TCTTTCGGGC TTCCTCTTAA TCTTTTTGAT GCAATCCGCT TTGCTTCTGA CTATAATAGT
 421 CAGGGTAAAG ACCTGATTTT TGATTTATGG TCATTCTCGT TTTCTGAACT GTTTAAAGCA
 481 TTTGAGGGGG ATTCAATGAA TATTTATGAC GATTCCGCAG TATTGGACGC TATCCAGTCT
 541 AAACATTTTA CTATTACCCC CTCTGGCAAA ACTTCTTTTG CAAAAGCCTC TCGCTATTTT
 601 GGTTTTTATC GTCGTCTGGT AAACGAGGGT TATGATAGTG TTGCTCTTAC TATGCCTCGT
 661 AATTCCTTTT GGCGTTATGT ATCTGCATTA GTTGAATGTG GTATTCCTAA ATCTCAACTG
 721 ATGAATCTTT CTACCTGTAA TAATGTTGTT CCGTTAGTTC GTTTTATTAA CGTAGATTTT
 781 TCTTCCCAAC GTCCTGACTG GTATAATGAG CCAGTTCTTA AAATCGCATA AGGTAATTCA
 841 CAATGATTAA AGTTGAAATT AAACCATCTC AAGCCCAATT TACTACTCGT TCTGGTGTTT
 901 CTCGTCAGGG CAAGCCTTAT TCACTGAATG AGCAGCTTTG TTACGTTGAT TTGGGTAATG
 961 AATATCCGGT TCTTGTCAAG ATTACTCTTG ATGAAGGTCA GCCAGCCTAT GCGCCTGGTC
1021 TGTACACCGT TCATCTGTCC TCTTTCAAAG TTGGTCAGTT CGGTTCCCTT ATGATTGACC
1081 GTCTGCGCCT CGTTCCGGCT AAGTAACATG GAGCAGGTCG CGGATTTCGA CACAATTTAT
1141 CAGGCGATGA TACAAATCTC CGTTGTACTT TGTTTCGCGC TTGGTATAAT CGCTGGGGGT
```

TABLE 21B-continued

Sequence of MALIA3, condensed LOCUS MALIA3 9532
CIRCULAR ORIGIN (SEQ ID NO: 451)

```
1201 CAAAGATGAG TGTTTTAGTG TATTCTTTCG CCTCTTTCGT TTTAGGTTGG TGCCTTCGTA

1261 GTGGCATTAC GTATTTTACC CGTTTAATGG AAACTTCCTC ATGAAAAAGT CTTTAGTCCT

1321 CAAAGCCTCT GTAGCCGTTG CTACCCTCGT TCCGATGCTG TCTTTCGCTG CTGAGGGTGA

1381 CGATCCCGCA AAAGCGGCCT TTAACTCCCT GCAAGCCTCA GCGACCGAAT ATATCGGTTA

1441 TGCGTGGGCG ATGGTTGTTG TCATTGTCGG CGCAACTATC GGTATCAAGC TGTTTAAGAA

1501 ATTCACCTCG AAAGCAAGCT GATAAACCGA TACAATTAAA GGCTCCTTTT GGAGCCTTTT

1561 TTTTTGGAGA TTTTCAACGT GAAAAATTA TTATTCGCAA TTCCTTTAGT TGTTCCTTTC

1621 TATTCTCACA GTGCACAGTC TGTCGTGACG CAGCCGCCCT CAGTGTCTGG GGCCCCAGGG

1681 CAGAGGGTCA CCATCTCCTG CACTGGGAGC AGCTCCAACA TCGGGCAGG TTATGATGTA

1741 CACTGGTACC AGCAGCTTCC AGGAACAGCC CCCAAACTCC TCATCTATGG AACAGCAAT

1801 CGGCCCTCAG GGGTCCCTGA CCGATTCTCT GGCTCCAAGT CTGGCACCTC AGCCTCCCTG

1861 GCCATCACTG GGCTCCAGGC TGAGGATGAG GCTGATTATT ACTGCCAGTC CTATGACAGC

1921 AGCCTGAGTG GCCTTTATGT CTTCGGAACT GGGACCAAGG TCACCGTCCT AGGTCAGCCC

1981 AAGGCCAACC CCACTGTCAC TCTGTTCCCG CCCTCCTCTG AGGAGCTCCA AGCCAACAAG

2041 GCCACACTAG TGTGTCTGAT CAGTGACTTC TACCCGGGAG CTGTGACAGT GGCCTGGAAG

2101 GCAGATAGCA GCCCCGTCAA GGCGGGAGTG GAGACCACCA CACCCTCCAA ACAAAGCAAC

2161 AACAAGTACG CGGCCAGCAG CTATCTGAGC CTGACGCCTG AGCAGTGGAA GTCCCACAGA

2221 AGCTACAGCT GCCAGGTCAC GCATGAAGGG AGCACCGTGG AGAAGACAGT GGCCCCTACA

2281 GAATGTTCAT AATAAACCGC CTCCACCGGG CGCGCCAATT CTATTTCAAG GAGACAGTCA

2341 TAATGAAATA CCTATTGCCT ACGGCAGCCG CTGGATTGTT ATTACTCGCG GCCCAGCCGG

2401 CCATGGCCGA AGTTCAATTG TTAGAGTCTG GTGGCGGTCT TGTTCAGCCT GGTGGTTCTT

2461 TACGTCTTTC TTGCGCTGCT TCCGGATTCA CTTTCTCTTC GTACGCTATG TCTTGGGTTC

2521 GCCAAGCTCC TGGTAAAGGT TTGGAGTGGG TTTCTGCTAT CTCTGGTTCT GGTGGCAGTA

2581 CTTACTATGC TGACTCCGTT AAAGGTCGCT TCACTATCTC TAGAGACAAC TCTAAGAATA

2641 CTCTCTACTT GCAGATGAAC AGCTTAAGGG CTGAGGACAC TGCAGTCTAC TATTGCGCTA

2701 AAGACTATGA AGGTACTGGT TATGCTTTCG ACATATGGGG TCAAGGTACT ATGGTCACCG

2761 TCTCTAGTGC CTCCACCAAG GGCCCATCGG TCTTCCCCCT GGCACCCTCC TCCAAGAGCA

2821 CCTCTGGGGG CACAGCGGCC CTGGGCTGCC TGGTCAAGGA CTACTTCCCC GAACCGGTGA

2881 CGGTGTCGTG GAACTCAGGC GCCCTGACCA GCGGCGTCCA CACCTTCCCG GCTGTCCTAC

2941 AGTCTAGCGG ACTCTACTCC CTCAGCAGCG TAGTGACCGT GCCCTCTTCT AGCTTGGGCA

3001 CCCAGACCTA CATCTGCAAC GTGAATCACA AGCCCAGCAA CACCAAGGTG GACAAGAAAG

3061 TTGAGCCCAA ATCTTGTGCG GCCGCTCATC ACCACCATCA TCACTCTGCT GAACAAAAAC

3121 TCATCTCAGA AGAGGATCTG AATGGTGCCG CAGATATCAA CGATGATCGT ATGGCTGGCG

3181 CCGCTGAAAC TGTTGAAAGT TGTTTAGCAA AACCCCATAC AGAAAATTCA TTTACTAACG

3241 TCTGGAAAGA CGACAAAACT TTAGATCGTT ACGCTAACTA TGAGGGTTGT CTGTGGAATG

3301 CTACAGGCGT TGTAGTTTGT ACTGGTGACG AAACTCAGTG TTACGGTACA TGGGTTCCTA

3361 TTGGGCTTGC TATCCCTGAA AATGAGGGTG GTGGCTCTGA GGGTGGCGGT TCTGAGGGTG

3421 GCGGTTCTGA GGGTGGCGGT ACTAAACCTC CTGAGTACGG TGATACACCT ATTCCGGGCT

3481 ATACTTATAT CAACCCTCTC GACGGCACTT ATCCGCCTGG TACTGAGCAA AACCCCGCTA
```

TABLE 21B-continued

Sequence of MALIA3, condensed LOCUS MALIA3 9532
CIRCULAR ORIGIN (SEQ ID NO: 451)

```
3541 ATCCTAATCC TTCTCTTGAG GAGTCTCAGC CTCTTAATAC TTTCATGTTT CAGAATAATA

3601 GGTTCCGAAA TAGGCAGGGG GCATTAACTG TTTATACGGG CACTGTTACT CAAGGCACTG

3661 ACCCCGTTAA AACTTATTAC CAGTACACTC CTGTATCATC AAAAGCCATG TATGACGCTT

3721 ACTGGAACGG TAAATTCAGA GACTGCGCTT TCCATTCTGG CTTTAATGAA GATCCATTCG

3781 TTTGTGAATA TCAAGGCCAA TCGTCTGACC TGCCTCAACC TCCTGTCAAT GCTGGCGGCG

3841 GCTCTGGTGG TGGTTCTGGT GGCGGCTCTG AGGGTGGTGG CTCTGAGGGT GGCGGTTCTG

3901 AGGGTGGCGG CTCTGAGGGA GGCGGTTCCG GTGGTGGCTC TGGTTCCGGT GATTTTGATT

3961 ATGAAAAGAT GGCAAACGCT AATAAGGGGG CTATGACCGA AAATGCCGAT GAAAACGCGC

4021 TACAGTCTGA CGCTAAAGGC AAACTTGATT CTGTCGCTAC TGATTACGGT GCTGCTATCG

4081 ATGGTTTCAT TGGTGACGTT TCCGGCCTTG CTAATGGTAA TGGTGCTACT GGTGATTTTG

4141 CTGGCTCTAA TTCCCAAATG GCTCAAGTCG GTGACGGTGA TAATTCACCT TTAATGAATA

4201 ATTTCCGTCA ATATTTACCT TCCCTCCCTC AATCGGTTGA ATGTCGCCCT TTTGTCTTTA

4261 GCGCTGGTAA ACCATATGAA TTTTCTATTG ATTGTGACAA AATAAACTTA TTCCGTGGTG

4321 TCTTTGCGTT TCTTTTATAT GTTGCCACCT TTATGTATGT ATTTTCTACG TTTGCTAACA

4381 TACTGCGTAA TAAGGAGTCT TAATCATGCC AGTTCTTTTG GGTATTCCGT TATTATTGCG

4441 TTTCCTCGGT TTCCTTCTGG TAACTTTGTT CGGCTATCTG CTTACTTTTC TTAAAAGGG

4501 CTTCGGTAAG ATAGCTATTG CTATTTCATT GTTTCTTGCT CTTATTATTG GGCTTAACTC

4561 AATTCTTGTG GGTTATCTCT CTGATATTAG CGCTCAATTA CCCTCTGACT TTGTTCAGGG

4621 TGTTCAGTTA ATTCTCCCGT CTAATGCGCT TCCCTGTTTT TATGTTATTC TCTCTGTAAA

4681 GGCTGCTATT TTCATTTTTG ACGTTAAACA AAAAATCGTT TCTTATTTGG ATTGGGATAA

4741 ATAATATGGC TGTTTATTTT GTAACTGGCA AATTAGGCTC TGGAAAGACG CTCGTTAGCG

4801 TTGGTAAGAT TCAGGATAAA ATTGTAGCTG GGTGCAAAAT AGCAACTAAT CTTGATTTAA

4861 GGCTTCAAAA CCTCCCGCAA GTCGGGAGGT TCGCTAAAAC GCCTCGCGTT CTTAGAATAC

4921 CGGATAAGCC TTCTATATCT GATTTGCTTG CTATTGGGCG CGGTAATGAT TCCTACGATG

4981 AAAATAAAAA CGGCTTGCTT GTTCTCGATG AGTGCGGTAC TTGGTTTAAT ACCCGTTCTT

5041 GGAATGATAA GGAAAGACAG CCGATTATTG ATTGGTTTCT ACATGCTCGT AAATTAGGAT

5101 GGGATATTAT TTTTCTTGTT CAGGACTTAT CTATTGTTGA TAAACAGGCG CGTTCTGCAT

5161 TAGCTGAACA TGTTGTTTAT TGTCGTCGTC TGGACAGAAT TACTTTACCT TTTGTCGGTA

5221 CTTTATATTC TCTTATTACT GGCTCGAAAA TGCCTCTGCC TAAATTACAT GTTGGCGTTG

5281 TTAAATATGG CGATTCTCAA TTAAGCCCTA CTGTTGAGCG TTGGCTTTAT ACTGGTAAGA

5341 ATTTGTATAA CGCATATGAT ACTAAACAGG CTTTTTCTAG TAATTATGAT TCCGGTGTTT

5401 ATTCTTATTT AACGCCTTAT TTATCACACG GTCGGTATTT CAAACCATTA AATTTAGGTC

5461 AGAAGATGAA ATTAACTAAA ATATATTTGA AAAAGTTTTC TCGCGTTCTT TGTCTTGCGA

5521 TTGGATTTGC ATCAGCATTT ACATATAGTT ATATAACCCA ACCTAAGCCG GAGGTTAAAA

5581 AGGTAGTCTC TCAGACCTAT GATTTTGATA AATTCACTAT TGACTCTTCT CAGCGTCTTA

5641 ATCTAAGCTA TCGCTATGTT TTCAAGGATT CTAAGGGAAA ATTAATTAAT AGCGACGATT

5701 TACAGAAGCA AGGTTATTCA CTCACATATA TTGATTTATG TACTGTTTCC ATTAAAAAAG

5761 GTAATTCAAA TGAAATTGTT AAATGTAATT AATTTTGTTT TCTTGATGTT TGTTTCATCA
```

TABLE 21B-continued

Sequence of MALIA3, condensed LOCUS MALIA3 9532
CIRCULAR ORIGIN (SEQ ID NO: 451)

```
5821 TCTTCTTTTG CTCAGGTAAT TGAAATGAAT AATTCGCCTC TGCGCGATTT TGTAACTTGG
5881 TATTCAAAGC AATCAGGCGA ATCCGTTATT GTTTCTCCCG ATGTAAAAGG TACTGTTACT
5941 GTATATTCAT CTGACGTTAA ACCTGAAAAT CTACGCAATT TCTTTATTTC TGTTTTACGT
6001 GCTAATAATT TTGATATGGT TGGTTCAATT CCTTCCATAA TTCAGAAGTA TAATCCAAAC
6061 AATCAGGATT ATATTGATGA ATTGCCATCA TCTGATAATC AGGAATATGA TGATAATTCC
6121 GCTCCTTCTG GTGGTTTCTT TGTTCCGCAA AATGATAATG TTACTCAAAC TTTTAAAATT
6181 AATAACGTTC GGGCAAAGGA TTTAATACGA GTTGTCGAAT TGTTTGTAAA GTCTAATACT
6241 TCTAAATCCT CAAATGTATT ATCTATTGAC GGCTCTAATC TATTAGTTGT TTCTGCACCT
6301 AAAGATATTT TAGATAACCT TCCTCAATTC CTTTCTACTG TTGATTTGCC AACTGACCAG
6361 ATATTGATTG AGGGTTTGAT ATTTGAGGTT CAGCAAGGTG ATGCTTTAGA TTTTTCATTT
6421 GCTGCTGGCT CTCAGCGTGG CACTGTTGCA GGCGGTGTTA ATACTGACCG CCTCACCTCT
6481 GTTTTATCTT CTGCTGGTGG TTCGTTCGGT ATTTTTAATG GCGATGTTTT AGGGCTATCA
6541 GTTCGCGCAT TAAAGACTAA TAGCCATTCA AAAATATTGT CTGTGCCACG TATTCTTACG
6601 CTTTCAGGTC AGAAGGGTTC TATCTCTGTT GGCCAGAATG TCCCTTTTAT TACTGGTCGT
6661 GTGACTGGTG AATCTGCCAA TGTAAATAAT CCATTTCAGA CGATTGAGCG TCAAAATGTA
6721 GGTATTTCCA TGAGCGTTTT TCCTGTTGCA ATGGCTGGCG GTAATATTGT TCTGGATATT
6781 ACCAGCAAGG CCGATAGTTT GAGTTCTTCT ACTCAGGCAA GTGATGTTAT TACTAATCAA
6841 AGAAGTATTG CTACAACGGT TAATTTGCGT GATGGACAGA CTCTTTTACT CGGTGGCCTC
6901 ACTGATTATA AAAACACTTC TCAAGATTCT GGCGTACCGT TCCTGTCTAA ATCCCTTTA
6961 ATCGGCCTCC TGTTTAGCTC CCGCTCTGAT TCCAACGAGG AAAGCACGTT ATACGTGCTC
7021 GTCAAAGCAA CCATAGTACG CGCCCTGTAG CGGCGCATTA AGCGCGGCGG GTGTGGTGGT
7081 TACGCGCAGC GTGACCGCTA CACTTGCCAG CGCCCTAGCG CCCGCTCCTT TCGCTTTCTT
7141 CCCTTCCTTT CTCGCCACGT TCGCCGGCTT TCCCCGTCAA GCTCTAAATC GGGGGCTCCC
7201 TTTAGGGTTC CGATTTAGTG CTTTACGGCA CCTCGACCCC AAAAAACTTG ATTTGGGTGA
7261 TGGTTCACGT AGTGGGCCAT CGCCCTGATA GACGGTTTTT CGCCCTTTGA CGTTGGAGTC
7321 CACGTTCTTT AATAGTGGAC TCTTGTTCCA AACTGGAACA ACACTCAACC CTATCTCGGG
7381 CTATTCTTTT GATTTATAAG GGATTTTGCC GATTTCGGAA CCACCATCAA ACAGGATTTT
7441 CGCCTGCTGG GGCAAACCAG CGTGGACCGC TTGCTGCAAC TCTCTCAGGG CCAGGCGGTG
7501 AAGGGCAATC AGCTGTTGCC CGTCTCACTG GTGAAAAGAA AAACCACCCT GGATCCAAGC
7561 TTGCAGGTGG CACTTTTCGG GGAAATGTGC GCGGAACCCC TATTTGTTTA TTTTTCTAAA
7621 TACATTCAAA TATGTATCCG CTCATGAGAC AATAACCCTG ATAAATGCTT CAATAATATT
7681 GAAAAAGGAA GAGTATGAGT ATTCAACATT TCCGTGTCGC CCTTATTCCC TTTTTTGCGG
7741 CATTTTGCCT TCCTGTTTTT GCTCACCCAG AAACGCTGGT GAAAGTAAAA GATGCTGAAG
7801 ATCAGTTGGG CGCACGAGTG GGTTACATCG AACTGGATCT CAACAGCGGT AAGATCCTTG
7861 AGAGTTTTCG CCCCGAAGAA CGTTTTCCAA TGATGAGCAC TTTTAAAGTT CTGCTATGTC
7921 ATACACTATT ATCCCGTATT GACGCCGGGC AAGAGCAACT CGGTCGCCGG GCGCGGTATT
7981 CTCAGAATGA CTTGGTTGAG TACTCACCAG TCACAGAAAA GCATCTTACG GATGGCATGA
8041 CAGTAAGAGA ATTATGCAGT GCTGCCATAA CCATGAGTGA TAACACTGCG GCCAACTTAC
8101 TTCTGACAAC GATCGGAGGA CCGAAGGAGC TAACCGCTTT TTTGCACAAC ATGGGGGATC
```

TABLE 21B-continued

Sequence of MALIA3, condensed LOCUS MALIA3 9532
CIRCULAR ORIGIN (SEQ ID NO: 451)

```
8161 ATGTAACTCG CCTTGATCGT TGGGAACCGG AGCTGAATGA AGCCATACCA AACGACGAGC

8221 GTGACACCAC GATGCCTGTA GCAATGCCAA CAACGTTGCG CAAACTATTA ACTGGCGAAC

8281 TACTTACTCT AGCTTCCCGG CAACAATTAA TAGACTGGAT GGAGGCGGAT AAAGTTGCAG

8341 GACCACTTCT GCGCTCGGCC CTTCCGGCTG GCTGGTTTAT TGCTGATAAA TCTGGAGCCG

8401 GTGAGCGTGG GTCTCGCGGT ATCATTGCAG CACTGGGGCC AGATGGTAAG CCCTCCCGTA

8461 TCGTAGTTAT CTACACGACG GGGAGTCAGG CAACTATGGA TGAACGAAAT AGACAGATCG

8521 CTGAGATAGG TGCCTCACTG ATTAAGCATT GGTAACTGTC AGACCAAGTT TACTCATATA

8581 TACTTTAGAT TGATTTAAAA CTTCATTTTT AATTTAAAAG GATCTAGGTG AAGATCCTTT

8641 TTGATAATCT CATGACCAAA ATCCCTTAAC GTGAGTTTTC GTTCCACTGT ACGTAAGACC

8701 CCCAAGCTTG TCGACTGAAT GGCGAATGGC GCTTTGCCTG GTTTCCGGCA CCAGAAGCGG

8761 TGCCGGAAAG CTGGCTGGAG TGCGATCTTC CTGAGGCCGA TACTGTCGTC GTCCCCTCAA

8821 ACTGGCAGAT GCACGGTTAC GATGCGCCCA TCTACACCAA CGTAACCTAT CCCATTACGG

8881 TCAATCCGCC GTTTGTTCCC ACGGAGAATC CGACGGGTTG TTACTCGCTC ACATTTAATG

8941 TTGATGAAAG CTGGCTACAG GAAGGCCAGA CGCGAATTAT TTTTGATGGC GTTCCTATTG

9001 GTTAAAAAAT GAGCTGATTT AACAAAAATT TAACGCGAAT TTTAACAAAA TATTAACGTT

9061 TACAATTTAA ATATTTGCTT ATACAATCTT CCTGTTTTTG GGGCTTTTCT GATTATCAAC

9121 CGGGGTACAT ATGATTGACA TGCTAGTTTT ACGATTACCG TTCATCGATT CTCTTGTTTG

9181 CTCCAGACTC TCAGGCAATG ACCTGATAGC CTTTGTAGAT CTCTCAAAAA TAGCTACCCT

9241 CTCCGGCATG AATTTATCAG CTAGAACGGT TGAATATCAT ATTGATGGTG ATTTGACTGT

9301 CTCCGGCCTT TCTCACCCTT TTGAATCTTT ACCTACACAT TACTCAGGCA TTGCATTTAA

9361 AATATATGAG GGTTCTAAAA ATTTTTATCC TTGCGTTGAA ATAAAGGCTT CTCCCGCAAA

9421 AGTATTACAG GGTCATAATG TTTTTGGTAC AACCGATTTA GCTTTATGCT CTGAGGCTTT

9481 ATTGCTTAAT TTTGCTAATT CTTTGCCTTG CCTGTATGAT TTATTGGATG TT
```

TABLE 22

Primers used in RACE amplification:

Heavy chain

| | |
|---|---|
| HuCµ-FOR (1st PCR) | 5'-TGG AAG AGG CAC GTT CTT TTC TTT-3' (SEQ ID NO: 457) |
| HuCµ-Nested (2nd PCR) | 5' CTT TTC TTT GTT GCC GTT GGG GTG-3' (SEQ ID NO: 458) |

Kappa light chain

| | |
|---|---|
| HuCkFor (1st PCR) | 5'-ACA CTC TCC CCT GTT GAA GCT CTT-3' (SEQ ID NO: 459) |
| HuCkForAscI (2nd PCR) | 5'-ACC GCC TCC ACC GGG CGC GCC TTA TTA ACA CTC TCC CCT GTT GAA GCT CTT-3' (SEQ ID NO: 460) |

Lambda light chain HuClambdaFor (1st PCR)

| | |
|---|---|
| HuCL2-FOR | 5'-TGA ACA TTC TGT AGG GGC CAC TG-3' (SEQ ID NO: 461) |
| HuCL7-FOR | 5'-AGA GCA TTC TGC AGG GGC CAC TG-3' (SEQ ID NO: 462) |

HuClambdaForAscI (2nd PCR)

| | |
|---|---|
| HuCL2-FOR-ASC | 5'-ACC GCC TCC ACC GGG CGC GCC TTA TTA TGA ACA TTC TGT AGG GGC CAC TG-3' (SEQ ID NO: 463) |
| HuCL7-FOR-ASC | 5'-ACC GCC TCC ACC GGG CGC GCC TTA TTA AGA GCA TTC TGC AGG GGC CAC TG-3' (SEQ ID NO: 464) |

TABLE 22-continued

Primers used in RACE amplification:

GeneRAcer 5' Primers provided with the kit (Invitrogen)

| | |
|---|---|
| 5'A 1st PCR | (SEQ ID NO: 465) 5'CGACTGGAGCACGAGGACACTGA 3' |
| 5'NA 2nd pCR | 5'GGACACTGACATGGACTGAAGGAGTA-3' (SEQ ID NO: 466) |

TABLE 23

ONs used in Capture of kappa light chains using CJ method and BsmAI

All ONs are written 5' to 3'.

REadapters (6)

| | |
|---|---|
| ON_20SK15O12 | gggAggATggAgAcTgggTc (SEQ ID NO: 467) |
| ON_20SK15L12 | gggAAgATggAgAcTgggTc (SEQ ID NO: 468) |
| ON_20SK15A17 | gggAgAgTggAgAcTgAgTc (SEQ ID NO: 469) |
| ON_20SK15A27 | gggTgccTggAgAcTgcgTc (SEQ ID NO: 470) |
| ON_20SK15A11 | gggTggcTggAgAcTgcgTc (SEQ ID NO: 471) |
| ON_20SK15B3 | gggAgTcTggAgAcTgggTc (residues 1-20 of SEQ ID NO: 477) |

Bridges (6)

| | |
|---|---|
| kapbri1O12 | gggAggATggAgAcTgggTcATcTggATgTcTTgTgcAcTgTgAcAgAgg (SEQ ID NO: 472) |
| kapbri1L12 | gggAAgATggAgAcTgggTcATcTggATgTcTTgTgcAcTgTgAcAgAgg (SEQ ID NO: 473) |
| kapbri1A17 | gggAgAgTggAgAcTgAgTcATcTggATgTcTTgTgcAcTgTgAcAgAgg (SEQ ID NO: 474) |
| kapbri1A27 | gggTgccTggAgAcTgcgTcATcTggATgTcTTgTgcAcTgTgAcAgAgg (SEQ ID NO: 475) |
| kapbri1A11 | gggTggcTggAgAcTgcgTcATcTggATgTcTTgTgcAcTgTgAcAgAgg (SEQ ID NO: 476) |
| kapbri1B3 | gggAgTcTggAgAcTgggTcATcTggATgTcTTgTgcAcTgTgAcAgAgg (SEQ ID NO: 477) |

Extender (5' biotinylated)

| | |
|---|---|
| kapext1bio | ccTcTgTcAcAgTgcAcAAgAcATccAgATgAcccAgTcTcc (SEQ ID NO: 478) |

Primers

| | |
|---|---|
| kaPCRt1 | ccTcTgTcAcAgTgcAcAAgAc (SEQ ID NO: 479) |
| kapfor | 5'-aca ctc tcc cct gtt gaa gct ctt-3' (SEQ ID NO: 480) |

TABLE 24

PCR program for amplification of kappa DNA

| | |
|---|---|
| 95° C. | 5 minutes |
| 95° C. | 15 seconds |
| 65° C. | 30 seconds |
| 72° C. | 1 minute |
| 72° C. | 7 minutes |
| 4° C. | hold |

TABLE 24-continued

PCR program for amplification of kappa DNA

Reagents (100 ul reaction):

| | |
|---|---|
| Template | 50 ng |
| 10x turbo PCR buffer | 1x |
| turbo Pfu | 4U |
| dNTPs | 200 μM each |
| kaPCRt1 | 300 nM |
| kapfor | 300 nM |

TABLE 25 h3401-h2 captured Via CJ with BsmAI
(Nucleotide sequence is SEQ ID NO: 481,
Amino acid sequence is SEQ ID NO: 482)

```
! 1   2   3   4   5   6   7   8   9   10  11  12  13  14  15
! S   A   Q   D   I   Q   M   T   Q   S   P   A   T   L   S
  aGT GCA Caa gac atc cag atg acc cag tct cca gcc acc ctg tct ! ApaLI... a gcc acc ! L25,L6,L20,L2,L16,A11
! Extender.............................. Bridge...

! 16  17  18  19  20  21  22  23  24  25  26  27  28  29  30
! V   S   P   G   E   R   A   T   L   S   C   R   A   S   Q
  gtg tct cca ggg gaa agg gcc acc ctc tcc tgc agg gcc agt cag
```

TABLE 25-continued h3401-h2 captured Via CJ with BsmAI
(Nucleotide sequence is SEQ ID NO: 481,
Amino acid sequence is SEQ ID NO: 482)

```
! 31  32  33  34  35  36  37  38  39  40  41  42  43  44  45
!  S   V   S   N   N   L   A   W   Y   Q   Q   K   P   G   Q
  agt gtt agt aac aac tta gcc tgg tac cag cag aaa cct ggc cag ! 46  47  48  49  50  51  52  53  54  55  56  57  58  59  60
!  V   P   R   L   L   I   Y   G   A   S   T   R   A   T   D
  gtt ccc agg ctc ctc atc tat ggt gca tcc acc agg gcc act gat ! 61  62  63  64  65  66  67  68  69  70  71  72  73  74  75
!  I   P   A   R   F   S   G   S   G   S   G   T   D   F   T
  atc cca gcc agg ttc agt ggc agt ggg tct ggg aca gac ttc act ! 76  77  78  79  80  81  82  83  84  85  86  87  88  89  90
!  L   T   I   S   R   L   E   P   E   D   F   A   V   Y   Y
  ctc acc atc agc aga ctg gag cct gaa gat ttt gca gtg tat tac ! 91  92  93  94  95  96  97  98  99 100 101 102 103 104 105
!  C   Q   R   Y   G   S   S   P   G   W   T   F   G   Q   G
  tgt cag cgg tat ggt agc tca ccg ggg tgg acg ttc ggc caa ggg ! 106 107 108 109 110 111 112 113 114 115 116 117 118 119 120
!  T   K   V   E   I   K   R   T   V   A   A   P   S   V   F
  acc aag gtg gaa atc aaa cga act gtg gct gca cca tct gtc ttc ! 121 122 123 124 125 126 127 128 129 130 131 132 133 134 135
!  I   F   P   P   S   D   E   Q   L   K   S   T   A   A   S
  atc ttc ccg cca tct gat gag cag ttg aaa tct gga act gcc tct ! 136 137 138 139 140 141 142 143 144 145 146 147 148 149 150
!  V   V   C   L   L   N   N   F   Y   P   R   E   A   K   V
  gtt gtg tgc ctg ctg aat aac ttc tat ccc aga gag gcc aaa gta ! 151 152 153 154 155 156 157 158 159 160 161 162 163 164 165
!  Q   W   K   V   D   N   A   L   Q   S   G   N   S   Q   E
  cag tgg aag gtg gat aac gcc ctc caa tcg ggt aac tcc cag gag ! 166 167 168 169 170 171 172 173 174 175 176 177 178 179 180
!  S   V   T   E   Q   D   S   K   D   S   T   Y   S   L   S
  agt gtc aca gag cag gac agc aag gac agc acc tac agc ctc agc ! 181 182 183 184 185 186 187 188 189 190 191 192 193 194 195
!  S   T   L   T   L   S   K   A   D   Y   E   K   H   K   V
  agc acc ctg acg ctg agc aaa gca gac tac gag aaa cac aaa gtc ! 196 197 198 199 200 201 202 203 204 205 206 207 208 209 210
!  Y   A   C   E   V   T   H   Q   G   L   S   S   P   V   T
  tac gcc tgc gaa gtc acc cat cag ggc ctg agc tcg cct gtc aca ! 211 212 213 214 215 216 217 218 219 220 221 222 223
!  K   S   F   N   K   G   E   C   K   G   E   F   A
  aag agc ttc aac aaa gga gag tgt aag ggc gaa ttc gc
```

TABLE 26 h3401-d8 KAPPA captured with CJ and BsmAI
(Nucleotide sequence is SEQ ID NO: 484;
Amino acid sequence is SEQ ID NO: 485)

```
!  1   2   3   4   5   6   7   8   9  10  11  12  13  14  15
!  S   A   Q   D   I   Q   M   T   Q   S   P   A   T   L   S
 aGT GCA Caa gac atc cag atg acc cag tct cct gcc acc ctg tct !ApaLI...Extender..........a gcc acc ! L25,L6,L20,L2,L16,A11
!A GCC ACC CTG TCT ! L2 (SEQ ID NO: 483)

! 16  17  18  19  20  21  22  23  24  25  26  27  28  29  30
!  V   S   P   G   E   R   A   T   L   S   C   R   A   S   Q
  gtg tct cca ggt gaa aga gcc acc ctc tcc tgc agg gcc agt cag
! GTG TCT CCA GGG GAA AGA GCC ACC CTC TCC TGC ! L2

! 31  32  33  34  35  36  37  38  39  40  41  42  43  44  45
   N   L   L   S   N   L   A   W   Y   Q   Q   K   P   G   Q
  aat ctt ctc agc aac tta gcc tgg tac cag cag aaa cct ggc cag
```

TABLE 26-continued h3401-d8 KAPPA captured with CJ and BsmAI
(Nucleotide sequence is SEQ ID NO: 484;
Amino acid sequence is SEQ ID NO: 485)

```
! 46  47  48  49  50  51  52  53  54  55  56  57  58  59  60
! A   P   R   L   L   I   Y   G   A   S   T   G   A   I   G
  gct ccc agg ctc ctc atc tat ggt gct tcc acc ggg gcc att ggt ! 61  62  63  64  65  66  67  68  69  70  71  72  73  74  75
! I   P   A   R   F   S   G   S   G   S   G   T   E   F   T
  atc cca gcc agg ttc agt ggc agt ggg tct ggg aca gag ttc act ! 76  77  78  79  80  81  82  83  84  85  86  87  88  89  90
! L   T   I   S   S   L   Q   S   E   D   F   A   V   Y   F
  ctc acc atc agc agc ctg cag tct gaa gat ttt gca gtg tat ttc ! 91  92  93  94  95  96  97  98  99  100 101 102 103 104 105
! C   Q   Q   Y   G   T   S   P   P   T   F   G   G   G   T
  tgt cag cag tat ggt acc tca ccg ccc act ttc ggc gga ggg acc ! 106 107 108 109 110 111 112 113 114 115 116 117 118 119 120
! K   V   E   I   K   R   T   V   A   A   P   S   V   F   I
  aag gtg gag atc aaa cga act gtg gct gca cca tct gtc ttc atc ! 121 122 123 124 125 126 127 128 129 130 131 132 133 134 135
  F   P   P   S   D   E   Q   L   K   S   G   T   A   S   V
  ttc ccg cca tct gat gag cag ttg aaa tct gga act gcc tct gtt ! 136 137 138 139 140 141 142 143 144 145 146 147 148 149 150
! V   C   P   L   N   N   F   Y   P   R   E   A   K   V   Q
  gtg tgc ccg ctg aat aac ttc tat ccc aga gag gcc aaa gta cag ! 151 152 153 154 155 156 157 158 159 160 161 162 163 164 165
! W   K   V   D   N   A   L   Q   S   G   N   S   Q   E   S
  tgg aag gtg gat aac gcc ctc caa tcg ggt aac tcc cag gag agt ! 166 167 168 169 170 171 172 173 174 175 176 177 178 179 180
! V   T   E   Q   D   N   K   D   S   T   Y   S   L   S   S
  gtc aca gag cag gac aac aag gac agc acc tac agc ctc agc agc ! 181 182 183 184 185 186 187 188 189 190 191 192 193 194 195
! T   L   T   L   S   K   V   D   Y   E   K   H   E   V   Y
  acc ctg acg ctg agc aaa gta gac tac gag aaa cac gaa gtc tac ! 196 197 198 199 200 201 202 203 204 205 206 207 208 209 210
! A   C   E   V   T   H   Q   G   L   S   S   P   V   T   K
  gcc tgc gaa gtc acc cat cag ggc ctt agc tcg ccc gtc acg aag ! 211 212 213 214 215 216 217 218 219 220 221 222 223
! S   F   N   R   G   E   C   K   K   E   F   V
  agc ttc aac agg gga gag tgt aag aaa gaa ttc gtt t
```

TABLE 27

V3-23 VH framework with variegated codons shown

```
!(Nucleotide sequence is SEQ ID NO: 486; Amino acid sequence is SEQ ID NO: 487)
!             17 18 19 20 21 22
!              A  Q  P  A  M  A
     5'-ctg tct gaa cG GCC cag ccG GCC atg gcc        29
     3'-gac aga ctt gc cgg gtc ggc cgg tac cgg
!          Scab.......SfiI........
!                     NgoMI....
!                       NcoI....

!                                FRI(DP47/V3-23---------------
!               !                23 24 25 26 27 28 29 30
!               !                 E  V  Q  L  L  E  S  G
!               !                gaa|gtt|CAA|TTG|tta|gag|tct|ggt|   53
!               !                ctt|caa|gtt|aac|aat|ctc|aga|cca|
!                                    |MfeI  |
```

TABLE 27-continued

V3-23 VH framework with variegated codons shown

```
! -------------FR1----------------------------------
! 31  32  33  34  35  36  37  38  39  40  41  42  43  44  45
!  G   G   L   V   Q   P   G   G   S   L   R   L   S   C   A
  |ggc|ggt|ctt|gtt|cag|cct|ggt|ggt|tct|tta|cgt|ctt|tct|tgc|gct|   98
! |ccg|cca|gaa|caa|gtc|gga|cca|cca|aga|aat|gca|gaa|aga|acg|cga|

! Sites to be varied--->      ***         ***         ***
! ----FR1-------------->|...CDR1............|--FR2------
! 46  47  48  49  50  51  52  53  54  55  56  57  58  59  60
!  A   S   G   F   T   F   S   S   Y   A   M   S   W   V   R
  |gct|TCC|GGA|ttc|act|ttc|tct|tCG|TAC|Gct|atg|tct|tgg|gtt|cgC|  143
! |cga|agg|cct|aag|tga|aag|aga|agc|atg|cga|tac|aga|acc|caa|gcg|
!    |BspEI|               |BsiWI|               |BstXI.

!               Sites to be varies--->***    *** ***
! ------FR2---------------------------->|..CDR2........
! 61  62  63  64  65  66  67  68  69  70  71  72  73  74  75
!  Q   A   P   G   K   G   L   E   W   V   S   A   I   S   G
  |CAa|gct|ccT|GGt|aaa|ggt|ttg|gag|tgg|gtt|tct|gct|atc|tct|ggt|  188
! |gtt|cga|gga|cca|ttt|cca|aac|ctc|acc|caa|aga|cga|tag|aga|cca|
! BstXI       |

!    ***          ***
! ..CDR2..............................|---FR3----
! 76  77  78  79  80  81  82  83  84  85  86  87  88  89  90
!  S   G   G   S   T   Y   Y   A   D   S   V   K   G   R   F
  |tct|ggt|ggc|agt|act|tac|tat|gct|gac|tcc|gtt|aaa|ggt|cgc|ttc|  233
! |aga|cca|ccg|tca|tga|atg|ata|cga|ctg|agg|caa|ttt|cca|gcg|aag|

! --------FR3---------------------------
!  91  92  93  94  95  96  97  98  99 100 101 102 103 104 105
!   T   I   S   R   D   N   S   K   N   T   L   Y   L   Q   M
  |act|atc|TCT|AGA|gac|aac|tct|aag|aat|act|ctc|tac|ttg|cag|atg|  278
! |tga|tag|aga|tct|ctg|ttg|aga|ttc|tta|tga|gag|atg|aac|gtc|tac|
!         |XbaI|

! ---FR3----------------------------------->|
! 106 107 108 109 110 111 112 113 114 115 116 117 118 119 120
!  N   S   L   R   A   E   D   T   A   V   Y   Y   C   A   K
  |aac|agC|TTA|AGg|gct|gag|gac|aCT|GCA|Gtc|tac|tat|tgc|gct|aaa|  323
! |ttg|tcg|aat|tcc|cga|ctc|ctg|tga|cgt|cag|atg|ata|acg|cga|ttt|
!         |AflII|            |PstI|

! ......CDR3..........|---FR4--------------------
!  121 122 123 124 125 126 127 128 129 130 131 132 133 134 135
!   D   Y   E   G   T   G   Y   A   F   D   I   W   G   Q   G
  |gac|tat|gaa|ggt|act|ggt|tat|gct|ttc|gaC|ATA|TGg|ggt|caa|ggt|  368
! |ctg|ata|ctt|cca|tga|cca|ata|cga|aag|ctg|tat|acc|cca|gtt|cca|
!                                     |NdeI|

! ------------FR4-----|
!  136 137 138 139 140 141 142
!   T   M   V   T   V   S   S
  |act|atG|GTC|ACC|gtc|tct|agt-  389
! |tga|tac|cag|tgg|cag|aga|tca-
!         |BstEII|

!                 ! 143 144 145 146 147 148 149 150 151 152
!                 !  A   S   T   K   G   P   S   V   F   P
!                 ! gcc tcc acc aaG GGC CCa tcg GTC TTC ccc-3'  419
                    cgg agg tgg ttc ccg ggt agc cag aag ggg-5'
!                       Bsp120I.    BbsI...(2/2)
!                       ApaI...
```

(SFPRMET) 5'-ctg tct gaa cG GCC cag ccG-3' (SEQ ID NO: 488)
(TOPFR1A) 5'-ctg tct gaa cG GCC cag ccG GCC atg gcc-
    gaa|gtt|CAA|TTG|tta|gag|tct|ggt|-
    |ggc|ggt|ctt|gtt|cag|cct|ggt|ggt|tct|tta-3' (SEQ ID NO: 489)
(BOTFR1B)            3'-caa|gtc|gga|cca|cca|aga|aat|gca|gaa|aga|acg|cga|-
    |cga|agg|cct|aag|tga|aag-5'! bottom strand (SEQ ID NO: 490)
(BOTFR2) 3'-acc|caa|gcg|-
    |gtt|cga|gga|cca|ttt|cca|aac|ctc|acc|caa|aga|-5'!bottom strand (SEQ ID NO: 491)

TABLE 27-continued

V3-23 VH framework with variegated codons shown

```
(BOTFR3)  3'-a|cga|ctg|agg|caa|ttt|cca|gcg|aag|-
             |tga|tag|aga|tct|ctg|ttg|aga|ttc|tta|tga|gag|atg|aac|gtc|tac|-
           |ttg|tcg|aat|tcc|cga|ctc|ctg|tga-5' (SEQ ID NO: 492)
(F06)    5'-gC|TTA|AGg|gct|gag|gac|aCT|GCA|Gtc|tac|tat|tgc|gct|aaa|-
             |gac|tat|gaa|ggt|act|ggt|tat|gct|ttc|gaC|ATA|TGg|ggt|c-3' (SEQ ID NO: 493)
(BOTFR4)  3'-cga|aag|ctg|tat|acc|cca|gtt|cca|-
             |tga|tac|cag|tgg|cag|aga|tca-
               cgg agg tgg ttc ccg ggt agc cag aag ggg-5' ! bottom strand (SEQ ID NO: 494)
(BOTPRCPRIM)            3'-gg-ttc ccg ggt agc cag aag ggg-5' (SE

TABLE 29

DNA sequence of pCES5

```
! pCES5 6680 bases = pCes4 with stuffers in CDR1-2 and CDR3 2000.12.13
!
! Ngene = 6680
! Useful REs (cut MAnoLI fewer than 3 times) 2000.06.05
!
! Non-cutters
!Acc65I Ggtacc            AfeI AGCgct           AvrII Cctagg
!BsaBI GATNNnnatc         BsiWI Cgtacg          Bsm-
                                                FI Nnnnnnnnnnnnnnngtccc
(SEQ ID NO: 499)                                    (SEQ ID NO: 500)
!BsrGI Tgtaca             BstAPI GCANNNNntgc BstBI Ttcgaa
                               (SEQ ID NO: 501)
!BstZ17I GTAtac           BtrI CACgtg           Ecl136I GAGctc
!EcoRV GATatc             FseI GGCCGGcc         KpnI GGTACc
!MscI TGGcca              NruI TCGcga           NsiI ATGCAt
!PacI TTAATtaa            PmeI GTTTaaac         PmlI CACgtg
!PpuMI RGgwccy            PshAI GACNNnngtc      SacI GAGCTc
                              (SEQ ID NO: 502)
!SacII CCGCgg             SbfI CCTGCAgg         SexAI Accwggt
!SgfI GCGATcgc            SnaBI TACgta          SpeI Actagt
!SphI GCATGc              Sse8387I CCTGCAgg     StuI AGGcct
!SwaI ATTTaaat            XmaI Cccggg
!
! cutters
! Enzymes that cut more than    3 times.
!AlwNI CAGNNNctg           5
!BsgI ctgcac               4
!BsrFI Rccggy              5
!EarI CTCTTCNnnn           4
(SEQ ID NO: 625)
!FauI nNNNNNGCGGG                     10
! (SEQ ID NO: 503)
!Enzymes that cut from 1 to    3 times.
!
!EcoO109I RGgnccy           3      7  2636  4208
!BssSI Ctcgtg               1     12
!-" - Cacgag                1   1703
!BspHI Tcatga               3     43   148  1156
!AatII GACGTc               1     65
!BciVI GTATCCNNNNNN                2    140  1667
(SEQ ID NO: 504)
!Eco57I CTGAAG              1    301
!-" - cttcag                2   1349
!AvaI Cycgrg                3    319  2347  6137
!BsiHKAI GWGCWc             3    401  2321  4245
!HgiAI GWGCWc               3    401  2321  4245
!BcgI gcannnnnntcg          1    461
(SEQ ID NO: 505)
!SacI AGTact                1    505
!PvuI CGATcg                3    616  3598  5926
!FspI TGCgca                2    763  5946
!BglI GCCNNNNNnggc          3    864  2771  5952
(SEQ ID NO: 506)
!BpmI CTGGAG                1    898
!-" - ctccag                1   4413
!BsaI GGTCTCNnnnn           1    916
(SEQ ID NO: 507)
!AhdI GACNNNnngtc           1    983
(SEQ ID NO: 508)
!Eam1105I GACNNNnngtc       1    983
(SEQ ID NO: 509)
!DrdI GACNNNNnngtc          3   1768  6197  6579
(SEQ ID NO: 510)
!SapI gaagagc               1   1998
!PvuII CAGctg               3   2054  3689  5896
!PflMI CCANNNNntgg          3   2233  3943  3991
(SEQ ID NO: 511)
!HindIII Aagctt             1   2235
!ApaLI Gtgcac               1   2321
!BspMI Nnnnnnnnnngcaggt     1   2328
(SEQ ID NO: 512)
!-" - ACCTGCNNNNn           2   3460
(SEQ ID NO: 513)
!PstI CTGCAg                1   2335
!AccI GTmkac                2   2341  2611
!HincII GTYrac              2   2341  3730
!SalI Gtcgac                1   2341
!TliI Ctcgag                1   2347
```

TABLE 29-continued

DNA sequence of pCES5

```
!XhoI Ctcgag                      1  2347
!BbsI gtcttc                      2  2383  4219
!BlpI GCtnagc                     1  2580
!EspI GCtnagc                     1  2580
!SgrAI CRccggyg                   1  2648
!AgeI Accggt                      2  2649  4302
!AscI GGcgcgcc                    1  2689
!BssHII Gcgcgc                    1  2690
!SfiI GGCCNNNNaggcc               1  2770
(SEQ ID NO: 514)
!NaeI GCCggc                      2  2776  6349
!NgoMIV Gccggc                    2  2776  6349
!BtgI Ccrygg                      3  2781  3553  5712
!DsaI Ccrygg                      3  2781  3553  5712
!NcoI Ccatgg                      1  2781
!StyI Ccwwgg                      3  2781  4205  4472
!MfeI Caattg                      1  2795
!BspEI Tccgga                     1  2861
!BglII Agatct                     1  2872
!BclI Tgatca                      1  2956
!Bsu36I CCtnagg                   3  3004  4143  4373
!XcmI CCANNNNNnnnntgg             1  3215
(SEQ ID NO: 515)
!MluI Acgcgt                      1  3527
!HpaI GTTaac                      1  3730
!XbaI Tctaga                      1  3767
!
!AflII Cttaag                     1  3811
!BsmI NGcattc                     1  3821
!-" - GAATGCN                     1  4695
!RsrII CGgwccg                    1  3827
!NheI Gctagc                      1  4166
!BstEII Ggtnacc                   1  4182
!BsmBI CGTCTCNnnnn                2  4188  6625
(SEQ ID NO: 516)
!-" - Nnnnnngagacg                1  6673
(SEQ ID NO: 517)
!ApaI GGGCCc                      1  4209
!BanII GRGCYc                     3  4209  4492  6319
!Bsp1201 Gggccc                   1  4209
!PspOMI Gggccc                    1  4209
!BseRI NNnnnnnnnnctcctc           1  4226
(SEQ ID NO: 518)
!-" - GAGGAGNNNNNNNNNN            1  4957
(SEQ ID NO: 519)
!EcoNI CCTNNnnnagg                1  4278
(SEQ ID NO: 520)
!PflFI GACNnngtc                  1  4308
!Tth111I GACNnngtc                1  4308
!KasI Ggcgcc                      2  4327  5967
!BstXI CCANNNNNntgg               1  4415
(SEQ ID NO: 521)
!NotI GCggccgc                    1  4507
!EagI Cggccg                      1  4508
!BamHI Ggatcc                     1  5169
!BspDI ATcgat                     1  5476
!NdeI CAtatg                      1  5672
!EcoRI Gaattc                     1  5806
!PsiI TTAtaa                      1  6118
!DraIII CACNNNgtg                 1  6243
!BsaAI YACgtr                     1  6246
!-------------------------------------
(Nucleotide sequence is SEQ ID NO: 522 and Amino acid sequence is
SEQ ID NO: 523, respectively)
    1   gacgaaaggg cCTCGTGata cgcctatttt tataggttaa tgtcatgata ataatggttt
!               BsssI.(1/2)
   61   cttaGACGTC aggtggcact tttcggggaa atgtgcgcgg aaccccctatt tgtttatttt
!           AatI.
  121   tctaaataca ttcaaatatG TATCCgctca tgagacaata accctgataa atgcttcaat
!                       BciVI..(1 of 2)
  181   aatattgaaa aaggaagagt
! Base # 201 to 1061 = ApR gene from pUC119 with some RE sites removed
!
!         1   2   3   4   5   6   7   8   9  10  11  12  13  14  15
!        fM   S   I   Q   H   F   R   V   A   L   I   P   F   F   A
  201   atg agt att caa cat ttc cgt gtc gcc ctt att ccc ttt ttt gcg
!
```

TABLE 29-continued

DNA sequence of pCES5

```
!         16  17  18  19  20  21  22  23  24  25  26  27  28  29  30
!          A   F   C   L   P   V   F   A   H   P   E   T   L   V   K
 246      gca ttt tgc ctt cct gtt ttt gct cac cca gaa acg ctg gtg aaa
!
!         31  32  33  34  35  36  37  38  39  40  41  42  43  44  45
!          V   K   D   A   E   D   Q   L   G   A   R   V   G   Y   I
 291      gta aaa gat gct gaa gat cag ttg ggt gcc cga gtg ggt tac atc
!
!         46  47  48  49  50  51  52  53  54  55  56  57  58  59  60
!          E   L   D   L   N   S   G   K   I   L   E   S   F   R   P
 336      gaa ctg gat ctc aac agc ggt aag atc ctt gag agt ttt cgc ccc
!
!         61  62  63  64  65  66  67  68  69  70  71  72  73  74  75
!          E   E   R   F   P   M   M   S   T   F   K   V   L   L   C
 381      gaa gaa cgt ttt cca atg atg agc act ttt aaa gtt ctg cta tgt
!
!         76  77  78  79  80  81  82  83  84  85  86  87  88  89  90
!          G   A   V   L   S   R   I   D   A   G   Q   E   Q   L   G
 426      ggc gcg gta tta tcc cgt att gac gcc ggg caa gaG CAa ctc ggT
!                                                        BcgI.........
!
!         91  92  93  94  95  96  97  98  99 100 101 102 103 104 105
!          R   R   I   H   Y   S   Q   N   D   L   V   E   Y   S   P
 471      CGc cgc ata cac tat tct cag aat gac ttg gtt gAG TAC Tca cca
!..BcgI....                                              ScaI....
!
!        106 107 108 109 110 111 112 113 114 115 116 117 118 119 120
!          V   T   E   K   H   L   T   D   G   M   T   V   R   E   L
 516      gtc aca gaa aag cat ctt acg gat ggc atg aca gta aga gaa tta
!
!        121 122 123 124 125 126 127 128 129 130 131 132 133 134 135
!          C   S   A   A   I   T   M   S   D   N   T   A   A   N   L
 561      tgc agt gct gcc ata acc atg agt gat aac act gcg gcc aac tta
!
!        136 137 138 139 140 141 142 143 144 145 146 147 148 149 150
!          L   L   T   T   I   G   G   P   K   E   L   T   A   F   L
 606      ctt ctg aca aCG ATC Gga gga ccg aag gag cta acc gct ttt ttg
!                     PvuI.... (1/2)
!
!        151 152 153 154 155 156 157 158 159 160 161 162 163 164 165
!          H   N   M   G   D   H   V   T   R   L   D   R   W   E   P
 651      cac aac atg ggg gat cat gta act cgc ctt gat cgt tgg gaa ccg
!
!        166 167 168 169 170 171 172 173 174 175 176 177 178 179 180
!          E   L   N   E   A   I   P   N   D   E   R   D   T   T   M
 696      gag ctg aat gaa gcc ata cca aac gac gag cgt gac acc acg atg
!
!        181 182 183 184 185 186 187 188 189 190 191 192 193 194 195
!          P   V   A   M   A   T   T   L   R   K   L   L   T   G   E
 741      cct gta GCA ATG gca aca acg tTG CGC Aaa cta tta act ggc gaa
!                 BsrDI..(1/2)   FspI.... (1/2)
!
!        196 197 198 199 200 201 202 203 204 205 206 207 208 209 210
!          L   L   T   L   A   S   R   Q   Q   L   I   D   W   M   E
 786      cta ctt act cta gct tcc cgg caa caa tta ata gac tgg atg gag
!
!        211 212 213 214 215 216 217 218 219 220 221 222 223 224 225
!          A   D   K   V   A   G   P   L   L   R   S   A   L   P   A
 831      gcg gat aaa gtt gca gga cca ctt ctg cgc tcg gcc ctt ccg gct
!
!        226 227 228 229 230 231 232 233 234 235 236 237 238 239 240
!          G   W   F   I   A   D   K   S   G   A   G   E   R   G   S
 876      ggc tgg ttt att gct gat aaa tCT GGA Gcc ggt gag cgt gGG TCT
!                                     BpmI....(1/2)      BsaI....
!
!        241 242 243 244 245 246 247 248 249 250 251 252 253 254 255
!          R   G   I   I   A   L   G   P   D   G   K   P   S   R
 921      Cgc ggt atC ATT GCa gca ctg ggg cca gat ggt aag ccc tcc cgt
!BsaI......      BsrDI...(2/2)
!
!        256 257 258 259 260 261 262 263 264 265 266 267 268 269 270
!          I   V   V   I   Y   T   T   G   S   Q   A   T   M   D   E
 966      atc gta gtt atc tac acG ACg ggg aGT Cag gca act atg gat gaa
!                                AhdI........
!
!        271 272 273 274 275 276 277 278 279 280 281 282 283 284 285
!          R   N   R   Q   I   A   E   I   G   A   S   L   K   H
1011      cga cct aga cag atc gct gag ata ggt gcc tca ctg agg aag cat
```

TABLE 29-continued

DNA sequence of pCES5

```
            286 287
            W
1056   tgg taa
1062                               ctgtcagac caagtttact
1081   catatatact ttagattgat ttaaaacttc atttttaatt taaaaggatc taggtgaaga
1141   tccttttga taatctcatg accaaaatcc cttaacgtga gttttcgttc cactgagcgt
1201   cagaccccgt agaaaagatc aaaggatctt cttgagatcc ttttttttctg cgcgtaatct
1261   gctgcttgca aacaaaaaaa ccaccgctac cagcggtggt ttgtttgccg gatcaagagc
1321   taccaactct ttttccgaag gtaactggct tcagcagagc gcagatacca aatactgtcc
1381   ttctagtgta gccgtagtta ggccaccact tcaagaactc tgtagcaccg cctacatacc
1441   tcgctctgct aatcctgtta ccagtggctg ctgccagtgg cgataagtcg tgtcttaccg
1501   ggttggactc aagacgatag ttaccggata aggcgcagcg gtcgggctga acggggggtt
1561   cgtgcataca gcccagcttg gagcgaacga cctacaccga actgagatac ctacagcgtg
1621   agcattgaga aagcgccacg cttcccgaag ggagaaaggc ggacagGTAT CCggtaagcg
                                        BciVI.. (2 of 2)
1681   gcagggtcgg aacaggagag cgCACGAGgg agcttccagg gggaaacgcc tggtatgttt
                    BsssI.(2/2)
1741   atagtcctgt cgggtttcgc cacctctgac ttgagcgtcg attttttgtga tgctcgtcag
1801   ggggcggag cctatggaaa aacgccagca acgcggcctt tttacggttc ctggccttt
1861   gctggccttt tgctcACATG Ttctttcctg cgttatcccc tgattctgtg gataaccgta
                    PciI...
1921   ttaccgcctt tgagtgagct gataccgctc gccgcagccg aacgaccgag cgcagcgagt
1981   cagtgagcga ggaagcgGAA GAGCgcccaa tacgcaaacc gcctctcccc gcgcgttggc
                    SapI....
2041   cgattcatta atgCAGCTGg cacgacaggt ttcccgactg gaaagcgggc agtgagcgca
                    PvuII.(1/3)
2101   acgcaaTAA TGTgagttag ctcactcatt aggcaccccca ggcTTTACAc tttatgcttc
           ..35..       Plac          ..-10.
2161   cggctcgtat gttgtgtgga attgtgagcg gataacaatt tcacaCAGGA AACAGCTATG
                                                     M13Rev_seq_primer
2221   ACcatgatta cgCCAAGCTT TGGagccttt tttttggaga ttttcaac
           PflMI.......
            Hind3.
!signal::linker::CLight (Amino acid sequence is SEQ ID NO: 524)
       1   2   3   4   5   6   7   8   9   10  11  12  13  14  15
       fM  K   K   L   L   F   A   I   P   L   V   V   P   F   Y
2269   gtg aaa aaa tta tta ttc gca att cct tta gtt gtt cct ttc tat Linker.................End of FR4
       16  17  18  19  20  21  22  23  24  25  26  27  28  29  30
       S   H   S   A   Q   V   Q   L   Q   V   D   L   E   I   K
2314   tct cac aGT GCA Cag gtc caa CTG CAG GTC GAC CTC GAG atc aaa
            ApaLI..... PstI...    XhoI...
                       BspMI...
                       SalI...
                       AccI...(1/2)
                       HincII.(1/2)

!Vlight domains could be cloned in as ApaLI-XhoI fragments.
!VL-CL(kappa) segments can be cloned in as ApaLI-AscI fragments. <------

31  32  33  34  35  36  37  38  39  40  41  42  43  44  45
       R   G   T   V   A   A   P   S   V   F   I   F   P   P   S
2359   cgt gga act gtg gct gca cca tct GTC TTC atc ttc ccg cca tct
                                   BbsI...(1/2)

46  47  48  49  50  51  52  53  54  55  56  57  58  59  60
       D   E   Q   L   K   S   G   T   A   S   V   V   C   L   L
2404   gat gag cag ttg aaa tct gga act gcc tct gtt gtg tgc ctg ctg 61  62  63  64  65  66  67  68  69  70  71  72  73  74  75
       N   N   F   Y   P   R   E   A   K   V   Q   W   K   V   D
2449   aat aac ttc tat ccc aga gag gcc aaa gta cag tgg aag gtg gat 76  77  78  79  80  81  82  83  84  85  86  87  88  89  90
       N   A   L   Q   S   G   N   S   Q   E   S   V   T   E   Q
2494   aac gcc ctc caa tcg ggt aac tcc cag gag agt gtc aca gag cag 91  92  93  94  95  96  97  98  99  100 101 102 103 104 105
       D   S   K   D   S   T   Y   S   L   S   S   T   L   T   L
2539   gac agc aag gac agc acc tac agc ctc agc agc acc ctg acG CTG
                                                          EspI...
```

TABLE 29-continued

DNA sequence of pCES5

```
!         106 107 108 109 110 111 112 113 114 115 116 117 118 119 120
!          S   K   A   D   Y   E   K   H   K   V   Y   A   C   E   V
2584      AGC aaa gca gac tac gag aaa cac aaa GTC TAC gcc tgc gaa gtc
!     ...EspI....              AccI...(2/2)
!
!         121 122 123 124 125 126 127 128 129 130 131 132 133 134 135
!          T   H   Q   G   L   S   P   V   T   K   S   F   N   R
2629      acc cat cag ggc ctg agt tcA CCG GTg aca aag agc ttc aag agg
!                                    AgeI....(1/2)
!
!         136 137 138 139 140
!          G   E   C   .   .
2674      gga gag tgt taa taa GG CGCGCCaatt
!                             AscI.....
!                              BssHII.
!
2701      ctatttcaag gagacagtca ta
!
!PelB::3-23(stuffed)::CH1::III fusion gene
!
!            (Amino acid sequence is SEQ ID NO: 525)
!          1   2   3   4   5   6   7   8   9  10  11  12  13  14  15
!          M   K   Y   L   L   P   T   A   A   A   G   L   L   L   L
2723      atg aaa tac cta ttg cct acg gca gcc gct gga ttg tta tta ctc
!
!-----------------------------------
!
!         16  17  18  19  20  21  22
!          A   A   Q   P   A   M   A
2768      gcG GCC cag ccG GCC atg gcc
!         SfiI..........
!             NgoMIV..(1/2)
!              NcoI....
!
!         FR1(DP47/V3-23)--------------
!         23  24  25  26  27  28  29  30
!          E   V   Q   L   L   E   S   G
2789      gaa|gtt|CAA|TTG|tta|gag|tct|ggt|
!            |MfeI|
!
!         ------------FR1----------------------------
!         31  32  33  34  35  36  37  38  39  40  41  42  43  44  45
!          G   G   L   V   Q   P   G   G   S   L   R   L   S   C   A
2813      |ggc|ggt|ctt|gtt|cag|cct|ggt|ggt|tct|tta|cgt|ctt|tct|tgc|gct|
!
!         ---FR1-----
!         46  47  48
!          A   S   G
2858      |gct|TCC|GGA|
!         |BspEI|
!
!         Stuffer for CDR1, FR2, and CDR2--------------------------------->
!         There are no stop codons in this stuffer.
2867                                    gcttcAGATC Tgtttgcctt
!                                            BglII..
2887      tttgtggggt ggtgcagatc gcgttacgga gatcgaccga ctgcttgagc aaaagccacg
2947      cttaactgcT GATCAggcat gggatgttat tcgccaaacc agtcgtcagg atcttaacct
!             BcII...
3007      gaggcttttt ttacctactc tgcaagcagc gacatctggt ttgacacaga gcgatccgcg
3067      tcgtcagttg gtagaaacat taacacgttg ggatggcatc aatttgctta atgatgatgg
3127      taaaacctgg cagcagccag gctctgccat cctgaacgtt tggctgacca gtatgttgaa
3187      gcgtaccgta gtggctgccg tacctatgCC Atttgataag TGGtacagcg ccagtggcta
!                                XcmI.........
3247      cgaaacaacc caggacggcc caactggttc gctgaatata agtgttggag caaaaatttt
3307      gtatgaggcg gtgcagggag acaaatcacc aatcccacag gcggttgatc tgtttgctgg
3367      gaaaccacag caggaggttg tgttggctgc gctggaagat acctgggaga ctcctttccaa
3427      acgctatggc aataatgtga gtaactggaa aacacctgca atggcttaa cgttccgggc
3487      aaataattte tttggtgtac cgcaggccgc agcggaagaa ACGCGTcatc aggcggagta
!                                                   MluI..
3547      tcaaaaccgt ggaacagaaa acgatatgat tgttttctca ccaacgacaa gcgatcgtcc
3607      tgtgcttgcc tgggatgtgg tcgcacccgg tcagtgtggg tttattgctc ccgatggaac
3667      agttgataag cactatgaag atcagctgaa aatgtacgaa aattttggcc gtaagtcgct
3727      ctgGTTAACg aagcaggatg tggaggcgca taaggagtcg
!            HpaI..
!            HincII(2/2)
!
```

TABLE 29-continued

DNA sequence of pCES5

```
! -----FR3-----------------------------------------
!      4   5   6   7   8   9  10  11  12  13  14  15  16
!     93  94  95  96  97  98  99 100 101 102 103 104 105
!      S   R   D   N   S   K   N   T   L   Y   L   Q   M   (Amino acid sequence is SEQ ID NO: 526
3767  |TCT|AGA|gac|aac|tct|aag|aat|act|ctc|tac|ttg|cag|atg|
!     |XbaI|
!
!   ------FR3---------------------------------->|
!        17  18  19  20
!       106 107 108 109
!        N   S L   s   l   s   i   r   s   g
3806   |aac|agC|TTA|AGt ctg agc att CGG TCC G
!           |AflII|        RsrII..
!
!        q   h   s    p   nt-.
3834   gg caa cat tct cca aac tga ccagacga cacaaacggc
3872   ttacgctaaa tcccgcgcat gggatggtaa agaggtggcg tctttgctgg cctggactca
3932   tcagatgaag gccaaaaatt ggcaggagtg gacacagcag gcagcgaaac aagcactgac
3992   catcaactgg tactatgctg atgtaaacgg caatattggt tatgttcata ctggtgctta
4052   tccagatcgt caatcaggcc atgatccgcg attacccgtt cctggtacgg gaaaatggga
4112   ctggaaaggg ctattgcctt ttgaaatgaa ccctaaggtg tataaccccc ag
4164       aa GCTAGC ctgcggcttc
!          NheI..
!
4182   G|GTC|ACC|  gtc tca agc
!      |BstEII|
!
!     (Amino acid sequence is SEQ ID NO: 527)
!     136 137 138 139 140 141 142 143 144 145 146 147 148 149 150
!      A   S   T   K   G   P   S   V   F   P   L   A   P   S   S
4198  gcc tcc acc aag ggc cca tcg gtc ttc ccc ctg gca ccc tcc tcc
!
!     151 152 153 154 155 156 157 158 159 160 161 162 163 164 165
!      K   S   T   S   G   G   T   A   A   L   G   C   L   V   K
4243  aag agc acc tct ggg ggc aca gcg gcc ctg ggc tgc ctg gtc aag
!
!     166 167 168 169 170 171 172 173 174 175 176 177 178 179 180
!      D   Y   F   P   E   P   V   T   V   S   W   N   S   G   A
4288  gac tac ttc ccc gaa ccg gtg acg gtg tcg tgg aac tca ggc gcc
!
!     181 182 183 184 185 186 187 188 189 190 191 192 193 194 195
!      L   T   S   G   V   H   T   F   P   A   V   L   Q   S   S
4333  ctg acc agc ggc gtc cac acc ttc ccg gct gtc cta cag tcc tca
!
!     196 197 198 199 200 201 202 203 204 205 206 207 208 209 210
!      G   L   Y   S   L   S   S   V   V   T   V   P   S   S   S
4378  gga Ctc tac tcc ctc agc agc gta gtg acc gtg ccc tcc agc agc
!
!     211 212 213 214 215 216 217 218 219 220 221 222 223 224 225
!      L   G   T   Q   T   Y   I   C   N   V   N   H   K   P   S
4423  ttg ggc acc cag acc tac atc tgc aac gtg aat cac aag ccc agc
!
!     226 227 228 229 230 231 232 233 234 235 236 237 238
!      N   T   K   V   D   K   K   V   E   P   K   S   C
4468  aac acc aag gtg gac aaG AAA GTT GAG CCC AAA TCT TGT
!                   ON-TQHCforw.............
!
!           Poly His linker
!     139 140 141 142 143 144 145 146 147 148 149 150
!      A   A   A   H   H   H   H   H   G   A   A
4507  GCG GCC GCa cat cat cat cac cat cac ggg gcc gca
!     NotI.....
!     EagI....
!
!     151 152 153 154 155 156 157 158 159 160 161 162 163 164 165
!      E   Q   K   L   I   S   E   E   D   L   N   G   A   A   .
4543  gaa caa aaa ctc atc tca gaa gag gat ctg aat ggg gcc gca tag
!
!      Mature III ---------------------------->...
!     166 167 168 169 170 171 172 173 174 175 176 177 178 179 180
!      T   V   E   S   C   L   A   K   P   H   T   E   N   S   F
4588  act gtt gaa agt tgt tta gca aaa cct cat aca gaa aat tca ttt
!
!     181 182 183 184 185 186 187 188 189 190 191 192 193 194 195
!      T   N   V   W   K   D   D   K   T   L   D   R   Y   A   N
4633  act aac gtc tgg aaa gac gac aaa act tta gat cgt tac gct aac
!
```

TABLE 29-continued

DNA sequence of pCES5

```
          196 197 198 199 200 201 202 203 204 205 206 207 208 209 210
           Y   E   G   C   L   W   N   A   T   G   V   V   C   T
    4678  tat gag ggc tgt ctg tgG AAT GCt aca ggc gtt gtg gtt tgt act
                                BsmI....

211 212 213 214 215 216 217 218 219 220 221 222 223 224 225
           G   D   E   T   Q   C   Y   G   T   W   V   P   I   G   L
    4723  ggt gac gaa act cag tgt tac ggt aca tgg gtt cct att ggg ctt 226 227 228 229 230 231 232 233 234 235 236 237 238 239 240
           A   I   P   E   N   E   G   G   G   S   E   G   G   G   S
    4768  gct atc cct gaa aat gag ggt ggt ggt tct gag ggt ggc ggt tct 241 242 243 244 245 246 247 248 249 250 251 252 253 254 255
           E   G   G   G   S   E   G   G   G   T   K   P   P   E   Y
    4813  gag ggt ggc ggt tct gag ggt ggc ggt act aaa cct cct gag tac 256 257 258 259 260 261 262 263 264 265 266 267 268 269 270
           G   D   T   P   I   P   G   Y   T   Y   I   N   P   L   D
    4858  ggt gat aca cct att ccg ggc tat act tat atc aac cct ctc gac 271 272 273 274 275 276 277 278 279 280 281 282 283 284 285
           G   T   Y   P   P   G   T   E   Q   N   P   A   N   P   N
    4903  ggc act tat ccg cct ggt act gag caa aac ccc gct aat cct aat 286 287 288 289 290 291 292 293 294 295 296 297 298 299 300
           P   S   L   E   E   S   Q   P   L   N   T   F   M   F   Q
    4948  cct tct ctt GAG GAG tct cag cct ctt aat act ttc atg ttt cag
                        BseRI..(2/2)

301 302 303 304 305 306 307 308 309 310 311 312 313 314 315
           N   N   R   F   R   N   R   Q   G   A   L   T   V   Y   T
    4993  aat aat agg ttc cga aat agg cag ggt gca tta act gtt tat acg 316 317 318 319 320 321 322 323 324 325 326 327 328 329 330
           G   T   V   T   Q   G   T   D   P   V   K   T   Y   Y   Q
    5038  ggc act gtt act caa ggc act gac ccc gtt aaa act tat tac cag 331 332 333 334 335 336 337 338 339 340 341 342 343 344 345
           Y   T   P   V   S   S   K   A   M   Y   D   A   Y   W   N
    5083  tac act cct gta tca tca aaa gcc atg tat gac gct tac tgg aac 346 347 348 349 350 351 352 353 354 355 356 357 358 359 360
           G   K   F   R   D   C   A   F   H   S   G   F   N   E   D
    5128  ggt aaa ttc aga gac tgc gct ttc cat tct ggc ttt aat gaG GAT
                                                              BamHI..

361 362 363 364 365 366 367 368 369 370 371 372 373 374 375
           P   F   V   C   E   Y   Q   G   Q   S   D   L   P   Q
    5173  CCa ttc gtt tgt gaa tat caa ggc caa tcg tct gAC CTG Cct caa
   !BamHI...                                        BspMI...(2/2)

376 377 378 379 380 381 382 383 384 385 386 387 388 389 390
           P   P   V   N   A   G   G   G   S   G   G   G   S   G   G
    5218  cct cct gtc aat gct ggc ggc ggc tct ggt ggt ggt tct ggt ggc 391 392 393 394 395 396 397 398 399 400 401 402 403 404 405
           G   S   E   G   G   G   S   E   G   G   G   S   E   G   G
    5263  ggc tct gag ggt ggc ggc tct gag ggt ggc ggt tct gag ggt ggc 406 407 408 409 410 411 412 413 414 415 416 417 418 419 420
           G   S   E   G   G   G   S   G   G   G   S   G   S   G   D
    5308  ggc tct gag ggt ggc ggt tcc ggt ggc ggc tcc ggt tcc ggt gat 421 422 423 424 425 426 427 428 429 430 431 432 433 434 435
           F   D   Y   E   K   M   A   N   A   N   K   G   A   M   T
    5353  ttt gat tat gaa aaa atg gca aac gct aat aag ggg gct atg acc 436 437 438 439 440 441 442 443 444 445 446 447 448 449 450
           E   N   A   D   E   N   A   L   Q   S   D   A   K   G   K
    5398  gaa aat gcc gat gaa aac gcg cta cag tct gac gct aaa ggc aaa 451 452 453 454 455 456 457 458 459 460 461 462 463 464 465
           L   D   S   V   A   T   D   Y   G   A   A   I   D   G   F
    5443  ctt gat tct gtc gct act gat tac ggt gct gct ATC GAT ggt ttc
                                                      BspDI..
```

TABLE 29-continued

DNA sequence of pCES5

```
!      466 467 468 469 470 471 472 473 474 475 476 477 478 479 480
!       I   G   D   V   S   G   L   A   N   G   N   G   A   T   G
5488   att ggt gac gtt tcc ggc ctt gct aat ggt aat ggt gct act ggt
!
!      481 482 483 484 485 486 487 488 489 490 491 492 493 494 495
!       D   F   A   G   S   N   S   Q   M   A   Q   V   G   D   G
5533   gat ttt gct ggc tct aat tcc caa atg gct caa gtc ggt gac ggt
!
!      496 497 498 499 500 501 502 503 504 505 506 507 508 509 510
!       D   N   S   P   L   M   N   N   F   R   Q   Y   L   P   S
5578   gat aat tca cct tta atg aat aat ttc cgt caa tat tta cct tct
!
!      511 512 513 514 515 516 517 518 519 520 521 522 523 524 525
!       L   P   Q   S   V   E   C   R   P   Y   V   F   G   A   G
5623   ttg cct cag tcg gtt gaa tgt cgc cct tat gtc ttt ggc gct ggt
!
!      526 527 528 529 530 531 532 533 534 535 536 537 538 539 540
!       K   P   Y   E   F   S   I   D   C   D   K   I   N   L   F
5668   aaa cCA TAT Gaa ttt tct att gat tgt gac aaa ata aac tta ttc
!          NdeI....
!
!      541 542 543 544 545 546 547 548 549 550 551 552 553 554 555
!       R   G   V   F   A   F   L   L   Y   V   A   T   F   M   Y
5713   cgt ggt gtc ttt gcg ttt ctt tta tat gtt gcc acc ttt atg tat
!
!      556 557 558 559 560 561 562 563 564 565 566 567 568 569 570
!       V   F   S   T   F   A   N   I   L   R   N   K   E   S   .
5758   gta ttt tcg acg ttt gct aac ata ctg cgt aat aag gag tct taa
!
!      571
!
5803   taa GAATTC
!          EcoRI.
5812   actggccgt cgttttacaa cgtcgtgact gggaaaaccc tggcgttacc caacttaatc
5871   gccttgcagc acatcccccct ttcgccagct ggcgtaatag cgaagaggcc cgcacCGATC
!                                                                  PvuI..
5931   Gcccttccca acagtTGCGC Agcctgaatg gcgaatGGCG CCtgatgcgg tattttctcc
!...PvuI... (3/3) FspI... (2/2) KasI...(2/2)
5991   ttacgcatct gtgcggtatt tcacaccgca tataaattgt aaacgttaat attttgttaa
6051   aattcgcgtt aaatttttgt taaatcagct cattttttaa ccaataggcc gaaatcggca
6111   aaatccccTTA TAAatcaaaa gaatagcccg ataggggtt gagtgttgtt ccagtttgga
!          PsiI...
6171   acaagagtcc actattaaag aacgtggact ccaacgtcaa agggcgaaaa accgtctatc
6231   agggcgatgg ccCACtacGT Gaaccatcac ccaaatcaag ttttttgggg tcgaggtgcc
!                DralTI....
6291   gtaaagcact aaatcggaac cctaaaggga gccccccgatt tagagcttga cggggaaaGC
!                                                                  NgoMIV..
6351   CGGCgaacgt ggcgagaaag gaagggaaga aagcgaaagg agcgggcgct agggcgctgg
! ..NgoMIV.(2/2)
6411   caagtgtagc ggtcacgctg cgcgtaacca ccacacccgc cgcgcttaat gcgccgctac
6471   agggcgcgta ctatggttgc tttgacgggt gcagtctcag tacaatctgc tctgatgccg
6531   catagttaag ccagccccga cacccgccaa cacccgctga cgcgccctga cgggcttgtc
6591   tgctcccggc atccgcttac agacaagctg tgaccgtctc cgggagctgc atgtgtcaga
6651   ggttttcacc gtcatcaccg aaacgcgcga
```

TABLE 30

Oligonucleotides used to clone CDR1/2 diversity

All sequences are 5' to 3'.

1) ON_CD1Bsp, 30 bases (SEQ ID NO: 528)

```
A c c T c A c T g g c T T c c g g A
1 2 3 4 5 6 7 8 9 10 11 12 13 14 15 16 17 18

T T c A c T T T c T c T
19 20 21 22 23 24 25 26 27 28 29 30
```

2) ON_Br12, 42 bases (SEQ ID NO: 529)

```
A g A A A c c c A c T c c A A A c c
1 2 3 4 5 6 7 8 9 10 11 12 13 14 15 16 17 18
```

TABLE 30-continued

Oligonucleotides used to clone CDR1/2 diversity

```
T T T A c c A g g A g c T T g g c
19 20 21 22 23 24 25 26 27 28 29 30 31 32 33 34 35 g A A c c c A
36 37 38 39 40 41 42
```

3) ON_CD2Xba, 51 bases (SEQ ID NO: 530)

```
g g A A g g c A g T g A T c T A g A
1 2 3 4 5 6 7 8 9 10 11 12 13 14 15 16 17 18 g A T A g T g A A g c g A c c T T
19 20 21 22 23 24 25 26 27 28 29 30 31 32 33 34 35

T A A c g g A g T c A g c A T A
36 37 38 39 40 41 42 43 44 45 46 47 48 49 50 51
```

TABLE 30-continued

Oligonucleotides used to clone CDR1/2 diversity

4) ON_BotXba, 23 bases (SEQ ID NO: 531)

g g A A g g c A g T g A T c T A g A
1 2 3 4 5 6 7 8 9 10 11 12 13 14 15 16 17 18 g A T A g
19 20 21 22 23

TABLE 31

Bridge/Extender Oligonucleotides
(SEQ ID NOS 532-546, respectively in order of appearance)

| | | |
|---|---|---|
| ON_Lam1aB7(rc) | ........................GTGCTGACTCAGCCACCCTC. | 20 |
| ON_Lam2aB7(rc) | ........................GCCCTGACTCAGCCTGCCTC. | 20 |
| ON_Lam31B7(rc) | ........................GAGCTGACTCAGG.ACCCTGC | 20 |
| ON_Lam3rB7(rc) | ........................GAGCTGACTCAGCCACCCTC. | 20 |
| ON_LamHf1cBrg(rc) | CCTCGACAGCGAAGTGCACAGAGCGTCTTGACTCAGCC....... | 38 |
| ON_LamHf1cExt | CCTCGACAGCGAAGTGCACAGAGCGTCTTG............... | 30 |
| ON_LamHf2b2Brg(rc) | CCTCGACAGCGAAGTGCACAGAGCGCTTTGACTCAGCC....... | 38 |
| ON_LamHf2b2Ext | CCTCGACAGCGAAGTGCACAGAGCGCTTTG............... | 30 |
| ON_LamHf2dBrg(rc) | CCTCGACAGCGTAAGTGCACAGAGCGCTTTGACTCAGCC....... | 38 |
| ON_LamHf2dExt | CCTCGACAGCGAAGTGCACAGAGCGCTTTG............... | 30 |
| ON_LamHf31Brg(rc) | CCTCGACAGCGAAGTGCACAGAGCGAATTGACTCAGCC....... | 38 |
| ON_LamHf31Ext | CCTCGACAGCGAAGTGCACAGAGCGAATTG............... | 30 |
| ON_LamHf3rBrg(rc) | CCTCGACAGCGAAGTGCACAGTACGAATTGACTCAGCC....... | 38 |
| ON_LamHf3rExt | CCTCGACAGCGAAGTGCACAGTACGAATTG............... | 30 |
| ON_lamPlePCR Consensus | CCTCGACAGCGAAGTGCACAG........................ | 21 |

TABLE 32

Oligonucleotides used to make SSDNA locally
double-stranded
(SEQ ID NOS 548-552,
respectively in order of appearance)

Adapters (8)

H43HF3.1?02#1    5'-cc gtg tat tac tgt gcg aga g-3'

H43.77.97.1-03#2 5'-ct gtg tat tac tgt gcg aga g-3'

H43.77.97.323#22 5'-cc gta tat tac tgt gcg aaa g-3'

H43.77.97.330#23 5'-ct gtg tat tac tgt gcg aaa g-3'

H43.77.97.439#44 5'-ct gtg tat tac tgt gcg aga c-3'

H43.77.97.551#48 5'-cc atg tat tac tgt gcg aga c-3'

TABLE 33

Bridge/extender pairs

Bridges (2)

H43.XABr1                                    (SEQ ID NO: 553)
5'ggtgtagtgaTCTAGtgacaactctaagaatactctctacttgcagat
gaacagCTTtAGggctgaggacaCTGCAGtctactattgtgcgaga-3'

H43.XABr2                                    (SEQ ID NO: 554)
5'ggtgtagtgaTCTAGtgacaactctaagaatactctctacttgcagat
gaacagCTTtAGggctgaggacaCTGCAGtctactattgtgcgaaa-3'

TABLE 33-continued

Bridge/extender pairs

Extender

H43.XAExt                                    (SEQ ID NO: 555)
5'ATAgTAgAcTgcAgTgTccTcAgcccTTAAgcTgTTcATcTgcAAgTA
gAgAgTATTcTTAgAgTTgTcTcTAgATcAcTAcAcc-3'

TABLE 34

PCR primers

Primers

H43.XAPCR2   gactgggTgTAgTgATcTAg (SEQ ID NO:556)

Hucmnest    cttttctttgttgccgttggggtg (SEQ ID NO:557)

TABLE 35

PCR program for amplification of
heavy chain CDR3 DNA

| | | |
|---|---|---|
| 95 degrees C. | 5 minutes | |
| 95 degrees C. | 20 seconds | |
| 60 degrees C. | 30 seconds | repeat 20× |
| 72 degrees C. | 1 minute | |
| 72 degrees C. | 7 minutes | |
| 4 degrees C. | hold | |
| Reagents (100 ul reaction): | | |
| Template | 5ul ligation mix | |
| 10× PCR buffer | 1× | |
| Taq | 5U | |
| dNTPs | 200 uM each | |
| $MgCl_2$ | 2 mM | |
| H43.XAPCR2-biotin | 400 nM | |
| Hucmnest | 200 nM | |

TABLE 36

```
! Annotated sequence of CJR DY3F7(CJR-A05) 10251 bases
!
! Non-cutters
!
!BclI  Tgatca        BsiWI Cgtacg        BssSI Cacgag
!BstZ17I GTAtac      BtrI  CACgtg        EcoRV GATatc
!FseI  GGCCGGcc      HpaI  GTTaac        MluI  Acgcgt
!PmeI  GTTTaaac      PmlI  CACgtg        PpuMI RGgwccy
!RsrII CGgwccg       SapI  GCTCTTC       SexAI Accwggt
!SgfI  GCGATcgc      SgrAI CRccggyg      SphI  GCATGc
!StuI  AGGcct        XmaI  Cccggg
!
! cutters
!
! Enzymes that cut from 1 to 4 times and other features
!
!End of genes II and X                   829
!Start gene V                            843
!BsrGI Tgtaca              1             1021
!BspMI Nnnnnnnnngcaggt     3             1104   5997   9183
 (SEQ ID NO: 558)
!-"-   ACCTGCNNNNn          1             2281
 (SEQ ID NO: 559)
!End of gene V                           1106
!Start gene VII                          1108
!BsaBI GATNNnnatc          2             1149   3967
 (SEQ ID NO: 560)
!Start gene IX                           1208
!End gene VII                            1211
!SnaBI TACgta              2             1268   7133
!BspHI Tcatga              3             1299   6085   7093
!Start gene VIII                         1301
!End gene IX                             1304
!End gene VIII                           1522
!Start gene III                          1578
!EagI  Cggccg              2             1630   8905
!XbaI  Tctaga              2             1643   8436
!KasI  Ggcgcc              4             1650   8724   9039   9120
!BsmI  GAATGCN             2             1769   9065
!BseRI GAGGAGNNNNNNNNNN    2             2031   8516
(SEQ ID NO: 561)
!-"-   NNnnnnnnnnctcctc    2             7603   8623
(SEQ ID NO: 562)
! AlwNI CAGNNNctg          3             2210   8072   8182
! BspDI ATcgat             2             2520   9883
! NdeI  CAtatg             3             2716   3796   9847
! End gene III                           2846
! Start gene VI                          2848
! AfeI  AGCgct             1             3032
! End gene VI                            3187
! Start gene I                           3189
! EarI  CTCTTCNnnn         2             4067   9274
(SEQ ID NO: 563)
! -"-Nnnnngaagag            2             6126   8953
(SEQ ID NO: 564)
! PacI  TTAATtaa           1             4125
! Start gene IV                          4213
! End gene I                             4235
! BsmFI Nnnnnnnnnnnnnnngtccc 2           5068   9515
(SEQ ID NO: 565)
! MscI  TGGcca             3             5073   7597   9160
! PsiI  TTAtaa             2             5349   5837
! End gene IV                            5493
! Start on                               5494
! NgoMIV Gccggc            3             5606   8213   9315
! BanII GRGCYc             4             5636   8080   8606   8889
! DraIII CACNNNgtg         1             5709
! DrdI  GACNNNNnngtc       1             5752
(SEQ ID NO: 566)
! AvaI  Cycgrg             2             5818   7240
! PvuII CAGctg             1             5953
! BsmBI CGTCTCNnnnn        3             5964   8585   9271
(SEQ ID NO: 567)
! End onregion                           5993
! BamHI Ggatcc             1             5994
! HindIII Aagctt           3             6000   7147   7384
! BciVI GTATCCNNNNNN       1             6077
(SEQ ID NO: 568)
! Start bla                              6138
! Eco57I CTGAAG            2             6238   7716
```

TABLE 36-continued

| | | | | |
|---|---|---|---|---|
| ! SpeI Actagt | 1 | 6257 | | |
| ! BcgI gcannnnnntcg | 1 | 6398 | | |
| (SEQ ID NO: 569) | | | | |
| ! ScaI AGTact | 1 | 6442 | | |
| ! PvuI CGATcg | 1 | 6553 | | |
| ! FspI TGCgca | 1 | 6700 | | |
| ! BglI GCCNNNNnggc | 3 | 6801 | 8208 | 8976 |
| (SEQ ID NO: 570) | | | | |
| ! BsaI GGTCTCNnnnn | 1 | 6853 | | |
| (SEQ ID NO: 571) | | | | |
| ! AhdI GACNNNnngtc | 1 | 6920 | | |
| (SEQ ID NO: 572) | | | | |
| ! Eam1105I GACNNNnngtc | 1 | 6920 | | |
| (SEQ ID NO: 573) | | | | |
| ! End bla | | 6998 | | |
| ! AccI GTmkac | 2 | 7153 | 8048 | |
| ! HincII GTYrac | 1 | 7153 | | |
| ! SalI Gtcgac | 1 | 7153 | | |
| ! XhoI Ctcgag | 1 | 7240 | | |
| ! Start PlacZ region | | 7246 | | |
| ! End PlacZ region | | 7381 | | |
| ! Pf1MI CCANNNNntgg | 1 | 7382 | | |
| (SEQ ID NO: 574) | | | | |
| ! RBS1 | | 7405 | | |
| ! start M13-iii signal seq for LC | | 7418 | | |
| ! ApaLI Gtgcac 1 | | 7470 | | |
| ! end M13-iii signal seq | | 7471 | | |
| ! Start light chain kappa L20:JK1 | | 7472 | | |
| ! Pf1FI GACNnngtc | 3 | 7489 | 8705 | 9099 |
| ! SbfI CCTGCAgg | 1 | 7542 | | |
| ! PstI CTGCAg | 1 | 7543 | | |
| ! KpnI GGTACc | 1 | 7581 | | |
| ! XcmI CCANNNNNnnnntgg | 2 | 7585 | 9215 | |
| (SEQ ID NO: 575) | | | | |
| ! NsiI ATGCAt | 2 | 7626 | 9503 | |
| ! BsgI ctgcac | 1 | 7809 | | |
| ! BbsI gtcttc | 2 | 7820 | 8616 | |
| ! BlpI GCtnagc | 1 | 8017 | | |
| ! EspI GCtnagc | 1 | 8017 | | |
| ! Eco0109I RGgnccy | 2 | 8073 | 8605 | |
| ! Ecl136I GAGctc | 1 | 8080 | | |
| ! SacI GAGCTc | 1 | 8080 | | |
| ! End light chain | | 8122 | | |
| ! AscI GGcgcgcc | 1 | 8126 | | |
| ! BssHII Gcgcgc | 1 | 8127 | | |
| ! RBS2 | | 8147 | | |
| ! SfiI GGCCNNNNnggcc | 1 | 8207 | | |
| (SEQ ID NO: 576) | | | | |
| ! NcoI Ccatgg | 1 | 8218 | | |
| ! Start 3-23, FR1 | | 8226 | | |
| ! MfeI Caattg | 1 | 8232 | | |
| ! BspEI Tccgga | 1 | 8298 | | |
| ! Start CDR1 | | 8316 | | |
| ! Statt FR2 | | 8331 | | |
| ! BstXI CCANNNNNntgg | 2 | 8339 | 8812 | |
| (SEQ ID NO: 577) | | | | |
| ! EcoNI CCTNNnnnagg | 2 | 8346 | 8675 | |
| (SEQ ID NO: 578) | | | | |
| ! Start FR3 | | 8373 | | |
| ! XbaI Tctaga | 2 | 8436 | 1643 | |
| ! AflII Cttaag | 1 | 8480 | | |
| ! Start CDR3 | | 8520 | | |
| ! AatII GACGTc | 1 | 8556 | | |
| ! Start FR4 | | 8562 | | |
| ! PshAI GACNNnngtc | 2 | 8573 | 9231 | |
| (SEQ ID NO: 579) | | | | |
| ! BstEII Ggtnacc | 1 | 8579 | | |
| ! Start CH1 | | 8595 | | |
| ! ApaI GGGCCc | 1 | 8606 | | |
| ! Bsp120I Gggccc | 1 | 8606 | | |
| ! PspOMI Gggccc | 1 | 8606 | | |
| ! AgeI Accggt | 1 | 8699 | | |
| ! Bsu36I CCtnagg | 2 | 8770 | 9509 | |
| ! End of CH1 | | 8903 | | |
| ! NotI GCggccgc | 1 | 8904 | | |
| ! Start His6 tag | | 8913 | | |
| (SEQ ID NO: 12) | | | | |
| ! Start cMyc tag | | 8931 | | |
| ! Amber codon | | 8982 | | |
| ! NheI Gctagc | 1 | 8985 | | |

TABLE 36-continued

```
! Start M13 III Domain            3      8997
! NruI TCGcga                     1      9106
! BstBI TTcgaa                    1      9197
! EcoRI Gaattc                    1      9200
! XcmI CCANNNNNnnnntgg            1      9215
  (SEQ ID NO: 580)
! BstAPI GCANNNNntgc              1      9337
  (SEQ ID NO: 581)
! SacII CCGCgg                    1      9365
! End IIIstump anchor                    9455
! AvrII Cctagg                    1      9462
! trp terminator                         9470
! SwaI ATTTaaat                   1      9784
! Start gene II                          9850
! BglII Agatct                    1      9936
!-----------------------------------------------------------------
!(SEQ ID NO: 582)
     1 aat gct act act att agt aga att gat gcc acc ttt tca gct cgc gcc
!      gene ii continued
    49 cca aat gaa aat ata gct aaa cag gtt att gac cat ttg cga aat gta
    97 tct aat ggt caa act aaa tct act cgt tcg cag aat tgg gaa tca act
   145 gtt aTa tgg aat gaa act tcc aga cac cgt act tta gtt gca tat tta
   193 aaa cat gtt gag cta cag caT TaT att cag caa tta agc tct aag cca
   241 tcc gca aaa atg acc tct tat caa aag gag caa tta aag gta ctc tct
   289 aat cct gac ctg ttg gag ttt gct tcc ggt ctg gtt cgc ttt gaa gct
   337 cga att aaa acg cga tat ttg aag tct ttc ggg ctt cct ctt aat ctt
   385 ttt gat gca atc cgc ttt gct tct gac tat aat agt cag ggt aaa gac
   433 ctg att ttt gat tta tgg tca ttc tcg ttt tct gaa ctg ttt aaa gca
   481 ttt gag ggg gat tca ATG aat att tat gac gat tcc gca gta ttg gac
!                            Start gene x, ii continues
   529 gct atc cag tct aaa cat ttt act att acc ccc tct ggc aaa act tct
   577 ttt gca aaa gcc tct cgc tat ttt ggt ttt tat cgt cgt ctg gta aac
   625 gag ggt tat gat agt gtt gct ctt act atg cct cgt aat tcc ttt tgg
   673 cgt tat gta tct gca tta gtt gaa tgt ggt att cct caa ctg
   721 atg aat ctt tct acc tgt aat aat gtt gtt ccg tta gtt cgt ttt att
   769 aac gta gat ttt tct tcc caa cgt cct gac tgg tat aat gag cca gtt
   817 ctt aaa atc gca TAA
!                         End X & II
   832 ggtaattca ca
!(SEQ ID NO: 626)
!      M1              E5               Q10                T15
   843 ATG att aaa gtt gaa att aaa cca tct caa gcc caa ttt act act cgt
!      Start gene V
!
!      S17             S20              P25                E30
   891 tct ggt gtt tct cgt cag ggc aag cct tat tca ctg aat gag cag ctt
!
!               V35          E40              V45
   939 tgt tac gtt gat ttg ggt aat gaa tat ccg gtt ctt gtc aag att act
!
!      D50             A55              L60
   987 ctt gat gaa ggt cag cca gcc tat gcg cct ggt cTGATAC Acc gtt cat
!                                                BsrGI...
!      L65             V70              S75                R80
  1035 ctg tcc tct ttc aaa gtt ggt cag ttc ggt tcc ctt atg att gac cgt
!
!                      P85     K87 end of V
! 1083 ctg cgc ctc gtt ccg gct aag TAA C
!
  1108 ATG gag cag gtc gcg gat ttc gac aca att tat cag gcg atg
!      Start gene VII
!
  1150 ata caa atc tcc gtt gta ctt tgt ttc gcg ctt ggt ata atc
!
!                       VII and IX overlap.
!                       ..... S2 V3 L4 V5 (SEQ ID NO: 621)  S10
  1192 gct ggg ggt caa agA TGA gt gtt tta gtg tat tct ttT gcc tct ttc
gtt
!                         End VII
!                         |start IX
!      L13        W15              G20                T25
E29
  1242 tta ggt tgg tgc  ctt cgt agt ggc att acg tat ttt acc cgt tta atg
gaa
!
  1293 act tcc tc
!
!      .... stop of IX, IX and VIII overlap by four bases
  1301 ATG aaa aag tct tta gtc ctc aaa gcc tct gta gcc gtt gct acc ctc
!      Start signal sequence of viii.
```

TABLE 36-continued

```
!
  1349 gtt ccg atg ctg tct ttc gct gct gag ggt gac gat ccc gca aaa gcg
!                                mature VIII --->
  1397 gcc ttt aac tcc ctg caa gcc tca gcg acc gaa tat atc ggt tat gcg
  1445 tgg gcg atg gtt gtt gtc att
  1466 gtc ggc gca act atc ggt atc aag ctg ttt aag
!
! bases 1499-1539 are probable promoter for iii
  1499 aaa ttc acc tcg aaa gca !  1515
!           ............ -35  ..
!
  1517 agc tga taaaccgat acaattaaag gctccttttg
!                                ..... -10   ...
!
  1552 gagccttttt ttt GGAGAt ttt !  S.D. uppercase, there may be 9 Ts
!
!          <------ III signal sequence--------------------------------->
 (SEQ ID NO: 583)
!         M   K   K   L   L   F   A   I   P   L   V   V   P   F
  1574 caac GTG aaa aaa tta tta ttc gca att cct tta gtt gtt cct ttc !
1620
!
!     Y   S   G   A   A   E   S   H   L   D   G   A
  1620 tat tct ggc gCG GCC Gaa tca caT CTA GAc ggc gcc
!                 EagI....         XbaI....
!
! Domain 1 -------------------------------------------------------------
!         A   E   T   V   E   S   C   L   A
  1656     gct gaa act gtt gaa agt tgt tta gca
!     K   S   H   T   E   I   S   F   T   N   V   W   K   D   D   K
T
  1683 aaA Tcc cat aca gaa aat tca ttt aCT AAC GTC TGG AAA GAC GAC AAA
ACt
!
!     L   D   R   Y   A   N   Y   E   G   S   L   W   N   A   T   G
V
  1734 tta gat cgt tac gct aac tat gag ggC tgt ctg tgG AAT GCt aca ggc
gtt
!                                                   BsmI....
!
!     V   V   C   T   G   D   E   T   Q   C   Y   G   T   W   V   P
I
  1785 gta gtt tgt act ggt GAC GAA ACT CAG TGT TAC GGT ACA TGG GTT cct
att
!
!     G   L   A   I   P   E   N
  1836 ggg ctt gct atc cct gaa aat
!
! L1 linker---------------------------------
!     E   G   G   G   S   E   G   G   G   S
  1857 gag ggt ggt ggc tct gag ggt ggc ggt tct
!
!     E   G   G   G   S   E   G   G   G   T
  1887 gag ggt ggc ggt tct gag ggt ggc ggt act
!
! Domain 2-----------------------------------
  1917 aaa cct cct gag tac ggt gat aca cct att ccg ggc tat act tat atc
aac
  1968 cct ctc gac ggc act tat ccg cct ggt act gag caa aac ccc gct aat
cct
  2019 aat cct tct ctt GAG GAG tct cag cct ctt aat act ttc atg ttt cag
aat
!                      BseRI..
  2070 aat agg ttc cga aat agg cag ggg gca tta act gtt tat acg ggc act
  2118 gtt act caa ggc act gac ccc gtt aaa act tat tac cag tac act cct
  2166 gta tca tca aaa gcc atg tat gac gct tac tgg aac ggt aaa ttC AGA
!                                                                 AlwNI
  2214 GAC TGc gct ttc cat tct ggc ttt aat gaG gat TTa ttT gtt tgt gaa
!     AlwNI
  2262 tat caa ggc caa tcg tct gac ctg cct caa cct cct gtc aat gct
!
  2307 ggc ggc ggc tct
! start L2
--------------------------------------------------------------
  2319 ggt ggt ggt tct
  2331 ggt ggc ggc tct
  2343 gag ggt ggt ggc tct gag gga ggc ggt tcc
  2373 ggt ggt ggc tct ggt    ! end L2
!
```

TABLE 36-continued

```
! Many published sequences of M13-derived phage have a longer linker
! than shown here by repeats of the EGGGS (SEQ ID NO:  589) motif two
more times.
!
! Domain 3
(SEQ ID NO:  584)
----------------------------------------------------------------
!       S    G    D    F    D    Y    E    K    M    A    N    A    N    K    G    A
  2388  tcc  ggt  gat  ttt  gat  tat  gaa  aag  atg  gca  aac  gct  aat  aag  ggg  gct
!
!       M    T    E    N    A    D    E    N    A    L    Q    S    D    A    K    G
  2436  atg  acc  gaa  aat  gcc  gat  gaa  aac  gcg  cta  cag  tct  gac  gct  aaa  ggc
!
!       K    L    D    S    V    A    T    D    Y    G    A    A    M    D    G    F
  2484  aaa  ctt  gat  tct  gtc  gct  act  gat  tac  ggt  gct  gct  atc  gat  ggt  ttc
!
!       I    G    D    V    S    G    L    A    N    G    N    G    A    T    G    D
  2532  att  ggt  gac  gtt  tcc  ggc  ctt  gct  aat  ggt  aat  ggt  gct  act  ggt  gat
!
!       F    A    G    S    N    S    Q    M    A    Q    V    G    D    G    D    N
  2580  ttt  gct  ggc  tct  aat  tcc  caa  atg  gct  caa  gtc  ggt  gac  ggt  gat  aat
!
!       S    P    L    M    N    N    F    R    Q    Y    L    P    S    L    P    Q
  2628  tca  cct  tta  atg  aat  aat  ttc  cgt  caa  tat  tta  cct  tcc  ctc  cct  caa
!
!       S    V    E    C    R    P    F    V    F    G    A    G    K    P    Y    E
  2676  tcg  gtt  gaa  tgt  cgc  cct  ttt  gtc  ttt  Ggc  gct  ggt  aaa  cca  tat  gaa
!
!       F    S    I    D    C    D    K    I    N    L    F    R
  2724  ttt  tct  att  gat  tgt  gac  aaa  ata  aac  tta  ttc  cgt
!                                                                   End Domain 3
!
!       G    V    F    A    F    L    L    Y    V    A    T    F    M    Y    V    F140
  2760  ggt  gtc  ttt  gcg  ttt  ctt  tta  tat  gtt  gcc  acc  ttt  atg  tat  gta  ttt
!       start transmembrane segment
!
!       S    T    F    A    N    I    L
  2808  tct  acg  ttt  gct  aac  ata  ctg
!
!       R    N    K    E    S
  2829  cgt  aat  aag  gag  tct  TAA !   stop of iii
!     Intracellular anchor.
!       (SEQ ID NO:  585)
!        M1   P2   V    L    L5   G    I    P    L    L10  L    R    F    L    G15
  2847  tc ATG  cca  gtt  ctt  ttg  ggt  att  ccg  tta  tta  ttg  cgt  ttc  ctc  ggt
!         Start VI
!
  2894  ttc  ctt  ctg  gta  act  ttg  ttc  ggc  tat  ctg  ctt  act  ttt  ctt  aaa  aag
  2942  ggc  ttc  ggt  aag  ata  gct  att  gct  att  tca  ttg  ttt  ctt  gct  ctt  att
  2990  att  ggg  ctt  aac  tca  att  ctt  gtg  ggt  tat  ctc  tct  gat  att  agc  gct
  3038  caa  tta  ccc  tct  gac  ttt  gtt  cag  ggt  gtt  cag  tta  att  ctc  ccg  tct
  3086  aat  gcg  ctt  ccc  tgt  ttt  tat  gtt  att  ctc  tct  gta  aag  gct  gct  att
  3134  ttc  att  ttt  gac  gtt  aaa  caa  aaa  atc  gtt  tct  tat  ttg  gat  tgg  gat
!
!                  M1   A2   V3        F5                  L10            G13
  3182  aaa  TAA  t ATG  gct  gtt  tat  ttt  gta  act  ggc  aaa  tta  ggc  tct  gga
!         end VI     Start gene I
(SEQ ID NO:  586)
!       K    T    L    V    S    V    G    K    I    Q    D    K    I    V    A
  3228  aag  acg  ctc  gtt  agc  gtt  ggt  aag  att  cag  gat  aaa  att  gta  gct
!
!       G    C    K    I    A    T    N    L    D    L    R    L    Q    N    L
  3273  ggg  tgc  aaa  ata  gca  act  aat  ctt  gat  tta  agg  ctt  caa  aac  ctc
!
!       P    Q    V    G    R    F    A    K    T    P    R    V    L    R    I
  3318  ccg  caa  gtc  ggg  agg  ttc  gct  aaa  acg  cct  cgc  gtt  ctt  aga  ata
!
!       P    D    K    P    S    I    S    D    L    L    A    I    G    R    G
  3363  ccg  gat  aag  cct  tct  ata  tct  gat  ttg  ctt  gct  att  ggg  cgc  ggt
!
!       N    D    S    Y    D    E    N    K    N    G    L    L    V    L    D
  3408  aat  gat  tcc  tac  gat  gaa  aat  aaa  aac  ggc  ttg  ctt  gtt  ctc  gat
!
!       E    C    G    T    W    F    N    T    R    S    W    N    D    K    E
  3453  gag  tgc  ggt  act  tgg  ttt  aat  acc  cgt  tct  tgg  aat  gat  aag  gaa
!
!       R    Q    P    I    I    D    W    F    L    H    A    R    K    L    G
  3498  aga  cag  ccg  att  att  gat  tgg  ttt  cta  cat  gct  cgt  aaa  tta  gga
!
```

TABLE 36-continued

```
!         W   D   I   I   F   L   V   Q   D   L   S   I   V   D   K
!  3543 tgg gat att att ttt ctt gtt cag gac tta tct att gtt gat aaa
!
!         Q   A   R   S   A   L   A   E   H   V   V   Y   C   R   R
!  3588 cag gcg cgt tct gca tta gct gaa cat gtt gtt tat tgt cgt cgt
!
!         L   D   R   I   T   L   P   F   V   G   T   L   Y   S   L
!  3633 ctg gac aga att act tta cct ttt gtc ggt act tta tat tct ctt
!
!         I   T   G   S   K   M   P   L   P   K   L   H   V   G   V
!  3678 att act ggc tcg aaa atg cct ctg cct aaa tta cat gtt ggc gtt
!
!         V   K   Y   G   D   S   Q   L   S   P   T   V   E   R   W
!  3723 gtt aaa tat ggc gat tct caa tta agc cct act gtt gag cgt tgg
!
!         L   Y   T   G   K   N   L   Y   N   A   Y   D   T   K   Q
!  3768 ctt tat act ggt aag aat ttg tat aac gca tat gat act aaa cag
!
!         A   F   S   S   N   Y   D   S   G   V   Y   S   Y   L   T
!  3813 gct ttt tct agt aat tat gat tcc ggt gtt tat tct tat tta acg
!
!         P   Y   L   S   H   G   R   Y   F   K   P   L   N   L   G
!  3858 cct tat tta tca cac ggt cgg tat ttc aaa cca tta aat tta ggt
!
!         Q   K   M   K   L   T   K   I   Y   L   K   K   F   S   R
!  3903 cag aag atg aaa tta act aaa ata tat ttg aaa aag ttt tct cgc
!
!         V   L   C   L   A   I   G   F   A   S   A   F   T   Y   S
!  3948 gtt ctt tgt ctt gcg att gga ttt gca tca gca ttt aca tat agt
!
!         Y   I   T   Q   P   K   P   E   V   K   K   V   S   Q
!  3993 tat ata acc caa cct aag ccg gag gtt aaa aag gta gtc tct cag
!
!         T   Y   D   F   D   K   F   T   I   D   S   S   Q   R   L
!  4038 acc tat gat ttt gat aaa ttc act att gac tct tct cag cgt ctt
!
!         N   L   S   Y   R   Y   V   F   K   D   S   K   G   K   L
!  4083 aat cta agc tat cgc tat gtt ttc aag gat tct aag gga aaa TTA
!                                                                 PacI
!
!         I   N   S   D   D   L   Q   K   Q   G   Y   S   L   T   Y
!  4128 ATT AAt agc gac gat tta cag aag caa ggt tat tca ctc aca tat
!      PacI
!
!         i   I   D   L   C   T   V   S   I   K   K   G   N   S   N   E
!         iv                                                      M1  K
!  4173     att gat tta tgt act gtt tcc att aaa aaa ggt aat tca aAT Gaa
!                                                                Start IV
! (SEQ ID NO: 527)
!         i   I   V   K   C   N  .End of I
!         iv  L3  L   N5  V   I7  N   F  V10
!  4218     att gtt aaa tgt aat TAA T TTT GTT
! IV continued.....
   4243 ttc ttg atg ttt gtt tca tca tct tct ttt gct cag gta att gaa atg
   4291 aat aat tcg cct ctg cgc gat ttt gta act tgg tat tca aag caa tca
   4339 ggc gaa tcc gtt att gtt tct ccc gat gta aaa ggt act gtt act gta
   4387 tat tca tct gac gtt aaa cct gaa aat cta cgc aat ttc ttt att tct
   4435 gtt tta cgt gcA aat aat ttt gat atg gtA ggt tcT aAC cct tcc atT
   4483 att cag aag tat aat cca aac aat cag gat tat att gat gaa ttg cca
   4531 tca tct gat aat cag gaa tat gat gat aat tcc gct cct tct ggt ggt
   4579 ttc ttt gtt ccg caa aat gat aat gtt act caa act ttt aaa att aat
   4627 aac gtt cgg gca aag gat tta ata cga gtt gtc gaa ttg ttt gta aag
   4675 tct aat act tct aaa tcc tca gta tta tct att gac ggc tct aat
   4723 cta tta gtt gtt agt gcT cct aaa gat att tta gat aac ctt cct caa
   4771 ttc ctt tcA act gtt gat ttg cca act gac cag ata ttg att gag ggt
   4819 ttg ata ttt gag gtt cag caa ggt gat gct tta gat ttt tca ttt gct
   4867 gct ggc tct cag cgt ggc act gtt gca ggc ggt gtt aat act gac cgc
   4915 ctc acc tct gtt tta tct tct ggt ggt tcg ttc ggt att ttt aat
   4963 ggc gat gtt tta ggg cta tca gtt cgc gca tta aag act aat agc cat
   5011 tca aaa ata ttg tct gtg cca cgt att ctt acg ctt tca ggt cag aag
   5059 ggt tct atc tct gtT GGC CAg aat gtc cct ttt att act ggt cgt gtg
!                           MscI....
   5107 act ggt gaa tct gcc aat gta aat aat cca ttt cag acg att gag cgt
   5155 caa aat gta ggt att tcc atg agc gtt ttt cct gtt gca atg gct ggc
   5203 ggt aat att gtt ctg gat att acc agc aag gcc gat agt ttg agt tct
   5251 tct act cag gca agt gat gtt att act aat caa aga agt att gct aca
   5299 acg gtt aat ttg cgt gat gga cag act ctt tta ctc ggt ggc ctc act
   5347 gat tat aaa aac act tct caG gat tct ggc gta ccg ttc ctg tct aaa
   5395 atc cct tta atc ggc ctc ctg ttt agc tcc cgc tct gat tcT aac gag
   5443 gaa agc acg tta tac gtg ctc gtc aaa gca acc ata gta cgc gcc ctg
```

TABLE 36-continued

```
  5491 TAG cggcgcatt
!      End IV
  5503 aagcgcggcg ggtgtggtgg ttacgcgcag cgtgaccgct acacttgcca
gcgccctagc
  5563 gcccgctcct ttcgctttct tcccttcctt tctcgccacg ttcGCCGGCt
ttccccgtca
!                                                      NgoMI.
  5623 agctctaaat cggggctcc ctttagggtt ccgatttagt gctttacggc
acctcgaccc
  5683 caaaaaactt gatttgggtg atggttCACG TAGTGggcca tcgccctgat
agacggtttt
!                            DraIII....
  5743 tcgccctttG ACGTTGGAGT Ccacgttctt taatagtgga ctcttgttcc
aaactggaac
!              DrdI..........
  5803 aacactcaac cctatctcgg gctattcttt tgatttataa gggattttgc
cgatttcgga
  5863 accaccatca acaggattt tcgcctgctg ggcaaaccaa gcgtggaccg
cttgctgcaa
  5923 ctctctcagg gccaggcggt gaagggcaat CAGCTGttgc cCGTCTCact
ggtgaaaaga
!                                      PvuII.     BsmBI.
  5983 aaaaccaccc tGGATCC AAGCTT
!               BamHI  HindIll (1/2)
!          Insert carrying bla gene
  6006    gcaggtg gcacttttcg gggaaatgtg cgcggaaccc
  6043 ctatttgttt attttctaa atacattcaa atatGTATCC gctcatgaga
caataaccct
!                                            BciVI
  6103 gataaatgct tcaataatat tgaaaaAGGA AGAgt
!                           RBS.?...
!    Start bla gene
  6138 ATG agt att caa cat ttc cgt gtc gcc ctt att ccc ttt ttt gcg gca
ttt
  6189 tgc ctt cct gtt ttt gct cac cca gaa acg ctg gtg aaa gta aaa gat
gct
  6240 gaa gat cag ttg ggC gcA CTA GTg ggt tac atc gaa ctg gat ctc aac
agc
!                         SpeI....
!               ApaLI & BssSI Removed
  6291 ggt aag atc ctt gag agt ttt cgc ccc gaa gaa cgt ttt cca atg atg
agc
  6342 act ttt aaa gtt ctg cta tgt GGC GcG Gta tta tcc cgt att gac gcc
ggg6393 caa gaG CAA CTC GGT CGc cgC ATA cAC tat tct cag aat gac ttg gtt
gAG
!                BcgI............
ScaI
  6444 TAC Tca cca gtc aca gaa aag cat ctt acg gat ggc atg aca gta aga
gaa
!     ScaI.
  6495 tta tgc agt gct gcc ata acc atg agt gat aac act gcg gcc aac tta
ctt
  6546 ctg aca aCG ATC Gga gga ccg aag gag cta acc gct ttt ttg cac aac
atg
!              PvuI....
  6597 ggg gat cat gta act cgc ctt gat cgt tgg gaa ccg gag ctg aat gaa
gcc
  6648 ata cca aac gac gag cgt gac acc acg atg cct gta gca atg Gca aca
acg
  6699 tTG CGC Aaa cta tta act ggc gaa cta ctt act cta gct tcc cgg caa
caa
!      FspI....
!
  6750 tta ata gac tgg atg gag gcg gat aaa gtt gca gga cca ctt ctg cgc
tcg
  6801 GCC ctt ccG GCt ggc tgg ttt att gct gat aaa tct gga gcc ggt gag
cgt
!     BglI..........
  6852 gGG TCT Cgc ggt atc att gca gca ctg ggg cca gat ggt aag ccc tcc
cgt
!     BsaI....
  6903 atc gta gtt atc tac acG ACg ggg aGT Cag gca act atg gat gaa cga
aat
!                        AhdI...........
  6954 aga cag atc gct gag ata  ggt gcc tca ctg att aag cat tgg TAA ctgt
!                                                               stop
  7003 cagaccaagt ttactcatat atactttaga ttgatttaaa acttcatttt
taatttaaaa
  7063 ggatctaggt gaagatcctt tttgataatc tcatgaccaa aatcccttaa
cgtgagtttt
```

TABLE 36-continued

```
7123 cgttccactg tacgtaagac cccc
7147 AAGCTT GTCGAC tgaa tggcgaatgg cgctttgcct
!    HindIII SalI..
!    (2/2)   HincII
7183 ggtttccggc accagaagcg gtgccggaaa gctggctgga gtgcgatctt
!
! Start of Fab-display cassette, the Fab DSR-A05, selected for
! binding to a protein antigen.
!
7233 CCTGAcG CTCGAG
!    xBsu36I XhoI..
!
! PlacZ promoter is in the following block
!
7246                         cgcaacgc aattaatgtg agttagctca
7274 ctcattaggc accccaggct ttacacttta tgcttccggc tcgtatgttg
7324 tgtggaattg tgagcggata acaatttcac acaggaaaca gctatgacca
7374 tgattacgCC AagcttTGGa gccttttttt tggagatttt caac
!            PflMI.......
!            Hind3. (there are 3)
! Gene iii signal sequence: (Amino acid sequence is SEQ ID NO: 587)
!    1  2  3  4  5  6  7  8  9 10 11 12 13 14 15
!    M  K  K  L  L  F  A  I  P  L  V  V  P  F  Y
7418 gtg aaa aaa tta tta ttc gca att cct tta gtt gtt cct ttc tat
!
!    16 17 18         Start light chain (L20:JK1)
!    S  H  S  A  Q  D  I  Q  M  T  Q  S  P  A
7463 tct cac aGT GCA Caa gac atc cag atg acc cag tct cca gcc
!            ApaLI...
!            Sequence supplied by extender............
!
!            T  L  S  L
7505         acc ctg tct ttg
!
!    S  P  G  E  R  A  T  L  S  C  R  A  S  Q  G
7517 tct cca ggg gaa aga gcc acc ctc tcc tgc agg gcc agt cag Ggt
!
!    V  S  S  Y  L  A  W  Y  Q  Q  K  P  G  Q  A
7562 gtt agc agc tac tta gcc tgg tac cag cag aaa cct ggc cag gct
!
!    P  R  L  L  I  Y  D  A  S  S  R  A  T  G  I
7607 ccc agg ctc ctc atc tat gAt gca tcc aAc agg gcc act ggc atc
!
!    P  A  R  F  S  G  S  G  P  G  T  D  F  T  L
7652 cca gCc agg ttc agt ggc agt ggg Cct ggg aca gac ttc act ctc
!
!    T  I  S  S  L  E  P  E  D  F  A  V  Y  Y  C
7697 acc atc agc agC ctA gag cct gaa gat ttt gca gtT tat tac tgt
!
!    Q  Q  R  S  W  H  P  W  T  F  G  Q  G  T  R
7742 cag cag CGt aAc tgg cat ccg tgg ACG TTC GGC CAA GGG ACC AAG
!
!    V  E  I  K  R  T  V  A  A  P  S  V  F  I  F
7787 gtg gaa atc aaa cga act gtg gCT GCA Cca tct gtc ttc atc ttc
!                                   BsgI....
!
!    P  P  S  D  E  Q  L  K  S  G  T  A  S  V  V
7832 ccg cca tct gat gag cag ttg aaa tct gga act gcc tct gtt gtg
!
!    C  L  L  N  N  F  Y  P  R  E  A  K  V  Q  W
7877 tgc ctg ctg aat aac ttc tat ccc aga gag gcc aaa gta cag tgg
!
!    K  V  D  N  A  L  Q  S  G  N  S  Q  E  S  V
7922 aag gtg gat aac gcc ctc caa tcg ggt aac tcc cag gag agt gtc
!
!    T  E  R  D  S  K  D  S  T  Y  S  L  S  S  T
7967 aca gag cgg gac agc aag gac agc acc tac agc ctc agc agc acc
!
!    L  T  L  S  K  A  D  Y  E  K  H  K  V  Y  A
8012 ctg acG CTG AGC aaa gca gac tac gag aaa cac aaa gtc tac gcc
!            EspI.....
!
!    C  E  V  T  H  Q  G  L  S  S  P  V  T  K  S
8057 tgc gaa gtc acc cat cag ggc ctG AGC TCg ccc gtc aca aag agc
!                                   SacI....
!
!    F  N  R  G  E  C  .  .
8102 ttc aac agg gga gag tgt taa taa
!
```

TABLE 36-continued

```
 8126       GGCGCG CCaattctat ttcaaGGAGA cagtcata
!           AscI.....            RBS2.
!     (Amino acid sequence is SEQ ID NO: 588)
!          PelB signal sequence------(22 codons)----->
!           1   2   3   4   5   6   7   8   9  10  11  12  13  14  15
!           M   K   Y   L   L   P   T   A   A   A   G   L   L   L   L
 8160       atg aaa tac cta ttg cct acg gca gcc gct gga ttg tta tta ctc
!
!           ...PelB signal------------> Start VH, FR1----------------->
!           16  17  18  19  20  21  22  23  24  25  26  27  28  29  30
!           A   A   Q   P   A   M   A   E   V   Q   L   L   E   S   G
 8205       gcG GCC cag ccG GCC atg gcc gaa gtt CAA TTG tta gag tct ggt
!              SfiI............              MfeI...
!                           NcoI....
!
!           31  32  33  34  35  36  37  38  39  40  41  42  43  44  45
!           G   G   L   V   Q   P   G   G   S   L   R   L   S   C   A
 8250       ggc ggt ctt gtt cag cct ggt ggt tct tta cgt ctt tct tgc gct
!
!           ...FR1--------------------> CDR1-------------> FR2-------->
!           46  47  48  49  50  51  52  53  54  55  56  57  58  59  60
!           A   S   G   F   T   F   S   T   Y   E   M   R   W   V   R
 8295       gct TCC GGA ttc act ttc tct act tac gag atg cgt tgg gtt cgC
!               BspEI..
BstXI...
!
!           FR2------------------------------------> CDR2----------->
!           61  62  63  64  65  66  67  68  69  70  71  72  73  74  75
!           Q   A   P   G   K   G   L   E   W   V   S   Y   I   A   P
 8340       CAa gct ccT GGt aaa ggt ttg gag tgg gtt tct tat atc gct cct
!  BstXI................
!
!           ...CDR2--------------------------------------------> FR3---->
!           76  77  78  79  80  81  82  83  84  85  86  87  88  89  90
!           S   G   G   D   T   A   Y   A   D   S   V   K   G   R   F
 8385       tct ggt ggc gat act gct tat gct gac tcc gtt aaa ggt cgc ttc
!
!           91  92  93  94  95  96  97  98  99 100 101 102 103 104 105
!           T   I   S   R   D   N   S   K   N   T   L   Y   L   Q   M
 8430       act atc TCT AGA gac aac tct aag aat act ctc tac ttg cag atg
!                   XbaI...
!                   Supplied by extender------------------------------
!
!           ------------------------------------------FR3-------------->
!           106 107 108 109 110 111 112 113 114 115 116 117 118 119 120
!           N   S   L   R   A   E   D   T   A   V   Y   Y   C   A   R
 8475       aac agC TTA AGg gct gag gac act gca gtc tac tat tgt gcg agg
!                   AflII...
!           from extender--------------------------->
!
!           CDR3-------------------------------------------------->
FR4-->
!           121 122 123 124 125 126 127 128 129 130 131 132 133 134 135
!           R   L   D   G   Y   I   S   Y   Y   Y   G   M   D   V   W
 8520       agg ctc gat ggc tat att tcc tac tac tac ggt atg GAC GTC tgg
!                                                           AatII..
!
!           136 137 138 139 140 141 142 143 144 145
!           G   Q   G   T   T   V   T   V   S   S
 8565       ggc caa ggg acc acG GTC ACC gtc tca agc
!                           BstEII...
!
!           CH1 of IgG1---------->
!           A   S   T   K   G   P   S   V   F   P   L   A   P   S   S
 8595       gcc tcc acc aag ggc cca tcg gtc ttc ccc ctg gca ccc tcc tcc
!
!           K   S   T   S   G   G   T   A   A   L   G   C   L   V   K
 8640       aag agc acc tct ggg ggc aca gcg gcc ctg ggc tgc ctg gtc aag
!
!           D   Y   F   P   E   P   V   T   V   S   W   N   S   G   A
 8685       gac tac ttc ccc gaa ccg gtg acg gtg tcg tgg aac tca ggc gcc
!
!           L   T   S   G   V   H   T   F   P   A   V   L   Q   S   S
 8730       ctg acc agc ggc gtc cac acc ttc ccg gct gtc cta cag tCC TCA
Bsu36I....
!
!           G   L   Y   S   L   S   S   V   V   T   V   P   S   S   S
 8775       GGa ctc tac tcc ctc agc agc gta gtg acc gtg ccc tcc agc agc
!  Bsu36I....
```

TABLE 36-continued

```
!          L   G   T   Q   T   Y   I   C   N   V   N   H   K   P   S
    8820   ttg ggc acc cag acc tac atc tgc aac gtg aat cac aag ccc agc
!
!          N   T   K   V   D   K   K   V   E   P   K   S   C   A   A
    8865   aac acc aag gtg gac aag aaa gtt gag ccc aaa tct tgt GCG GCC
! NotI......
!
!          A   H   H   H   H   H   H   G   A   A   E   Q   K   L   I
    8910   GCa cat cat cat cac cat cac ggg gcc gca gaa caa aaa ctc atc
!  ..NotI...  H6 tag.................   Myc-Tag........................
!
!          S   E   E   D   L   N   G   A   A   q   A   S   S   A
    8955   tca gaa gag gat ctg aat ggg gcc gca tag GCT AGC tct gct
!          Myc-Tag...................        ... NheI...
!                                            Amber
!
! III'stump
! Domain 3 of III
---------------------------------------------------------
!
!       S   G   D   F   D   Y   E   K   M   A   N   A   N   K   G   A
 8997  agt ggc gac ttc gac tac gag aaa atg gct aat gcc aac aaa GGC GCC
!      tcc t   t   t   t   a   g       a   c   t       g   g   t
!W.T.
!
KasI...(2/4)
!
!       M   T   E   N   A   D   E   N   A   L   Q   S   D   A   K   G
 9045  atG ACT GAG AAC GCT GAC GAG aat gct ttg caa agc gat gcc aag ggt
!          c   a   t   c   t   a   c   g   c   a   g tct c   t   a   c
!W.T.
!
!       K   L   D   S   V   A   T   D   Y   G   A   A   I   D   G   F
 9093  aag tta gac agc gTC GCG Acc gac tat GGC GCC gcc ATC GAc ggc ttt
!          a   c   t   t tct           t   t   t c   t   t       t   c
!W.T.                  NruI....            KasI...(3/4)
!
!       I   G   D   V   S   G   L   A   N   G   N   G   A   T   G   D
 9141  atc ggc gat gtc agt ggt tTG GCC Aac ggc aac gga gcc acc gga gac
!      t       t   c   t tcc cct t   t   t   t   t   t   t   t
!W.T.
!                              MscI....(3/3)
!
!       F   A   G   S   N   S   Q   M   A   Q   V   G   D   G   D   N
 9189  ttc GCA GGT tcG AAT TCt cag atg gcC CAG GTT GGA GAT GGg gac aac
!          t   c   t       c   a       t   a   c   t   c   t   t
!W.T.
!          BspMI.. (2/2)                      XcmI................
!              EcoRI...
!
!       S   P   L   M,  N   N   F   R   Q   Y   L   P   S   L   R   Q
 9237  agt ccg ctt atg aac aac ttt aga cag tac ctt ccg tct ctt ccg cag
!      tca t   t   a       t       c   c   t   a   t   t   a   t   c   c   t       a
!W.T.
!
!       S   V   E   C   R   P   F   V   F   S   A   G   K   P   Y   E
 9285  agt gtc gag tgc cgt cca ttc gtt ttc tct gcc ggc aag cct tac gag
!      tcg t       a       c       t   c       t       agc t       a   a       a
!W.T.
!
!       F   S   I   D   C   D   K   I   N   L   F   R
 9333  ttc aGC Atc gac TGC gat aag atc aat ctt ttC CGC
!      t tct t   t   t   c       a   a   cta       c   t  !W.T.
!          BstAPI........                  SacII...
!                                          End Domain 3
!
!       G   V   F   A   F   L   L   Y   V   A   T   F   M   Y   V   F
 9369  GGc gtt ttc gct ttc ttg cta tac gtc gct act ttc atg tac gtt ttc
!      t   c   t   g   tctta t       t   c   c   t       t   a   t
! W.T.
!      start transmembrane segment
!
!       S   T   F   A   N   I   L       R   N   K   E   S
 9417  aGC ACT TTC GCC AAT ATT TTA     Cgc aac aaa gaa agc
!      tct g   t   c   a   c   g       t   g   tct ! W.T.
!                                      Intracellular anchor.
!              .   .
```

TABLE 36-continued

```
 9453            tag tga tct CCT AGG
!                            AvrII..
!
!
 9468  aag ccc gcc taa tga gcg ggc ttt ttt ttt ct ggt
!          | Trp terminator                        |
!
! End Fab cassette
 9503  ATGCAT CCTGAGG ccgat actgtcgtcg tccccctcaaa ctggcagatg
!       NsiI.. Bsu36I.(3/3)
 9551  cacggttacg atgcgcccat ctacaccaac gtgacctatc ccattacggt
caatccgccg
 9611  tttgttccca cggagaatcc gacgggttgt tactcgctca catttaatgt
tgatgaaagc
 9671  tggctacagg aaggccagac gcgaattatt tttgatggcg ttcctattgg
ttaaaaaatg
 9731  agctgattta acaaaaattt aaTgcgaatt ttaacaaaat attaacgttt
acaATTTAAA
!
Swa1...
 9791  Tatttgctta tacaatcttc ctgtttttgg ggcttttctg attatcaacc GGGGTAcat
 9850  ATG att gac atg cta gtt tta cga tta ccg ttc atc gat tct ctt gtt
tgc
!      Start gene II
 9901  tcc aga ctc tca ggc aat gac ctg ata gcc ttt gtA GAT CTc tca aaa
ata
!                                                   BglII...
 9952  gct acc ctc tcc ggc atT aat tta tca gct aga acg gtt gaa tat cat
att
10003  gat ggt gat ttg act gtc tcc ggc ctt tct cac cct ttt gaa tct tta
cct
10054  aca cat tac tca ggc att gca ttt aaa ata tat gag ggt tct aaa aat
ttt
10105  tat cct tgc gtt gaa ata aag gct tct ccc gca aaa gta tta cag ggt
cat
10156  aat gtt ttt ggt aca acc gat tta gct tta tgc tct gag gct tta ttg
ctt
10207  aat ttt gct aat tct ttg cct tgc ctg tat gat tta ttg gat gtt !
! gene II continues
!------------------------End of Table--------------------------------
```

TABLE 37

! DNA seq of w.t. M13 gene iii
(Nucleotide sequenc is SEQ ID NO: 590;
Amino acid sequence is SEQ ID NO: 591)

```
!      1   2   3   4   5   6   7   8   9  10  11  12  13  14  15
!      fM  K   K   L   L   F   A   I   P   L   V   V   P   F   Y
1579   gtg aaa aaa tta tta ttc gca att cct tta gtt gtt cct ttc tat
!      Signal sequence..........................................

!     16  17  18  19  20  21  22  23  24  25  26  27  28  29  30
!      S   H   S   A   E   T   V   E   S   C   L   A   K   P   H
1624   tct cac tcc gct gaa act gtt gaa agt tgt tta gca aaa ccc cat
! Signal sequence> Domain 1-----------------------------------

!     31  32  33  34  35  36  37  38  39  40  41  42  43  44  45
!      T   E   N   S   F   T   N   V   W   K   D   D   K   T   L
1669   aca gaa aat tca ttt act aac gtc tgg aaa gac gac aaa act tta
!      Domain 1---------------------------------------------

!     46  47  48  49  50  51  52  53  54  55  56  57  58  59  60
!      D   R   Y   A   N   Y   E   G   C   L   W   N   A   T   G
1714   gat cgt tac gct aac tat gag ggt tgt ctg tgG AAT GCt aca ggc
!                                                 BsmI....
!      Domain 1---------------------------------------------

!     61  62  63  64  65  66  67  68  69  70  71  72  73  74  75
!      V   V   V   C   T   G   D   E   T   Q   C   Y   G   T   W
1759   gtt gta gtt tgt act ggt gac gaa act cag tgt tac ggt aca tgg
!      Domain 1---------------------------------------------

!     76  77  78  79  80  81  82  83  84  85  86  87  88  89  90
!      V   P   I   G   L   A   I   P   E   N   E   G   G   G   S
1804   gtt cct att ggg ctt gct atc cct gaa aat gag ggt ggt ggc tct
!      Domain 1----------------------------> Linker 1-----------
```

TABLE 37-continued

! DNA seq of w.t. M13 gene iii
(Nucleotide sequenc is SEQ ID NO: 590;
Amino acid sequence is SEQ ID NO: 591)

```
!      91  92  93  94  95  96  97  98  99  100 101 102 103 104 105
!       E   G   G   G   S   E   G   G   G   S   E   G   G   G   T
1849   gag ggt ggc ggt tct gag ggt ggc ggt tct gag ggt ggc ggt act
!      Linker 1--------------------------------------------------->

!      106 107 108 109 110 111 112 113 114 115 116 117 118 119 120
!       K   P   P   E   Y   G   D   T   P   I   P   G   Y   T   Y
1894   aaa cct cct gag tac ggt gat aca cct att ccg ggc tat act tat
!      Domain 2---------------------------------------------------

!      121 122 123 124 125 126 127 128 129 130 131 132 133 134 135
!       I   N   P   L   D   G   T   Y   P   P   G   T   E   Q   N
1939   atc aac cct ctc gac ggc act taT CCG CCt ggt act gag caa aac
!                                      EciI....
!      Domain 2---------------------------------------------------

!      136 137 138 139 140 141 142 143 144 145 146 147 148 149 150
!       P   A   N   P   N   P   S   L   E   E   S   Q   P   L   N
1984   ccc gct aat cct aat cct tct ctt GAG GAG tct cag cct ctt aat
!                                          BseRI..
!      Domain 2---------------------------------------------------

!      151 152 153 154 155 156 157 158 159 160 161 162 163 164 165
!       T   F   M   F   Q   N   N   R   F   R   N   R   Q   G   A
2029   act ttc atg ttt cag aat aat agg ttc cga aat agg cag ggg gca
!      Domain 2---------------------------------------------------

!      166 167 168 169 170 171 172 173 174 175 176 177 178 179 180
!       L   T   V   Y   T   G   T   V   T   Q   G   T   D   P   V
2074   tta act gtt tat acg ggc act gtt act caa ggc act gac ccc gtt
!      Domain 2---------------------------------------------------

!      181 182 183 184 185 186 187 188 189 190 191 192 193 194 195
!       K   T   Y   Y   Q   Y   T   P   V   S   S   K   A   M   Y
2119   aaa act tat tac cag tac act cct gta tca tca aaa gcc atg tat
!      Domain 2---------------------------------------------------

!      196 197 198 199 200 201 202 203 204 205 206 207 208 209 210
!       D   A   Y   W   N   G   K   F   R   D   C   A   F   H   S
2164   gac gct tac tgg aac ggt aaa ttC AGa gaC TGc gct ttc cat tct
!                                      AlwNI.......
!      Domain 2---------------------------------------------------

!      211 212 213 214 215 216 217 218 219 220 221 222 223 224 225
!       G   F   N   E   D   P   F   V   C   E   Y   Q   G   Q   S
2209   ggc ttt aat gaG GAT CCa ttc gtt tgt gaa tat caa ggc caa tcg
!                       BamHI...
!      Domain 2---------------------------------------------------

!      226 227 228 229 230 231 232 233 234 235 236 237 238 239 240
!       S   D   L   P   Q   P   P   V   N   A   G   G   G   S   G
2254   tct gac ctg cct caa cct cct gtc aat gct ggc ggc ggc tct ggt
!      Domain 2---------------------------> Linker 2-----------

!      241 242 243 244 245 246 247 248 249 250 251 252 253 254 255
!       G   G   S   G   G   G   S   E   G   G   S   E   G   G
2299   ggt ggt tct ggt ggc ggc tct gag ggt ggt ggc tct gag ggt ggc
!      Linker 2--------------------------------------------------

!      256 257 258 259 260 261 262 263 264 265 266 267 268 269 270
!       G   S   E   G   G   S   E   G   G   S   G   G
2344   ggt tct gag ggt ggc ggc tct gag gga ggc ggt tcc ggt ggt ggc
!      Linker 2--------------------------------------------------

!      271 272 273 274 275 276 277 278 279 280 281 282 283 284 285
2389    S   G   S   G   D   F   D   Y   E   K   M   A   N   A   N
       tct ggt tcc ggt gat ttt gat tat gaa aag atg gca aac gct aat
!Linker 2>   Domain 3---------------------------------------------

!      286 287 288 289 290 291 292 293 294 295 296 297 298 299 300
!       K   G   A   M   T   E   N   A   D   E   N   A   L   Q   S
2434   aag ggg gct atg acc gaa aat gcc gat gaa aac gcg cta cag tct
!      Domain 3---------------------------------------------------

!      301 302 303 304 305 306 307 308 309 310 311 312 313 314 315
!       D   A   K   G   K   L   D   S   V   A   T   D   Y   G   A
```

TABLE 37-continued

| | DNA seq of w.t. M13 gene iii |
| :--- | :--- |
| | (Nucleotide sequenc is SEQ ID NO: 590; |
| | Amino acid sequence is SEQ ID NO: 591) |

```
 2479  gac gct aaa ggc aaa ctt gat tct gtc gct act gat tac ggt gct
 !     Domain 3---------------------------------------------------

!     316 317 318 319 320 321 322 323 324 325 326 327 328 329 330
 !      A   I   D   G   F   I   G   D   V   S   G   L   A   N   G
 2524  gct atc gat ggt ttc att ggt gac gtt tcc ggc ctt gct aat ggt
 !     Domain 3---------------------------------------------------

!     331 332 333 334 335 336 337 338 339 340 341 342 343 344 345
 !      N   G   A   T   G   D   F   A   G   S   N   S   Q   M   A
 2569  aat ggt gct act ggt gat ttt gct ggc tct aat tcc caa atg gct
 !     Domain 3---------------------------------------------------

!     346 347 348 349 350 351 352 353 354 355 356 357 358 359 360
 !      Q   V   G   D   G   D   N   S   P   L   M   N   N   F   R
 2614  caa gtc ggt gac ggt gat aat tca cct tta atg aat aat ttc cgt
 !     Domain 3---------------------------------------------------

!     361 362 363 364 365 366 367 368 369 370 371 372 373 374 375
 !      Q   Y   L   P   S   L   P   Q   S   V   E   C   R   P   F
 2659  caa tat tta cct tcc ctc cct caa tcg gtt gaa tgt cgc cct ttt
 !     Domain 3---------------------------------------------------

!     376 377 378 379 380 381 382 383 384 385 386 387 388 389 390
 !      V   F   S   A   G   K   P   Y   E   F   S   I   D   C   D
 2704  gtc ttt agc gct ggt aaa cca tat gaa ttt tct att gat tgt gac
 !     Domain 3---------------------------------------------------

!     391 392 393 394 395 396 397 398 399 400 401 402 403 404 405
 !      K   I   N   L   F   R   G   V   F   A   F   L   L   Y   V
 2749  aaa ata aac tta ttc cgt ggt gtc ttt gcg ttt ctt tta tat gtt
 !     Domain 3--------------> Transmembrane segment--------------

!     406 407 408 409 410 411 412 413 414 415 416 417 418 419 420
 !      A   T   F   M   Y   V   F   S   T   F   A   N   I   L   R
 2794  gcc acc ttt atg tat gta ttt tct acg ttt gct aac ata ctg cgt
 !     Transmembrane segment--------------------------------> ICA--

!     421 422 423 424 425
 !      N   K   E   S   .
 2839  aat aag gag tct taa ! 2853
 !     ICA----------->

!------------------End of Table
 ---------------------------------------
```

ICA = intracellular anchor

TABLE 38

Whole mature III anchor M13-III derived anchor with recoded DNA

```
 !
 !         1   2   3
 !         A   A   A                    (SEQ ID NO: 594)
 !    1   GCG gcc gca                   (SEQ ID NO: 593)
 !        NotI . . .
 !         4   5   6   7   8   9  10  11  12  13  14  15  16  17
 !         H   H   H   H   H   H   G   A   A   E   Q   K   L   I
 !   10   cat cat cat cac cat cac ggg gcc gca gaa caa aaa ctc atc
 !
 !        18  19  20  21  22  23  24  25  26  27  28  29
 !
 !         S   E   E   D   L   N   G   A   A   .   A   S
 !   52   tca gaa gag gat ctg aat ggg gcc gca Tag GCT AGC
 !                                            NheI...
 !
 !        30  31  32  33  34  35  36  37  38  39
 !         D   I   N   D   D   R   M   A   S   T
 !   88   GAT ATC aac gat gat cgt atg gct tct act
 ! (ON_G37bot) [RC] 5'-c aac gat gat cgt atg gcG CAt Gct gcc gag aca g-3'
 !        EcoRV.. (SEQ ID NO: 592)
 !        Enterokinase cleavage site.
```

TABLE 38-continued

Whole mature III anchor M13-III derived anchor with recoded DNA

```
!
! Start mature III (recoded) Domain 1---->
!            40  41  42  43
!             A   E   T   V
 118         |gcC|gaG|acA|gtC|
!               t   a   t   t ! W.T.
!
!
!        44  45  46  47  48  49  50  51  52  53  54  55  56  57  58
!         E   S   C   L   A   K   P   H   T   E   N   S   F   T   N
 130     |gaa|TCC|tgC|CTG|GCC|AaG|ccT|caC|acT|gaG|aat|AGT|ttC|acA|Aat|
!           agt tta  a   c   t   a   a     tca  t   t   c ! W.T.
!               MscI....
!
!        59  60  61  62  63  64  65  66  67  68  69  70  71  72  73
!         V   W   K   D   D   K   T   L   D   R   Y   A   N   Y   E
 175     |gtg|TGG|aaG|gaT|gaT|aaG|acC|CtT|gAT|CGA|TaT|gcC|aaT|taC|gaA|
!           c       a   c   c   a  tta          t   c   t   c   g ! W.T.
!                                       BspDI...
!
!        74  75  76  77  78  79  80  81  82  83  84  85  86  87  88
!         G   C   L   W   N   A   T   G   V   V   V   C   T   G   D
 220     |ggC|tgC|TtA|tgg|aat|gcC|ACC|GGC|GtC|gtT|gtC|TGC|ACG|ggC|gaT|
!           t  tcg          t   a       t   a   t   t   t   c ! W.T.
!                               SgrAI......       BsgI....
!
!        89  90  91  92  93  94  95  96  97  98  99 100 101 102 103
!         E   T   Q   C   Y   G   T   W   V   P   I   G   L   A   I
 265     |gaG|acA|caA|tgC|taT|ggC|ACG|TGg|gtG|ccG|atA|gGC|TTA|GCC|atA|
!           a   t   g   t   c   a           t   t  gc t   t   c ! W.T.
!                           PmlI....                 BlpI.....
!
!    Domain 1----->  Linker 1--------------->
!       104 105 106 107 108 109 110 111 112 113 114 115 116 117 118
!         P   E   N   E   G   G   G   S   E   G   G   G   S   E   G
 310     |ccG|gaG|aaC|gaA|ggC|ggC|ggT|AGC|gaA|ggC|ggT|ggC|AGC|gaA|ggC|
!           t   a   g   t       c tct   g   t   c  ttct   g   t ! W.T.
!
!       Linker 1--------------------->  Domain 2-------------->
!       119 120 121 122 123 124 125 126 127 128 129 130 131 132 133
!         G   G   S   E   G   G   G   T   K   P   P   E   Y   G   D
 355     |ggT|GGA|TCC|gaa|ggA|ggT|ggA|acC|aaG|ccG|gaA|taT|ggC|gaC|
!           c   t   t   g   t   c   t   t   a   t   g   c   t ! W.T.
!               BamHI..(2/2)
!
!       134 135 136 137 138 139 140 141 142 143 144 145 146 147 148
!         T   P   I   P   G   Y   T   Y   I   N   P   L   D   G   T
 400     |acT|ccG|atA|CCT|GGT|taC|acC|taC|atT|aaT|ccG|TtA|gaT|ggA|acC|
!           a   t   g   c   t   t   c   c  tcc  c   c   t ! W.T.
!                       SexAI....
!
!       149 150 151 152 153 154 155 156 157 158 159 160 161 162 163
!         Y   P   P   G   T   E   Q   N   P   A   N   P   N   P   S
 445     |taC|ccT|ccG|ggC|acC|gaA|caG|aaT|ccT|gcC|aaC|ccG|aaC|ccA|AGC|
!           T   G   t   t   t   g   a   c   c   t   t   t  ttct ! W.T.
!                                                           HindIII...
!
!       164 165 166 167 168 169 170 171 172 173 174 175 176 177 178
!         L   E   S   Q   P   L   N   T   F   M   F   Q   N   N
 490     |TTA|gaA|gaA|AGC|caA|ccG|TtA|aaC|acC|ttT|atg|ttC|caA|aaC|aaC|
!           c  t   G  Gtct  g   t  tct  t   c        t   g   t   t ! W.T.
! HindIII.
!
!       179 180 181 182 183 184 185 186 187 188 189 190 191 192 193
!         R   F   R   N   R   Q   G   A   L   T   V   Y   T   G   T
 535     |CgT|ttT|AgG|aaC|CgT|caA|gGT|GCT|CtT|acC|gTG|TAC|AcT|ggA|acC|
!           a   g   c   c   a  tag  g   g  ata  t   t   t   g   c   t ! W.T.
!                                       HgiAI...     BsrGI...
!
!       209 210 211 212 213 214 215 216 217 218 219 220 221 222 223
!         P   V   S   S   K   A   M   Y   D   A   Y   W   N   G   K
 625     |ccG|gtC|TCG|AGt|aaG|gcT|atg|taC|gaT|gcC|taT|tgg|aaT|ggC|acG|
!           t   a  atca  a   c       t   c   t   c       c   t   a ! W.T.
!           BsaI ....
!               XhoI ....
!
!       224 225 226 227 228 229 230 231 232 233 234 235 236 237 238
!         F   R   D   C   A   F   H   S   G   F   N   E   D   P   F
 670     |ttT|CgT|gaT|tgT|gcC|ttT|caC|AGC|ggT|ttC|aaC|gaa|gac|CCt|ttT|
!           C   Aa   C    c   t  ttct  c   t   G   T   a   c ! W.T.
!
!       239 240 241 242 243 244 245 246 247 248 249 250 251 252 253
!         V   C   E   Y   Q   G   Q   S   S   D   L   P   Q   P   P
 715     |gtC|tgC|gaG|taC|caG|ggT|caG|AGT|AGC|gaT|TtA|ccG|caG|ccA|CCG|
!           t   t   a   t   a   c  atcg tct  ccg  t   a   t ! W.T.
! DrdI......                                              AgeI.....
```

TABLE 38-continued

Whole mature III anchor M13-III derived anchor with recoded DNA

```
!  Domain 2--------->  Linker 2--------------------->
!        254 255 256 257 258 259 260 261 262 263 264 265 266 267 268
!         V   N   A   G   G   S   G   G   G   S   G   G   G   S
  760   |GTT|AAC|gcG|ggT|ggT|ggT|AGC|ggC|ggA|ggC|AGC|ggT|ggT|AGC|
!         c   t   t   c   c   c tct   t   t t tct   t   c   c tct ! W.T.
! AgeI.....
!        HpaI...
!        HincII.
!
!        Linker 2-----------------------------------------> Domain 3-->
!        269 270 271 272 273 274 275 276 277 278 279 280 281 282 283
!         E   G   G   S   E   G   G   G   S   G   G   G   S
  805   |gaA|ggC|ggA|ggT|AGC|gaA|ggA|ggT|ggC|AGC|ggA|ggT|ggT|AGC|ggC|
!         g   t   t   c tct   g   t   c tct   g   t   c tct   t  ! W.T.
!
!        ------------Domain 3-------------------->
!        284 284 286 287 288 289 290 291 292 293 294 295 296 297 298
!         S   G   D   F   D   Y   E   K   M   A   N   A   N   K   G
  850   |AGT|ggC|gac|ttc|gac|tac|gag|aaa|atg|gct|aat|gcc|aac|aaa|GGC|
!         tcc   t   t   t   t   a   g       a   c   t   g   g ! W.T.
!                                                          KasI....
!
!        299 300 301 302 303 304 305 306 307 308 309 310 311 312 313
!         A   M   T   E   N   A   D   E   N   A   L   Q   S   D   A
  895   |GCC|atg|act|gag|aac|gct|gac|gaG|AAT|GCA|ctg|caa|agt|gat|gCC|
!         t   c   act   t   c   a   c   g       a gtc   c   t ! W.T.
! KasI....                              BsmI....                    StyI...
!
!        314 315 316 317 318 319 320 321 322 323 324 325 326 327 328
!         K   G   K   L   D   S   V   A   T   D   Y   G   A   A   I
  940   |AAG|GGt|aag|tta|gac|agc|gTC|GCc|Aca|gac|tat|ggT|GCt|gcc|atc|
!         a   c   act   t tct       t       t   t           t      ! W.T.
! StyI......         PflFI......
!        329 330 331 332 333 334 335 336 337 338 339 340 341 342 343
!         D   G   F   I   G   D   V   S   G   L   A   N   G   N
  985   |gac|ggc|ttt|atc|ggc|gat|gtc|agt|ggt|ctg|gct|aac|ggc|aac|gga|
!         t   t   c   t   t   c   t tcc   c   t       t   t   t ! W.T.
!
!        344 345 346 347 348 349 350 351 352 353
!         A   T   G   D   F   A   G   S   N   S
 1030   |gcc|acc|gga|gac|ttc|GCA|GGT|tcG|AAT|TCt|
!         t   t   t   t   t   c   t       c ! W.T.
!                                      BstBI...
!                                         EcoRI...
!                              BspMI..
!
!        354 355 356 357 358 359 360 361 362 363
!         Q   M   A   Q   V   G   D   G   D   N
 1060     cag atg gcC CAG GTT GGA GAT GGg gac aac
!          a       t   a   c   t   c   t   t ! W.T.
!                  XcmI................
!
!        364 365 366 367 368 369 370 371 372 373 374 375 376 377 378 379
!         S   P   L   M   N   N   F   R   Q   Y   L   P   S   L   P   Q
 1090     agt ccg ctt atg aac aac ttt aga cag tac ctt ccg tct ctt ccg cag
!         tca     tta     t       t   cct     a   tta     t   c       a ! W.T.
!
!        380 381 382 383 384 385 386 387 388 389 390 391 392 393 394 395
!         S   V   E   C   R   P   F   V   F   S   A   G   K   P   Y   E
 1138     agt gtc gag tgc cgt cca ttc gtt ttc tct gcc ggc aag cct tac gag
!         tcg   t   a   t   c   t   t   c   t agc t       a   a   t   a ! W.T.
!
!        Domain 3------------------------------------ >
!        396 397 398 399 400 401 402 403 404 405 406 407
!         F   S   I   D   C   D   K   I   N   L   F   R
 1186     ttc aGC Atc gac TGC gat aag atc aat ctt ttC CGC
!           t tct   t       t   c   a   a   cta       t
!             BstAPI                              SacII...
!
!        transmembrane segment-------------->
!        408 409 410 411 412 413 414 415 416 417 418 419 420 421 422 423
!         G   V   F   A   F   L   L   Y   V   A   T   F   M   Y   V   F
 1222     GGc gtt ttc gct ttc ttg cta tac gtc gct act ttc atg tac gtt ttc
!           t   c   t   g   tctta   t       c   c   t           t   a   t ! W.T.
!
!        424 425 426 427 428 429 430                 431 432 433 434 435
!         S   T   F   A   N   I   L                   R   N   K   E   S
 1270     aGC ACT TTC GCC AAT ATT TTA                 Cgc aac aaa gaa agc
!         tct   g   t   c   a   c   g                     t   g gtct ! W.T.
!                                         Intracellular anchor.
```

TABLE 38-continued

Whole mature III anchor M13-III derived anchor with recoded DNA

```
   1306            tag tga tct CCT AGG
!                                 AvrII..
 1321  aag ccc gcc taa tga gcg ggc ttt ttt ttt ct  ggt
!          | Trp terminator                  |
! End Fab cassette
!---------------------------End of Table----------------------------
```

TABLE 39

ONs to make deletions in III

```
! ONs for use with NheI
!                                                                    N
(SEQ ID NO: 595)
(ON_G29bot)                    5'-c gTT gAT ATc gcT Agc cTA Tgc-3'    ! 22
! this is the reverse complement of  5'-gca tag gct agc gat atc aac g-3'
!                         NheI... scab..........
(ON_G104top) 5' -g|ata|ggc|tta|gcT|aGC|ccg|gag|aac|gaa|gg-3'          ! 30
(SEQ ID NO: 596)
!            Scab..........NheI... 104 105 106 107 108
(ON_G236tCS) 5'-c|ttt|cac|agc|ggt|ttc|GCT|AGC|gac|cct|ttt|gtc|tgc-3'  ! 37
(SEQ ID NO: 597)
!                         NheI... 236 237 238 239 240
(ON_G236tCS) 5'-c|ttt|cac|agc|ggt|ttc|GCT|AGC|gac|cct|ttt|gtc|Agc-
!                         NheI... 236 237 238 239 240
         gag|tac|cag|ggt|c-3'  (SEQ ID NO: 598)
! 50
! ONs for use with SphI G CAT Gc
(ON_X37bot)        5'-gAc TgT cTc ggc Agc ATg cgc CAT Acg ATc ATc gTT g-3'  ! 37
(SEQ ID NO: 599)
!          N D D R M A H A (SEQ ID NO:  601)
! (ON_X37bot) = [RC]  5'-c aac gat gat cgt atg gcG CAt Gct gcc gag aca gtc-3'
(SEQ ID NO: 600)
!                         SphI... Scab..........
(ON_X104top) 5' -g|gtG ccg|ata|ggc|ttG|CAT|GCa|ccg|gag|aac|gaa|gg-3'  ! 36
(SEQ ID NO: 617)
!            Scab................SphI.... 104 105 106 107 108
(ON_X236top) 5'-c|ttt|cac|agc|ggc|ttG|CaT|gCa|gac|cct|ttt|gtc|tgc-3'  ! 37
(SEQ ID NO: 602)
!                         SphI...   236 237 238 239 240
(ON_G236tCS) 5'-c|ttt|cac|agc|ggt|ttG|CaT|gCa|gac|cct|ttt|gtc|Agc-
!                         NheI... 236 237 238 239 240
         gag|tac|cag|ggt|c-3'  (SEQ ID NO: 603)
! 50
```

TABLE 40

Phage titers and enrichments of selections with a DY3F31-based human Fab library

| | Input (total cfu) | Output (total cfu) | Output/input ratio |
|---|---|---|---|
| R1-ox selected on phOx-BSA | $4.5 \times 10^{12}$ | $3.4 \times 10^{5}$ | $7.5 \times 10^{-8}$ |
| R2-Strep selected on Strep-beads | $9.2 \times 10^{12}$ | $3 \times 10^{8}$ | $3.3 \times 10^{-5}$ |

TABLE 41

Frequency of ELISA positives in DY3F31-based Fab libraries

| | Anti-M13 HRP | 9E10/RAM-HRP | Anti-CK/CL Gar-HRP |
|---|---|---|---|
| R2-ox (with IPTG induction) | 18/44 | 10/44 | 10/44 |
| R2-ox (without IPTG) | 13/44 | ND | ND |
| R3-strep (with IPTG) | 39/44 | 38/44 | 36/44 |
| R3-strep (without IPTG) | 33/44 | ND | ND |

SEQUENCE LISTING

<160> NUMBER OF SEQ ID NOS: 637

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catgtgtatt actgtgc                                                    17

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cacatccgtg cttcttgcac ggatgtggca cagtaataca catg                      44

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgtattaga ctgctgcc                                                   18

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcagcagtc taatacacca catccgtgtt cttcacggat gtg                       43

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacatccgtg tttgttacac ggatgtggtg tcttacagtc cattctg                   47

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagaatggac tgtaagacac                                                        20

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atcgagtctc actgagccac atccgtggtt ttccacggat gtg                              43

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctcagtgag actcgat                                                           17

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(24)
<223> OTHER INFORMATION: a, t, c, g, unknown or other

<400> SEQUENCE: 9
cacgaggagn nnnnnnnnnn nnnn                                                   24

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgaccgaat tgctacaag                                                         19

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gactcctcag cttcttgctg aggagtcctt gtagcaattc ggtcat                           46

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: 6 His tag

<400> SEQUENCE: 12

His His His His His His
1               5

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 13 gtctcnnnnn                                                            10

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 14
nnnnnngaga c                                                          11

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(24)
<223> OTHER INFORMATION: a, t, c, g, unknown or other

<400> SEQUENCE: 15
cacggatgtg nnnnnnnnnn nnnn                                            24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(14)
<223> OTHER INFORMATION: a, t, c, g, unknown or other

<400> SEQUENCE: 16
nnnnnnnnnn nnnncacatc cgtg                                            24

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
gtgtattact gtgc                                                        14

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cacatccgtg cacggatgtg gcacagtaat acac                                  34

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgtattaga ctgc                                                        14

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcagtctaat acaccacatc cgtgcacgga tgtg                                  34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacatccgtg cacggatgtg gtgtcttaca gtcc                                  34

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggactgtaag acac                                                        14

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```
gagtctcact gagccacatc cgtgcacgga tgtg 34

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 24
gctcagtgag actc 14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 25
gtgtattact gtgc 14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 26
gtatattact gtgc 14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 27
gtgtattact gtaa 14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 28
gtgtattact gtac 14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 29
ttgtattact gtgc 14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgtatcact gtgc                                                         14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acatattact gtgc                                                         14

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acgtattact gtgc                                                         14

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgtattact gtgc                                                         14

<210> SEQ ID NO 34
<211> LENGTH: 101
<212> TYPE: DNA
<213> ORGANISM: Homo sapiens

<400> SEQUENCE: 34
agggtcacca tgaccaggga cacgtccatc agcacagcct acatgabcga gctgagcagg        60
ctgagatctg acgacacggc cgtgtattac tgtgcgagag a                          101

<210> SEQ ID NO 35
<211> LENGTH: 98
<212> TYPE: DNA
<213> ORGANISM: Homo sapiens

<400> SEQUENCE: 35
agagtcacca ttaccaggga cacatccgcg agcacagcct acatggagct gagcagcctg        60
agatctgaag acacggctgt gtattactgt gcgagaga                               98

<210> SEQ ID NO 36
<211> LENGTH: 98

```
<212> TYPE: DNA
<213> ORGANISM: Homo sapiens

<400> SEQUENCE: 36
agagtcacca tgaccaggaa cacctccata agcacagcct acatggagct gagcagcctg     60
agatctgagg acacggccgt gtattactgt gcgagagg                             98

<210> SEQ ID NO 37
<211> LENGTH: 98
<212> TYPE: DNA
<213> ORGANISM: Homo sapiens

<400> SEQUENCE: 37
agagtcacca tgaccacaga cacatccacg agcacagcct acatggagct gaggagcctg     60
agatctgacg acacggccgt gtattactgt gcgagaga                             98

<210> SEQ ID NO 38
<211> LENGTH: 98
<212> TYPE: DNA
<213> ORGANISM: Homo sapiens

<400> SEQUENCE: 38
agagtcacca tgaccgagga cacatctaca gacacagcct acatggagct gagcagcctg     60
agatctgagg acacggccgt gtattactgt gcaacaga                             98

<210> SEQ ID NO 39
<211> LENGTH: 98
<212> TYPE: DNA
<213> ORGANISM: Homo sapiens

<400> SEQUENCE: 39
agagtcacca ttaccaggga caggtctatg agcacagcct acatggagct gagcagcctg     60
agatctgagg acacagccat gtattactgt gcaagata                             98

<210> SEQ ID NO 40
<211> LENGTH: 98
<212> TYPE: DNA
<213> ORGANISM: Homo sapiens

<400> SEQUENCE: 40
agagtcacca tgaccaggga cacgtccacg agcacagtct acatggagct gagcagcctg     60
agatctgagg acacggccgt gtattactgt gcgagaga                             98

<210> SEQ ID NO 41
<211> LENGTH: 98
<212> TYPE: DNA
<213> ORGANISM: Homo sapiens

<400> SEQUENCE: 41
agagtcacca ttaccaggga catgtccaca agcacagcct acatggagct gagcagcctg     60
agatccgagg acacggccgt gtattactgt gcggcaga                             98

<210> SEQ ID NO 42
<211> LENGTH: 98
<212> TYPE: DNA
<213> ORGANISM: Homo sapiens

<400> SEQUENCE: 42
agagtcacga ttaccgcgga cgaatccacg agcacagcct acatggagct gagcagcctg     60
agatctgagg acacggccgt gtattactgt gcgagaga                             98
```

<210> SEQ ID NO 43
<211> LENGTH: 98
<212> TYPE: DNA
<213> ORGANISM: Homo sapiens

<400> SEQUENCE: 43
agagtcacga ttaccgcgga caaatccacg agcacagcct acatggagct gagcagcctg    60
agatctgagg acacggccgt gtattactgt gcgagaga    98

<210> SEQ ID NO 44
<211> LENGTH: 98
<212> TYPE: DNA
<213> ORGANISM: Homo sapiens

<400> SEQUENCE: 44
agagtcacca taaccgcgga cacgtctaca gacacagcct acatggagct gagcagcctg    60
agatctgagg acacggccgt gtattactgt gcaacaga    98

<210> SEQ ID NO 45
<211> LENGTH: 100
<212> TYPE: DNA
<213> ORGANISM: Homo sapiens

<400> SEQUENCE: 45
aggctcacca tcaccaagga cacctccaaa aaccaggtgg tccttacaat gaccaacatg    60
gaccctgtgg acacagccac atattactgt gcacacagac    100

<210> SEQ ID NO 46
<211> LENGTH: 100
<212> TYPE: DNA
<213> ORGANISM: Homo sapiens

<400> SEQUENCE: 46
aggctcacca tctccaagga cacctccaaa agccaggtgg tccttaccat gaccaacatg    60
gaccctgtgg acacagccac atattactgt gcacggatac    100

<210> SEQ ID NO 47
<211> LENGTH: 100
<212> TYPE: DNA
<213> ORGANISM: Homo sapiens

<400> SEQUENCE: 47
aggctcacca tctccaagga cacctccaaa aaccaggtgg tccttacaat gaccaacatg    60
gaccctgtgg acacagccac gtattactgt gcacggatac    100

<210> SEQ ID NO 48
<211> LENGTH: 98
<212> TYPE: DNA
<213> ORGANISM: Homo sapiens

<400> SEQUENCE: 48
cgattcacca tctccagaga caacgccaag aactcactgt atctgcaaat gaacagcctg    60
agagccgagg acacggctgt gtattactgt gcgagaga    98

<210> SEQ ID NO 49
<211> LENGTH: 100
<212> TYPE: DNA
<213> ORGANISM: Homo sapiens

<400> SEQUENCE: 49

-continued

```
cgattcacca tctccagaga caacgccaag aactccctgt atctgcaaat gaacagtctg    60
agagctgagg acacggcctt gtattactgt gcaaaagata                         100
```

<210> SEQ ID NO 50
<211> LENGTH: 98
<212> TYPE: DNA
<213> ORGANISM: Homo sapiens

<400> SEQUENCE: 50

```
cgattcacca tctccaggga caacgccaag aactcactgt atctgcaaat gaacagcctg    60
agagccgagg acacggccgt gtattactgt gcgagaga                           98
```

<210> SEQ ID NO 51
<211> LENGTH: 98
<212> TYPE: DNA
<213> ORGANISM: Homo sapiens

<400> SEQUENCE: 51

```
cgattcacca tctccagaga aaatgccaag aactccttgt atcttcaaat gaacagcctg    60
agagccgggg acacggctgt gtattactgt gcaagaga                           98
```

<210> SEQ ID NO 52
<211> LENGTH: 98
<212> TYPE: DNA
<213> ORGANISM: Homo sapiens

<400> SEQUENCE: 52

```
agattcacca tctcaagaga tgattcaaaa aacacgctgt atctgcaaat gaacagcctg    60
aaaaccgagg acacagccgt gtattactgt accacaga                           98
```

<210> SEQ ID NO 53
<211> LENGTH: 98
<212> TYPE: DNA
<213> ORGANISM: Homo sapiens

<400> SEQUENCE: 53

```
cgattcacca tctccagaga caacgccaag aactccctgt atctgcaaat gaacagtctg    60
agagccgagg acacggcctt gtatcactgt gcgagaga                           98
```

<210> SEQ ID NO 54
<211> LENGTH: 98
<212> TYPE: DNA
<213> ORGANISM: Homo sapiens

<400> SEQUENCE: 54

```
cgattcacca tctccagaga caacgccaag aactcactgt atctgcaaat gaacagcctg    60
agagccgagg acacggctgt gtattactgt gcgagaga                           98
```

<210> SEQ ID NO 55
<211> LENGTH: 98
<212> TYPE: DNA
<213> ORGANISM: Homo sapiens

<400> SEQUENCE: 55

```
cggttcacca tctccagaga caattccaag aacacgctgt atctgcaaat gaacagcctg    60
agagccgagg acacggccgt atattactgt gcgaaaga                           98
```

<210> SEQ ID NO 56
<211> LENGTH: 98

```
<212> TYPE: DNA
<213> ORGANISM: Homo sapiens

<400> SEQUENCE: 56
cgattcacca tctccagaga caattccaag aacacgctgt atctgcaaat gaacagcctg      60
agagctgagg acacggctgt gtattactgt gcgaaaga                              98

<210> SEQ ID NO 57
<211> LENGTH: 98
<212> TYPE: DNA
<213> ORGANISM: Homo sapiens

<400> SEQUENCE: 57
cgattcacca tctccagaga caattccaag aacacgctgt atctgcaaat gaacagcctg      60
agagctgagg acacggctgt gtattactgt gcgagaga                              98

<210> SEQ ID NO 58
<211> LENGTH: 98
<212> TYPE: DNA
<213> ORGANISM: Homo sapiens

<400> SEQUENCE: 58
cgattcacca tctccagaga caattccaag aacacgctgt atctgcaaat gaacagcctg      60
agagctgagg acacggctgt gtattactgt gcgaaaga                              98

<210> SEQ ID NO 59
<211> LENGTH: 98
<212> TYPE: DNA
<213> ORGANISM: Homo sapiens

<400> SEQUENCE: 59
cgattcacca tctccagaga caattccaag aacacgctgt atctgcaaat gaacagcctg      60
agagccgagg acacggctgt gtattactgt gcgagaga                              98

<210> SEQ ID NO 60
<211> LENGTH: 100
<212> TYPE: DNA
<213> ORGANISM: Homo sapiens

<400> SEQUENCE: 60
cgattcacca tctccagaga caacagcaaa aactccctgt atctgcaaat gaacagtctg      60
agaactgagg acaccgcctt gtattactgt gcaaaagata                           100

<210> SEQ ID NO 61
<211> LENGTH: 98
<212> TYPE: DNA
<213> ORGANISM: Homo sapiens

<400> SEQUENCE: 61
cgattcacca tctccagaga caatgccaag aactcactgt atctgcaaat gaacagcctg      60
agagacgagg acacggctgt gtattactgt gcgagaga                              98

<210> SEQ ID NO 62
<211> LENGTH: 98
<212> TYPE: DNA
<213> ORGANISM: Homo sapiens

<400> SEQUENCE: 62
agattcacca tctcaagaga tggttccaaa agcatcgcct atctgcaaat gaacagcctg      60
aaaaccgagg acacagccgt gtattactgt actagaga                              98
```

<210> SEQ ID NO 63
<211> LENGTH: 98
<212> TYPE: DNA
<213> ORGANISM: Homo sapiens

<400> SEQUENCE: 63
cgattcacca tctccagaga caattccaag aacacgctgt atcttcaaat gaacagcctg    60
agagccgagg acacggccgt gtattactgt gcgagaga                            98

<210> SEQ ID NO 64
<211> LENGTH: 98
<212> TYPE: DNA
<213> ORGANISM: Homo sapiens

<400> SEQUENCE: 64
agattcacca tctccagaga caattccaag aacacgctgt atcttcaaat gggcagcctg    60
agagctgagg acatggctgt gtattactgt gcgagaga                            98

<210> SEQ ID NO 65
<211> LENGTH: 98
<212> TYPE: DNA
<213> ORGANISM: Homo sapiens

<400> SEQUENCE: 65
agattcacca tctccagaga caattccaag aacacgctgt atcttcaaat gaacagcctg    60
agagctgagg acacggctgt gtattactgt gcgagaga                            98

<210> SEQ ID NO 66
<211> LENGTH: 98
<212> TYPE: DNA
<213> ORGANISM: Homo sapiens

<400> SEQUENCE: 66
agattcacca tctcaagaga tgattcaaag aactcactgt atctgcaaat gaacagcctg    60
aaaaccgagg acacggccgt gtattactgt gctagaga                            98

<210> SEQ ID NO 67
<211> LENGTH: 98
<212> TYPE: DNA
<213> ORGANISM: Homo sapiens

<400> SEQUENCE: 67
aggttcacca tctccagaga tgattcaaag aacacggcgt atctgcaaat gaacagcctg    60
aaaaccgagg acacggccgt gtattactgt actagaca                            98

<210> SEQ ID NO 68
<211> LENGTH: 98
<212> TYPE: DNA
<213> ORGANISM: Homo sapiens

<400> SEQUENCE: 68
cgattcacca tctccagaga caacgccaag aacacgctgt atctgcaaat gaacagtctg    60
agagccgagg acacggctgt gtattactgt gcaagaga                            98

<210> SEQ ID NO 69
<211> LENGTH: 98
<212> TYPE: DNA
<213> ORGANISM: Homo sapiens

<400> SEQUENCE: 69

```
agattcacca tctccagaga caattccaag aacacgctgc atcttcaaat gaacagcctg    60
agagctgagg acacggctgt gtattactgt aagaaaga                           98
```

<210> SEQ ID NO 70
<211> LENGTH: 98
<212> TYPE: DNA
<213> ORGANISM: Homo sapiens

<400> SEQUENCE: 70

```
cgagtcacca tatcagtaga caagtccaag aaccagttct ccctgaagct gagctctgtg    60
accgccgcgg acacggccgt gtattactgt gcgagaga                           98
```

<210> SEQ ID NO 71
<211> LENGTH: 98
<212> TYPE: DNA
<213> ORGANISM: Homo sapiens

<400> SEQUENCE: 71

```
cgagtcacca tgtcagtaga cacgtccaag aaccagttct ccctgaagct gagctctgtg    60
accgccgtgg acacggccgt gtattactgt gcgagaaa                           98
```

<210> SEQ ID NO 72
<211> LENGTH: 98
<212> TYPE: DNA
<213> ORGANISM: Homo sapiens

<400> SEQUENCE: 72

```
cgagttacca tatcagtaga cacgtctaag aaccagttct ccctgaagct gagctctgtg    60
actgccgcgg acacggccgt gtattactgt gcgagaga                           98
```

<210> SEQ ID NO 73
<211> LENGTH: 98
<212> TYPE: DNA
<213> ORGANISM: Homo sapiens

<400> SEQUENCE: 73

```
cgagtcacca tatcagtaga caggtccaag aaccagttct ccctgaagct gagctctgtg    60
accgccgcgg acacggccgt gtattactgt gccagaga                           98
```

<210> SEQ ID NO 74
<211> LENGTH: 98
<212> TYPE: DNA
<213> ORGANISM: Homo sapiens

<400> SEQUENCE: 74

```
cgagttacca tatcagtaga cacgtccaag aaccagttct ccctgaagct gagctctgtg    60
actgccgcag acacggccgt gtattactgt gccagaga                           98
```

<210> SEQ ID NO 75
<211> LENGTH: 98
<212> TYPE: DNA
<213> ORGANISM: Homo sapiens

<400> SEQUENCE: 75

```
cgagttacca tatcagtaga cacgtctaag aaccagttct ccctgaagct gagctctgtg    60
actgccgcgg acacggccgt gtattactgt gcgagaga                           98
```

<210> SEQ ID NO 76
<211> LENGTH: 98

```
<212> TYPE: DNA
<213> ORGANISM: Homo sapiens

<400> SEQUENCE: 76
cgagtcacca tatcagtaga cacgtccaag aaccagttct ccctgaagct gagctctgtg      60
accgccgcgg acacggctgt gtattactgt gcgagaga                             98

<210> SEQ ID NO 77
<211> LENGTH: 98
<212> TYPE: DNA
<213> ORGANISM: Homo sapiens

<400> SEQUENCE: 77
cgagtcacca tatccgtaga cacgtccaag aaccagttct ccctgaagct gagctctgtg      60
accgccgcag acacggctgt gtattactgt gcgagaca                             98

<210> SEQ ID NO 78
<211> LENGTH: 98
<212> TYPE: DNA
<213> ORGANISM: Homo sapiens

<400> SEQUENCE: 78
cgagtcacca tatcagtaga cacgtccaag aaccagttct ccctgaagct gagctctgtg      60
accgctgcgg acacggccgt gtattactgt gcgagaga                             98

<210> SEQ ID NO 79
<211> LENGTH: 98
<212> TYPE: DNA
<213> ORGANISM: Homo sapiens

<400> SEQUENCE: 79
cgagtcacca tatcagtaga cacgtccaag aaccagttct ccctgaagct gagctctgtg      60
accgctgcgg acacggccgt gtattactgt gcgagaga                             98

<210> SEQ ID NO 80
<211> LENGTH: 98
<212> TYPE: DNA
<213> ORGANISM: Homo sapiens

<400> SEQUENCE: 80
cgagtcacca tatcagtaga cacgtccaag aaccagttct ccctgaagct gagctctgtg      60
accgccgcag acacggccgt gtattactgt gcgagaga                             98

<210> SEQ ID NO 81
<211> LENGTH: 98
<212> TYPE: DNA
<213> ORGANISM: Homo sapiens

<400> SEQUENCE: 81
caggtcacca tctcagccga caagtccatc agcaccgcct acctgcagtg gagcagcctg      60
aaggcctcgg acaccgccat gtattactgt gcgagaca                             98

<210> SEQ ID NO 82
<211> LENGTH: 96
<212> TYPE: DNA
<213> ORGANISM: Homo sapiens

<400> SEQUENCE: 82
cacgtcacca tctcagctga caagtccatc agcactgcct acctgcagtg gagcagcctg      60
aaggcctcgg acaccgccat gtattactgt gcgaga                               96
```

<210> SEQ ID NO 83
<211> LENGTH: 98
<212> TYPE: DNA
<213> ORGANISM: Homo sapiens

<400> SEQUENCE: 83
cgaataacca tcaacccaga cacatccaag aaccagttct ccctgcagct gaactctgtg    60
actcccgagg acacggctgt gtattactgt gcaagaga                           98

<210> SEQ ID NO 84
<211> LENGTH: 98
<212> TYPE: DNA
<213> ORGANISM: Homo sapiens

<400> SEQUENCE: 84
cggtttgtct tctccttgga cacctctgtc agcacggcat atctgcagat ctgcagccta    60
aaggctgagg acactgccgt gtattactgt gcgagaga                           98

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, t, c, g, unknown or other

<400> SEQUENCE: 85
gcnnnnnnng c                                                        11

<210> SEQ ID NO 86
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 86 caynnnnrtg                                                          10

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 87
gagtcnnnnn n                                                        11

<210> SEQ ID NO 88
<211> LENGTH: 11
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 88
nnnnnngaga c                                                             11

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 89 gaannnnttc                                                               10

<210> SEQ ID NO 90
<211> LENGTH: 90
<212> TYPE: DNA
<213> ORGANISM: Artificial Sequence
<220> FEATURE:
<223> OTHER INFORMATION: Description of Artificial Sequence: Synthetic
      3-23 FR3 nucleotide sequence
<220> FEATURE:
<221> NAME/KEY: CDS
<222> LOCATION: (1)..(90)
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (9)
<223> OTHER INFORMATION: a, t, c or g
<220> FEATURE:
<221> NAME/KEY: modified_base
<222> LOCATION: (12)
<223> OTHER INFORMATION: a, t, c or g
<220> FEATURE:
<221> NAME/KEY: modified_base
<222> LOCATION: (21)
<223> OTHER INFORMATION: a, t, c or g
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (33)
<223> OTHER INFORMATION: a, t, c or g
<220> FEATURE:
<221> NAME/KEY: modified_base
<222> LOCATION: (39)
<223> OTHER INFORMATION: a, t, c or g
<220> FEATURE:
<221> NAME/KEY: modified_base
<222> LOCATION: (51)
<223> OTHER INFORMATION: a, t, c or g
<220> FEATURE:
<221> NAME/KEY: modified_base
<222> LOCATION: (57)
<223> OTHER INFORMATION: a, t, c or g
<220> FEATURE:
<221> NAME/KEY: modified_base
<222> LOCATION: (60)
```

```
<223> OTHER INFORMATION: a, t, c or g
<220> FEATURE:
<221> NAME/KEY: modified_base
<222> LOCATION: (69)
<223> OTHER INFORMATION: a, t, c or g
<220> FEATURE:
<221> NAME/KEY: modified_base
<222> LOCATION: (72)
<223> OTHER INFORMATION: a, t, c or g
<220> FEATURE:
<221> NAME/KEY: modified_base
<222> LOCATION: (75)
<223> OTHER INFORMATION: a, t, c or g
<220> FEATURE:
<221> NAME/KEY: modified_base
<222> LOCATION: (87)
<223> OTHER INFORMATION: a, t, c or g

<400> SEQUENCE: 90 acn ath wsn mgn gay aay wsn aar aay acn ytn tay ttn car atg aay      48
Thr Ile Ser Arg Asp

```
<400> SEQUENCE: 94
ccctgtatct gcaaatgaac ag                                              22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ccgcctacct gcagtggagc ag                                              22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
cgctgtatct gcaaatgaac ag                                              22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cggcatatct gcagatctgc ag                                              22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
cggcgtatct gcaaatgaac ag                                              22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ctgcctacct gcagtggagc ag                                              22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
```

```
tcgcctatct gcaaatgaac ag                                             22
```

<210> SEQ ID NO 101
<211> LENGTH: 63
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 101

```
cgcttcacta agtctagaga caactctaag aatactctct acttgcagat gaacagctta   60
agg                                                                  63
```

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 102

```
caagtagaga gtattcttag agttgtctct agacttagtg aagcg                    45
```

<210> SEQ ID NO 103
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 103

```
cgcttcacta agtctagaga caactctaag aatactctct acttgcagct gaac          54
```

<210> SEQ ID NO 104
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 104

```
cgcttcacta agtctagaga caactctaag aatactctct acttgcaaat gaac          54
```

<210> SEQ ID NO 105
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 105

```
cgcttcacta agtctagaga caactctaag aatactctct acttgcagtg gagc          54
```

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 106

-continued

```
cgcttcacta agtctagaga c                                              21
```

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107

```
acatggagct gagcagcctg ag                                             22
```

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108

```
acatggagct gagcaggctg ag                                             22
```

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109

```
acatggagct gaggagcctg ag                                             22
```

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110

```
acctgcagtg gagcagcctg aa                                             22
```

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111

```
atctgcaaat gaacagcctg aa                                             22
```

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112

```
atctgcaaat gaacagcctg ag                                             22
```

```
<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
atctgcaaat gaacagtctg ag                                              22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
atctgcagat ctgcagccta aa                                              22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
atcttcaaat gaacagcctg ag                                              22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
atcttcaaat gggcagcctg ag                                              22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ccctgaagct gagctctgtg ac                                              22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
ccctgcagct gaactctgtg ac                                              22

<210> SEQ ID NO 119
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
tccttacaat gaccaacatg ga                                              22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
tccttaccat gaccaacatg ga                                              22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
acatggagct gagcagcctg ag                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccctgaagct gagctctgtg ac                                              22

<210> SEQ ID NO 123
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgcttcacta agtctagaga caactctaag aatactctct acttgcagat gaac           54

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cgcttcactc agtctagaga taacagtaaa aatactttgt acttgcagct gagcagcctg     60

<210> SEQ ID NO 125
<211> LENGTH: 60
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 125
cgcttcactc agtctagaga taacagtaaa aatactttgt acttgcagct gagctctgtg    60

<210> SEQ ID NO 126
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tcagctgcaa gtacaaagta tttttactgt tatctctaga ctgagtgaag cg            52

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cgcttcactc agtctagaga taac                                           24

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccgtgtatta ctgtgcgaga ga                                             22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ctgtgtatta ctgtgcgaga ga                                             22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccgtgtatta ctgtgcgaga gg                                             22

<210> SEQ ID NO 131
<211> LENGTH: 22
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 131
ccgtgtatta ctgtgcaaca ga                                                  22

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccatgtatta ctgtgcaaga ta                                                  22

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ccgtgtatta ctgtgcggca ga                                                  22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccacatatta ctgtgcacac ag                                                  22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ccacatatta ctgtgcacgg at                                                  22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccacgtatta ctgtgcacgg at                                                  22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 137
ccttgtatta ctgtgcaaaa ga                                              22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctgtgtatta ctgtgcaaga ga                                              22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ccgtgtatta ctgtaccaca ga                                              22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccttgtatca ctgtgcgaga ga                                              22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgtatatta ctgtgcgaaa ga                                              22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ctgtgtatta ctgtgcgaaa ga                                              22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
```

```
ccgtgtatta ctgtactaga ga                                              22
```

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144

```
ccgtgtatta ctgtgctaga ga                                              22
```

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145

```
ccgtgtatta ctgtactaga ca                                              22
```

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146

```
ctgtgtatta ctgtaagaaa ga                                              22
```

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147

```
ccgtgtatta ctgtgcgaga aa                                              22
```

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148

```
ccgtgtatta ctgtgccaga ga                                              22
```

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149

```
ctgtgtatta ctgtgcgaga ca                                              22
```

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ccatgtatta ctgtgcgaga ca                                              22

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ccatgtatta ctgtgcgaga                                                 20

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ccgtgtatta ctgtgcgaga g                                               21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctgtgtatta ctgtgcgaga g                                               21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ccgtgtatta ctgtgcgaga g                                               21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgtatatta ctgtgcgaaa g                                               21

```
<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ctgtgtatta ctgtgcgaaa g                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctgtgtatta ctgtgcgaga c                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ccatgtatta ctgtgcgaga c                                              21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ccatgtatta ctgtgcgaga                                                20

<210> SEQ ID NO 160
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggtgtagtga tctagtgaca actctaagaa tactctctac ttgcagatga acagctttag    60
ggctgaggac actgcagtct actattgtgc gaga                                94

<210> SEQ ID NO 161
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtgtagtga tctagtgaca actctaagaa tactctctac ttgcagatga acagctttag    60
ggctgaggac actgcagtct actattgtgc gaaa                                94
```

<210> SEQ ID NO 162
<211> LENGTH: 85
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 162
atagtagact gcagtgtcct cagcccttaa gctgttcatc tgcaagtaga gagtattctt    60
agagttgtct ctagatcact acacc                                         85

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 163
ggtgtagtga tctagagaca ac                                            22

<210> SEQ ID NO 164
<211> LENGTH: 55
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 164
ggtgtagtga aacagcttta gggctgagga cactgcagtc tactattgtg cgaga         55

<210> SEQ ID NO 165
<211> LENGTH: 55
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 165
ggtgtagtga aacagcttta gggctgagga cactgcagtc tactattgtg cgaaa         55

<210> SEQ ID NO 166
<211> LENGTH: 46
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 166
atagtagact gcagtgtcct cagcccttaa gctgtttcac tacacc                  46

<210> SEQ ID NO 167
<211> LENGTH: 46
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 167
ggtgtagtga aacagcttaa gggctgagga cactgcagtc tactat                  46

```
<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggtgtagtga aacagcttaa gggctg                                          26

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
agttctccct gcagctgaac tc                                              22

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
cactgtatct gcaaatgaac ag                                              22

<210> SEQ ID NO 171
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
ccctgtatct gcaaatgaac ag                                              22

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
ccgcctacct gcagtggagc ag                                              22

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
cgctgtatct gcaaatgaac ag                                              22
```

```
<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
cggcatatct gcagatctgc ag                                              22

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
cggcgtatct gcaaatgaac ag                                              22

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ctgcctacct gcagtggagc ag                                              22

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
tcgcctatct gcaaatgaac ag                                              22

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
acatggagct gagcagcctg ag                                              22

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
acatggagct gagcaggctg ag                                              22

<210> SEQ ID NO 180
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
acatggagct gaggagcctg ag                                        22

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
acctgcagtg gagcagcctg aa                                        22

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atctgcaaat gaacagcctg aa                                        22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atctgcaaat gaacagcctg ag                                        22

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
atctgcaaat gaacagtctg ag                                        22

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
atctgcagat ctgcagccta aa                                        22

<210> SEQ ID NO 186
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 186
atcttcaaat gaacagcctg ag                                                  22

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atcttcaaat gggcagcctg ag                                                  22

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ccctgaagct gagctctgtg ac                                                  22

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ccctgcagct gaactctgtg ac                                                  22

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tccttacaat gaccaacatg ga                                                  22

<210> SEQ ID NO 191
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tccttaccat gaccaacatg ga                                                  22

<210> SEQ ID NO 192
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 192
ccgtgtatta ctgtgcgaga ga                                           22

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctgtgtatta ctgtgcgaga ga                                           22

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccgtgtatta ctgtgcgaga gg                                           22

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ccgtgtatta ctgtgcaaca ga                                           22

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ccatgtatta ctgtgcaaga ta                                           22

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ccgtgtatta ctgtgcggca ga                                           22

<210> SEQ ID NO 198
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 198
ccacatatta ctgtgcacac ag                                              22

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ccacatatta ctgtgcacgg at                                              22

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ccacgtatta ctgtgcacgg at                                              22

<210> SEQ ID NO 201
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ccttgtatta ctgtgcaaaa ga                                              22

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctgtgtatta ctgtgcaaga ga                                              22

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ccgtgtatta ctgtaccaca ga                                              22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
```

```
ccttgtatca ctgtgcgaga ga                                              22
```

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205

```
ccgtatatta ctgtgcgaaa ga                                              22
```

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206

```
ctgtgtatta ctgtgcgaaa ga                                              22
```

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

```
ccgtgtatta ctgtactaga ga                                              22
```

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208

```
ccgtgtatta ctgtgctaga ga                                              22
```

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209

```
ccgtgtatta ctgtactaga ca                                              22
```

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210

```
ctgtgtatta ctgtaagaaa ga                                              22
```

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ccgtgtatta ctgtgcgaga aa                                          22

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ccgtgtatta ctgtgccaga ga                                          22

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ctgtgtatta ctgtgcgaga ca                                          22

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ccatgtatta ctgtgcgaga ca                                          22

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ccatgtatta ctgtgcgaga aa                                          22

<210> SEQ ID NO 216
<211> LENGTH: 90
<212> TYPE: DNA
<213> ORGANISM: Homo sapiens

<400> SEQUENCE: 216
caggtgcagc tggtgcagtc tggggctgag gtgaagaagc ctggggcctc agtgaaggtc    60
tcctgcaagg cttctggata caccttcacc                                    90

<210> SEQ ID NO 217
<211> LENGTH: 90

```
<212> TYPE: DNA
<213> ORGANISM: Homo sapiens

<400> SEQUENCE: 217
caggtccagc ttgtgcagtc tggggctgag gtgaagaagc ctggggcctc agtgaaggtt      60
tcctgcaagg cttctggata caccttcact                                      90

<210> SEQ ID NO 218
<211> LENGTH: 90
<212> TYPE: DNA
<213> ORGANISM: Homo sapiens

<400> SEQUENCE: 218
caggtgcagc tggtgcagtc tggggctgag gtgaagaagc ctggggcctc agtgaaggtc      60
tcctgcaagg cttctggata caccttcacc                                      90

<210> SEQ ID NO 219
<211> LENGTH: 90
<212> TYPE: DNA
<213> ORGANISM: Homo sapiens

<400> SEQUENCE: 219
caggttcagc tggtgcagtc tggagctgag gtgaagaagc ctggggcctc agtgaaggtc      60
tcctgcaagg cttctggtta cacctttacc                                      90

<210> SEQ ID NO 220
<211> LENGTH: 90
<212> TYPE: DNA
<213> ORGANISM: Homo sapiens

<400> SEQUENCE: 220
caggtccagc tggtacagtc tggggctgag gtgaagaagc ctggggcctc agtgaaggtc      60
tcctgcaagg tttccggata caccctcact                                      90

<210> SEQ ID NO 221
<211> LENGTH: 90
<212> TYPE: DNA
<213> ORGANISM: Homo sapiens

<400> SEQUENCE: 221
cagatgcagc tggtgcagtc tggggctgag gtgaagaaga ctgggtcctc agtgaaggtt      60
tcctgcaagg cttccggata caccttcacc                                      90

<210> SEQ ID NO 222
<211> LENGTH: 90
<212> TYPE: DNA
<213> ORGANISM: Homo sapiens

<400> SEQUENCE: 222
caggtgcagc tggtgcagtc tggggctgag gtgaagaagc ctggggcctc agtgaaggtt      60
tcctgcaagg catctggata caccttcacc                                      90

<210> SEQ ID NO 223
<211> LENGTH: 90
<212> TYPE: DNA
<213> ORGANISM: Homo sapiens

<400> SEQUENCE: 223
caaatgcagc tggtgcagtc tgggcctgag gtgaagaagc ctgggacctc agtgaaggtc      60
tcctgcaagg cttctggatt caccttact                                       90
```

<210> SEQ ID NO 224
<211> LENGTH: 90
<212> TYPE: DNA
<213> ORGANISM: Homo sapiens

<400> SEQUENCE: 224
caggtgcagc tggtgcagtc tggggctgag gtgaagaagc ctgggtcctc ggtgaaggtc      60
tcctgcaagg cttctggagg caccttcagc                                      90

<210> SEQ ID NO 225
<211> LENGTH: 90
<212> TYPE: DNA
<213> ORGANISM: Homo sapiens

<400> SEQUENCE: 225
caggtgcagc tggtgcagtc tggggctgag gtgaagaagc ctgggtcctc ggtgaaggtc      60
tcctgcaagg cttctggagg caccttcagc                                      90

<210> SEQ ID NO 226
<211> LENGTH: 90
<212> TYPE: DNA
<213> ORGANISM: Homo sapiens

<400> SEQUENCE: 226
gaggtccagc tggtacagtc tggggctgag gtgaagaagc ctggggctac agtgaaaatc      60
tcctgcaagg tttctggata caccttcacc                                      90

<210> SEQ ID NO 227
<211> LENGTH: 90
<212> TYPE: DNA
<213> ORGANISM: Homo sapiens

<400> SEQUENCE: 227
cagatcacct tgaaggagtc tggtcctacg ctggtgaaac ccacacagac cctcacgctg      60
acctgcacct tctctgggtt ctcactcagc                                      90

<210> SEQ ID NO 228
<211> LENGTH: 90
<212> TYPE: DNA
<213> ORGANISM: Homo sapiens

<400> SEQUENCE: 228
caggtcacct tgaaggagtc tggtcctgtg ctggtgaaac ccacagagac cctcacgctg      60
acctgcaccg tctctgggtt ctcactcagc                                      90

<210> SEQ ID NO 229
<211> LENGTH: 90
<212> TYPE: DNA
<213> ORGANISM: Homo sapiens

<400> SEQUENCE: 229
caggtcacct tgaaggagtc tggtcctgcg ctggtgaaac ccacacagac cctcacactg      60
acctgcacct tctctgggtt ctcactcagc                                      90

<210> SEQ ID NO 230
<211> LENGTH: 90
<212> TYPE: DNA
<213> ORGANISM: Homo sapiens

<400> SEQUENCE: 230

```
gaggtgcagc tggtggagtc tggggggaggc ttggtccagc ctgggggtc cctgagactc      60 tcctgtgcag cctctggatt cacctttagt                                       90
```

<210> SEQ ID NO 231
<211> LENGTH: 90
<212> TYPE: DNA
<213> ORGANISM: Homo sapiens

<400> SEQUENCE: 231

```
gaagtgcagc tggtggagtc tggggggaggc ttggtacagc ctggcaggtc cctgagactc      60
tcctgtgcag cctctggatt cacctttgat                                       90
```

<210> SEQ ID NO 232
<211> LENGTH: 90
<212> TYPE: DNA
<213> ORGANISM: Homo sapiens

<400> SEQUENCE: 232

```
caggtgcagc tggtggagtc tggggggaggc ttggtcaagc ctggagggtc cctgagactc      60
tcctgtgcag cctctggatt caccttcagt                                       90
```

<210> SEQ ID NO 233
<211> LENGTH: 90
<212> TYPE: DNA
<213> ORGANISM: Homo sapiens

<400> SEQUENCE: 233

```
gaggtgcagc tggtggagtc tggggggaggc ttggtacagc ctgggggtc cctgagactc      60 tcctgtgcag cctctggatt caccttcagt                                       90
```

<210> SEQ ID NO 234
<211> LENGTH: 90
<212> TYPE: DNA
<213> ORGANISM: Homo sapiens

<400> SEQUENCE: 234

```
gaggtgcagc tggtggagtc tggggggaggc ttggtaaagc ctgggggtc ccttagactc      60 tcctgtgcag cctctggatt cactttcagt                                       90
```

<210> SEQ ID NO 235
<211> LENGTH: 90
<212> TYPE: DNA
<213> ORGANISM: Homo sapiens

<400> SEQUENCE: 235

```
gaggtgcagc tggtggagtc tggggggaggt gtggtacggc ctgggggtc cctgagactc      60 tcctgtgcag cctctggatt cacctttgat                                       90
```

<210> SEQ ID NO 236
<211> LENGTH: 90
<212> TYPE: DNA
<213> ORGANISM: Homo sapiens

<400> SEQUENCE: 236

```
gaggtgcagc tggtggagtc tggggggaggc ctggtcaagc ctgggggtc cctgagactc      60 tcctgtgcag cctctggatt caccttcagt                                       90
```

<210> SEQ ID NO 237
<211> LENGTH: 90

```
<212> TYPE: DNA
<213> ORGANISM: Homo sapiens

<400> SEQUENCE: 237
gaggtgcagc tgttggagtc tgggggaggc ttggtacagc ctgggggtc cctgagactc    60 tcctgtgcag cctctggatt cacctttagc                                    90

<210> SEQ ID NO 238
<211> LENGTH: 90
<212> TYPE: DNA
<213> ORGANISM: Homo sapiens

<400> SEQUENCE: 238
caggtgcagc tggtggagtc tgggggaggc gtggtccagc ctgggaggtc cctgagactc    60
tcctgtgcag cctctggatt cacctttcagt                                   90

<210> SEQ ID NO 239
<211> LENGTH: 90
<212> TYPE: DNA
<213> ORGANISM: Homo sapiens

<400> SEQUENCE: 239
caggtgcagc tggtggagtc tgggggaggc gtggtccagc ctgggaggtc cctgagactc    60
tcctgtgcag cctctggatt caccttcagt                                    90

<210> SEQ ID NO 240
<211> LENGTH: 90
<212> TYPE: DNA
<213> ORGANISM: Homo sapiens

<400> SEQUENCE: 240
caggtgcagc tggtggagtc tgggggaggc gtggtccagc ctgggaggtc cctgagactc    60
tcctgtgcag cctctggatt caccttcagt                                    90

<210> SEQ ID NO 241
<211> LENGTH: 90
<212> TYPE: DNA
<213> ORGANISM: Homo sapiens

<400> SEQUENCE: 241
caggtgcagc tggtggagtc tgggggaggc gtggtccagc ctgggaggtc cctgagactc    60
tcctgtgcag cgtctggatt caccttcagt                                    90

<210> SEQ ID NO 242
<211> LENGTH: 90
<212> TYPE: DNA
<213> ORGANISM: Homo sapiens

<400> SEQUENCE: 242
gaagtgcagc tggtggagtc tgggggagtc gtggtacagc ctgggggtc cctgagactc    60 tcctgtgcag cctctggatt cacctttgat                                    90

<210> SEQ ID NO 243
<211> LENGTH: 90
<212> TYPE: DNA
<213> ORGANISM: Homo sapiens

<400> SEQUENCE: 243
gaggtgcagc tggtggagtc tgggggaggc ttggtacagc ctgggggtc cctgagactc    60 tcctgtgcag cctctggatt caccttcagt                                    90
```

<210> SEQ ID NO 244
<211> LENGTH: 90
<212> TYPE: DNA
<213> ORGANISM: Homo sapiens

<400> SEQUENCE: 244
gaggtgcagc tggtggagtc tggggggaggc ttggtacagc cagggcggtc cctgagactc      60
tcctgtacag cttctggatt cacctttggt                                        90

<210> SEQ ID NO 245
<211> LENGTH: 90
<212> TYPE: DNA
<213> ORGANISM: Homo sapiens

<400> SEQUENCE: 245
gaggtgcagc tggtggagac tggaggaggc ttgatccagc ctgggggagtc cctgagactc      60 tcctgtgcag cctctgggtt caccgtcagt                                        90

<210> SEQ ID NO 246
<211> LENGTH: 90
<212> TYPE: DNA
<213> ORGANISM: Homo sapiens

<400> SEQUENCE: 246
gaggtgcagc tggtggagtc tggggggaggc ttggtccagc ctgggggagtc cctgagactc      60 tcctgtgcag cctctggatt caccttcagt                                        90

<210> SEQ ID NO 247
<211> LENGTH: 90
<212> TYPE: DNA
<213> ORGANISM: Homo sapiens

<400> SEQUENCE: 247
gaggtgcagc tggtggagtc tggggggaggc ttggtccagc ctgggggagtc cctgagactc      60 tcctgtgcag cctctggatt caccgtcagt                                        90

<210> SEQ ID NO 248
<211> LENGTH: 90
<212> TYPE: DNA
<213> ORGANISM: Homo sapiens

<400> SEQUENCE: 248
gaggtgcagc tggtggagtc tggggggaggc ttggtccagc ctggagggtc cctgagactc      60
tcctgtgcag cctctggatt caccttcagt                                        90

<210> SEQ ID NO 249
<211> LENGTH: 90
<212> TYPE: DNA
<213> ORGANISM: Homo sapiens

<400> SEQUENCE: 249
gaggtgcagc tggtggagtc tggggggaggc ttggtccagc ctgggggagtc cctgaaactc      60 tcctgtgcag cctctgggtt caccttcagt                                        90

<210> SEQ ID NO 250
<211> LENGTH: 90
<212> TYPE: DNA
<213> ORGANISM: Homo sapiens

<400> SEQUENCE: 250

```
gaggtgcagc tggtggagtc cgggggaggc ttagttcagc ctgggggtc cctgagactc      60 tcctgtgcag cctctggatt caccttcagt                                       90

<210> SEQ ID NO 251
<211> LENGTH: 90
<212> TYPE: DNA
<213> ORGANISM: Homo sapiens

<400> SEQUENCE: 251
gaggtgcagc tggtggagtc tcggggagtc ttggtacagc ctgggggtc cctgagactc      60 tcctgtgcag cctctggatt caccgtcagt                                       90

<210> SEQ ID NO 252
<211> LENGTH: 90
<212> TYPE: DNA
<213> ORGANISM: Homo sapiens

<400> SEQUENCE: 252
caggtgcagc tgcaggagtc gggcccagga ctggtgaagc cttcggggac cctgtccctc      60
acctgcgctg tctctggtgg ctccatcagc                                       90

<210> SEQ ID NO 253
<211> LENGTH: 90
<212> TYPE: DNA
<213> ORGANISM: Homo sapiens

<400> SEQUENCE: 253
caggtgcagc tgcaggagtc gggcccagga ctggtgaagc cttcggacac cctgtccctc      60
acctgcgctg tctctggtta ctccatcagc                                       90

<210> SEQ ID NO 254
<211> LENGTH: 90
<212> TYPE: DNA
<213> ORGANISM: Homo sapiens

<400> SEQUENCE: 254
caggtgcagc tgcaggagtc gggcccagga ctggtgaagc cttcacagac cctgtccctc      60
acctgcactg tctctggtgg ctccatcagc                                       90

<210> SEQ ID NO 255
<211> LENGTH: 90
<212> TYPE: DNA
<213> ORGANISM: Homo sapiens

<400> SEQUENCE: 255
cagctgcagc tgcaggagtc cggctcagga ctggtgaagc cttcacagac cctgtccctc      60
acctgcgctg tctctggtgg ctccatcagc                                       90

<210> SEQ ID NO 256
<211> LENGTH: 90
<212> TYPE: DNA
<213> ORGANISM: Homo sapiens

<400> SEQUENCE: 256
caggtgcagc tgcaggagtc gggcccagga ctggtgaagc cttcacagac cctgtccctc      60
acctgcactg tctctggtgg ctccatcagc                                       90

<210> SEQ ID NO 257
<211> LENGTH: 90
```

```
<212> TYPE: DNA
<213> ORGANISM: Homo sapiens

<400> SEQUENCE: 257
caggtgcagc tgcaggagtc gggcccagga ctggtgaagc cttcacagac cctgtccctc    60
acctgcactg tctctggtgg ctccatcagc                                    90

<210> SEQ ID NO 258
<211> LENGTH: 90
<212> TYPE: DNA
<213> ORGANISM: Homo sapiens

<400> SEQUENCE: 258
caggtgcagc tacagcagtg gggcgcagga ctgttgaagc cttcggagac cctgtccctc    60
acctgcgctg tctatggtgg gtccttcagt                                    90

<210> SEQ ID NO 259
<211> LENGTH: 90
<212> TYPE: DNA
<213> ORGANISM: Homo sapiens

<400> SEQUENCE: 259
cagctgcagc tgcaggagtc gggcccagga ctggtgaagc cttcggagac cctgtccctc    60
acctgcactg tctctggtgg ctccatcagc                                    90

<210> SEQ ID NO 260
<211> LENGTH: 90
<212> TYPE: DNA
<213> ORGANISM: Homo sapiens

<400> SEQUENCE: 260
caggtgcagc tgcaggagtc gggcccagga ctggtgaagc cttcggagac cctgtccctc    60
acctgcactg tctctggtgg ctccatcagt                                    90

<210> SEQ ID NO 261
<211> LENGTH: 90
<212> TYPE: DNA
<213> ORGANISM: Homo sapiens

<400> SEQUENCE: 261
caggtgcagc tgcaggagtc gggcccagga ctggtgaagc cttcggagac cctgtccctc    60
acctgcactg tctctggtgg ctccgtcagc                                    90

<210> SEQ ID NO 262
<211> LENGTH: 90
<212> TYPE: DNA
<213> ORGANISM: Homo sapiens

<400> SEQUENCE: 262
caggtgcagc tgcaggagtc gggcccagga ctggtgaagc cttcggagac cctgtccctc    60
acctgcgctg tctctggtta ctccatcagc                                    90

<210> SEQ ID NO 263
<211> LENGTH: 90
<212> TYPE: DNA
<213> ORGANISM: Homo sapiens

<400> SEQUENCE: 263
gaggtgcagc tggtgcagtc tggagcagag gtgaaaaagc ccggggagtc tctgaagatc    60
tcctgtaagg gttctggata cagctttacc                                    90
```

<210> SEQ ID NO 264
<211> LENGTH: 90
<212> TYPE: DNA
<213> ORGANISM: Homo sapiens

<400> SEQUENCE: 264
gaagtgcagc tggtgcagtc tggagcagag gtgaaaaagc ccggggagtc tctgaggatc    60
tcctgtaagg gttctggata cagctttacc                                    90

<210> SEQ ID NO 265
<211> LENGTH: 90
<212> TYPE: DNA
<213> ORGANISM: Homo sapiens

<400> SEQUENCE: 265
caggtacagc tgcagcagtc aggtccagga ctggtgaagc cctcgcagac cctctcactc    60
acctgtgcca tctccgggga cagtgtctct                                    90

<210> SEQ ID NO 266
<211> LENGTH: 90
<212> TYPE: DNA
<213> ORGANISM: Homo sapiens

<400> SEQUENCE: 266
caggtgcagc tggtgcaatc tgggtctgag ttgaagaagc ctggggcctc agtgaaggtt    60
tcctgcaagg cttctggata caccttcact                                    90

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ccgtgtatta ctgtgcgaga ga                                            22

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctgtgtatta ctgtgcgaga ga                                            22

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ccgtgtatta ctgtgcgaga gg                                            22

<210> SEQ ID NO 270
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 270
ccgtatatta ctgtgcgaaa ga                                           22

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ctgtgtatta ctgtgcgaaa ga                                           22

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctgtgtatta ctgtgcgaga ca                                           22

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ccatgtatta ctgtgcgaga ca                                           22

<210> SEQ ID NO 274
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ccatgtatta ctgtgcgaga aa                                           22

<210> SEQ ID NO 275
<211> LENGTH: 69
<212> TYPE: DNA
<213> ORGANISM: Homo sapiens

<400> SEQUENCE: 275
gacatccaga tgacccagtc tccatcctcc ctgtctgcat ctgtaggaga cagagtcacc   60
atcacttgc                                                          69

<210> SEQ ID NO 276
<211> LENGTH: 69
<212> TYPE: DNA
<213> ORGANISM: Homo sapiens

<400> SEQUENCE: 276
```

```
gacatccaga tgacccagtc tccatcctcc ctgtctgcat ctgtaggaga cagagtcacc    60
atcacttgc                                                             69

<210> SEQ ID NO 277
<211> LENGTH: 69
<212> TYPE: DNA
<213> ORGANISM: Homo sapiens

<400> SEQUENCE: 277
gacatccaga tgacccagtc tccatcctcc ctgtctgcat ctgtaggaga cagagtcacc    60
atcacttgc                                                             69

<210> SEQ ID NO 278
<211> LENGTH: 69
<212> TYPE: DNA
<213> ORGANISM: Homo sapiens

<400> SEQUENCE: 278
gacatccaga tgacccagtc tccatcctcc ctgtctgcat ctgtaggaga cagagtcacc    60
atcacttgc                                                             69

<210> SEQ ID NO 279
<211> LENGTH: 69
<212> TYPE: DNA
<213> ORGANISM: Homo sapiens

<400> SEQUENCE: 279
gacatccaga tgacccagtc tccatcctcc ctgtctgcat ctgtaggaga cagagtcacc    60
atcacttgc                                                             69

<210> SEQ ID NO 280
<211> LENGTH: 69
<212> TYPE: DNA
<213> ORGANISM: Homo sapiens

<400> SEQUENCE: 280
gacatccaga tgacccagtc tccatcctcc ctgtctgcat ctgtaggaga cagagtcacc    60
atcacttgc                                                             69

<210> SEQ ID NO 281
<211> LENGTH: 69
<212> TYPE: DNA
<213> ORGANISM: Homo sapiens

<400> SEQUENCE: 281
aacatccaga tgacccagtc tccatctgcc atgtctgcat ctgtaggaga cagagtcacc    60
atcacttgt                                                             69

<210> SEQ ID NO 282
<211> LENGTH: 69
<212> TYPE: DNA
<213> ORGANISM: Homo sapiens

<400> SEQUENCE: 282
gacatccaga tgacccagtc tccatcctca ctgtctgcat ctgtaggaga cagagtcacc    60
atcacttgt                                                             69

<210> SEQ ID NO 283
<211> LENGTH: 69
```

```
<212> TYPE: DNA
<213> ORGANISM: Homo sapiens

<400> SEQUENCE: 283
gacatccaga tgacccagtc tccatcctca ctgtctgcat ctgtaggaga cagagtcacc    60
atcacttgt                                                            69

<210> SEQ ID NO 284
<211> LENGTH: 69
<212> TYPE: DNA
<213> ORGANISM: Homo sapiens

<400> SEQUENCE: 284
gccatccagt tgacccagtc tccatcctcc ctgtctgcat ctgtaggaga cagagtcacc    60
atcacttgc                                                            69

<210> SEQ ID NO 285
<211> LENGTH: 69
<212> TYPE: DNA
<213> ORGANISM: Homo sapiens

<400> SEQUENCE: 285
gccatccagt tgacccagtc tccatcctcc ctgtctgcat ctgtaggaga cagagtcacc    60
atcacttgc                                                            69

<210> SEQ ID NO 286
<211> LENGTH: 69
<212> TYPE: DNA
<213> ORGANISM: Homo sapiens

<400> SEQUENCE: 286
gacatccaga tgacccagtc tccatcttcc gtgtctgcat ctgtaggaga cagagtcacc    60
atcacttgt                                                            69

<210> SEQ ID NO 287
<211> LENGTH: 69
<212> TYPE: DNA
<213> ORGANISM: Homo sapiens

<400> SEQUENCE: 287
gacatccaga tgacccagtc tccatcttct gtgtctgcat ctgtaggaga cagagtcacc    60
atcacttgt                                                            69

<210> SEQ ID NO 288
<211> LENGTH: 69
<212> TYPE: DNA
<213> ORGANISM: Homo sapiens

<400> SEQUENCE: 288
gacatccagt tgacccagtc tccatccttc ctgtctgcat ctgtaggaga cagagtcacc    60
atcacttgc                                                            69

<210> SEQ ID NO 289
<211> LENGTH: 69
<212> TYPE: DNA
<213> ORGANISM: Homo sapiens

<400> SEQUENCE: 289
gccatccgga tgacccagtc tccattctcc ctgtctgcat ctgtaggaga cagagtcacc    60
atcacttgc                                                            69
```

<210> SEQ ID NO 290
<211> LENGTH: 69
<212> TYPE: DNA
<213> ORGANISM: Homo sapiens

<400> SEQUENCE: 290
gccatccgga tgacccagtc tccatcctca ttctctgcat ctacaggaga cagagtcacc     60
atcacttgt                                                             69

<210> SEQ ID NO 291
<211> LENGTH: 69
<212> TYPE: DNA
<213> ORGANISM: Homo sapiens

<400> SEQUENCE: 291
gtcatctgga tgacccagtc tccatcctta ctctctgcat ctacaggaga cagagtcacc     60
atcagttgt                                                             69

<210> SEQ ID NO 292
<211> LENGTH: 69
<212> TYPE: DNA
<213> ORGANISM: Homo sapiens

<400> SEQUENCE: 292
gccatccaga tgacccagtc tccatcctcc ctgtctgcat ctgtaggaga cagagtcacc     60
atcacttgc                                                             69

<210> SEQ ID NO 293
<211> LENGTH: 69
<212> TYPE: DNA
<213> ORGANISM: Homo sapiens

<400> SEQUENCE: 293
gacatccaga tgacccagtc tccttccacc ctgtctgcat ctgtaggaga cagagtcacc     60
atcacttgc                                                             69

<210> SEQ ID NO 294
<211> LENGTH: 69
<212> TYPE: DNA
<213> ORGANISM: Homo sapiens

<400> SEQUENCE: 294
gatattgtga tgacccagac tccactctcc ctgcccgtca cccctggaga gccggcctcc     60
atctcctgc                                                             69

<210> SEQ ID NO 295
<211> LENGTH: 69
<212> TYPE: DNA
<213> ORGANISM: Homo sapiens

<400> SEQUENCE: 295
gatattgtga tgacccagac tccactctcc ctgcccgtca cccctggaga gccggcctcc     60
atctcctgc                                                             69

<210> SEQ ID NO 296
<211> LENGTH: 69
<212> TYPE: DNA
<213> ORGANISM: Homo sapiens

<400> SEQUENCE: 296

```
gatgttgtga tgactcagtc tccactctcc ctgcccgtca cccttggaca gccggcctcc    60
atctcctgc                                                           69
```

<210> SEQ ID NO 297
<211> LENGTH: 69
<212> TYPE: DNA
<213> ORGANISM: Homo sapiens

<400> SEQUENCE: 297

```
gatgttgtga tgactcagtc tccactctcc ctgcccgtca cccttggaca gccggcctcc    60
atctcctgc                                                           69
```

<210> SEQ ID NO 298
<211> LENGTH: 69
<212> TYPE: DNA
<213> ORGANISM: Homo sapiens

<400> SEQUENCE: 298

```
gatattgtga tgacccagac tccactctct ctgtccgtca cccctggaca gccggcctcc    60
atctcctgc                                                           69
```

<210> SEQ ID NO 299
<211> LENGTH: 69
<212> TYPE: DNA
<213> ORGANISM: Homo sapiens

<400> SEQUENCE: 299

```
gatattgtga tgacccagac tccactctct ctgtccgtca cccctggaca gccggcctcc    60
atctcctgc                                                           69
```

<210> SEQ ID NO 300
<211> LENGTH: 69
<212> TYPE: DNA
<213> ORGANISM: Homo sapiens

<400> SEQUENCE: 300

```
gatattgtga tgactcagtc tccactctcc ctgcccgtca cccctggaga gccggcctcc    60
atctcctgc                                                           69
```

<210> SEQ ID NO 301
<211> LENGTH: 69
<212> TYPE: DNA
<213> ORGANISM: Homo sapiens

<400> SEQUENCE: 301

```
gatattgtga tgactcagtc tccactctcc ctgcccgtca cccctggaga gccggcctcc    60
atctcctgc                                                           69
```

<210> SEQ ID NO 302
<211> LENGTH: 69
<212> TYPE: DNA
<213> ORGANISM: Homo sapiens

<400> SEQUENCE: 302

```
gatattgtga tgacccagac tccactctcc tcacctgtca cccttggaca gccggcctcc    60
atctcctgc                                                           69
```

<210> SEQ ID NO 303
<211> LENGTH: 69

```
<212> TYPE: DNA
<213> ORGANISM: Homo sapiens

<400> SEQUENCE: 303
gaaattgtgt tgacgcagtc tccaggcacc ctgtctttgt ctccagggga aagagccacc    60
ctctcctgc                                                           69

<210> SEQ ID NO 304
<211> LENGTH: 69
<212> TYPE: DNA
<213> ORGANISM: Homo sapiens

<400> SEQUENCE: 304
gaaattgtgt tgacgcagtc tccagccacc ctgtctttgt ctccagggga aagagccacc    60
ctctcctgc                                                           69

<210> SEQ ID NO 305
<211> LENGTH: 69
<212> TYPE: DNA
<213> ORGANISM: Homo sapiens

<400> SEQUENCE: 305
gaaatagtga tgacgcagtc tccagccacc ctgtctgtgt ctccagggga aagagccacc    60
ctctcctgc                                                           69

<210> SEQ ID NO 306
<211> LENGTH: 69
<212> TYPE: DNA
<213> ORGANISM: Homo sapiens

<400> SEQUENCE: 306
gaaatagtga tgacgcagtc tccagccacc ctgtctgtgt ctccagggga aagagccacc    60
ctctcctgc                                                           69

<210> SEQ ID NO 307
<211> LENGTH: 69
<212> TYPE: DNA
<213> ORGANISM: Homo sapiens

<400> SEQUENCE: 307
gaaattgtgt tgacacagtc tccagccacc ctgtctttgt ctccagggga aagagccacc    60
ctctcctgc                                                           69

<210> SEQ ID NO 308
<211> LENGTH: 69
<212> TYPE: DNA
<213> ORGANISM: Homo sapiens

<400> SEQUENCE: 308
gaaattgtgt tgacacagtc tccagccacc ctgtctttgt ctccagggga aagagccacc    60
ctctcctgc                                                           69

<210> SEQ ID NO 309
<211> LENGTH: 69
<212> TYPE: DNA
<213> ORGANISM: Homo sapiens

<400> SEQUENCE: 309
gaaattgtaa tgacacagtc tccagccacc ctgtctttgt ctccagggga aagagccacc    60
ctctcctgc                                                           69
```

<210> SEQ ID NO 310
<211> LENGTH: 69
<212> TYPE: DNA
<213> ORGANISM: Homo sapiens

<400> SEQUENCE: 310
gacatcgtga tgacccagtc tccagactcc ctggctgtgt ctctgggcga gagggccacc    60
atcaactgc                                                            69

<210> SEQ ID NO 311
<211> LENGTH: 69
<212> TYPE: DNA
<213> ORGANISM: Homo sapiens

<400> SEQUENCE: 311
gaaacgacac tcacgcagtc tccagcattc atgtcagcga ctccaggaga caaagtcaac    60
atctcctgc                                                            69

<210> SEQ ID NO 312
<211> LENGTH: 69
<212> TYPE: DNA
<213> ORGANISM: Homo sapiens

<400> SEQUENCE: 312
gaaattgtgc tgactcagtc tccagacttt cagtctgtga ctccaaagga gaaagtcacc    60
atcacctgc                                                            69

<210> SEQ ID NO 313
<211> LENGTH: 69
<212> TYPE: DNA
<213> ORGANISM: Homo sapiens

<400> SEQUENCE: 313
gaaattgtgc tgactcagtc tccagacttt cagtctgtga ctccaaagga gaaagtcacc    60
atcacctgc                                                            69

<210> SEQ ID NO 314
<211> LENGTH: 69
<212> TYPE: DNA
<213> ORGANISM: Homo sapiens

<400> SEQUENCE: 314
gatgttgtga tgacacagtc tccagctttc ctctctgtga ctccagggga gaaagtcacc    60
atcacctgc                                                            69

<210> SEQ ID NO 315
<211> LENGTH: 66
<212> TYPE: DNA
<213> ORGANISM: Homo sapiens

<400> SEQUENCE: 315
cagtctgtgc tgactcagcc accctcggtg tctgaagccc ccaggcagag ggtcaccatc    60
tcctgt                                                               66

<210> SEQ ID NO 316
<211> LENGTH: 66
<212> TYPE: DNA
<213> ORGANISM: Homo sapiens

<400> SEQUENCE: 316

```
cagtctgtgc tgacgcagcc gccctcagtg tctggggccc cagggcagag ggtcaccatc    60
tcctgc                                                                66

<210> SEQ ID NO 317
<211> LENGTH: 66
<212> TYPE: DNA
<213> ORGANISM: Homo sapiens

<400> SEQUENCE: 317
cagtctgtgc tgactcagcc accctcagcg tctgggaccc ccgggcagag ggtcaccatc    60
tcttgt                                                                66

<210> SEQ ID NO 318
<211> LENGTH: 66
<212> TYPE: DNA
<213> ORGANISM: Homo sapiens

<400> SEQUENCE: 318
cagtctgtgc tgactcagcc accctcagcg tctgggaccc ccgggcagag ggtcaccatc    60
tcttgt                                                                66

<210> SEQ ID NO 319
<211> LENGTH: 66
<212> TYPE: DNA
<213> ORGANISM: Homo sapiens

<400> SEQUENCE: 319
cagtctgtgt tgacgcagcc gccctcagtg tctgcggccc caggacagaa ggtcaccatc    60
tcctgc                                                                66

<210> SEQ ID NO 320
<211> LENGTH: 66
<212> TYPE: DNA
<213> ORGANISM: Homo sapiens

<400> SEQUENCE: 320
cagtctgccc tgactcagcc tccctccgcg tccgggtctc ctggacagtc agtcaccatc    60
tcctgc                                                                66

<210> SEQ ID NO 321
<211> LENGTH: 66
<212> TYPE: DNA
<213> ORGANISM: Homo sapiens

<400> SEQUENCE: 321
cagtctgccc tgactcagcc tcgctcagtg tccgggtctc ctggacagtc agtcaccatc    60
tcctgc                                                                66

<210> SEQ ID NO 322
<211> LENGTH: 66
<212> TYPE: DNA
<213> ORGANISM: Homo sapiens

<400> SEQUENCE: 322
cagtctgccc tgactcagcc tgcctccgtg tctgggtctc ctggacagtc gatcaccatc    60
tcctgc                                                                66

<210> SEQ ID NO 323
<211> LENGTH: 66
```

```
<212> TYPE: DNA
<213> ORGANISM: Homo sapiens

<400> SEQUENCE: 323
cagtctgccc tgactcagcc tccctccgtg tccgggtctc ctggacagtc agtcaccatc      60
tcctgc                                                                 66

<210> SEQ ID NO 324
<211> LENGTH: 66
<212> TYPE: DNA
<213> ORGANISM: Homo sapiens

<400> SEQUENCE: 324
cagtctgccc tgactcagcc tgcctccgtg tctgggtctc ctggacagtc gatcaccatc      60
tcctgc                                                                 66

<210> SEQ ID NO 325
<211> LENGTH: 66
<212> TYPE: DNA
<213> ORGANISM: Homo sapiens

<400> SEQUENCE: 325
tcctatgagc tgactcagcc accctcagtg tccgtgtccc caggacagac agccagcatc      60
acctgc                                                                 66

<210> SEQ ID NO 326
<211> LENGTH: 66
<212> TYPE: DNA
<213> ORGANISM: Homo sapiens

<400> SEQUENCE: 326
tcctatgagc tgactcagcc actctcagtg tcagtggccc tgggacagac ggccaggatt      60
acctgt                                                                 66

<210> SEQ ID NO 327
<211> LENGTH: 66
<212> TYPE: DNA
<213> ORGANISM: Homo sapiens

<400> SEQUENCE: 327
tcctatgagc tgacacagcc accctcggtg tcagtgtccc caggacaaac ggccaggatc      60
acctgc                                                                 66

<210> SEQ ID NO 328
<211> LENGTH: 66
<212> TYPE: DNA
<213> ORGANISM: Homo sapiens

<400> SEQUENCE: 328
tcctatgagc tgacacagcc accctcggtg tcagtgtccc taggacagat ggccaggatc      60
acctgc                                                                 66

<210> SEQ ID NO 329
<211> LENGTH: 66
<212> TYPE: DNA
<213> ORGANISM: Homo sapiens

<400> SEQUENCE: 329
tcttctgagc tgactcagga ccctgctgtg tctgtggcct gggacagac agtcaggatc       60 acatgc                                                                 66
```

<210> SEQ ID NO 330
<211> LENGTH: 66
<212> TYPE: DNA
<213> ORGANISM: Homo sapiens

<400> SEQUENCE: 330
tcctatgtgc tgactcagcc accctcagtg tcagtggccc caggaaagac ggccaggatt    60
acctgt                                                              66

<210> SEQ ID NO 331
<211> LENGTH: 66
<212> TYPE: DNA
<213> ORGANISM: Homo sapiens

<400> SEQUENCE: 331
tcctatgagc tgacacagct accctcggtg tcagtgtccc caggacagac agccaggatc    60
acctgc                                                              66

<210> SEQ ID NO 332
<211> LENGTH: 66
<212> TYPE: DNA
<213> ORGANISM: Homo sapiens

<400> SEQUENCE: 332
tcctatgagc tgatgcagcc accctcggtg tcagtgtccc caggacagac ggccaggatc    60
acctgc                                                              66

<210> SEQ ID NO 333
<211> LENGTH: 66
<212> TYPE: DNA
<213> ORGANISM: Homo sapiens

<400> SEQUENCE: 333
tcctatgagc tgacacagcc atcctcagtg tcagtgtctc cgggacagac agccaggatc    60
acctgc                                                              66

<210> SEQ ID NO 334
<211> LENGTH: 66
<212> TYPE: DNA
<213> ORGANISM: Homo sapiens

<400> SEQUENCE: 334
ctgcctgtgc tgactcagcc cccgtctgca tctgccttgc tgggagcctc gatcaagctc    60
acctgc                                                              66

<210> SEQ ID NO 335
<211> LENGTH: 66
<212> TYPE: DNA
<213> ORGANISM: Homo sapiens

<400> SEQUENCE: 335
cagcctgtgc tgactcaatc atcctctgcc tctgcttccc tgggatcctc ggtcaagctc    60
acctgc                                                              66

<210> SEQ ID NO 336
<211> LENGTH: 66
<212> TYPE: DNA
<213> ORGANISM: Homo sapiens

<400> SEQUENCE: 336

```
cagcttgtgc tgactcaatc gccctctgcc tctgcctccc tgggagcctc ggtcaagctc      60
acctgc                                                                 66

<210> SEQ ID NO 337
<211> LENGTH: 66
<212> TYPE: DNA
<213> ORGANISM: Homo sapiens

<400> SEQUENCE: 337
cagcctgtgc tgactcagcc accttcctcc tccgcatctc ctggagaatc cgccagactc      60
acctgc                                                                 66

<210> SEQ ID NO 338
<211> LENGTH: 66
<212> TYPE: DNA
<213> ORGANISM: Homo sapiens

<400> SEQUENCE: 338
caggctgtgc tgactcagcc ggcttccctc tctgcatctc ctggagcatc agccagtctc      60
acctgc                                                                 66

<210> SEQ ID NO 339
<211> LENGTH: 66
<212> TYPE: DNA
<213> ORGANISM: Homo sapiens

<400> SEQUENCE: 339
cagcctgtgc tgactcagcc atcttcccat tctgcatctt ctggagcatc agtcagactc      60
acctgc                                                                 66

<210> SEQ ID NO 340
<211> LENGTH: 66
<212> TYPE: DNA
<213> ORGANISM: Homo sapiens

<400> SEQUENCE: 340
aattttatgc tgactcagcc ccactctgtg tcggagtctc cggggaagac ggtaaccatc      60
tcctgc                                                                 66

<210> SEQ ID NO 341
<211> LENGTH: 66
<212> TYPE: DNA
<213> ORGANISM: Homo sapiens

<400> SEQUENCE: 341
cagactgtgg tgactcagga gccctcactg actgtgtccc caggagggac agtcactctc      60
acctgt                                                                 66

<210> SEQ ID NO 342
<211> LENGTH: 66
<212> TYPE: DNA
<213> ORGANISM: Homo sapiens

<400> SEQUENCE: 342
caggctgtgg tgactcagga gccctcactg actgtgtccc caggagggac agtcactctc      60
acctgt                                                                 66

<210> SEQ ID NO 343
<211> LENGTH: 66
```

```
<212> TYPE: DNA
<213> ORGANISM: Homo sapiens

<400> SEQUENCE: 343
cagactgtgg tgacccagga gccatcgttc tcagtgtccc ctggagggac agtcacactc    60
acttgt                                                               66

<210> SEQ ID NO 344
<211> LENGTH: 66
<212> TYPE: DNA
<213> ORGANISM: Homo sapiens

<400> SEQUENCE: 344
cagcctgtgc tgactcagcc accttctgca tcagcctccc tgggagcctc ggtcacactc    60
acctgc                                                               66

<210> SEQ ID NO 345
<211> LENGTH: 66
<212> TYPE: DNA
<213> ORGANISM: Homo sapiens

<400> SEQUENCE: 345
caggcagggc tgactcagcc accctcggtg tccaagggct tgagacagac cgccacactc    60
acctgc                                                               66

<210> SEQ ID NO 346
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 346
nnnnnngact c                                                         11

<210> SEQ ID NO 347
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 347
gagtcnnnnn n                                                         11

<210> SEQ ID NO 348
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, t, c, g, unknown or other
```

-continued

<400> SEQUENCE: 348
gcnnnnnnng c                                                                 11

<210> SEQ ID NO 349
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 349
acctgcnnnn n                                                                 11

<210> SEQ ID NO 350
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
cacatccgtg ttgttcacgg atgtg                                                  25

<210> SEQ ID NO 351
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
aatagtagac tgcagtgtcc tcagccctta agctgttcat ctgcaagtag agagtattct            60
tagagttgtc tctagactta gtgaagcg                                               88

<210> SEQ ID NO 352
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
cgcttcacta agtctagaga caactctaag aatactctct acttgcagat gaacagctta            60
agggctgagg acactgcagt ctactatt                                               88

<210> SEQ ID NO 353
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
cgcttcacta agtctagaga caactctaag aatactctct acttgcagat gaacagctta            60
agggctgagg acactgcagt ctactattgt gcgag                                       95

-continued

<210> SEQ ID NO 354
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
cgcttcacta agtctagaga caactctaag aatactctct acttgcagat gaacagctta    60
agggctgagg acactgcagt ctactattgt acgag                               95

<210> SEQ ID NO 355
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cgcttcacta agtctagaga caac                                           24

<210> SEQ ID NO 356
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(15)
<223> OTHER INFORMATION: a, t, c, g, unknown or other

<400> SEQUENCE: 356
cacctgcnnn nnnnn                                                     15

<210> SEQ ID NO 357
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 357
cagctcnnnn nnnnnnn                                                   17

<210> SEQ ID NO 358
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 358
gaagacnnnn nnnnnnn                                                   17

<210> SEQ ID NO 359

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, t, c, g, unknown or other

<400> SEQUENCE: 359 gcagcnnnn nnnnnnn                                                      17

<210> SEQ ID NO 360
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 360
gaagacnnnn nn                                                          12

<210> SEQ ID NO 361
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 361
cttgagnnnn nnnnnnnnnn nn                                               22

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 362 acggcnnnn nnnnnnnnn                                                    19

<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, t, c, g, unknown or other

<400> SEQUENCE: 363
```

```
acggcnnnn nnnnnnnn                                          18

<210> SEQ ID NO 364
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 364
gtatccnnnn nn                                               12

<210> SEQ ID NO 365
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 365
actgggnnnn n                                                11

<210> SEQ ID NO 366
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 366 ggatcnnnnn                                                  10

<210> SEQ ID NO 367
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 367 gcatcnnnn n                                                 11

<210> SEQ ID NO 368
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (7)..(16)
<223> OTHER INFORMATION: a, t, c, g, unknown or other

<400> SEQUENCE: 368
gaggagnnnn nnnnnn                                                     16

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 369
gggacnnnnn nnnnnnnnn                                                  19

<210> SEQ ID NO 370
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(14)
<223> OTHER INFORMATION: a, t, c, g, unknown or other

<400> SEQUENCE: 370
acctgcnnnn nnnn                                                       14

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 371
ggcggannnn nnnnnnn                                                    17

<210> SEQ ID NO 372
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 372
ctgaagnnnn nnnnnnnnnn nn                                              22

<210> SEQ ID NO 373
<211> LENGTH: 11
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, t, c, g, unknown or other

<400> SEQUENCE: 373
cccgcnnnnn n                                                           11

<210> SEQ ID NO 374
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, t, c, g, unknown or other

<400> SEQUENCE: 374
ggatgnnnnn nnnnnnnn                                                    18

<210> SEQ ID NO 375
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, t, c, g, unknown or other

<400> SEQUENCE: 375
ctggagnnnn nnnnnnnnnn nn                                               22

<210> SEQ ID NO 376
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, t, c, g, unknown or other

<400> SEQUENCE: 376
gacgcnnnnn nnnnn                                                       15

<210> SEQ ID NO 377
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 377
ggtgannnnn nnn                                                         13

```
<210> SEQ ID NO 378
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 378
gaagannnnn nnn                                                          13

<210> SEQ ID NO 379
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, t, c, g, unknown or other

<400> SEQUENCE: 379 gagtcnnnnn                                                              10

<210> SEQ ID NO 380
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(26)
<223> OTHER INFORMATION: a, t, c, g, unknown or other

<400> SEQUENCE: 380
tccracnnnn nnnnnnnnnn nnnnnn                                            26

<210> SEQ ID NO 381
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(11)
<223> OTHER INFORMATION: a, t, c, g, unknown or other

<400> SEQUENCE: 381
cctcnnnnnn n                                                            11

<210> SEQ ID NO 382
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
```

<223> OTHER INFORMATION: a, t, c, g, unknown or other

<400> SEQUENCE: 382 gagtcnnnnn                                                        10

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(18)
<223> OTHER INFORMATION: a, t, c, g, unknown or other

<400> SEQUENCE: 383
cccacannnn nnnnnnnn                                               18

<210> SEQ ID NO 384
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, t, c, g, unknown or other

<400> SEQUENCE: 384
gcatcnnnnn nnnn                                                   14

<210> SEQ ID NO 385
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, t, c, g, unknown or other

<400> SEQUENCE: 385
ggtgannnnn nnn                                                    13

<210> SEQ ID NO 386
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, t, c, g, unknown or other

<400> SEQUENCE: 386
cccgnnnnnn nn                                                     12

<210> SEQ ID NO 387
<211> LENGTH: 19
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, t, c, g, unknown or other

<400> SEQUENCE: 387
ggatgnnnnn nnnnnnnnn                                                      19

<210> SEQ ID NO 388
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 388
gaccgannnn nnnnnnn                                                        17

<210> SEQ ID NO 389
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 389
cacccannnn nnnnnnn                                                        17

<210> SEQ ID NO 390
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, t, c, g, unknown or other

<400> SEQUENCE: 390
caarcannnn nnnnnnn                                                        17

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
gctgtgtatt actgtgcgag                                                     20

<210> SEQ ID NO 392
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 392
gccgtgtatt actgtgcgag                                                 20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 393
gccgtatatt actgtgcgag                                                 20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394
gccgtgtatt actgtacgag                                                 20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395
gccatgtatt actgtgcgag                                                 20

<210> SEQ ID NO 396
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
cacatccgtg ttgttcacgg atgtg                                           25

<210> SEQ ID NO 397
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
aatagtagac tgcagtgtcc tcagcccttca agctgttcat ctgcaagtag agagtattct    60
tagagttgtc tctagactta gtgaagcg                                        88

<210> SEQ ID NO 398
<211> LENGTH: 95
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 398
cgcttcacta agtctagaga caactctaag aatactctct acttgcagat gaacagctta    60
agggctgagg acactgcagt ctactattgt gcgag    95

<210> SEQ ID NO 399
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cgcttcacta agtctagaga caac    24

<210> SEQ ID NO 400
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
cacatccgtg ttgttcacgg atgtgggagg atggagactg ggtc    44

<210> SEQ ID NO 401
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
cacatccgtg ttgttcacgg atgtgggaga gtggagactg agtc    44

<210> SEQ ID NO 402
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
cacatccgtg ttgttcacgg atgtgggtgc ctggagactg cgtc    44

<210> SEQ ID NO 403
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
cacatccgtg ttgttcacgg atgtgggtgg ctggagactg cgtc    44

<210> SEQ ID NO 404
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 404
cctctactct tgtcacagtg cacaagacat ccag                              34

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
cctctactct tgtcacagtg                                              20

<210> SEQ ID NO 406
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ggaggatgga ctggatgtct tgtgcactgt gacaagagta gagg                   44

<210> SEQ ID NO 407
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ggagagtgga ctggatgtct tgtgcactgt gacaagagta gagg                   44

<210> SEQ ID NO 408
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ggtgcctgga ctggatgtct tgtgcactgt gacaagagta gagg                   44

<210> SEQ ID NO 409
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ggtggctgga ctggatgtct tgtgcactgt gacaagagta gagg                   44

<210> SEQ ID NO 410
<211> LENGTH: 44
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 410
cacatccgtg ttgttcacgg atgtggatcg actgtccagg agac                    44

<210> SEQ ID NO 411
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cacatccgtg ttgttcacgg atgtggactg tctgtcccaa ggcc                    44

<210> SEQ ID NO 412
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
cacatccgtg ttgttcacgg atgtggactg actgtccagg agac                    44

<210> SEQ ID NO 413
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
cacatccgtg ttgttcacgg atgtggaccc tctgccctgg ggcc                    44

<210> SEQ ID NO 414
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
cctctgactg agtgcacaga gtgctttaac ccaaccggct agtgttagcg gttccccgg    59

<210> SEQ ID NO 415
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
cctctgactg agtgcacaga gtgctttaac ccaaccggct agtgttagcg gttccccggg   60
acagtcgat                                                           69

<210> SEQ ID NO 416
<211> LENGTH: 69
<212> TYPE: DNA
<213> ORGANISM: Artificial Sequence
<220> FEATURE:
<223> OTHER INFORMATION: Description of Artificial Sequence: Synthetic

```
                              -continued
        oligonucleotide

<400> SEQUENCE: 416
cctctgactg agtgcacaga gtgctttaac ccaaccggct agtgttagcg gttccccggg    60
acagacagt                                                            69

<210> SEQ ID NO 417
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
cctctgactg agtgcacaga gtgctttaac ccaaccggct agtgttagcg gttccccggg    60
acagtcagt                                                            69

<210> SEQ ID NO 418
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
cctctgactg agtgcacaga gtgctttaac ccaaccggct agtgttagcg gtstcccgg     60 ggcagagggt                                                           70

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
cctctgactg agtgcacaga gtgc                                           24

<210> SEQ ID NO 420
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 420
ggccnnnnng gcc                                                       13

<210> SEQ ID NO 421
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other
```

```
<400> SEQUENCE: 421
ccannnnnnn nntgg                                               15

<210> SEQ ID NO 422
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 422
cgannnnnnt gc                                                  12

<210> SEQ ID NO 423
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 423
gccnnnnngg c                                                   11

<210> SEQ ID NO 424
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 424 gatnnnnatc                                                     10

<210> SEQ ID NO 425
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 425
gacnnnnngt c                                                   11

<210> SEQ ID NO 426
<211> LENGTH: 11
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 426
gcannnnntg c                                                          11

<210> SEQ ID NO 427
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 427
gtatccnnnn nn                                                         12

<210> SEQ ID NO 428
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 428
gacnnnnnng tc                                                         12

<210> SEQ ID NO 429
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 429
ccannnnntg g                                                          11

<210> SEQ ID NO 430
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 430
nnnnnngaga cg                                                         12

<210> SEQ ID NO 431

```
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 431
ccannnnnnt gg                                                             12

<210> SEQ ID NO 432
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 432 gaannnnttc                                                                10

<210> SEQ ID NO 433
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 433
ggtctcnnnn n                                                              11

<210> SEQ ID NO 434
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 434
nnnnnnnnnn ctcctc                                                         16

<210> SEQ ID NO 435
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 435
```
nnnnnnnnnt ccgcc                                          15

<210> SEQ ID NO 436
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 436
ggccnnnnng gcc                                            13

<210> SEQ ID NO 437
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 437
ccannnnnnt gg                                             12

<210> SEQ ID NO 438
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 438
gacnnnnnng tc                                             12

<210> SEQ ID NO 439
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 439
cgannnnnnt gc                                             12

<210> SEQ ID NO 440
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)..(8)
<223> OTHER INFORMATION: a, t, c, g, unknown or other

<400> SEQUENCE: 440
gcannnnntg c                                                          11

<210> SEQ ID NO 441
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 441
ccannnnntg g                                                          11

<210> SEQ ID NO 442
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 442 gaannnnttc                                                            10

<210> SEQ ID NO 443
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, t, c, g, unknown or other

<400> SEQUENCE: 443
nnnnnngaga cg                                                         12

<210> SEQ ID NO 444
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 444
gtatccnnnn nn                                                         12

<210> SEQ ID NO 445
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 445
gacnnnnngt c                                                           11

<210> SEQ ID NO 446
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 446
ggtctcnnnn n                                                           11

<210> SEQ ID NO 447
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 447
gccnnnnngg c                                                           11

<210> SEQ ID NO 448
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 448
ccannnnnnn nntgg                                                       15

<210> SEQ ID NO 449
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 449
nnnnnnnnnn ctcctc                                                      16
```

```
<210> SEQ ID NO 450
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 450
nnnnnnnnnt ccgcc                                                      15

<210> SEQ ID NO 451
<211> LENGTH: 9532
<212> TYPE: DNA
<213> ORGANISM: Unknown
<220> FEATURE:
<223> OTHER INFORMATION: Description of Unknown: MALIA3 nucleotide
      sequence
<220> FEATURE:
<221> NAME/KEY: CDS
<222> LOCATION: (1579)..(1638)
<220> FEATURE:
<221> NAME/KEY: CDS
<222> LOCATION: (2343)..(3443)
<220> FEATURE:
<221> NAME/KEY: CDS
<222> LOCATION: (3945)..(4400)
<220> FEATURE:
<221> NAME/KEY: CDS
<222> LOCATION: (4406)..(4450)
<220> FEATURE:
<221> NAME/KEY: CDS
<222> LOCATION: (4746)..(5789)

<400> SEQUENCE: 451
aatgctacta ctattagtag aattgatgcc acctttcag ctcgcgcccc aaatgaaaat        60
atagctaaac aggttattga ccatttgcga aatgtatcta atggtcaaac taaatctact      120
cgttcgcaga attgggaatc aactgttaca tggaatgaaa cttccagaca ccgtacttta      180
gttgcatatt taaaacatgt tgagctacag caccagattc agcaattaag ctctaagcca      240
tccgcaaaaa tgacctctta tcaaaaggag caattaaagg tactctctaa tcctgacctg      300
ttggagtttg cttccggtct ggttcgcttt gaagctcgaa ttaaaacgcg atatttgaag      360
tctttcgggc ttcctcttaa tcttttttgat gcaatccgct ttgcttctga ctataatagt     420
cagggtaaag acctgatttt tgatttatgg tcattctcgt tttctgaact gtttaaagca      480 tttgagggg attcaatgaa tatttatgac gattccgcag tattggacgc tatccagtct       540 aaacattta ctattacccc ctctggcaaa acttctttg caaaagcctc tcgctatttt        600 ggttttatc gtcgtctggt aaacgagggt tatgatagtg ttgctcttac tatgcctcgt       660 aattccttt ggcgttatgt atctgcatta gttgaatgtg gtattcctaa atctcaactg       720
atgaatcttt ctacctgtaa taatgttgtt ccgttagttc gttttattaa cgtagatttt     780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
```

```
gtctgcgcct cgttccggct aagtaacatg gagcaggtcg cggatttcga cacaatttat    1140
caggcgatga tacaaatctc cgttgtactt tgtttcgcgc ttggtataat cgctgggggt    1200
caaagatgag tgtttagtg tattctttcg cctctttcgt tttaggttgg tgccttcgta    1260
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
tttttggaga tttcaac gtg aaa aaa tta tta ttc gca att cct tta gtt    1611
                    Met Lys Lys Leu Leu Phe Ala Ile Pro Leu Val
                      1               5                  10 gtt cct ttc tat tct cac agt gca cag tctgtcgtga cgcagccgcc          1658
Val Pro Phe Tyr Ser His Ser Ala Gln
             15                  20 ctcagtgtct ggggcccag gcagagggt caccatctcc tgcactggga gcagctccaa     1718
catcggggca ggttatgatg tacactggta ccagcagctt ccaggaacag cccccaaact    1778
cctcatctat ggtaacagca atcggccctc aggggtccct gaccgattct ctggctccaa   1838
gtctggcacc tcagcctccc tggccatcac tgggctccag gctgaggatg aggctgatta   1898
ttactgccag tcctatgaca gcagcctgag tggcctttat gtcttcggaa ctgggaccaa   1958
ggtcaccgtc ctaggtcagc ccaaggccaa ccccactgtc actctgttcc cgccctcctc   2018
tgaggagctc aagccaaca aggccacact agtgtgtctg atcagtgact tctacccggg    2078
agctgtgaca gtggcctgga aggcagatag cagccccgtc aaggcgggag tggagaccac   2138
cacaccctcc aaacaaagca caacaagta cgcggccagc agctatctga gcctgacgcc    2198
tgagcagtgg aagtcccaca gaagctcag ctgccaggtc acgcatgaag ggagcaccgt    2258
ggagaagaca gtggccccta cagaatgttc ataataaacc gcctccaccg ggcgcgccaa   2318
ttctatttca aggagacagt cata atg aaa tac cta ttg cct acg gca gcc     2369
                          Met Lys Tyr Leu Leu Pro Thr Ala Ala
                                            25 gct gga ttg tta tta ctc gcg gcc cag ccg gcc atg gcc gaa gtt caa    2417
Ala Gly Leu Leu Leu Leu Ala Ala Gln Pro Ala Met Ala Glu Val Gln
 30               35                  40                  45 ttg tta gag tct ggt ggc ggt ctt gtt cag cct ggt ggt tct tta cgt    2465
Leu Leu Glu Ser Gly Gly Gly Leu Val Gln Pro Gly Gly Ser Leu Arg
             50                  55                  60 ctt tct tgc gct gct tcc gga ttc act ttc tct tcg tac gct atg tct    2513
Leu Ser Cys Ala Ala Ser Gly Phe Thr Phe Ser Ser Tyr Ala Met Ser
         65                  70                  75 tgg gtt cgc caa gct cct ggt aaa ggt ttg gag tgg gtt tct gct atc    2561
Trp Val Arg Gln Ala Pro Gly Lys Gly Leu Glu Trp Val Ser Ala Ile
             80                  85                  90 tct ggt tct ggt ggc agt act tac tat gct gac tcc gtt aaa ggt cgc    2609
Ser Gly Ser Gly Gly Ser Thr Tyr Tyr Ala Asp Ser Val Lys Gly Arg
     95                  100                 105 ttc act atc tct aga gac aac tct aag aat act ctc tac ttg cag atg    2657
Phe Thr Ile Ser Arg Asp Asn Ser Lys Asn Thr Leu Tyr Leu Gln Met
110             115                 120                 125 aac agc tta agg gct gag gac act gca gtc tac tat tgc gct aaa gac    2705
Asn Ser Leu Arg Ala Glu Asp Thr Ala Val Tyr Tyr Cys Ala Lys Asp
                 130                 135                 140 tat gaa ggt act ggt tat gct ttc gac ata tgg ggt caa ggt act atg    2753
Tyr Glu Gly Thr Gly Tyr Ala Phe Asp Ile Trp Gly Gln Gly Thr Met
```

```
                     145                 150                 155
gtc acc gtc tct agt gcc tcc acc aag ggc cca tcg gtc ttc ccc ctg      2801
Val Thr Val Ser Ser Ala Ser Thr Lys Gly Pro Ser Val Phe Pro Leu
            160                 165                 170 gca ccc tcc tcc aag agc acc tct ggg ggc aca gcg gcc ctg ggc tgc      2849
Ala Pro Ser Ser Lys Ser Thr Ser Gly Gly Thr Ala Ala Leu Gly Cys
        175                 180                 185 ctg gtc aag gac tac ttc ccc gaa ccg gtg acg gtg tcg tgg aac tca      2897
Leu Val Lys Asp Tyr Phe Pro Glu Pro Val Thr Val Ser Trp Asn Ser
190                 195                 200                 205 ggc gcc ctg acc agc ggc gtc cac acc ttc ccg gct gtc cta cag tct      2945
Gly Ala Leu Thr Ser Gly Val His Thr Phe Pro Ala Val Leu Gln Ser
                210                 215                 220 agc gga ctc tac tcc ctc agc agc gta gtg acc gtg ccc tct tct agc      2993
Ser Gly Leu Tyr Ser Leu Ser Ser Val Val Thr Val Pro Ser Ser Ser
            225                 230                 235 ttg ggc acc cag acc tac atc tgc aac gtg aat cac aag ccc agc aac      3041
Leu Gly Thr Gln Thr Tyr Ile Cys Asn Val Asn His Lys Pro Ser Asn
        240                 245                 250 acc aag gtg gac aag aaa gtt gag ccc aaa tct tgt gcg gcc gct cat      3089
Thr Lys Val Asp Lys Lys Val Glu Pro Lys Ser Cys Ala Ala Ala His
255                 260                 265 cac cac cat cat cac tct gct gaa caa aaa ctc atc tca gaa gag gat      3137
His His His His His Ser Ala Glu Gln Lys Leu Ile Ser Glu Glu Asp
270                 275                 280                 285 ctg aat ggt gcc gca gat atc aac gat gat cgt atg gct ggc gcc gct      3185
Leu Asn Gly Ala Ala Asp Ile Asn Asp Asp Arg Met Ala Gly Ala Ala
                290                 295                 300 gaa act gtt gaa agt tgt tta gca aaa ccc cat aca gaa aat tca ttt      3233
Glu Thr Val Glu Ser Cys Leu Ala Lys Pro His Thr Glu Asn Ser Phe
            305                 310                 315 act aac gtc tgg aaa gac gac aaa act tta gat cgt tac gct aac tat      3281
Thr Asn Val Trp Lys Asp Asp Lys Thr Leu Asp Arg Tyr Ala Asn Tyr
        320                 325                 330 gag ggt tgt ctg tgg aat gct aca ggc gtt gta gtt tgt act ggt gac      3329
Glu Gly Cys Leu Trp Asn Ala Thr Gly Val Val Val Cys Thr Gly Asp
335                 340                 345 gaa act cag tgt tac ggt aca tgg gtt cct att ggg ctt gct atc cct      3377
Glu Thr Gln Cys Tyr Gly Thr Trp Val Pro Ile Gly Leu Ala Ile Pro
350                 355                 360                 365 gaa aat gag ggt ggt ggc tct gag ggt ggc ggt tct gag ggt ggc ggt      3425
Glu Asn Glu Gly Gly Gly Ser Glu Gly Gly Gly Ser Glu Gly Gly Gly
                370                 375                 380 tct gag ggt ggc ggt act aaacctcctg agtacggtga tacacctatt             3473
Ser Glu Gly Gly Gly Thr
            385 ccgggctata cttatatcaa ccctctcgac ggcacttatc cgcctggtac tgagcaaaac    3533 cccgctaatc ctaatccttc tcttgaggag tctcagcctc ttaatacttt catgtttcag    3593 aataataggt tccgaaatag gcagggggca ttaactgttt atacgggcac tgttactcaa    3653 ggcactgacc ccgttaaaac ttattaccag tacactcctg tatcatcaaa agccatgtat    3713 gacgcttact ggaacggtaa attcagagac tgcgctttcc attctggctt taatgaagat    3773 ccattcgttt gtgaatatca aggccaatcg tctgacctgc tcaacctcc tgtcaatgct     3833 ggcggcggct ctggtggtgg ttctggtggc ggctctgagg tggtggctc tgagggtggc     3893 ggttctgagg gtggcggctc tgagggaggc ggttccggtg gtggctctgg t tcc ggt     3950
                                                          Ser Gly gat ttt gat tat gaa aag atg gca aac gct aat aag ggg gct atg acc      3998
```

```
Asp Phe Asp Tyr Glu Lys Met Ala Asn Ala Asn Lys Gly Ala Met Thr
390                 395                 400                 405 gaa aat gcc gat gaa aac gcg cta cag tct gac gct aaa ggc aaa ctt    4046
Glu Asn Ala Asp Glu Asn Ala Leu Gln Ser Asp Ala Lys Gly Lys Leu
                410                 415                 420 gat tct gtc gct act gat tac ggt gct gct atc gat ggt ttc att ggt    4094
Asp Ser Val Ala Thr Asp Tyr Gly Ala Ala Ile Asp Gly Phe Ile Gly
            425                 430                 435 gac gtt tcc ggc ctt gct aat ggt aat ggt gct act ggt gat ttt gct    4142
Asp Val Ser Gly Leu Ala Asn Gly Asn Gly Ala Thr Gly Asp Phe Ala
        440                 445                 450 ggc tct aat tcc caa atg gct caa gtc ggt gac ggt gat aat tca cct    4190
Gly Ser Asn Ser Gln Met Ala Gln Val Gly Asp Gly Asp Asn Ser Pro
    455                 460                 465 tta atg aat aat ttc cgt caa tat tta cct tcc ctc cct caa tcg gtt    4238
Leu Met Asn Asn Phe Arg Gln Tyr Leu Pro Ser Leu Pro Gln Ser Val
470                 475                 480                 485 gaa tgt cgc cct ttt gtc ttt agc gct ggt aaa cca tat gaa ttt tct    4286
Glu Cys Arg Pro Phe Val Phe Ser Ala Gly Lys Pro Tyr Glu Phe Ser
                490                 495                 500 att gat tgt gac aaa ata aac tta ttc cgt ggt gtc ttt gcg ttt ctt    4334
Ile Asp Cys Asp Lys Ile Asn Leu Phe Arg Gly Val Phe Ala Phe Leu
            505                 510                 515 tta tat gtt gcc acc ttt atg tat gta ttt tct acg ttt gct aac ata    4382
Leu Tyr Val Ala Thr Phe Met Tyr Val Phe Ser Thr Phe Ala Asn Ile
        520                 525                 530 ctg cgt aat aag gag tct taatc atg cca gtt ctt ttg ggt att ccg tta  4432
Leu Arg Asn Lys Glu Ser       Met Pro Val Leu Leu Gly Ile Pro Leu
535                               540                 545 tta ttg cgt ttc ctc ggt ttccttctgg taactttgtt cggctatctg           4480
Leu Leu Arg Phe Leu Gly
        550 cttactttc ttaaaaggg cttcggtaag atagctattg ctatttcatt gtttcttgct    4540
cttattattg ggcttaactc aattcttgtg ggttatctct ctgatattag cgctcaatta  4600
ccctctgact tgttcaggg tgttcagtta attctcccgt ctaatgcgct tccctgtttt   4660
tatgttattc tctctgtaaa ggctgctatt ttcattttg acgttaaaca aaaaatcgtt   4720
tcttatttgg attgggataa ataat atg gct gtt tat ttt gta act ggc aaa    4772
                            Met Ala Val Tyr Phe Val Thr Gly Lys
                            555                 560 tta ggc tct gga aag acg ctc gtt agc gtt ggt aag att cag gat aaa    4820
Leu Gly Ser Gly Lys Thr Leu Val Ser Val Gly Lys Ile Gln Asp Lys
565                 570                 575 att gta gct ggg tgc aaa ata gca act aat ctt gat tta agg ctt caa    4868
Ile Val Ala Gly Cys Lys Ile Ala Thr Asn Leu Asp Leu Arg Leu Gln
580                 585                 590                 595 aac ctc ccg caa gtc ggg agg ttc gct aaa acg cct cgc gtt ctt aga    4916
Asn Leu Pro Gln Val Gly Arg Phe Ala Lys Thr Pro Arg Val Leu Arg
                600                 605                 610 ata ccg gat aag cct tct ata tct gat ttg ctt gct att ggg cgc ggt    4964
Ile Pro Asp Lys Pro Ser Ile Ser Asp Leu Leu Ala Ile Gly Arg Gly
            615                 620                 625 aat gat tcc tac gat gaa aat aaa aac ggc ttg ctt gtt ctc gat gag    5012
Asn Asp Ser Tyr Asp Glu Asn Lys Asn Gly Leu Leu Val Leu Asp Glu
        630                 635                 640 tgc ggt act tgg ttt aat acc cgt tct tgg aat gat aag gaa aga cag    5060
Cys Gly Thr Trp Phe Asn Thr Arg Ser Trp Asn Asp Lys Glu Arg Gln
    645                 650                 655 ccg att att gat tgg ttt cta cat gct cgt aaa tta gga tgg gat att    5108
```

```
                Pro Ile Ile Asp Trp Phe Leu His Ala Arg Lys Leu Gly Trp Asp Ile
                660                 665                 670                 675 att ttt ctt gtt cag gac tta tct att gtt gat aaa cag gcg cgt tct         5156
Ile Phe Leu Val Gln Asp Leu Ser Ile Val Asp Lys Gln Ala Arg Ser
                            680                 685                 690 gca tta gct gaa cat gtt gtt tat tgt cgt cgt ctg gac aga att act         5204
Ala Leu Ala Glu His Val Val Tyr Cys Arg Arg Leu Asp Arg Ile Thr
                695                 700                 705 tta cct ttt gtc ggt act tta tat tct att act ggc tcg aaa atg             5252
Leu Pro Phe Val Gly Thr Leu Tyr Ser Leu Ile Thr Gly Ser Lys Met
            710                 715                 720 cct ctg cct aaa tta cat gtt ggc gtt gtt aaa tat ggc gat tct caa         5300
Pro Leu Pro Lys Leu His Val Gly Val Val Lys Tyr Gly Asp Ser Gln
        725                 730                 735 tta agc cct act gtt gag cgt tgg ctt tat act ggt aag aat ttg tat         5348
Leu Ser Pro Thr Val Glu Arg Trp Leu Tyr Thr Gly Lys Asn Leu Tyr
740                 745                 750                 755 aac gca tat gat act aaa cag gct ttt tct agt aat tat gat tcc ggt         5396
Asn Ala Tyr Asp Thr Lys Gln Ala Phe Ser Ser Asn Tyr Asp Ser Gly
                760                 765                 770 gtt tat tct tat tta acg cct tat tta tca cac ggt cgg tat ttc aaa         5444
Val Tyr Ser Tyr Leu Thr Pro Tyr Leu Ser His Gly Arg Tyr Phe Lys
                    775                 780                 785 cca tta aat tta ggt cag aag atg aaa tta act aaa ata tat ttg aaa         5492
Pro Leu Asn Leu Gly Gln Lys Met Lys Leu Thr Lys Ile Tyr Leu Lys
                790                 795                 800 aag ttt tct cgc gtt ctt tgt ctt gcg att gga ttt gca tca gca ttt         5540
Lys Phe Ser Arg Val Leu Cys Leu Ala Ile Gly Phe Ala Ser Ala Phe
805                 810                 815 aca tat agt tat ata acc caa cct aag ccg gag gtt aaa aag gta gtc         5588
Thr Tyr Ser Tyr Ile Thr Gln Pro Lys Pro Glu Val Lys Lys Val Val
820                 825                 830                 835 tct cag acc tat gat ttt gat aaa ttc act att gac tct tct cag cgt         5636
Ser Gln Thr Tyr Asp Phe Asp Lys Phe Thr Ile Asp Ser Ser Gln Arg
                840                 845                 850 ctt aat cta agc tat cgc tat gtt ttc aag gat tct aag gga aaa tta         5684
Leu Asn Leu Ser Tyr Arg Tyr Val Phe Lys Asp Ser Lys Gly Lys Leu
                855                 860                 865 att aat agc gac gat tta cag aag caa ggt tat tca ctc aca tat att         5732
Ile Asn Ser Asp Asp Leu Gln Lys Gln Gly Tyr Ser Leu Thr Tyr Ile
            870                 875                 880 gat tta tgt act gtt tcc att aaa aaa ggt aat tca aat gaa att gtt         5780
Asp Leu Cys Thr Val Ser Ile Lys Lys Gly Asn Ser Asn Glu Ile Val
885                 890                 895 aaa tgt aat taattttgtt tcttgatgt tgtttcatc atcttctttt                   5829
Lys Cys Asn
900 gctcaggtaa ttgaaatgaa taattcgcct ctgcgcgatt ttgtaacttg gtattcaaag       5889 caatcaggcg aatccgttat tgtttctccc gatgtaaaag gtactgttac tgtatattca       5949 tctgacgtta aacctgaaaa tctacgcaat ttctttattt ctgttttacg tgctaataat       6009 tttgatatgg ttggttcaat tccttccata attcagaagt ataatccaaa caatcaggat       6069 tatattgatg aattgccatc atctgataat caggaatatg atgataattc cgctccttct       6129 ggtggtttct ttgttccgca aaatgataat gttactcaaa cttttaaaat taataacgtt       6189 cgggcaaagg atttaatacg agttgtcgaa ttgtttgtaa agtctaatac ttctaaatcc       6249 tcaaatgtat tatctattga cggctctaat ctattagttg tttctgcacc taaagatatt       6309 ttagataacc ttcctcaatt cctttctact gttgatttgc caactgacca gatattgatt       6369
```

```
gagggtttga tatttgaggt tcagcaaggt gatgctttag attttcatt tgctgctggc    6429
tctcagcgtg gcactgttgc aggcggtgtt aatactgacc gcctcacctc tgttttatct    6489
tctgctggtg gttcgttcgg tatttttaat ggcgatgttt tagggctatc agttcgcgca    6549
ttaaagacta atagccattc aaaaatattg tctgtgccac gtattcttac gctttcaggt    6609
cagaagggtt ctatctctgt tggccagaat gtcccttta ttactggtcg tgtgactggt     6669
gaatctgcca atgtaaataa tccatttcag acgattgagc gtcaaaatgt aggtatttcc    6729
atgagcgttt ttcctgttgc aatggctggc ggtaatattg ttctggatat taccagcaag    6789
gccgatagtt tgagttcttc tactcaggca agtgatgtta ttactaatca agaagtatt     6849
gctacaacgg ttaatttgcg tgatggacag actcttttac tcggtggcct cactgattat    6909
aaaaacactt ctcaagattc tggcgtaccg ttcctgtcta aatcccttt aatcggcctc     6969
ctgtttagct cccgctctga ttccaacgag gaaagcacgt tatacgtgct cgtcaaagca    7029
accatagtac gcgccctgta gcggcgcatt aagcgcggcg ggtgtggtgg ttacgcgcag    7089
cgtgaccgct acacttgcca gcgccctagc gcccgctcct ttcgctttct tcccttcctt    7149
tctcgccacg ttcgccggct ttccccgtca agctctaaat cgggggctcc ctttagggtt    7209
ccgatttagt gctttacggc acctcgaccc caaaaaactt gatttgggtg atggttcacg    7269
tagtgggcca tcgccctgat agacggtttt tcgccctttg acgttggagt ccacgttctt    7329
taatagtgga ctcttgttcc aaactggaac aacactcaac cctatctcgg gctattcttt    7389
tgatttataa gggattttgc cgatttcgga accaccatca acaggattt tcgcctgctg     7449
gggcaaacca gcgtggaccg cttgctgcaa ctctctcagg gccaggcggt gaagggcaat    7509
cagctgttgc ccgtctcact ggtgaaaaga aaaaccaccc tggatccaag cttgcaggtg    7569
gcacttttcg gggaaatgtg cgcggaaccc ctatttgttt attttctaa atacattcaa     7629
atatgtatcc gctcatgaga caataacccct gataaatgct tcaataatat tgaaaaagga   7689
agagtatgag tattcaacat ttccgtgtcg cccttattcc cttttttgcg gcattttgcc    7749
ttcctgttt tgctcaccca gaaacgctgg tgaaagtaaa agatgctgaa gatcagttgg     7809
gcgcacgagt gggttacatc gaactggatc tcaacagcgg taagatcctt gagagttttc    7869
gccccgaaga acgttttcca atgatgagca cttttaaagt tctgctatgt catacactat    7929
tatcccgtat tgacgccggg caagagcaac tcggtcgccg ggcgcggtat tctcagaatg    7989
acttggttga gtactcacca gtcacagaaa agcatcttac ggatggcatg acagtaagag    8049
aattatgcag tgctgccata accatgagtg ataacactgc ggccaactta cttctgacaa    8109
cgatcggagg accgaaggag ctaaccgctt ttttgcacaa catgggggat catgtaactc    8169
gccttgatcg ttgggaaccg gagctgaatg aagccatacc aaacgacgag cgtgacacca    8229
cgatgcctgt agcaatgcca acaacgttgc gcaaactatt aactggcgaa ctacttactc    8289
tagcttcccg gcaacaatta atagactgga tggaggcgga taaagttgca ggaccacttc    8349
tgcgctcggc ccttccggct ggctggttta ttgctgataa atctggagcc ggtgagcgtg    8409
ggtctcgcgg tatcattgca gcactggggc cagatggtaa gccctcccgt atcgtagtta    8469
tctacacgac ggggagtcag gcaactatgg atgaacgaaa tagacagatc gctgagatag    8529
gtgcctcact gattaagcat tggtaactgt cagaccaagt ttactcatat atactttaga    8589
ttgatttaaa acttcatttt taatttaaaa ggatctaggt gaagatcctt tttgataatc    8649
tcatgaccaa aatcccttaa cgtgagtttt cgttccactg tacgtaagac ccccaagctt    8709
gtcgactgaa tggcgaatgg cgctttgcct ggtttccggc accagaagcg gtgccggaaa    8769
```

```
gctggctgga gtgcgatctt cctgaggccg atactgtcgt cgtcccctca aactggcaga    8829
tgcacggtta cgatgcgccc atctacacca acgtaaccta tcccattacg gtcaatccgc    8889
cgtttgttcc cacggagaat ccgacggggt gttactcgct cacatttaat gttgatgaaa    8949
gctggctaca ggaaggccag acgcgaatta ttttgatgg cgttcctatt ggttaaaaaa    9009
tgagctgatt taacaaaaat ttaacgcgaa ttttaacaaa atattaacgt ttacaattta    9069
aatatttgct tatacaatct tcctgttttt ggggcttttc tgattatcaa ccggggtaca    9129
tatgattgac atgctagttt tacgattacc gttcatcgat tctcttgttt gctccagact    9189
ctcaggcaat gacctgatag cctttgtaga tctctcaaaa atagctaccc tctccggcat    9249
gaatttatca gctagaacgg ttgaatatca tattgatggt gatttgactg tctccggcct    9309
ttctcaccct tttgaatctt tacctacaca ttactcaggc attgcattta aaatatgatga   9369 gggttctaaa aattttatc cttgcgttga ataaaggct tctcccgcaa agtattaca      9429 gggtcataat gttttggta caaccgattt agctttatgc tctgaggctt tattgcttaa    9489
ttttgctaat tctttgcctt gcctgtatga tttattggat gtt                     9532
```

<210> SEQ ID NO 452
<211> LENGTH: 20
<212> TYPE: PRT
<213> ORGANISM: Unknown
<220> FEATURE:
<223> OTHER INFORMATION: Description of Unknown: MALIA3 peptide
      sequence

<400> SEQUENCE: 452

Met Lys Lys Leu Leu Phe Ala Ile Pro Leu Val Val Pro Phe Tyr Ser
 1               5                  10                  15

His Ser Ala Gln
            20

<210> SEQ ID NO 453
<211> LENGTH: 367
<212> TYPE: PRT
<213> ORGANISM: Unknown
<220> FEATURE:
<223> OTHER INFORMATION: Description of Unknown: MALIA3 protein
      sequence

<400> SEQUENCE: 453

Met Lys Tyr Leu Leu Pro Thr Ala Ala Ala Gly Leu Leu Leu Leu Ala
 1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Tyr Glu Gly Thr Gly Tyr Ala
        115                 120                 125

Phe Asp Ile Trp Gly Gln Gly Thr Met Val Thr Val Ser Ser Ala Ser

```
                130                 135                 140
Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Ala Ala His His His His His His Ser Ala
                245                 250                 255

Glu Gln Lys Leu Ile Ser Glu Glu Asp Leu Asn Gly Ala Ala Asp Ile
                260                 265                 270

Asn Asp Asp Arg Met Ala Gly Ala Ala Glu Thr Val Glu Ser Cys Leu
    275                 280                 285

Ala Lys Pro His Thr Glu Asn Ser Phe Thr Asn Val Trp Lys Asp Asp
    290                 295                 300

Lys Thr Leu Asp Arg Tyr Ala Asn Tyr Glu Gly Cys Leu Trp Asn Ala
305                 310                 315                 320

Thr Gly Val Val Val Cys Thr Gly Asp Glu Thr Gln Cys Tyr Gly Thr
                325                 330                 335

Trp Val Pro Ile Gly Leu Ala Ile Pro Glu Asn Glu Gly Gly Gly Ser
                340                 345                 350

Glu Gly Gly Gly Ser Glu Gly Gly Gly Ser Glu Gly Gly Gly Thr
    355                 360                 365

<210> SEQ ID NO 454
<211> LENGTH: 152
<212> TYPE: PRT
<213> ORGANISM: Unknown
<220> FEATURE:
<223> OTHER INFORMATION: Description of Unknown: MALIA3 protein
      sequence

<400> SEQUENCE: 454

Ser Gly Asp Phe Asp Tyr Glu Lys Met Ala Asn Ala Asn Lys Gly Ala
1               5                   10                  15

Met Thr Glu Asn Ala Asp Glu Asn Ala Leu Gln Ser Asp Ala Lys Gly
                20                  25                  30

Lys Leu Asp Ser Val Ala Thr Asp Tyr Gly Ala Ala Ile Asp Gly Phe
            35                  40                  45

Ile Gly Asp Val Ser Gly Leu Ala Asn Gly Asn Gly Ala Thr Gly Asp
        50                  55                  60

Phe Ala Gly Ser Asn Ser Gln Met Ala Gln Val Gly Asp Gly Asp Asn
65                  70                  75                  80

Ser Pro Leu Met Asn Asn Phe Arg Gln Tyr Leu Pro Ser Leu Pro Gln
                85                  90                  95

Ser Val Glu Cys Arg Pro Phe Val Phe Ser Ala Gly Lys Pro Tyr Glu
                100                 105                 110

Phe Ser Ile Asp Cys Asp Lys Ile Asn Leu Phe Arg Gly Val Phe Ala
            115                 120                 125

Phe Leu Leu Tyr Val Ala Thr Phe Met Tyr Val Phe Ser Thr Phe Ala
```

```
            130                 135                 140
Asn Ile Leu Arg Asn Lys Glu Ser
145                 150
```

<210> SEQ ID NO 455
<211> LENGTH: 15
<212> TYPE: PRT
<213> ORGANISM: Unknown
<220> FEATURE:
<223> OTHER INFORMATION: Description of Unknown: MALIA3 peptide
      sequence

<400> SEQUENCE: 455

```
Met Pro Val Leu Leu Gly Ile Pro Leu Leu Arg Phe Leu Gly
 1               5                  10                  15
```

<210> SEQ ID NO 456
<211> LENGTH: 348
<212> TYPE: PRT
<213> ORGANISM: Unknown
<220> FEATURE:
<223> OTHER INFORMATION: Description of Unknown: MALIA3 protein
      sequence

<400> SEQUENCE: 456

```
Met Ala Val Tyr Phe Val Thr Gly Lys Leu Gly Ser Gly Lys Thr Leu
 1               5                  10                  15

Val Ser Val Gly Lys Ile Gln Asp Lys Ile Val Ala Gly Cys Lys Ile
                20                  25                  30

Ala Thr Asn Leu Asp Leu Arg Leu Gln Asn Leu Pro Gln Val Gly Arg
            35                  40                  45

Phe Ala Lys Thr Pro Arg Val Leu Arg Ile Pro Asp Lys Pro Ser Ile
        50                  55                  60

Ser Asp Leu Leu Ala Ile Gly Arg Gly Asn Asp Ser Tyr Asp Glu Asn
 65                  70                  75                  80

Lys Asn Gly Leu Leu Val Leu Asp Glu Cys Gly Thr Trp Phe Asn Thr
                85                  90                  95

Arg Ser Trp Asn Asp Lys Glu Arg Gln Pro Ile Ile Asp Trp Phe Leu
            100                 105                 110

His Ala Arg Lys Leu Gly Trp Asp Ile Ile Phe Leu Val Gln Asp Leu
        115                 120                 125

Ser Ile Val Asp Lys Gln Ala Arg Ser Ala Leu Ala Glu His Val Val
130                 135                 140

Tyr Cys Arg Arg Leu Asp Arg Ile Thr Leu Pro Phe Val Gly Thr Leu
145                 150                 155                 160

Tyr Ser Leu Ile Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
        195                 200                 205

Ala Phe Ser Ser Asn Tyr Asp Ser Gly Val Tyr Ser Tyr Leu Thr Pro
    210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270
```

```
Pro Lys Pro Glu Val Lys Lys Val Val Ser Gln Thr Tyr Asp Phe Asp
        275                 280                 285

Lys Phe Thr Ile Asp Ser Ser Gln Arg Leu Asn Leu Ser Tyr Arg Tyr
        290                 295                 300

Val Phe Lys Asp Ser Lys Gly Lys Leu Ile Asn Ser Asp Leu Gln
305                 310                 315                 320

Lys Gln Gly Tyr Ser Leu Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 457
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
tggaagaggc acgttctttt cttt                                          24

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
cttttctttg ttgccgttgg ggtg                                          24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
acactctccc ctgttgaagc tctt                                          24

<210> SEQ ID NO 460
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
accgcctcca ccgggcgcgc cttattaaca ctctcccctg ttgaagctct t            51

<210> SEQ ID NO 461
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
tgaacattct gtagggggcca ctg                                          23
```

<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
agagcattct gcaggggcca ctg                                              23

<210> SEQ ID NO 463
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
accgcctcca ccgggcgcgc cttattatga acattctgta ggggccactg                 50

<210> SEQ ID NO 464
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
accgcctcca ccgggcgcgc cttattaaga gcattctgca ggggccactg                 50

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
cgactggagc acgaggacac tga                                              23

<210> SEQ ID NO 466
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
ggacactgac atggactgaa ggagta                                           26

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
gggaggatgg agactgggtc                                                  20

```
<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
gggaagatgg agactgggtc                                                 20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
gggagagtgg agactgagtc                                                 20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gggtgcctgg agactgcgtc                                                 20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
gggtggctgg agactgcgtc                                                 20

<210> SEQ ID NO 472
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gggaggatgg agactgggtc atctggatgt cttgtgcact gtgacagagg                50

<210> SEQ ID NO 473
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gggaagatgg agactgggtc atctggatgt cttgtgcact gtgacagagg                50

<210> SEQ ID NO 474
<211> LENGTH: 50
```

<210> SEQ ID NO 474
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
gggagagtgg agactgggtc atctggatgt cttgtgcact gtgacagagg           50

<210> SEQ ID NO 475
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gggtgcctgg agactgggtc atctggatgt cttgtgcact gtgacagagg           50

<210> SEQ ID NO 476
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gggtggctgg agactgggtc atctggatgt cttgtgcact gtgacagagg           50

<210> SEQ ID NO 477
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gggagtctgg agactgggtc atctggatgt cttgtgcact gtgacagagg           50

<210> SEQ ID NO 478
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
cctctgtcac agtgcacaag acatccagat gacccagtct cc                   42

<210> SEQ ID NO 479
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
cctctgtcac agtgcacaag ac                                         22

<210> SEQ ID NO 480
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 480
acactctccc ctgttgaagc tctt                                                   24

<210> SEQ ID NO 481
<211> LENGTH: 669
<212> TYPE: DNA
<213> ORGANISM: Homo sapiens
<220> FEATURE:
<221> NAME/KEY: CDS
<222> LOCATION: (1)..(669)
<220> FEATURE:
<221> NAME/KEY: modified_base
<222> LOCATION: (669)..(669)
<223> OTHER INFORMATION: a, c, t or g

<400> SEQUENCE: 481
```

| | | | | | | | | | | | | | | | | |
|---|---|---|---|---|---|---|---|---|---|---|---|---|---|---|---|---|
| agt | gca | caa | gac | atc | cag | atg | acc | cag | tct | cca | gcc | acc | ctg | tct | gtg | 48 |
| Ser | Ala | Gln | Asp | Ile | Gln | Met | Thr | Gln | Ser | Pro | Ala | Thr | Leu | Ser | Val | |
| 1 | | | | 5 | | | | | 10 | | | | | 15 | | |
| tct | cca | ggg | gaa | agg | gcc | acc | ctc | tcc | tgc | agg | gcc | agt | cag | agt | gtt | 96 |
| Ser | Pro | Gly | Glu | Arg | Ala | Thr | Leu | Ser | Cys | Arg | Ala | Ser | Gln | Ser | Val | |
| | | | 20 | | | | | 25 | | | | | 30 | | | |
| agt | aac | aac | tta | gcc | tgg | tac | cag | cag | aaa | cct | ggc | cag | gtt | ccc | agg | 144 |
| Ser | Asn | Asn | Leu | Ala | Trp | Tyr | Gln | Gln | Lys | Pro | Gly | Gln | Val | Pro | Arg | |
| | | 35 | | | | | 40 | | | | | 45 | | | | |
| ctc | ctc | atc | tat | ggt | gca | tcc | acc | agg | gcc | act | gat | atc | cca | gcc | agg | 192 |
| Leu | Leu | Ile | Tyr | Gly | Ala | Ser | Thr | Arg | Ala | Thr | Asp | Ile | Pro | Ala | Arg | |
| | 50 | | | | | 55 | | | | | 60 | | | | | |
| ttc | agt | ggc | agt | ggg | tct | ggg | aca | gac | ttc | act | ctc | acc | atc | agc | aga | 240 |
| Phe | Ser | Gly | Ser | Gly | Ser | Gly | Thr | Asp | Phe | Thr | Leu | Thr | Ile | Ser | Arg | |
| 65 | | | | | 70 | | | | | 75 | | | | | 80 | |
| ctg | gag | cct | gaa | gat | ttt | gca | gtg | tat | tac | tgt | cag | cgg | tat | ggt | agc | 288 |
| Leu | Glu | Pro | Glu | Asp | Phe | Ala | Val | Tyr | Tyr | Cys | Gln | Arg | Tyr | Gly | Ser | |
| | | | | 85 | | | | | 90 | | | | | 95 | | |
| tca | ccg | ggg | tgg | acg | ttc | ggc | caa | ggg | acc | aag | gtg | gaa | atc | aaa | cga | 336 |
| Ser | Pro | Gly | Trp | Thr | Phe | Gly | Gln | Gly | Thr | Lys | Val | Glu | Ile | Lys | Arg | |
| | | | 100 | | | | | 105 | | | | | 110 | | | |
| act | gtg | gct | gca | cca | tct | gtc | ttc | atc | ttc | ccg | cca | tct | gat | gag | cag | 384 |
| Thr | Val | Ala | Ala | Pro | Ser | Val | Phe | Ile | Phe | Pro | Pro | Ser | Asp | Glu | Gln | |
| | | 115 | | | | | 120 | | | | | 125 | | | | |
| ttg | aaa | tct | gga | act | gcc | tct | gtt | gtg | tgc | ctg | ctg | aat | aac | ttc | tat | 432 |
| Leu | Lys | Ser | Gly | Thr | Ala | Ser | Val | Val | Cys | Leu | Leu | Asn | Asn | Phe | Tyr | |
| | 130 | | | | | 135 | | | | | 140 | | | | | |
| ccc | aga | gag | gcc | aaa | gta | cag | tgg | aag | gtg | gat | aac | gcc | ctc | caa | tcg | 480 |
| Pro | Arg | Glu | Ala | Lys | Val | Gln | Trp | Lys | Val | Asp | Asn | Ala | Leu | Gln | Ser | |
| 145 | | | | | 150 | | | | | 155 | | | | | 160 | |
| ggt | aac | tcc | cag | gag | agt | gtc | aca | gag | cag | gac | agc | aag | gac | agc | acc | 528 |
| Gly | Asn | Ser | Gln | Glu | Ser | Val | Thr | Glu | Gln | Asp | Ser | Lys | Asp | Ser | Thr | |
| | | | | 165 | | | | | 170 | | | | | 175 | | |
| tac | agc | ctc | agc | agc | acc | ctg | acg | ctg | agc | aaa | gca | gac | tac | gag | aaa | 576 |
| Tyr | Ser | Leu | Ser | Ser | Thr | Leu | Thr | Leu | Ser | Lys | Ala | Asp | Tyr | Glu | Lys | |
| | | | 180 | | | | | 185 | | | | | 190 | | | |
| cac | aaa | gtc | tac | gcc | tgc | gaa | gtc | acc | cat | cag | ggc | ctg | agc | tcg | cct | 624 |
| His | Lys | Val | Tyr | Ala | Cys | Glu | Val | Thr | His | Gln | Gly | Leu | Ser | Ser | Pro | |
| | | 195 | | | | | 200 | | | | | 205 | | | | |
| gtc | aca | aag | agc | ttc | aac | aaa | gga | gag | tgt | aag | ggc | gaa | ttc | gcn | | 669 |
| Val | Thr | Lys | Ser | Phe | Asn | Lys | Gly | Glu | Cys | Lys | Gly | Glu | Phe | Ala | | |
| | 210 | | | | | 215 | | | | | 220 | | | | | |

```
<210> SEQ ID NO 482
<211> LENGTH: 223
<212> TYPE: PRT
<213> ORGANISM: Homo sapiens

<400> SEQUENCE: 482

Ser Ala Gln Asp Ile Gln Met Thr Gln Ser Pro Ala Thr Leu Ser Val
 1               5                  10                  15

Ser Pro Gly Glu Arg Ala Thr Leu Ser Cys Arg Ala Ser Gln Ser Val
            20                  25                  30

Ser Asn Asn Leu Ala Trp Tyr Gln Gln Lys Pro Gly Gln Val Pro Arg
        35                  40                  45

Leu Leu Ile Tyr Gly Ala Ser Thr Arg Ala Thr Asp Ile Pro Ala Arg
 50                  55                  60

Phe Ser Gly Ser Gly Ser Gly Thr Asp Phe Thr Leu Thr Ile Ser Arg
 65                  70                  75                  80

Leu Glu Pro Glu Asp Phe Ala Val Tyr Tyr Cys Gln Arg Tyr Gly Ser
                85                  90                  95

Ser Pro Gly Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Lys Gly Glu Cys Lys Gly Glu Phe Ala
    210                 215                 220

<210> SEQ ID NO 483
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
agccaccctg tct                                                         13

<210> SEQ ID NO 484
<211> LENGTH: 700
<212> TYPE: DNA
<213> ORGANISM: Homo sapiens
<220> FEATURE:
<221> NAME/KEY: CDS
<222> LOCATION: (1)..(699)

<400> SEQUENCE: 484 agt gca caa gac atc cag atg acc cag tct cct gcc acc ctg tct gtg      48
Ser Ala Gln Asp Ile Gln Met Thr Gln Ser Pro Ala Thr Leu Ser Val
 1               5                  10                  15 tct cca ggt gaa aga gcc acc ctc tcc tgc agg gcc agt cag gtg tct      96
Ser Pro Gly Glu Arg Ala Thr Leu Ser Cys Arg Ala Ser Gln Val Ser
            20                  25                  30
```

```
cca ggg gaa aga gcc acc ctc tcc tgc aat ctt ctc agc aac tta gcc      144
Pro Gly Glu Arg Ala Thr Leu Ser Cys Asn Leu Leu Ser Asn Leu Ala
             35                  40                  45 tgg tac cag cag aaa cct ggc cag gct ccc agg ctc ctc atc tat ggt      192
Trp Tyr Gln Gln Lys Pro Gly Gln Ala Pro Arg Leu Leu Ile Tyr Gly
     50                  55                  60 gct tcc acc ggg gcc att ggt atc cca gcc agg ttc agt ggc agt ggg      240
Ala Ser Thr Gly Ala Ile Gly Ile Pro Ala Arg Phe Ser Gly Ser Gly
 65                  70                  75                  80 tct ggg aca gag ttc act ctc acc atc agc agc ctg cag tct gaa gat      288
Ser Gly Thr Glu Phe Thr Leu Thr Ile Ser Ser Leu Gln Ser Glu Asp
                 85                  90                  95 ttt gca gtg tat ttc tgt cag cag tat ggt acc tca ccg ccc act ttc      336
Phe Ala Val Tyr Phe Cys Gln Gln Tyr Gly Thr Ser Pro Pro Thr Phe
            100                 105                 110 ggc gga ggg acc aag gtg gag atc aaa cga act gtg gct gca cca tct      384
Gly Gly Gly Thr Lys Val Glu Ile Lys Arg Thr Val Ala Ala Pro Ser
            115                 120                 125 gtc ttc atc ttc ccg cca tct gat gag cag ttg aaa tct gga act gcc      432
Val Phe Ile Phe Pro Pro Ser Asp Glu Gln Leu Lys Ser Gly Thr Ala
130                 135                 140 tct gtt gtg tgc ctg ctg aat aac ttc tat ccc aga gag gcc aaa gta      480
Ser Val Val Cys Pro Leu Asn Asn Phe Tyr Pro Arg Glu Ala Lys Val
145                 150                 155                 160 cag tgg aag gtg gat aac gcc ctc caa tcg ggt aac tcc cag gag agt      528
Gln Trp Lys Val Asp Asn Ala Leu Gln Ser Gly Asn Ser Gln Glu Ser
                165                 170                 175 gtc aca gag cag gac aac aag gac agc acc tac agc ctc agc agc acc      576
Val Thr Glu Gln Asp Asn Lys Asp Ser Thr Tyr Ser Leu Ser Ser Thr
            180                 185                 190 ctg acg ctg agc aaa gta gac tac gag aaa cac gaa gtc tac gcc tgc      624
Leu Thr Leu Ser Lys Val Asp Tyr Glu Lys His Glu Val Tyr Ala Cys
            195                 200                 205 gaa gtc acc cat cag ggc ctt agc tcg ccc gtc acg aag agc ttc aac      672
Glu Val Thr His Gln Gly Leu Ser Ser Pro Val Thr Lys Ser Phe Asn
210                 215                 220 agg gga gag tgt aag aaa gaa ttc gtt t                                700
Arg Gly Glu Cys Lys Lys Glu Phe Val
225                 230
```

<210> SEQ ID NO 485
<211> LENGTH: 233
<212> TYPE: PRT
<213> ORGANISM: Homo sapiens

<400> SEQUENCE: 485

```
Ser Ala Gln Asp Ile Gln Met Thr Gln Ser Pro Ala Thr Leu Ser Val
 1               5                  10                  15

Ser Pro Gly Glu Arg Ala Thr Leu Ser Cys Arg Ala Ser Gln Val Ser
            20                  25                  30

Pro Gly Glu Arg Ala Thr Leu Ser Cys Asn Leu Leu Ser Asn Leu Ala
            35                  40                  45

Trp Tyr Gln Gln Lys Pro Gly Gln Ala Pro Arg Leu Leu Ile Tyr Gly
     50                  55                  60

Ala Ser Thr Gly Ala Ile Gly Ile Pro Ala Arg Phe Ser Gly Ser Gly
 65                  70                  75                  80

Ser Gly Thr Glu Phe Thr Leu Thr Ile Ser Ser Leu Gln Ser Glu Asp
                 85                  90                  95

Phe Ala Val Tyr Phe Cys Gln Gln Tyr Gly Thr Ser Pro Pro Thr Phe
```

-continued

```
                100                 105                 110
Gly Gly Gly Thr Lys Val Glu Ile Lys Arg Thr Val Ala Ala Pro Ser
            115                 120                 125

Val Phe Ile Phe Pro Pro Ser Asp Glu Gln Leu Lys Ser Gly Thr Ala
130                 135                 140

Ser Val Val Cys Pro Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
            165                 170                 175

Val Thr Glu Gln Asp Asn Lys Asp Ser Thr Tyr Ser Leu Ser Ser Thr
            180                 185                 190

Leu Thr Leu Ser Lys Val Asp Tyr Glu Lys His Glu Val Tyr Ala Cys
            195                 200                 205

Glu Val Thr His Gln Gly Leu Ser Ser Pro Val Thr Lys Ser Phe Asn
            210                 215                 220

Arg Gly Glu Cys Lys Lys Glu Phe Val
225                 230
```

<210> SEQ ID NO 486
<211> LENGTH: 419
<212> TYPE: DNA
<213> ORGANISM: Artificial Sequence
<220> FEATURE:
<223> OTHER INFORMATION: Description of Artificial Sequence: Synthetic 3-23 VH nucleotide sequence
<220> FEATURE:
<221> NAME/KEY: CDS
<222> LOCATION: (12)..(419)

<400> SEQUENCE: 486

```
ctgtctgaac g gcc cag ccg gcc atg gcc gaa gtt caa ttg tta gag tct       50
            Ala Gln Pro Ala Met Ala Glu Val Gln Leu Leu Glu Ser
              1               5                  10 ggt ggc ggt ctt gtt cag cct ggt ggt tct tta cgt ctt tct tgc gct       98
Gly Gly Gly Leu Val Gln Pro Gly Gly Ser Leu Arg Leu Ser Cys Ala
 15                  20                  25 gct tcc gga ttc act ttc tct tcg tac gct atg tct tgg gtt cgc caa     146
Ala Ser Gly Phe Thr Phe Ser Ser Tyr Ala Met Ser Trp Val Arg Gln
 30                  35                  40                  45 gct cct ggt aaa ggt ttg gag tgg gtt tct gct atc tct ggt tct ggt     194
Ala Pro Gly Lys Gly Leu Glu Trp Val Ser Ala Ile Ser Gly Ser Gly
                 50                  55                  60 ggc agt act tac tat gct gac tcc gtt aaa ggt cgc ttc act atc tct     242
Gly Ser Thr Tyr Tyr Ala Asp Ser Val Lys Gly Arg Phe Thr Ile Ser
                 65                  70                  75 aga gac aac tct aag aat act ctc tac ttg cag atg aac agc tta agg     290
Arg Asp Asn Ser Lys Asn Thr Leu Tyr Leu Gln Met Asn Ser Leu Arg
         80                  85                  90 gct gag gac act gca gtc tac tat tgc gct aaa gac tat gaa ggt act     338
Ala Glu Asp Thr Ala Val Tyr Tyr Cys Ala Lys Asp Tyr Glu Gly Thr
     95                 100                 105 ggt tat gct ttc gac ata tgg ggt caa ggt act atg gtc acc gtc tct     386
Gly Tyr Ala Phe Asp Ile Trp Gly Gln Gly Thr Met Val Thr Val Ser
110                 115                 120                 125 agt gcc tcc acc aag ggc cca tcg gtc ttc ccc                         419
Ser Ala Ser Thr Lys Gly Pro Ser Val Phe Pro
                130                 135
```

<210> SEQ ID NO 487
<211> LENGTH: 136
<212> TYPE: PRT

<213> ORGANISM: Artificial Sequence
<220> FEATURE:
<223> OTHER INFORMATION: Description of Artificial Sequence: Synthetic
     3-23 VH protein sequence

<400> SEQUENCE: 487

Ala Gln Pro Ala Met Ala Glu Val Gln Leu Leu Glu Ser Gly Gly Gly
 1               5                  10                  15

Leu Val Gln Pro Gly Gly Ser Leu Arg Leu Ser Cys Ala Ala Ser Gly
             20                  25                  30

Phe Thr Phe Ser Ser Tyr Ala Met Ser Trp Val Arg Gln Ala Pro Gly
         35                  40                  45

Lys Gly Leu Glu Trp Val Ser Ala Ile Ser Gly Ser Gly Gly Ser Thr
     50                  55                  60

Tyr Tyr Ala Asp Ser Val Lys Gly Arg Phe Thr Ile Ser Arg Asp Asn
 65                  70                  75                  80

Ser Lys Asn Thr Leu Tyr Leu Gln Met Asn Ser Leu Arg Ala Glu Asp
                 85                  90                  95

Thr Ala Val Tyr Tyr Cys Ala Lys Asp Tyr Glu Gly Thr Gly Tyr Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro
    130                 135

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 488
ctgtctgaac ggcccagccg                                           20

<210> SEQ ID NO 489
<211> LENGTH: 83
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 489
ctgtctgaac ggcccagccg gccatggccg aagttcaatt gttagagtct ggtggcggtc   60
ttgttcagcc tggtggttct tta                                          83

<210> SEQ ID NO 490
<211> LENGTH: 54
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 490
gaaagtgaat ccggaagcag cgcaagaaag acgtaaagaa ccaccaggct gaac        54

<210> SEQ ID NO 491
<211> LENGTH: 42
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 491
agaaacccac tccaaacctt taccaggagc ttggcgaacc ca                          42

<210> SEQ ID NO 492
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
agtgtcctca gcccttaagc tgttcatctg caagtagaga gtattcttag agttgtctct      60
agagatagtg aagcgacctt taacggagtc agca                                  94

<210> SEQ ID NO 493
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gcttaagggc tgaggacact gcagtctact attgcgctaa agactatgaa ggtactggtt      60
atgctttcga catatggggt c                                                81

<210> SEQ ID NO 494
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
ggggaagacc gatgggccct tggtggaggc actagagacg gtgaccatag taccttgacc      60
tatgtcgaaa gc                                                          72

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ggggaagacc gatgggccct tgg                                              23

<210> SEQ ID NO 496
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(24)
<223> OTHER INFORMATION: a, t, c, g, unknown or other
<220> FEATURE:
<221> NAME/KEY: modified_base
```

```
<222> LOCATION: (28)..(30)
<223> OTHER INFORMATION: a, t, c, g, unknown or other
<220> FEATURE:
<221> NAME/KEY: modified_base
<222> LOCATION: (34)..(36)
<223> OTHER INFORMATION: a, t, c, g, unknown or other
<220> FEATURE:
<223> OTHER INFORMATION: nnn codes for any amino acid but Cys

<400> SEQUENCE: 496
gcttccggat tcactttctc tnnntacnnn atgnnntggg ttcgccaagc tcctgg        56

<210> SEQ ID NO 497
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, t, c or g
<220> FEATURE:
<221> NAME/KEY: modified_base
<222> LOCATION: (25)..(30)
<223> OTHER INFORMATION: a, t, c or g
<220> FEATURE:
<221> NAME/KEY: modified_base
<222> LOCATION: (40)..(42)
<223> OTHER INFORMATION: a, t, c or g
<220> FEATURE:
<221> NAME/KEY: modified_base
<222> LOCATION: (46)..(48)
<223> OTHER INFORMATION: a, t, c or g

<400> SEQUENCE: 497
ggtttggagt gggtttctnn natcnnnnnn tctggtggcn nnactnnnta tgctgactcc    60
gttaaagg                                                             68

<210> SEQ ID NO 498
<211> LENGTH: 912
<212> TYPE: DNA
<213> ORGANISM: Escherichia coli

<400> SEQUENCE: 498
tccggagctt cagatctgtt tgccttttg tggggtggtg cagatcgcgt tacggagatc    60
gaccgactgc ttgagcaaaa gccacgctta actgctgatc aggcatggga tgttattcgc   120
caaaccagtc gtcaggatct taacctgagg ctttttttac ctactctgca agcagcgaca   180
tctggtttga cacagagcga tccgcgtcgt cagttggtag aaacattaac acgttgggat   240
ggcatcaatt tgcttaatga tgatggtaaa acctggcagc agccaggctc tgccatcctg   300
aacgtttggc tgaccagtat gttgaagcgt accgtagtgg ctgccgtacc tatgccattt   360
gataagtggt acagcgccag tggctacgaa acaacccagg acggcccaac tggttcgctg   420
aatataagtg ttggagcaaa aatttgtat gaggcggtgc agggagacaa atcaccaatc   480
ccacaggcgg ttgatctgtt tgctgggaaa ccacagcagg aggttgtgtt ggctgcgctg   540
gaagatacct gggagactct ttccaaacgc tatggcaata atgtgagtaa ctggaaaaca   600
cctgcaatgg ccttaacgtt ccgggcaaat aatttctttg gtgtaccgca ggccgcagcg   660
gaagaaacgc gtcatcaggc ggagtatcaa aaccgtggaa cagaaaacga tatgattgtt   720
ttctcaccaa cgacaagcga tcgtcctgtg cttgcctggg atgtggtcgc acccggtcag   780
agtgggttta ttgctcccga tggaacagtt gataagcact atgaagatca gctgaaaatg   840
```

```
tacgaaaatt ttggccgtaa gtcgctctgg ttaacgaagc aggatgtgga ggcgcataag      900
gagtcgtcta ga                                                         912

<210> SEQ ID NO 499
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 499 gatnnnnatc                                                            10

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, t, c, g, unknown or other

<400> SEQUENCE: 500
nnnnnnnnnn nnnnngtccc                                                 20

<210> SEQ ID NO 501
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 501
gcannnnntg c                                                          11

<210> SEQ ID NO 502
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 502 gacnnnngtc                                                            10

<210> SEQ ID NO 503
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(7)
<223> OTHER INFORMATION: a, t, c, g, unknown or other

<400> SEQUENCE: 503
nnnnnnngcg gg                                                              12

<210> SEQ ID NO 504
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 504
gtatccnnnn nn                                                              12

<210> SEQ ID NO 505
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 505
gcannnnnnt cg                                                              12

<210> SEQ ID NO 506
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 506
gccnnnnngg c                                                               11

<210> SEQ ID NO 507
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 507
ggtctcnnnn n                                                               11

<210> SEQ ID NO 508
<211> LENGTH: 11
```

<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 508
gacnnnnngt c                                                          11

<210> SEQ ID NO 509
<211> LENGTH: 11
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 509
gacnnnnngt c                                                          11

<210> SEQ ID NO 510
<211> LENGTH: 12
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 510
gacnnnnnng tc                                                         12

<210> SEQ ID NO 511
<211> LENGTH: 11
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 511
ccannnnntg g                                                          11

<210> SEQ ID NO 512
<211> LENGTH: 15
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 512
nnnnnnnnng caggt 15

<210> SEQ ID NO 513
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 513
acctgcnnnn n 11

<210> SEQ ID NO 514
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 514
ggccnnnnng gcc 13

<210> SEQ ID NO 515
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 515
ccannnnnnn nntgg 15

<210> SEQ ID NO 516
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 516
cgtctcnnnn n 11

<210> SEQ ID NO 517
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(6)
<223> OTHER INFORMATION: a, t, c, g, unknown or other

<400> SEQUENCE: 517
nnnnnngaga cg                                                           12

<210> SEQ ID NO 518
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 518
nnnnnnnnnn ctcctc                                                       16

<210> SEQ ID NO 519
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, t, c, g, unknown or other

<400> SEQUENCE: 519
gaggagnnnn nnnnnn                                                       16

<210> SEQ ID NO 520
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 520
cctnnnnnag g                                                            11

<210> SEQ ID NO 521
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 521
ccannnnnnt gg                                                           12

<210> SEQ ID NO 522
<211> LENGTH: 6680
<212> TYPE: DNA
<213> ORGANISM: Artificial Sequence
```

-continued

```
<220> FEATURE:
<223> OTHER INFORMATION: Description of Artificial Sequence: Vector pCES5
      nucleotide sequence
<220> FEATURE:
<221> NAME/KEY: CDS
<222> LOCATION: (201)..(1058)
<220> FEATURE:
<221> NAME/KEY: CDS
<222> LOCATION: (2269)..(2682)
<220> FEATURE:
<221> NAME/KEY: CDS
<222> LOCATION: (2723)..(2866)
<220> FEATURE:
<221> NAME/KEY: CDS
<222> LOCATION: (3767)..(3850)
<220> FEATURE:
<221> NAME/KEY: CDS
<222> LOCATION: (4198)..(5799)

<400> SEQUENCE: 522
gacgaaaggg cctcgtgata cgcctatttt tataggttaa tgtcatgata ataatggttt      60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aggaagagt atg agt att caa cat ttc cgt gtc gcc ctt att     233
                     Met Ser Ile Gln His Phe Arg Val Ala Leu Ile
                      1               5                  10 ccc ttt ttt gcg gca ttt tgc ctt cct gtt ttt gct cac cca gaa acg      281
Pro Phe Phe Ala Ala Phe Cys Leu Pro Val Phe Ala His Pro Glu Thr
             15                  20                  25 ctg gtg aaa gta aaa gat gct gaa gat cag ttg ggt gcc cga gtg ggt      329
Leu Val Lys Val Lys Asp Ala Glu Asp Gln Leu Gly Ala Arg Val Gly
         30                  35                  40 tac atc gaa ctg gat ctc aac agc ggt aag atc ctt gag agt ttt cgc      377
Tyr Ile Glu Leu Asp Leu Asn Ser Gly Lys Ile Leu Glu Ser Phe Arg
     45                  50                  55 ccc gaa gaa cgt ttt cca atg atg agc act ttt aaa gtt ctg cta tgt      425
Pro Glu Glu Arg Phe Pro Met Met Ser Thr Phe Lys Val Leu Leu Cys
 60                  65                  70                  75 ggc gcg gta tta tcc cgt att gac gcc ggg caa gag caa ctc ggt cgc      473
Gly Ala Val Leu Ser Arg Ile Asp Ala Gly Gln Glu Gln Leu Gly Arg
                 80                  85                  90 cgc ata cac tat tct cag aat gac ttg gtt gag tac tca cca gtc aca      521
Arg Ile His Tyr Ser Gln Asn Asp Leu Val Glu Tyr Ser Pro Val Thr
             95                 100                 105 gaa aag cat ctt acg gat ggc atg aca gta aga gaa tta tgc agt gct      569
Glu Lys His Leu Thr Asp Gly Met Thr Val Arg Glu Leu Cys Ser Ala
        110                 115                 120 gcc ata acc atg agt gat aac act gcg gcc aac tta ctt ctg aca acg      617
Ala Ile Thr Met Ser Asp Asn Thr Ala Ala Asn Leu Leu Leu Thr Thr
    125                 130                 135 atc gga gga ccg aag gag cta acc gct ttt ttg cac aac atg ggg gat      665
Ile Gly Gly Pro Lys Glu Leu Thr Ala Phe Leu His Asn Met Gly Asp
140                 145                 150                 155 cat gta act cgc ctt gat cgt tgg gaa ccg gag ctg aat gaa gcc ata      713
His Val Thr Arg Leu Asp Arg Trp Glu Pro Glu Leu Asn Glu Ala Ile
                160                 165                 170 cca aac gac gag cgt gac acc acg atg cct gta gca atg gca aca acg      761
Pro Asn Asp Glu Arg Asp Thr Thr Met Pro Val Ala Met Ala Thr Thr
            175                 180                 185 ttg cgc aaa cta tta act ggc gaa cta ctt act cta gct tcc cgg caa      809
Leu Arg Lys Leu Leu Thr Gly Glu Leu Leu Thr Leu Ala Ser Arg Gln
        190                 195                 200 caa tta ata gac tgg atg gag gcg gat aaa gtt gca gga cca ctt ctg      857
```

-continued

```
          Gln Leu Ile Asp Trp Met Glu Ala Asp Lys Val Ala Gly Pro Leu Leu
              205                 210                 215 cgc tcg gcc ctt ccg gct ggc tgg ttt att gct gat aaa tct gga gcc        905
Arg Ser Ala Leu Pro Ala Gly Trp Phe Ile Ala Asp Lys Ser Gly Ala
220                 225                 230                 235 ggt gag cgt ggg tct cgc ggt atc att gca gca ctg ggg cca gat ggt        953
Gly Glu Arg Gly Ser Arg Gly Ile Ile Ala Ala Leu Gly Pro Asp Gly
                240                 245                 250 aag ccc tcc cgt atc gta gtt atc tac acg acg ggg agt cag gca act       1001
Lys Pro Ser Arg Ile Val Val Ile Tyr Thr Thr Gly Ser Gln Ala Thr
            255                 260                 265 atg gat gaa cga aat aga cag atc gct gag ata ggt gcc tca ctg att       1049
Met Asp Glu Arg Asn Arg Gln Ile Ala Glu Ile Gly Ala Ser Leu Ile
        270                 275                 280 aag cat tgg taactgtcag accaagttta ctcatatata ctttagattg               1098
Lys His Trp
        285 atttaaaact tcatttttaa tttaaaagga tctaggtgaa gatccttttt gataatctca     1158 tgaccaaaat cccttaacgt gagttttcgt tccactgagc gtcagacccc gtagaaaga      1218 tcaaaggatc ttcttgagat cctttttttc tgcgcgtaat ctgctgcttg caaacaaaaa     1278 aaccaccgct accagcggtg gtttgtttgc cggatcaaga gctaccaact ctttttccga     1338 aggtaactgg cttcagcaga gcgcagatac caaatactgt ccttctagtg tagccgtagt     1398 taggccacca cttcaagaac tctgtagcac cgcctacata cctcgctctg ctaatcctgt     1458 taccagtggc tgctgccagt ggcgataagt cgtgtcttac cgggttggac tcaagacgat     1518 agttaccgga taaggcgcag cggtcgggct gaacggggggg ttcgtgcata cagcccagct    1578 tggagcgaac gacctacacc gaactgagat acctacagcg tgagcattga aaagcgcca      1638 cgcttcccga agggagaaag gcggacaggt atccggtaag cggcagggtc ggaacaggag     1698 agcgcacgag ggagcttcca gggggaaacg cctggtatct ttatagtcct gtcgggtttc    1758 gccacctctg acttgagcgt cgatttttgt gatgctcgtc agggggggcgg agcctatgga   1818 aaaacgccag caacgcggcc ttttacggtt cctggccttt tgctggcctt tttgctcaca    1878 tgttctttcc tgcgttatcc cctgattctg tggataaccg tattaccgcc tttgagtgag    1938 ctgataccgc tcgccgcagc cgaacgaccg agcgcagcga gtcagtgagc gaggaagcgg    1998 aagagcgccc aatacgcaaa ccgcctctcc ccgcgcgttg gccgattcat taatgcagct    2058 ggcacgacag gtttcccgac tggaaagcgg gcagtgagcg caacgcaatt aatgtgagtt    2118 agctcactca ttaggcaccc caggctttac actttatgct tccggctcgt atgttgtgtg    2178 gaattgtgag cggataacaa tttcacacag gaaacagcta tgaccatgat tacgccaagc    2238 tttggagcct tttttttgga gattttcaac gtg aaa aaa tta tta ttc gca att     2292
                                Met Lys Lys Leu Leu Phe Ala Ile
                                                290 cct tta gtt gtt cct ttc tat tct cac agt gca cag gtc caa ctg cag       2340
Pro Leu Val Val Pro Phe Tyr Ser His Ser Ala Gln Val Gln Leu Gln
295                 300                 305                 310 gtc gac ctc gag atc aaa cgt gga act gtg gct gca cca tct gtc ttc       2388
Val Asp Leu Glu Ile Lys Arg Gly Thr Val Ala Ala Pro Ser Val Phe
                315                 320                 325 atc ttc ccg cca tct gat gag cag ttg aaa tct gga act gcc tct gtt       2436
Ile Phe Pro Pro Ser Asp Glu Gln Leu Lys Ser Gly Thr Ala Ser Val
            330                 335                 340 gtg tgc ctg ctg aat aac ttc tat ccc aga gag gcc aaa gta cag tgg       2484
Val Cys Leu Leu Asn Asn Phe Tyr Pro Arg Glu Ala Lys Val Gln Trp
        345                 350                 355
```

| | | |
|---|---|---|
| aag gtg gat aac gcc ctc caa tcg ggt aac tcc cag gag agt gtc aca<br>Lys Val Asp Asn Ala Leu Gln Ser Gly Asn Ser Gln Glu Ser Val Thr<br>360                    365                    370 | | 2532 |
| gag cag gac agc aag gac agc acc tac agc ctc agc agc acc ctg acg<br>Glu Gln Asp Ser Lys Asp Ser Thr Tyr Ser Leu Ser Ser Thr Leu Thr<br>375                    380                    385                    390 | | 2580 |
| ctg agc aaa gca gac tac gag aaa cac aaa gtc tac gcc tgc gaa gtc<br>Leu Ser Lys Ala Asp Tyr Glu Lys His Lys Val Tyr Ala Cys Glu Val<br>                    395                    400                    405 | | 2628 |
| acc cat cag ggc ctg agt tca ccg gtg aca aag agc ttc aac agg gga<br>Thr His Gln Gly Leu Ser Ser Pro Val Thr Lys Ser Phe Asn Arg Gly<br>410                    415                    420 | | 2676 |
| gag tgt taataaggcg cgccaattct atttcaagga gacagtcata atg aaa tac<br>Glu Cys                                                          Met Lys Tyr<br>                                                                                            425 | | 2731 |
| cta ttg cct acg gca gcc gct gga ttg tta tta ctc gcg gcc cag ccg<br>Leu Leu Pro Thr Ala Ala Ala Gly Leu Leu Leu Leu Ala Ala Gln Pro<br>          430                    435                    440 | | 2779 |
| gcc atg gcc gaa gtt caa ttg tta gag tct ggt ggc ggt ctt gtt cag<br>Ala Met Ala Glu Val Gln Leu Leu Glu Ser Gly Gly Gly Leu Val Gln<br>445                    450                    455 | | 2827 |
| cct ggt ggt tct tta cgt ctt tct tgc gct gct tcc gga gcttcagatc<br>Pro Gly Gly Ser Leu Arg Leu Ser Cys Ala Ala Ser Gly<br>460                    465                    470 | | 2876 |
| tgtttgcctt tttgtggggt ggtgcagatc gcgttacgga gatcgaccga ctgcttgagc | | 2936 |
| aaaagccacg cttaactgct gatcaggcat gggatgttat tcgccaaacc agtcgtcagg | | 2996 |
| atcttaacct gaggctttt ttacctactc tgcaagcagc gacatctggt ttgacacaga | | 3056 |
| gcgatccgcg tcgtcagttg gtagaaacat taacacgttg ggatggcatc aatttgctta | | 3116 |
| atgatgatgg taaaacctgg cagcagccag gctctgccat cctgaacgtt ggctgacca | | 3176 |
| gtatgttgaa gcgtaccgta gtggctgccg tacctatgcc atttgataag tggtacagcg | | 3236 |
| ccagtggcta cgaaacaacc caggacggcc caactggttc gctgaatata agtgttggag | | 3296 |
| caaaaatttt gtatgaggcg gtgcaggag acaaatcacc aatcccacag gcggttgatc | | 3356 |
| tgtttgctgg gaaaccacag caggaggttg tgttggctgc gctggaagat acctgggaga | | 3416 |
| ctctttccaa acgctatggc aataatgtga gtaactggaa acacctgca atggccttaa | | 3476 |
| cgttccgggc aaataatttc tttggtgtac cgcaggccgc agcggaagaa acgcgtcatc | | 3536 |
| aggcggagta tcaaaaccgt ggaacagaaa acgatatgat tgttttctca ccaacgacaa | | 3596 |
| gcgatcgtcc tgtgcttgcc tgggatgtgg tcgcacccgg tcagagtggg tttattgctc | | 3656 |
| ccgatggaac agttgataag cactatgaag atcagctgaa aatgtacgaa aattttggcc | | 3716 |
| gtaagtcgct ctggttaacg aagcaggatg tggaggcgca taggagtcg tct aga | | 3772 |
|                                                                                                                              Ser Arg | | |
| gac aac tct aag aat act ctc tac ttg cag atg aac agc tta agt ctg<br>Asp Asn Ser Lys Asn Thr Leu Tyr Leu Gln Met Asn Ser Leu Ser Leu<br>475                    480                    485                    490 | | 3820 |
| agc att cgg tcc ggg caa cat tct cca aac tgaccagacg acacaaacgg<br>Ser Ile Arg Ser Gly Gln His Ser Pro Asn<br>                    495                    500 | | 3870 |
| cttacgctaa atcccgcgca tgggatggta aagaggtggc gtctttgctg gcctggactc | | 3930 |
| atcagatgaa ggccaaaaat tggcaggagt ggacacagca ggcagcgaaa caagcactga | | 3990 |
| ccatcaactg gtactatgct gatgtaaacg gcaatattgg ttatgttcat actggtgctt | | 4050 |
| atccagatcg tcaatcaggc catgatccgc gattacccgt tcctggtacg ggaaaatggg | | 4110 |

```
                                                       -continued actggaaagg gctattgcct tttgaaatga accctaaggt gtataacccc cagaagctag    4170
cctgcggctt cggtcaccgt ctcaagc gcc tcc acc aag ggc cca tcg gtc ttc    4224
                                Ala Ser Thr Lys Gly Pro Ser Val Phe
                                                505 ccc ctg gca ccc tcc tcc aag agc acc tct ggg ggc aca gcg gcc ctg     4272
Pro Leu Ala Pro Ser Ser Lys Ser Thr Ser Gly Gly Thr Ala Ala Leu
510                 515                 520                 525 ggc tgc ctg gtc aag gac tac ttc ccc gaa ccg gtg acg gtg tcg tgg     4320
Gly Cys Leu Val Lys Asp Tyr Phe Pro Glu Pro Val Thr Val Ser Trp
                530                 535                 540 aac tca ggc gcc ctg acc agc ggc gtc cac acc ttc ccg gct gtc cta     4368
Asn Ser Gly Ala Leu Thr Ser Gly Val His Thr Phe Pro Ala Val Leu
545                 550                 555 cag tcc tca gga ctc tac tcc ctc agc agc gta gtg acc gtg ccc tcc     4416
Gln Ser Ser Gly Leu Tyr Ser Leu Ser Ser Val Val Thr Val Pro Ser
        560                 565                 570 agc agc ttg ggc acc cag acc tac atc tgc aac gtg aat cac aag ccc     4464
Ser Ser Leu Gly Thr Gln Thr Tyr Ile Cys Asn Val Asn His Lys Pro
    575                 580                 585 agc aac acc aag gtg gac aag aaa gtt gag ccc aaa tct tgt gcg gcc     4512
Ser Asn Thr Lys Val Asp Lys Lys Val Glu Pro Lys Ser Cys Ala Ala
590                 595                 600                 605 gca cat cat cat cac cat cac ggg gcc gca gaa caa aaa ctc atc tca     4560
Ala His His His His His His Gly Ala Ala Glu Gln Lys Leu Ile Ser
                610                 615                 620 gaa gag gat ctg aat ggg gcc gca tag act gtt gaa agt tgt tta gca     4608
Glu Glu Asp Leu Asn Gly Ala Ala     Thr Val Glu Ser Cys Leu Ala
            625                             630                 635 aaa cct cat aca gaa aat tca ttt act aac gtc tgg aaa gac gac aaa     4656
Lys Pro His Thr Glu Asn Ser Phe Thr Asn Val Trp Lys Asp Asp Lys
        640                 645                 650 act tta gat cgt tac gct aac tat gag ggc tgt ctg tgg aat gct aca     4704
Thr Leu Asp Arg Tyr Ala Asn Tyr Glu Gly Cys Leu Trp Asn Ala Thr
    655                 660                 665 ggc gtt gtg gtt tgt act ggt gac gaa act cag tgt tac ggt aca tgg     4752
Gly Val Val Val Cys Thr Gly Asp Glu Thr Gln Cys Tyr Gly Thr Trp
670                 675                 680 gtt cct att ggg ctt gct atc cct gaa aat gag ggt ggt ggc tct gag     4800
Val Pro Ile Gly Leu Ala Ile Pro Glu Asn Glu Gly Gly Gly Ser Glu
685                 690                 695                 700 ggt ggc ggt tct gag ggt ggc ggt tct gag ggt ggc ggt act aaa cct     4848
Gly Gly Gly Ser Glu Gly Gly Gly Ser Glu Gly Gly Gly Thr Lys Pro
                705                 710                 715 cct gag tac ggt gat aca cct att ccg ggc tat act tat atc aac cct     4896
Pro Glu Tyr Gly Asp Thr Pro Ile Pro Gly Tyr Thr Tyr Ile Asn Pro
            720                 725                 730 ctc gac ggc act tat ccg cct ggt act gag caa aac ccc gct aat cct     4944
Leu Asp Gly Thr Tyr Pro Pro Gly Thr Glu Gln Asn Pro Ala Asn Pro
        735                 740                 745 aat cct tct ctt gag gag tct cag cct ctt aat act ttc atg ttt cag     4992
Asn Pro Ser Leu Glu Glu Ser Gln Pro Leu Asn Thr Phe Met Phe Gln
    750                 755                 760 aat aat agg ttc cga aat agg cag ggt gca tta act gtt tat acg ggc     5040
Asn Asn Arg Phe Arg Asn Arg Gln Gly Ala Leu Thr Val Tyr Thr Gly
765                 770                 775                 780 act gtt act caa ggc act gac ccc gtt aaa act tat tac cag tac act     5088
Thr Val Thr Gln Gly Thr Asp Pro Val Lys Thr Tyr Tyr Gln Tyr Thr
                785                 790                 795 cct gta tca tca aaa gcc atg tat gac gct tac tgg aac ggt aaa ttc     5136
Pro Val Ser Ser Lys Ala Met Tyr Asp Ala Tyr Trp Asn Gly Lys Phe
```

-continued

```
                    800              805             810
aga gac tgc gct ttc cat tct ggc ttt aat gag gat cca ttc gtt tgt    5184
Arg Asp Cys Ala Phe His Ser Gly Phe Asn Glu Asp Pro Phe Val Cys
            815              820             825 gaa tat caa ggc caa tcg tct gac ctg cct caa cct cct gtc aat gct    5232
Glu Tyr Gln Gly Gln Ser Ser Asp Leu Pro Gln Pro Pro Val Asn Ala
        830              835             840 ggc ggc ggc tct ggt ggt ggt tct ggt ggc ggc tct gag ggt ggc ggc    5280
Gly Gly Gly Ser Gly Gly Gly Ser Gly Gly Gly Ser Glu Gly Gly Gly
845             850             855                 860 tct gag ggt ggc ggt tct gag ggt ggc ggc tct gag ggt ggc ggt tcc    5328
Ser Glu Gly Gly Gly Ser Glu Gly Gly Gly Ser Glu Gly Gly Gly Ser
            865             870             875 ggt ggc ggc tcc ggt tcc ggt gat ttt gat tat gaa aaa atg gca aac    5376
Gly Gly Gly Ser Gly Ser Gly Asp Phe Asp Tyr Glu Lys Met Ala Asn
        880             885             890 gct aat aag ggg gct atg acc gaa aat gcc gat gaa aac gcg cta cag    5424
Ala Asn Lys Gly Ala Met Thr Glu Asn Ala Asp Glu Asn Ala Leu Gln
    895             900             905 tct gac gct aaa ggc aaa ctt gat tct gtc gct act gat tac ggt gct    5472
Ser Asp Ala Lys Gly Lys Leu Asp Ser Val Ala Thr Asp Tyr Gly Ala
910             915             920 gct atc gat ggt ttc att ggt gac gtt tcc ggc ctt gct aat ggt aat    5520
Ala Ile Asp Gly Phe Ile Gly Asp Val Ser Gly Leu Ala Asn Gly Asn
925             930             935             940 ggt gct act ggt gat ttt gct ggc tct aat tcc caa atg gct caa gtc    5568
Gly Ala Thr Gly Asp Phe Ala Gly Ser Asn Ser Gln Met Ala Gln Val
            945             950             955 ggt gac ggt gat aat tca cct tta atg aat aat ttc cgt caa tat tta    5616
Gly Asp Gly Asp Asn Ser Pro Leu Met Asn Asn Phe Arg Gln Tyr Leu
        960             965             970 cct tct ttg cct cag tcg gtt gaa tgt cgc cct tat gtc ttt ggc gct    5664
Pro Ser Leu Pro Gln Ser Val Glu Cys Arg Pro Tyr Val Phe Gly Ala
    975             980             985 ggt aaa cca tat gaa ttt tct att gat tgt gac aaa ata aac tta ttc    5712
Gly Lys Pro Tyr Glu Phe Ser Ile Asp Cys Asp Lys Ile Asn Leu Phe
990             995             1000 cgt ggt gtc ttt gcg ttt ctt tta tat gtt gcc acc ttt atg tat gta    5760
Arg Gly Val Phe Ala Phe Leu Leu Tyr Val Ala Thr Phe Met Tyr Val
1005            1010            1015            1020 ttt tcg acg ttt gct aac ata ctg cgt aat aag gag tct taataagaat     5809
Phe Ser Thr Phe Ala Asn Ile Leu Arg Asn Lys Glu Ser
            1025            1030 tcactggccg tcgttttaca acgtcgtgac tgggaaaacc ctggcgttac ccaacttaat  5869
cgccttgcag cacatccccc tttcgccagc tggcgtaata gcgaagaggc ccgcaccgat  5929
cgcccttccc aacagttgcg cagcctgaat ggcgaatggc gcctgatgcg gtattttctc  5989
cttacgcatc tgtgcggtat ttcacaccgc atataaattg taaacgttaa tattttgtta  6049
aaattcgcgt taaattttg ttaaatcagc tcatttttta accaataggc cgaaatcggc   6109
aaaatccctt ataaatcaaa agaatagccc gagataggt tgagtgttgt tccagtttgg   6169
aacaagagtc cactattaaa gaacgtggac tccaacgtca aagggcgaaa aaccgtctat   6229
cagggcgatg gcccactacg tgaaccatca cccaaatcaa gttttttggg gtcgaggtgc   6289
cgtaaagcac taaatcggaa ccctaaaggg agcccccgat ttagagcttg acggggaaag   6349
ccggcgaacg tggcgagaaa ggaagggaag aaagcgaaag gagcgggcgc tagggcgctg   6409
gcaagtgtag cggtcacgct gcgcgtaacc accacacccg ccgcgcttaa tgcgccgcta   6469
```

```
cagggcgcgt actatggttg cttttgacggg tgcagtctca gtacaatctg ctctgatgcc     6529
gcatagttaa gccagccccg acacccgcca acacccgctg acgcgccctg acgggcttgt     6589
ctgctcccgg catccgctta cagacaagct gtgaccgtct ccgggagctg catgtgtcag     6649
aggttttcac cgtcatcacc gaaacgcgcg a                                     6680
```

<210> SEQ ID NO 523
<211> LENGTH: 286
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 523

```
Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 524
<211> LENGTH: 138
<212> TYPE: PRT
<213> ORGANISM: Artificial Sequence
<220> FEATURE:
<223> OTHER INFORMATION: Description of Artificial Sequence: Vector pCES5 protein sequence

<400> SEQUENCE: 524

Met Lys Lys Leu Leu Phe Ala Ile Pro Leu Val Val Pro Phe Tyr Ser
1               5                   10                  15

His Ser Ala Gln Val Gln Leu Gln Val Asp Leu Glu Ile Lys Arg Gly
            20                  25                  30

Thr Val Ala Ala Pro Ser Val Phe Ile Phe Pro Pro Ser Asp Glu Gln
        35                  40                  45

Leu Lys Ser Gly Thr Ala Ser Val Val Cys Leu Leu Asn Asn Phe Tyr
    50                  55                  60

Pro Arg Glu Ala Lys Val Gln Trp Lys Val Asp Asn Ala Leu Gln Ser
65                  70                  75                  80

Gly Asn Ser Gln Glu Ser Val Thr Glu Gln Asp Ser Lys Asp Ser Thr
                85                  90                  95

Tyr Ser Leu Ser Ser Thr Leu Thr Leu Ser Lys Ala Asp Tyr Glu Lys
            100                 105                 110

His Lys Val Tyr Ala Cys Glu Val Thr His Gln Gly Leu Ser Ser Pro
        115                 120                 125

Val Thr Lys Ser Phe Asn Arg Gly Glu Cys
    130                 135

<210> SEQ ID NO 525
<211> LENGTH: 48
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 525

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

<210> SEQ ID NO 526
<211> LENGTH: 28
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 526

Ser Arg Asp Asn Ser Lys Asn Thr Leu Tyr Leu Gln Met Asn Ser Leu
1               5                   10                  15

Ser Leu Ser Ile Arg Ser Gly Gln His Ser Pro Asn
            20                  25

<210> SEQ ID NO 527
<211> LENGTH: 533
<212> TYPE: PRT
<213> ORGANISM: Artificial Sequence
<220> FEATURE:
<223> OTHER INFORMATION: Description of Artificial Sequence: Vector
      pCES5 protein sequence

<400> SEQUENCE: 527

Ala Ser Thr Lys Gly Pro Ser Val Phe Pro Leu Ala Pro Ser Ser Lys

```
            1               5              10              15
Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Ala Ala Ala His His His His His His
            100             105             110

Gly Ala Ala Glu Gln Lys Leu Ile Ser Glu Glu Asp Leu Asn Gly Ala
            115             120             125

Ala Thr Val Glu Ser Cys Leu Ala Lys Pro His Thr Glu Asn Ser Phe
            130             135             140

Thr Asn Val Trp Lys Asp Asp Lys Thr Leu Asp Arg Tyr Ala Asn Tyr
145             150             155             160

Glu Gly Cys Leu Trp Asn Ala Thr Gly Val Val Cys Thr Gly Asp
                165             170             175

Glu Thr Gln Cys Tyr Gly Thr Trp Val Pro Ile Gly Leu Ala Ile Pro
            180             185             190

Glu Asn Glu Gly Gly Gly Ser Glu Gly Gly Ser Glu Gly Gly Gly
                195             200             205

Ser Glu Gly Gly Gly Thr Lys Pro Pro Glu Tyr Gly Asp Thr Pro Ile
            210             215             220

Pro Gly Tyr Thr Tyr Ile Asn Pro Leu Asp Gly Thr Tyr Pro Pro Gly
225             230             235             240

Thr Glu Gln Asn Pro Ala Asn Pro Asn Pro Ser Leu Glu Glu Ser Gln
            245             250             255

Pro Leu Asn Thr Phe Met Phe Gln Asn Asn Arg Phe Arg Asn Arg Gln
            260             265             270

Gly Ala Leu Thr Val Tyr Thr Gly Thr Val Thr Gln Gly Thr Asp Pro
            275             280             285

Val Lys Thr Tyr Tyr Gln Tyr Thr Pro Val Ser Ser Lys Ala Met Tyr
            290             295             300

Asp Ala Tyr Trp Asn Gly Lys Phe Arg Asp Cys Ala Phe His Ser Gly
305             310             315             320

Phe Asn Glu Asp Pro Phe Val Cys Glu Tyr Gln Gly Gln Ser Ser Asp
            325             330             335

Leu Pro Gln Pro Pro Val Asn Ala Gly Gly Ser Gly Gly Gly Ser
            340             345             350

Gly Gly Gly Ser Glu Gly Gly Ser Glu Gly Gly Ser Glu Gly
            355             360             365

Gly Gly Ser Glu Gly Gly Ser Gly Gly Ser Gly Ser Gly Asp
            370             375             380

Phe Asp Tyr Glu Lys Met Ala Asn Ala Asn Lys Gly Ala Met Thr Glu
385             390             395             400

Asn Ala Asp Glu Asn Ala Leu Gln Ser Asp Ala Lys Gly Lys Leu Asp
            405             410             415

Ser Val Ala Thr Asp Tyr Gly Ala Ala Ile Asp Gly Phe Ile Gly Asp
            420             425             430
```

```
Val Ser Gly Leu Ala Asn Gly Asn Gly Ala Thr Gly Asp Phe Ala Gly
        435                 440                 445

Ser Asn Ser Gln Met Ala Gln Val Gly Asp Gly Asp Asn Ser Pro Leu
    450                 455                 460

Met Asn Asn Phe Arg Gln Tyr Leu Pro Ser Leu Pro Gln Ser Val Glu
465                 470                 475                 480

Cys Arg Pro Tyr Val Phe Gly Ala Gly Lys Pro Tyr Glu Phe Ser Ile
                485                 490                 495

Asp Cys Asp Lys Ile Asn Leu Phe Arg Gly Val Phe Ala Phe Leu Leu
                500                 505                 510

Tyr Val Ala Thr Phe Met Tyr Val Phe Ser Thr Phe Ala Asn Ile Leu
            515                 520                 525

Arg Asn Lys Glu Ser
        530

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
acctcactgg cttccggatt cactttctct                                    30

<210> SEQ ID NO 529
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
agaaacccac tccaaacctt taccaggagc ttggcgaacc ca                      42

<210> SEQ ID NO 530
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ggaaggcagt gatctagaga tagtgaagcg acctttaacg gagtcagcat a            51

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ggaaggcagt gatctagaga tag                                           23

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
      oligonucleotide

<400> SEQUENCE: 532
gtgctgactc agccaccctc                                               20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gccctgactc agcctgcctc                                               20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gagctgactc aggaccctgc                                               20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
gagctgactc agccaccctc                                               20

<210> SEQ ID NO 536
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
cctcgacagc gaagtgcaca gagcgtcttg actcagcc                           38

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
cctcgacagc gaagtgcaca gagcgtcttg                                    30

<210> SEQ ID NO 538
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 538
cctcgacagc gaagtgcaca gagcgctttg actcagcc                              38

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
cctcgacagc gaagtgcaca gagcgctttg                                        30

<210> SEQ ID NO 540
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
cctcgacagc taagtgcaca gagcgctttg actcagcc                              38

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
cctcgacagc gaagtgcaca gagcgctttg                                        30

<210> SEQ ID NO 542
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
cctcgacagc gaagtgcaca gagcgaattg actcagcc                              38

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
cctcgacagc gaagtgcaca gagcgaattg                                        30

<210> SEQ ID NO 544
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
```

```
cctcgacagc gaagtgcaca gtacgaattg actcagcc                              38
```

<210> SEQ ID NO 545
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 545

```
cctcgacagc gaagtgcaca gtacgaattg                                       30
```

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 546

```
cctcgacagc gaagtgcaca g                                                21
```

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 547

```
ccgtgtatta ctgtgcgaga g                                                21
```

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 548

```
ctgtgtatta ctgtgcgaga g                                                21
```

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 549

```
ccgtatatta ctgtgcgaaa g                                                21
```

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 550

```
ctgtgtatta ctgtgcgaaa g                                                21
```

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
ctgtgtatta ctgtgcgaga c                                               21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
ccatgtatta ctgtgcgaga c                                               21

<210> SEQ ID NO 553
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
ggtgtagtga tctagtgaca actctaagaa tactctctac ttgcagatga acagctttag     60
ggctgaggac actgcagtct actattgtgc gaga                                 94

<210> SEQ ID NO 554
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ggtgtagtga tctagtgaca actctaagaa tactctctac ttgcagatga acagctttag     60
ggctgaggac actgcagtct actattgtgc gaaa                                 94

<210> SEQ ID NO 555
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
atagtagact gcagtgtcct cagcccttaa gctgttcatc tgcaagtaga gagtattctt     60
agagttgtct ctagatcact acacc                                           85

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 556
gactgggtgt agtgatctag                                              20

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
cttttctttg ttgccgttgg ggtg                                         24

<210> SEQ ID NO 558
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, t, c, g, unknown or other

<400> SEQUENCE: 558
nnnnnnnnng caggt                                                   15

<210> SEQ ID NO 559
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 559
acctgcnnnn n                                                       11

<210> SEQ ID NO 560
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 560 gatnnnnatc                                                         10

<210> SEQ ID NO 561
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, t, c, g, unknown or other
```

```
<400> SEQUENCE: 561
gaggagnnnn nnnnnn                                                    16

<210> SEQ ID NO 562
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, t, c, g, unknown or other

<400> SEQUENCE: 562
nnnnnnnnnn ctcctc                                                    16

<210> SEQ ID NO 563
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c, g, unknown or other

<400> SEQUENCE: 563 ctcttcnnnn                                                           10

<210> SEQ ID NO 564
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, t, c, g, unknown or other

<400> SEQUENCE: 564
nnnnngaaga g                                                         11

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, t, c, g, unknown or other

<400> SEQUENCE: 565
nnnnnnnnnn nnnnngtccc                                                20

<210> SEQ ID NO 566
<211> LENGTH: 12
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 566
gacnnnnnng tc                                                            12

<210> SEQ ID NO 567
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 567
cgtctcnnnn n                                                             11

<210> SEQ ID NO 568
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, t, c, g, unknown or other

<400> SEQUENCE: 568
gtatccnnnn nn                                                            12

<210> SEQ ID NO 569
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 569
gcannnnnnt cg                                                            12

<210> SEQ ID NO 570
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 570
gccnnnnngg c                                                             11

<210> SEQ ID NO 571
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, t, c, g, unknown or other

<400> SEQUENCE: 571
ggtctcnnnn n                                                            11

<210> SEQ ID NO 572
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 572
gacnnnnngt c                                                            11

<210> SEQ ID NO 573
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 573
gacnnnnngt c                                                            11

<210> SEQ ID NO 574
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 574
ccannnnntg g                                                            11

<210> SEQ ID NO 575
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, t, c, g, unknown or other

<400> SEQUENCE: 575
```

```
ccannnnnnn nntgg                                                    15

<210> SEQ ID NO 576
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, t, c, g, unknown or other

<400> SEQUENCE: 576
ggccnnnnng gcc                                                      13

<210> SEQ ID NO 577
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, t, c, g, unknown or other

<400> SEQUENCE: 577
ccannnnnnt gg                                                       12

<210> SEQ ID NO 578
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 578
cctnnnnnag g                                                        11

<210> SEQ ID NO 579
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 579 gacnnnngtc                                                          10

<210> SEQ ID NO 580
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (4)..(12)
<223> OTHER INFORMATION: a, t, c, g, unknown or other

<400> SEQUENCE: 580
ccannnnnnn nntgg                                                    15

<210> SEQ ID NO 581
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, t, c, g, unknown or other

<400> SEQUENCE: 581
gcannnnntg c                                                        11

<210> SEQ ID NO 582
<211> LENGTH: 10251
<212> TYPE: DNA
<213> ORGANISM: Artificial Sequence
<220> FEATURE:
<223> OTHER INFORMATION: Description of Artificial Sequence: CJRA05
      nucleotide sequence
<220> FEATURE:
<221> NAME/KEY: CDS
<222> LOCATION: (1578)..(1916)
<220> FEATURE:
<221> NAME/KEY: CDS
<222> LOCATION: (2388)..(2843)
<220> FEATURE:
<221> NAME/KEY: CDS
<222> LOCATION: (2849)..(2893)
<220> FEATURE:
<221> NAME/KEY: CDS
<222> LOCATION: (3189)..(4232)
<220> FEATURE:
<221> NAME/KEY: CDS
<222> LOCATION: (7418)..(8119)
<220> FEATURE:
<221> NAME/KEY: CDS
<222> LOCATION: (8160)..(9452)

<400> SEQUENCE: 582
aatgctacta ctattagtag aattgatgcc acctttcag ctcgcgcccc aaatgaaaat     60
atagctaaac aggttattga ccatttgcga aatgtatcta atggtcaaac taatctact   120 cgttcgcaga attgggaatc aactgttata tggaatgaaa cttccagaca ccgtacttta   180
gttgcatatt taaacatgt tgagctacag cattatattc agcaattaag ctctaagcca   240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tcttttgat gcaatccgct tgcttctga ctataatagt    420 cagggtaaag acctgatttt tgatttatgg tcattctcgt tttctgaact gtttaaagca   480 tttgagggg attcaatgaa tatttatgac gattccgcag tattggacgc tatccagtct   540
aaacatttta ctattacccc ctctggcaaa acttcttttg caaaagcctc tcgctatttt   600
ggtttttatc gtcgtctggt aaacgagggt tatgatagtg ttgctcttac tatgcctcgt   660
aattcctttt ggcgttatgt atctgcatta gttgaatgtg gtattcctaa atctcaactg   720
atgaatcttt ctacctgtaa taatgttgtt ccgttagttc gttttattaa cgtagatttt   780
```

```
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg agcaggtcg cggatttcga cacaatttat   1140
caggcgatga tacaaatctc cgttgtactt tgtttcgcgc ttggtataat cgctgggggt   1200
caaagatgag tgtttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggagat tttcaac gtg aaa aaa tta tta ttc gca att cct tta gtt      1610
                   Met Lys Lys Leu Leu Phe Ala Ile Pro Leu Val
                     1               5                  10 gtt cct ttc tat tct ggc gcg gcc gaa tca cat cta gac ggc gcc gct     1658
Val Pro Phe Tyr Ser Gly Ala Ala Glu Ser His Leu Asp Gly Ala Ala
             15                  20                  25 gaa act gtt gaa agt tgt tta gca aaa tcc cat aca gaa aat tca ttt     1706
Glu Thr Val Glu Ser Cys Leu Ala Lys Ser His Thr Glu Asn Ser Phe
     30                  35                  40 act aac gtc tgg aaa gac gac aaa act tta gat cgt tac gct aac tat    1754
Thr Asn Val Trp Lys Asp Asp Lys Thr Leu Asp Arg Tyr Ala Asn Tyr
 45                  50                  55 gag ggc tgt ctg tgg aat gct aca ggc gtt gta gtt tgt act ggt gac    1802
Glu Gly Cys Leu Trp Asn Ala Thr Gly Val Val Val Cys Thr Gly Asp
 60                  65                  70                  75 gaa act cag tgt tac ggt aca tgg gtt cct att ggg ctt gct atc cct    1850
Glu Thr Gln Cys Tyr Gly Thr Trp Val Pro Ile Gly Leu Ala Ile Pro
         80                  85                  90 gaa aat gag ggt ggt ggc tct gag ggt ggc ggt tct gag ggt ggc ggt    1898
Glu Asn Glu Gly Gly Gly Ser Glu Gly Gly Gly Ser Glu Gly Gly Gly
             95                 100                 105 tct gag ggt ggc ggt act aaacctcctg agtacggtga tacacctatt            1946
Ser Glu Gly Gly Gly Thr
            110 ccgggctata cttatatcaa ccctctcgac ggcacttatc cgcctggtac tgagcaaaac   2006 cccgctaatc ctaatccttc tcttgaggag tctcagcctc ttaatacttt catgtttcag   2066 aataataggt tccgaaatag gcagggggca ttaactgttt atacgggcac tgttactcaa   2126 ggcactgacc ccgttaaaac ttattaccag tacactcctg tatcatcaaa agccatgtat   2186 gacgcttact ggaacggtaa attcagagac tgcgctttcc attctggctt taatgaggat   2246 ttatttgttt gtgaatatca aggccaatcg tctgacctgc ctcaacctcc tgtcaatgct   2306 ggcggcggct ctggtggtgg ttctggtggc ggctctgagg gtggtggctc tgagggaggc   2366 ggttccggtg gtggctctgg t tcc ggt gat ttt gat tat gaa aag atg gca    2417
                       Ser Gly Asp Phe Asp Tyr Glu Lys Met Ala
                                  115                 120 aac gct aat aag ggg gct atg acc gaa aat gcc gat gaa aac gcg cta    2465
Asn Ala Asn Lys Gly Ala Met Thr Glu Asn Ala Asp Glu Asn Ala Leu
         125                 130                 135
```

```
                                                        -continued
cag tct gac gct aaa ggc aaa ctt gat tct gtc gct act gat tac ggt    2513
Gln Ser Asp Ala Lys Gly Lys Leu Asp Ser Val Ala Thr Asp Tyr Gly
140             145                 150                 155 gct gct atc gat ggt ttc att ggt gac gtt tcc ggc ctt gct aat ggt    2561
Ala Ala Ile Asp Gly Phe Ile Gly Asp Val Ser Gly Leu Ala Asn Gly
            160                 165                 170 aat ggt gct act ggt gat ttt gct ggc tct aat tcc caa atg gct caa    2609
Asn Gly Ala Thr Gly Asp Phe Ala Gly Ser Asn Ser Gln Met Ala Gln
        175                 180                 185 gtc ggt gac ggt gat aat tca cct tta atg aat aat ttc cgt caa tat    2657
Val Gly Asp Gly Asp Asn Ser Pro Leu Met Asn Asn Phe Arg Gln Tyr
    190                 195                 200 tta cct tcc ctc cct caa tcg gtt gaa tgt cgc cct ttt gtc ttt ggc    2705
Leu Pro Ser Leu Pro Gln Ser Val Glu Cys Arg Pro Phe Val Phe Gly
205                 210                 215 gct ggt aaa cca tat gaa ttt tct att gat tgt gac aaa ata aac tta    2753
Ala Gly Lys Pro Tyr Glu Phe Ser Ile Asp Cys Asp Lys Ile Asn Leu
220                 225                 230                 235 ttc cgt ggt gtc ttt gcg ttt ctt tta tat gtt gcc acc ttt atg tat    2801
Phe Arg Gly Val Phe Ala Phe Leu Leu Tyr Val Ala Thr Phe Met Tyr
            240                 245                 250 gta ttt tct acg ttt gct aac ata ctg cgt aat aag gag tct taatc atg  2851
Val Phe Ser Thr Phe Ala Asn Ile Leu Arg Asn Lys Glu Ser           Met
        255                 260                 265 cca gtt ctt ttg ggt att ccg tta tta ttg cgt ttc ctc ggt            2893
Pro Val Leu Leu Gly Ile Pro Leu Leu Leu Arg Phe Leu Gly
270                 275                 280 ttccttctgg taactttgtt cggctatctg cttacttttc ttaaaaaggg cttcggtaag   2953
atagctattg ctatttcatt gtttcttgct cttattattg ggcttaactc aattcttgtg   3013
ggttatctct ctgatattag cgctcaatta ccctctgact ttgttcaggg tgttcagtta   3073
attctcccgt ctaatgcgct tccctgtttt tatgttattc tctctgtaaa ggctgctatt   3133
ttcatttttg acgttaaaca aaaaatcgtt tcttatttgg attgggataa ataat atg    3191
                                                              Met gct gtt tat ttt gta act ggc aaa tta ggc tct gga aag acg ctc gtt    3239
Ala Val Tyr Phe Val Thr Gly Lys Leu Gly Ser Gly Lys Thr Leu Val
            285                 290                 295 agc gtt ggt aag att cag gat aaa att gta gct ggg tgc aaa ata gca    3287
Ser Val Gly Lys Ile Gln Asp Lys Ile Val Ala Gly Cys Lys Ile Ala
        300                 305                 310 act aat ctt gat tta agg ctt caa aac ctc ccg caa gtc ggg agg ttc    3335
Thr Asn Leu Asp Leu Arg Leu Gln Asn Leu Pro Gln Val Gly Arg Phe
315                 320                 325 gct aaa acg cct cgc gtt ctt aga ata ccg gat aag cct tct ata tct    3383
Ala Lys Thr Pro Arg Val Leu Arg Ile Pro Asp Lys Pro Ser Ile Ser
330             335                 340                 345 gat ttg ctt gct att ggg cgc ggt aat gat tcc tac gat gaa aat aaa    3431
Asp Leu Leu Ala Ile Gly Arg Gly Asn Asp Ser Tyr Asp Glu Asn Lys
            350                 355                 360 aac ggc ttg ctt gtt ctc gat gag tgc ggt act tgg ttt aat acc cgt    3479
Asn Gly Leu Leu Val Leu Asp Glu Cys Gly Thr Trp Phe Asn Thr Arg
        365                 370                 375 tct tgg aat gat aag gaa aga cag ccg att att gat tgg ttt cta cat    3527
Ser Trp Asn Asp Lys Glu Arg Gln Pro Ile Ile Asp Trp Phe Leu His
380                 385                 390 gct cgt aaa tta gga tgg gat att att ttt ctt gtt cag gac tta tct    3575
Ala Arg Lys Leu Gly Trp Asp Ile Ile Phe Leu Val Gln Asp Leu Ser
395                 400                 405 att gtt gat aaa cag gcg cgt tct gca tta gct gaa cat gtt gtt tat    3623
Ile Val Asp Lys Gln Ala Arg Ser Ala Leu Ala Glu His Val Val Tyr
```

```
                  Ile Val Asp Lys Gln Ala Arg Ser Ala Leu Ala Glu His Val Val Tyr
                  410                 415                 420                 425 tgt cgt cgt ctg gac aga att act tta cct ttt gtc ggt act tta tat                3671
Cys Arg Arg Leu Asp Arg Ile Thr Leu Pro Phe Val Gly Thr Leu Tyr
                430                 435                 440 tct ctt att act ggc tcg aaa atg cct ctg cct aaa tta cat gtt ggc                3719
Ser Leu Ile Thr Gly Ser Lys Met Pro Leu Pro Lys Leu His Val Gly
                445                 450                 455 gtt gtt aaa tat ggc gat tct caa tta agc cct act gtt gag cgt tgg                3767
Val Val Lys Tyr Gly Asp Ser Gln Leu Ser Pro Thr Val Glu Arg Trp
                460                 465                 470 ctt tat act ggt aag aat ttg tat aac gca tat gat act aaa cag gct                3815
Leu Tyr Thr Gly Lys Asn Leu Tyr Asn Ala Tyr Asp Thr Lys Gln Ala
                475                 480                 485 ttt tct agt aat tat gat tcc ggt gtt tat tct tat tta acg cct tat                3863
Phe Ser Ser Asn Tyr Asp Ser Gly Val Tyr Ser Tyr Leu Thr Pro Tyr
490                 495                 500                 505 tta tca cac ggt cgg tat ttc aaa cca tta aat tta ggt cag aag atg                3911
Leu Ser His Gly Arg Tyr Phe Lys Pro Leu Asn Leu Gly Gln Lys Met
                510                 515                 520 aaa tta act aaa ata tat ttg aaa aag ttt tct cgc gtt ctt tgt ctt                3959
Lys Leu Thr Lys Ile Tyr Leu Lys Lys Phe Ser Arg Val Leu Cys Leu
                525                 530                 535 gcg att gga ttt gca tca gca ttt aca tat agt tat ata acc caa cct                4007
Ala Ile Gly Phe Ala Ser Ala Phe Thr Tyr Ser Tyr Ile Thr Gln Pro
                540                 545                 550 aag ccg gag gtt aaa aag gta gtc tct cag acc tat gat ttt gat aaa                4055
Lys Pro Glu Val Lys Lys Val Val Ser Gln Thr Tyr Asp Phe Asp Lys
555                 560                 565 ttc act att gac tct tct cag cgt ctt aat cta agc tat cgc tat gtt                4103
Phe Thr Ile Asp Ser Ser Gln Arg Leu Asn Leu Ser Tyr Arg Tyr Val
570                 575                 580                 585 ttc aag gat tct aag gga aaa tta att aat agc gac gat tta cag aag                4151
Phe Lys Asp Ser Lys Gly Lys Leu Ile Asn Ser Asp Asp Leu Gln Lys
                590                 595                 600 caa ggt tat tca ctc aca tat att gat tta tgt act gtt tcc att aaa                4199
Gln Gly Tyr Ser Leu Thr Tyr Ile Asp Leu Cys Thr Val Ser Ile Lys
                605                 610                 615 aaa ggt aat tca aat gaa att gtt aaa tgt aat taattttgtt ttcttgatgt              4252
Lys Gly Asn Ser Asn Glu Ile Val Lys Cys Asn
                620                 625 ttgtttcatc atcttctttt gctcaggtaa ttgaaatgaa taattcgcct ctgcgcgatt              4312
ttgtaacttg gtattcaaag caatcaggcg aatccgttat tgtttctccc gatgtaaaag              4372
gtactgttac tgtatattca tctgacgtta aacctgaaaa tctacgcaat ttctttattt              4432
ctgttttacg tgcaaataat tttgatatgg taggttctaa cccttccatt attcagaagt              4492
ataatccaaa caatcaggat tatattgatg aattgccatc atctgataat caggaatatg              4552
atgataattc cgctccttct ggtggtttct tgttccgca aatgataat gttactcaaa                4612 ctttttaaaat taataacgtt cgggcaaagg atttaatacg agttgtcgaa ttgtttgtaa             4672
agtctaatac ttctaaatcc tcaaatgtat tatctattga cggctctaat ctattagttg              4732
ttagtgctcc taaagatatt ttagataacc ttcctcaatt cctttcaact gttgatttgc              4792
caactgacca gatattgatt gagggtttga tatttgaggt tcagcaaggt gatgctttag              4852
atttttcatt tgctgctggc tctcagcgtg gcactgttgc aggcggtgtt aatactgacc              4912
gcctcacctc tgtttatct tctgctggtg gttcgtcgg tatttttaat ggcgatgttt                4972
tagggctatc agttcgcgca ttaaagacta atagccattc aaaaatattg tctgtgccac              5032
```

```
gtattcttac gctttcaggt cagaagggtt ctatctctgt tggccagaat gtcccttta   5092
ttactggtcg tgtgactggt gaatctgcca atgtaaataa tccatttcag acgattgagc   5152
gtcaaaatgt aggtatttcc atgagcgttt ttcctgttgc aatggctggc ggtaatattg   5212
ttctggatat taccagcaag gccgatagtt tgagttcttc tactcaggca agtgatgtta   5272
ttactaatca agaagtatt gctacaacgg ttaatttgcg tgatggacag actcttttac    5332
tcggtggcct cactgattat aaaaacactt ctcaggattc tggcgtaccg ttcctgtcta   5392
aaatcccttt aatcggcctc ctgtttagct cccgctctga ttctaacgag gaaagcacgt   5452
tatacgtgct cgtcaaagca accatagtac gcgccctgta gcggcgcatt aagcgcggcg   5512
ggtgtggtgg ttacgcgcag cgtgaccgct acacttgcca gcgccctagc gcccgctcct   5572
ttcgctttct tcccttcctt tctcgccacg ttcgccggct ttccccgtca gctctaaat    5632
cgggggctcc ctttagggtt ccgatttagt gctttacggc acctcgaccc caaaaaactt   5692
gatttgggtg atggttcacg tagtgggcca tcgccctgat agacggtttt tcgccctttg   5752
acgttggagt ccacgttctt taatagtgga ctcttgttcc aaactggaac aacactcaac   5812
cctatctcgg gctattcttt tgatttataa gggattttgc cgatttcgga accaccatca   5872
aacaggattt cgcctgctg gggcaaacca gcgtggaccg cttgctgcaa ctctctcagg    5932
gccaggcggt gaagggcaat cagctgttgc ccgtctcact ggtgaaaaga aaaccaccc    5992
tggatccaag cttgcaggtg gcacttttcg gggaaatgtg cgcggaaccc ctatttgttt   6052
attttttctaa atacattcaa atatgtatcc gctcatgaga caataaccct gataaatgct   6112
tcaataatat tgaaaaagga agagtatgag tattcaacat ttccgtgtcg cccttattcc   6172
cttttttgcg gcattttgcc ttcctgtttt tgctcaccca gaaacgctgg tgaaagtaaa   6232
agatgctgaa gatcagttgg gcgcactagt gggttacatc gaactggatc tcaacagcgg   6292
taagatcctt gagagttttc gccccgaaga acgttttcca atgatgagca cttttaaagt   6352
tctgctatgt ggcgcggtat tatcccgtat tgacgccggg caagagcaac tcggtcgccg   6412
catacactat tctcagaatg acttggttga gtactcacca gtcacagaaa agcatcttac   6472
ggatggcatg acagtaagag aattatgcag tgctgccata accatgagtg ataacactgc   6532
ggccaactta cttctgacaa cgatcggagg accgaaggag ctaaccgctt ttttgcacaa   6592
catggggat catgtaactc gccttgatcg ttgggaaccg gagctgaatg aagccatacc    6652
aaacgacgag cgtgacacca cgatgcctgt agcaatggca acaacgttgc gcaaactatt   6712
aactggcgaa ctacttactc tagcttcccg gcaacaatta atagactgga tggaggcgga   6772
taaagttgca ggaccacttc tgcgctcggc ccttccggct ggctggttta ttgctgataa   6832
atctggagcc ggtgagcgtg ggtctcgcgg tatcattgca gcactgggc cagatggtaa   6892
gccctcccgt atcgtagtta tctacacgac ggggagtcag gcaactatgg atgaacgaaa   6952
tagacagatc gctgagatag gtgcctcact gattaagcat tggtaactgt cagaccaagt   7012
ttactcatat atactttaga ttgatttaaa acttcatttt taatttaaaa ggatctaggt   7072
gaagatcctt tttgataatc tcatgaccaa atcccttaa cgtgagtttt cgttccactg    7132
tacgtaagac ccccaagctt gtcgactgaa tggcgaatgg cgctttgcct ggtttccggc   7192
accagaagcg gtgccggaaa gctggctgga gtgcgatctt cctgacgctc gagcgcaacg   7252
caattaatgt gagttagctc actcattagg caccccaggc tttacacttt atgcttccgg   7312
ctcgtatgtt gtgtggaatt gtgagcggat aacaatttca cacaggaaac agctatgacc   7372
atgattacgc caagctttgg agcctttttt ttggagattt tcaac gtg aaa aaa tta   7429
```

```
                                    Met Lys Lys Leu
                                             630
tta ttc gca att cct tta gtt gtt cct ttc tat tct cac agt gca caa    7477
Leu Phe Ala Ile Pro Leu Val Val Pro Phe Tyr Ser His Ser Ala Gln
            635                 640                 645 gac atc cag atg acc cag tct cca gcc acc ctg tct ttg tct cca ggg    7525
Asp Ile Gln Met Thr Gln Ser Pro Ala Thr Leu Ser Leu Ser Pro Gly
        650                 655                 660 gaa aga gcc acc ctc tcc tgc agg gcc agt cag ggt gtt agc agc tac    7573
Glu Arg Ala Thr Leu Ser Cys Arg Ala Ser Gln Gly Val Ser Ser Tyr
665                 670                 675                 680 tta gcc tgg tac cag cag aaa cct ggc cag gct ccc agg ctc ctc atc    7621
Leu Ala Trp Tyr Gln Gln Lys Pro Gly Gln Ala Pro Arg Leu Leu Ile
                685                 690                 695 tat gat gca tcc aac agg gcc act ggc atc cca gcc agg ttc agt ggc    7669
Tyr Asp Ala Ser Asn Arg Ala Thr Gly Ile Pro Ala Arg Phe Ser Gly
            700                 705                 710 agt ggg cct ggg aca gac ttc act ctc acc atc agc agc cta gag cct    7717
Ser Gly Pro Gly Thr Asp Phe Thr Leu Thr Ile Ser Ser Leu Glu Pro
        715                 720                 725 gaa gat ttt gca gtt tat tac tgt cag cag cgt aac tgg cat ccg tgg    7765
Glu Asp Phe Ala Val Tyr Tyr Cys Gln Gln Arg Asn Trp His Pro Trp
730                 735                 740 acg ttc ggc caa ggg acc aag gtg gaa atc aaa cga act gtg gct gca    7813
Thr Phe Gly Gln Gly Thr Lys Val Glu Ile Lys Arg Thr Val Ala Ala
745                 750                 755                 760 cca tct gtc ttc atc ttc ccg cca tct gat gag cag ttg aaa tct gga    7861
Pro Ser Val Phe Ile Phe Pro Pro Ser Asp Glu Gln Leu Lys Ser Gly
                765                 770                 775 act gcc tct gtt gtg tgc ctg ctg aat aac ttc tat ccc aga gag gcc    7909
Thr Ala Ser Val Val Cys Leu Leu Asn Asn Phe Tyr Pro Arg Glu Ala
            780                 785                 790 aaa gta cag tgg aag gtg gat aac gcc ctc caa tcg ggt aac tcc cag    7957
Lys Val Gln Trp Lys Val Asp Asn Ala Leu Gln Ser Gly Asn Ser Gln
        795                 800                 805 gag agt gtc aca gag cgg gac agc aag gac agc acc tac agc ctc agc    8005
Glu Ser Val Thr Glu Arg Asp Ser Lys Asp Ser Thr Tyr Ser Leu Ser
810                 815                 820 agc acc ctg acg ctg agc aaa gca gac tac gag aaa cac aaa gtc tac    8053
Ser Thr Leu Thr Leu Ser Lys Ala Asp Tyr Glu Lys His Lys Val Tyr
825                 830                 835                 840 gcc tgc gaa gtc acc cat cag ggc ctg agc tcg ccc gtc aca aag agc    8101
Ala Cys Glu Val Thr His Gln Gly Leu Ser Ser Pro Val Thr Lys Ser
                845                 850                 855 ttc aac agg gga gag tgt taataaggcg cgccaattct atttcaagga            8149
Phe Asn Arg Gly Glu Cys
                860 gacagtcata atg aaa tac cta ttg cct acg gca gcc gct gga ttg tta    8198
           Met Lys Tyr Leu Leu Pro Thr Ala Ala Ala Gly Leu Leu
                    865                 870                 875 tta ctc gcg gcc cag ccg gcc atg gcc gaa gtt caa ttg tta gag tct    8246
Leu Leu Ala Ala Gln Pro Ala Met Ala Glu Val Gln Leu Leu Glu Ser
                880                 885                 890 ggt ggc ggt ctt gtt cag cct ggt ggt tct tta cgt ctt tct tgc gct    8294
Gly Gly Gly Leu Val Gln Pro Gly Gly Ser Leu Arg Leu Ser Cys Ala
            895                 900                 905 gct tcc gga ttc act ttc tct act tac gag atg cgt tgg gtt cgc caa    8342
Ala Ser Gly Phe Thr Phe Ser Thr Tyr Glu Met Arg Trp Val Arg Gln
        910                 915                 920 gct cct ggt aaa ggt ttg gag tgg gtt tct tat atc gct cct tct ggt    8390
```

-continued

```
                Ala Pro Gly Lys Gly Leu Glu Trp Val Ser Tyr Ile Ala Pro Ser Gly
                    925                 930                 935 ggc gat act gct tat gct gac tcc gtt aaa ggt cgc ttc act atc tct        8438
Gly Asp Thr Ala Tyr Ala Asp Ser Val Lys Gly Arg Phe Thr Ile Ser
940                 945                 950                 955 aga gac aac tct aag aat act ctc tac ttg cag atg aac agc tta agg        8486
Arg Asp Asn Ser Lys Asn Thr Leu Tyr Leu Gln Met Asn Ser Leu Arg
                960                 965                 970 gct gag gac act gca gtc tac tat tgt gcg agg agg ctc gat ggc tat        8534
Ala Glu Asp Thr Ala Val Tyr Tyr Cys Ala Arg Arg Leu Asp Gly Tyr
            975                 980                 985 att tcc tac tac tac ggt atg gac gtc tgg ggc caa ggg acc acg gtc        8582
Ile Ser Tyr Tyr Tyr Gly Met Asp Val Trp Gly Gln Gly Thr Thr Val
        990                 995                 1000 acc gtc tca agc gcc tcc acc aag ggc cca tcg gtc ttc ccc ctg gca        8630
Thr Val Ser Ser Ala Ser Thr Lys Gly Pro Ser Val Phe Pro Leu Ala
    1005                1010                1015 ccc tcc tcc aag agc acc tct ggg ggc aca gcg gcc ctg ggc tgc ctg        8678
Pro Ser Ser Lys Ser Thr Ser Gly Gly Thr Ala Ala Leu Gly Cys Leu
1020                1025                1030                1035 gtc aag gac tac ttc ccc gaa ccg gtg acg gtg tcg tgg aac tca ggc        8726
Val Lys Asp Tyr Phe Pro Glu Pro Val Thr Val Ser Trp Asn Ser Gly
                1040                1045                1050 gcc ctg acc agc ggc gtc cac acc ttc ccg gct gtc cta cag tcc tca        8774
Ala Leu Thr Ser Gly Val His Thr Phe Pro Ala Val Leu Gln Ser Ser
            1055                1060                1065 gga ctc tac tcc ctc agc agc gta gtg acc gtg ccc tcc agc agc ttg        8822
Gly Leu Tyr Ser Leu Ser Ser Val Val Thr Val Pro Ser Ser Ser Leu
        1070                1075                1080 ggc acc cag acc tac atc tgc aac gtg aat cac aag ccc agc aac acc        8870
Gly Thr Gln Thr Tyr Ile Cys Asn Val Asn His Lys Pro Ser Asn Thr
    1085                1090                1095 aag gtg gac aag aaa gtt gag ccc aaa tct tgt gcg gcc gca cat cat        8918
Lys Val Asp Lys Lys Val Glu Pro Lys Ser Cys Ala Ala Ala His His
1100                1105                1110                1115 cat cac cat cac ggg gcc gca gaa caa aaa ctc atc tca gaa gag gat        8966
His His His His Gly Ala Ala Glu Gln Lys Leu Ile Ser Glu Glu Asp
                1120                1125                1130 ctg aat ggg gcc gca tag gct agc tct gct wsy ggy gay tty gay tay        9014
Leu Asn Gly Ala Ala Gln Ala Ser Ser Ala Ser Gly Asp Phe Asp Tyr
            1135                1140                1145 gar aar atg gct aaw gcy aay aar ggs gcy atg acy gar aay gcy gay        9062
Glu Lys Met Ala Asn Ala Asn Lys Gly Ala Met Thr Glu Asn Ala Asp
        1150                1155                1160 gar aay gck ytr car wsy gay gcy aar ggy aar ytw gay wsy gtc gck        9110
Glu Asn Ala Leu Gln Ser Asp Ala Lys Gly Lys Leu Asp Ser Val Ala
    1165                1170                1175 acy gay tay ggy gcy gcc atc gay ggy tty aty ggy gay gtc wsy ggy        9158
Thr Asp Tyr Gly Ala Ala Ile Asp Gly Phe Ile Gly Asp Val Ser Gly
1180                1185                1190                1195 ytk gcy aay ggy aay ggy gcy acy ggw gay tty gcw ggy tck aat tcy        9206
Leu Ala Asn Gly Asn Gly Ala Thr Gly Asp Phe Ala Gly Ser Asn Ser
                1200                1205                1210 car atg gcy car gty ggw gay ggk gay aay wsw cck ytw atg aay aay        9254
Gln Met Ala Gln Val Gly Asp Gly Asp Asn Ser Pro Leu Met Asn Asn
            1215                1220                1225 tty mgw car tay ytw cck tcy cty cck car wsk gty gar tgy cgy ccw        9302
Phe Arg Gln Tyr Leu Pro Ser Leu Pro Gln Ser Val Glu Cys Arg Pro
        1230                1235                1240 tty gty tty wsy gcy ggy aar ccw tay gar tty wsy aty gay tgy gay        9350
```

```
Phe Val Phe Ser Ala Gly Lys Pro Tyr Glu Phe Ser Ile Asp Cys Asp
   1245                1250                1255 aar atm aay ytw tty cgy ggy gty tty gck tty ytk yta tay gty gcy    9398
Lys Ile Asn Leu Phe Arg Gly Val Phe Ala Phe Leu Leu Tyr Val Ala
   1260                1265                1270                1275 acy tty atg tay gtw tty wsy ack tty gcy aay atw ytr cgy aay aar    9446
Thr Phe Met Tyr Val Phe Ser Thr Phe Ala Asn Ile Leu Arg Asn Lys
                    1280                1285                1290 gar wsy tagtgatctc ctaggaagcc cgcctaatga gcgggctttt ttttctggt      9502
Glu Ser atgcatcctg aggccgatac tgtcgtcgtc ccctcaaact ggcagatgca cggttacgat  9562
gcgcccatct acaccaacgt gacctatccc attacggtca atccgccgtt tgttcccacg  9622
gagaatccga cggggtgtta ctcgctcaca tttaatgttg atgaaagctg gctacaggaa  9682
ggccagacgc gaattatttt tgatggcgtt cctattggtt aaaaaatgag ctgatttaac  9742
aaaaatttaa tgcgaatttt aacaaaatat taacgtttac aatttaaata tttgcttata  9802
caatcttcct gttttggggg cttttctgat tatcaaccgg ggtacatatg attgacatgc  9862
tagttttacg attaccgttc atcgattctc ttgtttgctc cagactctca ggcaatgacc  9922
tgatagcctt tgtagatctc tcaaaaatag ctaccctctc cggcattaat ttatcagcta  9982
gaacggttga atatcatatt gatggtgatt tgactgtctc cggcctttct cacccttttg 10042 aatctttacc tacacattac tcaggcattg catttaaaat atatgagggt tctaaaaatt 10102 tttatccttg cgttgaaata aaggcttctc ccgcaaaagt attacagggt cataatgttt 10162 ttggtacaac cgatttagct ttatgctctg aggctttatt gcttaatttt gctaattctt 10222 tgccttgcct gtatgattta ttggatgtt                                  10251

<210> SEQ ID NO 583
<211> LENGTH: 113
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 583

Met Lys Lys Leu Leu Phe Ala Ile Pro Leu Val Val Pro Phe Tyr Ser
  1               5                  10                  15

Gly Ala Ala Glu Ser His Leu Asp Gly Ala Ala Glu Thr Val Glu Ser
             20                  25                  30

Cys Leu Ala Lys Ser His Thr Glu Asn Ser Phe Thr Asn Val Trp Lys
         35                  40                  45

Asp Asp Lys Thr Leu Asp Arg Tyr Ala Asn Tyr Glu Gly Cys Leu Trp
     50                  55                  60

Asn Ala Thr Gly Val Val Val Cys Thr Gly Asp Glu Thr Gln Cys Tyr
 65                  70                  75                  80

Gly Thr Trp Val Pro Ile Gly Leu Ala Ile Pro Glu Asn Glu Gly Gly
                 85                  90                  95

Gly Ser Glu Gly Gly Gly Ser Glu Gly Gly Gly Ser Glu Gly Gly Gly
            100                 105                 110

Thr

<210> SEQ ID NO 584
<211> LENGTH: 152
<212> TYPE: PRT
<213> ORGANISM: Artificial Sequence
<220> FEATURE:
```

<223> OTHER INFORMATION: Description of Artificial Sequence: CJRA05
      protein sequence

<400> SEQUENCE: 584

Ser Gly Asp Phe Asp Tyr Glu Lys Met Ala Asn Ala Asn Lys Gly Ala
1               5                   10                  15

Met Thr Glu Asn Ala Asp Glu Asn Ala Leu Gln Ser Asp Ala Lys Gly
            20                  25                  30

Lys Leu Asp Ser Val Ala Thr Asp Tyr Gly Ala Ala Ile Asp Gly Phe
        35                  40                  45

Ile Gly Asp Val Ser Gly Leu Ala Asn Gly Asn Gly Ala Thr Gly Asp
    50                  55                  60

Phe Ala Gly Ser Asn Ser Gln Met Ala Gln Val Gly Asp Gly Asp Asn
65                  70                  75                  80

Ser Pro Leu Met Asn Asn Phe Arg Gln Tyr Leu Pro Ser Leu Pro Gln
                85                  90                  95

Ser Val Glu Cys Arg Pro Phe Val Phe Gly Ala Gly Lys Pro Tyr Glu
            100                 105                 110

Phe Ser Ile Asp Cys Asp Lys Ile Asn Leu Phe Arg Gly Val Phe Ala
        115                 120                 125

Phe Leu Leu Tyr Val Ala Thr Phe Met Tyr Val Phe Ser Thr Phe Ala
130                 135                 140

Asn Ile Leu Arg Asn Lys Glu Ser
145                 150

<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: CJRA05
      peptide sequence

<400> SEQUENCE: 585

Met Pro Val Leu Leu Gly Ile Pro Leu Leu Leu Arg Phe Leu Gly
1               5                   10                  15

<210> SEQ ID NO 586
<211> LENGTH: 348
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 586

Met Ala Val Tyr Phe Val Thr Gly Lys Leu Gly Ser Gly Lys Thr Leu
1               5                   10                  15

Val Ser Val Gly Lys Ile Gln Asp Lys Ile Val Ala Gly Cys Lys Ile
            20                  25                  30

Ala Thr Asn Leu Asp Leu Arg Leu Gln Asn Leu Pro Gln Val Gly Arg
        35                  40                  45

Phe Ala Lys Thr Pro Arg Val Leu Arg Ile Pro Asp Lys Pro Ser Ile
    50                  55                  60

Ser Asp Leu Leu Ala Ile Gly Arg Gly Asn Asp Ser Tyr Asp Glu Asn
65                  70                  75                  80

Lys Asn Gly Leu Leu Val Leu Asp Glu Cys Gly Thr Trp Phe Asn Thr
                85                  90                  95

Arg Ser Trp Asn Asp Lys Glu Arg Gln Pro Ile Ile Asp Trp Phe Leu
            100                 105                 110

```
His Ala Arg Lys Leu Gly Trp Asp Ile Ile Phe Leu Val Gln Asp Leu
            115                 120                 125

Ser Ile Val Asp Lys Gln Ala Arg Ser Ala Leu Ala Glu His Val Val
    130                 135                 140

Tyr Cys Arg Arg Leu Asp Arg Ile Thr Leu Pro Phe Val Gly Thr Leu
145                 150                 155                 160

Tyr Ser Leu Ile Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
        195                 200                 205

Ala Phe Ser Ser Asn Tyr Asp Ser Gly Val Tyr Ser Tyr Leu Thr Pro
    210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270

Pro Lys Pro Glu Val Lys Lys Val Val Ser Gln Thr Tyr Asp Phe Asp
        275                 280                 285

Lys Phe Thr Ile Asp Ser Ser Gln Arg Leu Asn Leu Ser Tyr Arg Tyr
    290                 295                 300

Val Phe Lys Asp Ser Lys Gly Lys Leu Ile Asn Ser Asp Asp Leu Gln
305                 310                 315                 320

Lys Gln Gly Tyr Ser Leu Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 587
<211> LENGTH: 234
<212> TYPE: PRT
<213> ORGANISM: Artificial Sequence
<220> FEATURE:
<223> OTHER INFORMATION: Description of Artificial Sequence: CJRA05
      protein sequence

<400> SEQUENCE: 587

Met Lys Lys Leu Leu Phe Ala Ile Pro Leu Val Val Pro Phe Tyr Ser
1               5                   10                  15

His Ser Ala Gln Asp Ile Gln Met Thr Gln Ser Pro Ala Thr Leu Ser
            20                  25                  30

Leu Ser Pro Gly Glu Arg Ala Thr Leu Ser Cys Arg Ala Ser Gln Gly
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Pro Gly Thr Asp Phe Thr Leu Thr Ile Ser
                85                  90                  95

Ser Leu Glu Pro Glu Asp Phe Ala Val Tyr Tyr Cys Gln Gln Arg Asn
            100                 105                 110

Trp His Pro Trp Thr Phe Gly Gln Gly Thr Lys Val Glu Ile Lys Arg
        115                 120                 125
```

```
Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Arg Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 588
<211> LENGTH: 431
<212> TYPE: PRT
<213> ORGANISM: Artificial Sequence
<220> FEATURE:
<223> OTHER INFORMATION: Description of Artificial Sequence: CJRA05
    protein sequence

<400> SEQUENCE: 588

```
Met Lys Tyr Leu Leu Pro Thr Ala Ala Ala Gly Leu Leu Leu Leu Ala
 1               5                  10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Thr Tyr Glu Met Arg Trp Val Arg Gln Ala Pro Gly
    50                  55                  60

Lys Gly Leu Glu Trp Val Ser Tyr Ile Ala Pro Ser Gly Gly Asp Thr
65                  70                  75                  80

Ala Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Arg Leu Asp Gly Tyr Ile Ser Tyr
        115                 120                 125

Tyr Tyr Gly Met Asp Val Trp Gly Gln Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Ala Ala Ala His His His His His
                245                 250                 255
```

His Gly Ala Ala Glu Gln Lys Leu Ile Ser Glu Glu Asp Leu Asn Gly
            260                 265                 270

Ala Ala Gln Ala Ser Ser Ala Ser Gly Asp Phe Asp Tyr Glu Lys Met
        275                 280                 285

Ala Asn Ala Asn Lys Gly Ala Met Thr Glu Asn Ala Asp Glu Asn Ala
    290                 295                 300

Leu Gln Ser Asp Ala Lys Gly Lys Leu Asp Ser Val Ala Thr Asp Tyr
305                 310                 315                 320

Gly Ala Ala Ile Asp Gly Phe Ile Gly Asp Val Ser Gly Leu Ala Asn
                325                 330                 335

Gly Asn Gly Ala Thr Gly Asp Phe Ala Gly Ser Asn Ser Gln Met Ala
            340                 345                 350

Gln Val Gly Asp Gly Asp Asn Ser Pro Leu Met Asn Asn Phe Arg Gln
        355                 360                 365

Tyr Leu Pro Ser Leu Pro Gln Ser Val Glu Cys Arg Pro Phe Val Phe
    370                 375                 380

Ser Ala Gly Lys Pro Tyr Glu Phe Ser Ile Asp Cys Asp Lys Ile Asn
385                 390                 395                 400

Leu Phe Arg Gly Val Phe Ala Phe Leu Leu Tyr Val Ala Thr Phe Met
                405                 410                 415

Tyr Val Phe Ser Thr Phe Ala Asn Ile Leu Arg Asn Lys Glu Ser
            420                 425                 430

<210> SEQ ID NO 589
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 589

Glu Gly Gly Gly Ser
 1               5

<210> SEQ ID NO 590
<211> LENGTH: 1275
<212> TYPE: DNA
<213> ORGANISM: Unknown
<220> FEATURE:
<221> NAME/KEY: CDS
<222> LOCATION: (1)..(1272)
<220> FEATURE:
<223> OTHER INFORMATION: Description of Unknown: M13 nucleotide
      sequence

<400> SEQUENCE: 590 gtg aaa aaa tta tta ttc gca att cct tta gtt gtt cct ttc tat tct      48
Met Lys Lys Leu Leu Phe Ala Ile Pro Leu Val Val Pro Phe Tyr Ser
 1               5                  10                  15 cac tcc gct gaa act gtt gaa agt tgt tta gca aaa ccc cat aca gaa      96
His Ser Ala Glu Thr Val Glu Ser Cys Leu Ala Lys Pro His Thr Glu
                20                  25                  30 aat tca ttt act aac gtc tgg aaa gac gac aaa act tta gat cgt tac     144
Asn Ser Phe Thr Asn Val Trp Lys Asp Asp Lys Thr Leu Asp Arg Tyr
            35                  40                  45 gct aac tat gag ggt tgt ctg tgg aat gct aca ggc gtt gta gtt tgt     192
Ala Asn Tyr Glu Gly Cys Leu Trp Asn Ala Thr Gly Val Val Val Cys
        50                  55                  60 act ggt gac gaa act cag tgt tac ggt aca tgg gtt cct att ggg ctt     240
Thr Gly Asp Glu Thr Gln Cys Tyr Gly Thr Trp Val Pro Ile Gly Leu

```
                65                  70                  75                  80
gct atc cct gaa aat gag ggt ggt ggc tct gag ggt ggc ggt tct gag        288
Ala Ile Pro Glu Asn Glu Gly Gly Gly Ser Glu Gly Gly Gly Ser Glu
                    85                  90                  95 ggt ggc ggt tct gag ggt ggc ggt act aaa cct cct gag tac ggt gat        336
Gly Gly Gly Ser Glu Gly Gly Gly Thr Lys Pro Pro Glu Tyr Gly Asp
            100                 105                 110 aca cct att ccg ggc tat act tat atc aac cct ctc gac ggc act tat        384
Thr Pro Ile Pro Gly Tyr Thr Tyr Ile Asn Pro Leu Asp Gly Thr Tyr
        115                 120                 125 ccg cct ggt act gag caa aac ccc gct aat cct aat cct tct ctt gag        432
Pro Pro Gly Thr Glu Gln Asn Pro Ala Asn Pro Asn Pro Ser Leu Glu
    130                 135                 140 gag tct cag cct ctt aat act ttc atg ttt cag aat aat agg ttc cga        480
Glu Ser Gln Pro Leu Asn Thr Phe Met Phe Gln Asn Asn Arg Phe Arg
145                 150                 155                 160 aat agg cag ggg gca tta act gtt tat acg ggc act gtt act caa ggc        528
Asn Arg Gln Gly Ala Leu Thr Val Tyr Thr Gly Thr Val Thr Gln Gly
                    165                 170                 175 act gac ccc gtt aaa act tat tac cag tac act cct gta tca tca aaa        576
Thr Asp Pro Val Lys Thr Tyr Tyr Gln Tyr Thr Pro Val Ser Ser Lys
            180                 185                 190 gcc atg tat gac gct tac tgg aac ggt aaa ttc aga gac tgc gct ttc        624
Ala Met Tyr Asp Ala Tyr Trp Asn Gly Lys Phe Arg Asp Cys Ala Phe
        195                 200                 205 cat tct ggc ttt aat gag gat cca ttc gtt tgt gaa tat caa ggc caa        672
His Ser Gly Phe Asn Glu Asp Pro Phe Val Cys Glu Tyr Gln Gly Gln
    210                 215                 220 tcg tct gac ctg cct caa cct cct gtc aat gct ggc ggc ggt tct ggt        720
Ser Ser Asp Leu Pro Gln Pro Pro Val Asn Ala Gly Gly Gly Ser Gly
225                 230                 235                 240 ggt ggt tct ggt ggc ggc tct gag ggt ggc ggc tct gag ggt ggc ggt        768
Gly Gly Ser Gly Gly Gly Ser Glu Gly Gly Gly Ser Glu Gly Gly Gly
                    245                 250                 255 tct gag ggt ggc ggc tct gag gga ggc ggt tcc ggt ggt ggc tct ggt        816
Ser Glu Gly Gly Gly Ser Glu Gly Gly Gly Ser Gly Gly Gly Ser Gly
            260                 265                 270 tcc ggt gat ttt gat tat gaa aag atg gca aac gct aat aag ggg gct        864
Ser Gly Asp Phe Asp Tyr Glu Lys Met Ala Asn Ala Asn Lys Gly Ala
        275                 280                 285 atg acc gaa aat gcc gat gaa aac gcg cta cag tct gac gct aaa ggc        912
Met Thr Glu Asn Ala Asp Glu Asn Ala Leu Gln Ser Asp Ala Lys Gly
    290                 295                 300 aaa ctt gat tct gtc gct act gat tac ggt gct gct atc gat ggt ttc        960
Lys Leu Asp Ser Val Ala Thr Asp Tyr Gly Ala Ala Ile Asp Gly Phe
305                 310                 315                 320 att ggt gac gtt tcc ggc ctt gct aat ggt aat ggt gct act ggt gat       1008
Ile Gly Asp Val Ser Gly Leu Ala Asn Gly Asn Gly Ala Thr Gly Asp
                    325                 330                 335 ttt gct ggc tct aat tcc caa atg gct caa gtc ggt gac ggt gat aat       1056
Phe Ala Gly Ser Asn Ser Gln Met Ala Gln Val Gly Asp Gly Asp Asn
            340                 345                 350 tca cct tta atg aat aat ttc cgt caa tat tta cct tcc ctc cct caa       1104
Ser Pro Leu Met Asn Asn Phe Arg Gln Tyr Leu Pro Ser Leu Pro Gln
        355                 360                 365 tcg gtt gaa tgt cgc cct ttt gtc ttt agc gct ggt aaa cca tat gaa       1152
Ser Val Glu Cys Arg Pro Phe Val Phe Ser Ala Gly Lys Pro Tyr Glu
    370                 375                 380 ttt tct att gat tgt gac aaa ata aac tta ttc cgt ggt gtc ttt gcg       1200
Phe Ser Ile Asp Cys Asp Lys Ile Asn Leu Phe Arg Gly Val Phe Ala
```

```
                385                 390                 395                 400
ttt ctt tta tat gtt gcc acc ttt atg tat gta ttt tct acg ttt gct          1248
Phe Leu Leu Tyr Val Ala Thr Phe Met Tyr Val Phe Ser Thr Phe Ala
                405                 410                 415 aac ata ctg cgt aat aag gag tct taa                                       1275
Asn Ile Leu Arg Asn Lys Glu Ser
        420
```

<210> SEQ ID NO 591
<211> LENGTH: 424
<212> TYPE: PRT
    <213> ORGANISM: Unknown
<220> FEATURE:
<223> OTHER INFORMATION: Description of Unknown: M13 protein
      sequence

<400> SEQUENCE: 591

```
Met Lys Lys Leu Leu Phe Ala Ile Pro Leu Val Val Pro Phe Tyr Ser
  1               5                  10                  15

His Ser Ala Glu Thr Val Glu Ser Cys Leu Ala Lys Pro His Thr Glu
             20                  25                  30

Asn Ser Phe Thr Asn Val Trp Lys Asp Asp Lys Thr Leu Asp Arg Tyr
         35                  40                  45

Ala Asn Tyr Glu Gly Cys Leu Trp Asn Ala Thr Gly Val Val Val Cys
     50                  55                  60

Thr Gly Asp Glu Thr Gln Cys Tyr Gly Thr Trp Val Pro Ile Gly Leu
 65                  70                  75                  80

Ala Ile Pro Glu Asn Glu Gly Gly Gly Ser Glu Gly Gly Gly Ser Glu
                 85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125

Pro Pro Gly Thr Glu Gln Asn Pro Ala Asn Pro Asn Pro Ser Leu Glu
    130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Gly Ser Glu Gly Gly Gly
                245                 250                 255

Ser Glu Gly Gly Gly Ser Glu Gly Gly Gly Ser Gly Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320
```

```
Ile Gly Asp Val Ser Gly Leu Ala Asn Gly Asn Gly Ala Thr Gly Asp
            325                 330                 335

Phe Ala Gly Ser Asn Ser Gln Met Ala Gln Val Gly Asp Gly Asp Asn
        340                 345                 350

Ser Pro Leu Met Asn Asn Phe Arg Gln Tyr Leu Pro Ser Leu Pro Gln
    355                 360                 365

Ser Val Glu Cys Arg Pro Phe Val Phe Ser Ala Gly Lys Pro Tyr Glu
370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420
```

<210> SEQ ID NO 592
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
caacgatgat cgtatggcgc atgctgccga gacag                               35

<210> SEQ ID NO 593
<211> LENGTH: 1355
<212> TYPE: DNA
<213> ORGANISM: Artificial Sequence
<220> FEATURE:
<223> OTHER INFORMATION: Description of Artificial Sequence: M13-III
      nucleotide sequence
<220> FEATURE:
<221> NAME/KEY: CDS
<222> LOCATION: (1)..(1305)

<400> SEQUENCE: 593

```
gcg gcc gca cat cat cat cac cat cac ggg gcc gca gaa caa aaa ctc        48
Ala Ala Ala His His His His His His Gly Ala Ala Glu Gln Lys Leu
 1               5                  10                  15 atc tca gaa gag gat ctg aat ggg gcc gca tag gct agc gat atc aac        96
Ile Ser Glu Glu Asp Leu Asn Gly Ala Ala     Ala Ser Asp Ile Asn
             20                  25                  30 gat gat cgt atg gct tct act gcy gar acw gty gaa wsy tgy ytr gcm       144
Asp Asp Arg Met Ala Ser Thr Ala Glu Thr Val Glu Ser Cys Leu Ala
         35                  40                  45 aar ccy cay acw gar aat wsw tty acw aay gts tgg aar gay gay aar       192
Lys Pro His Thr Glu Asn Ser Phe Thr Asn Val Trp Lys Asp Asp Lys
     50                  55                  60 acy ytw gat cgw tay gcy aay tay gar ggy tgy ytr tgg aat gcy acm       240
Thr Leu Asp Arg Tyr Ala Asn Tyr Glu Gly Cys Leu Trp Asn Ala Thr
 65                  70                  75 ggc gty gtw gty tgy ack ggy gay gar acw car tgy tay ggy acr tgg       288
Gly Val Val Val Cys Thr Gly Asp Glu Thr Gln Cys Tyr Gly Thr Trp
             80                  85                  90                  95 gtk cck atw ggs ytw gcy atm cck gar aay gar ggy ggy wsy gar           336
Val Pro Ile Gly Leu Ala Ile Pro Glu Asn Glu Gly Gly Ser Glu
                100                 105                 110 ggy ggy ggy wsy gar ggy ggy ggw tcy gar ggw ggy ggw acy aar cck       384
Gly Gly Gly Ser Glu Gly Gly Gly Ser Glu Gly Gly Gly Thr Lys Pro
             115                 120                 125
```

```
cck gar tay ggy gay acw cck atw cck ggy tay acy tay aty aay cck      432
Pro Glu Tyr Gly Asp Thr Pro Ile Pro Gly Tyr Thr Tyr Ile Asn Pro
        130                 135                 140 ytm gay ggm acy tay cck cck ggy acy gar car aay ccy gcy aay cck      480
Leu Asp Gly Thr Tyr Pro Pro Gly Thr Glu Gln Asn Pro Ala Asn Pro
    145                 150                 155 aay ccw wsy ytw gar gar wsy car cck ytw aay acy tty atg tty car      528
Asn Pro Ser Leu Glu Glu Ser Gln Pro Leu Asn Thr Phe Met Phe Gln
160                 165                 170                 175 aay aay mgk tty mgr aay mgk car ggk gcw ytw acy gtk tay ack ggm      576
Asn Asn Arg Phe Arg Asn Arg Gln Gly Ala Leu Thr Val Tyr Thr Gly
                180                 185                 190 acy gty acy car ggy acy gay ccy gty aar acy tay tay car tay acy      624
Thr Val Thr Gln Gly Thr Asp Pro Val Lys Thr Tyr Tyr Gln Tyr Thr
            195                 200                 205 cck gtm tcr wsw aar gcy atg tay gay gcy tay tgg aay ggy aar tty      672
Pro Val Ser Ser Lys Ala Met Tyr Asp Ala Tyr Trp Asn Gly Lys Phe
        210                 215                 220 mgw gay tgy gcy tty cay wsy ggy tty aay gar gay ccw tty gty tgy      720
Arg Asp Cys Ala Phe His Ser Gly Phe Asn Glu Asp Pro Phe Val Cys
    225                 230                 235 gar tay car ggy car wsk wsy gay ytr cck car ccw cck gty aay gck      768
Glu Tyr Gln Gly Gln Ser Ser Asp Leu Pro Gln Pro Pro Val Asn Ala
240                 245                 250                 255 ggy ggy ggy wsy ggy ggw ggy wsy ggy ggy ggy wsy gar ggy ggw ggy      816
Gly Gly Gly Ser Gly Gly Gly Ser Gly Gly Gly Ser Glu Gly Gly Gly
                260                 265                 270 wsy gar ggw ggy ggy wsy ggr ggy ggy wsy ggy wsy ggy gay tty gay      864
Ser Glu Gly Gly Gly Ser Gly Gly Gly Ser Gly Ser Gly Asp Phe Asp
            275                 280                 285 tay gar aar atg gcw aay gcy aay aar ggs gcy atg acy gar aay gcy      912
Tyr Glu Lys Met Ala Asn Ala Asn Lys Gly Ala Met Thr Glu Asn Ala
        290                 295                 300 gay gar aay gcr ctr car wst gay gcy aar ggy aar ytw gay wsy gtc      960
Asp Glu Asn Ala Leu Gln Ser Asp Ala Lys Gly Lys Leu Asp Ser Val
    305                 310                 315 gcy acw gay tay ggt gct gcy atc gay ggy tty aty ggy gay gty wsy     1008
Ala Thr Asp Tyr Gly Ala Ala Ile Asp Gly Phe Ile Gly Asp Val Ser
320                 325                 330                 335 ggy ctk gct aay ggy aay ggw gcy acy ggw gay tty gcw ggy tck aat     1056
Gly Leu Ala Asn Gly Asn Gly Ala Thr Gly Asp Phe Ala Gly Ser Asn
                340                 345                 350 tcy car atg gcy car gty ggw gay ggk gay aay wsw cck ytw atg aay     1104
Ser Gln Met Ala Gln Val Gly Asp Gly Asp Asn Ser Pro Leu Met Asn
            355                 360                 365 aay tty mgw car tay ytw cck tcy cty cck car wsk gty gar tgy cgy     1152
Asn Phe Arg Gln Tyr Leu Pro Ser Leu Pro Gln Ser Val Glu Cys Arg
        370                 375                 380 ccw tty gty tty wsy gcy ggy aar ccw tay gar tty wsy aty gay tgy     1200
Pro Phe Val Phe Ser Ala Gly Lys Pro Tyr Glu Phe Ser Ile Asp Cys
    385                 390                 395 gay aar atm aay ytw ttc cgy ggy gty tty gck tty ytk yta tay gty     1248
Asp Lys Ile Asn Leu Phe Arg Gly Val Phe Ala Phe Leu Leu Tyr Val
400                 405                 410                 415 gcy acy tty atg tay gtw tty wsy ack tty gcy aay atw ytr cgy aay     1296
Ala Thr Phe Met Tyr Val Phe Ser Thr Phe Ala Asn Ile Leu Arg Asn
                420                 425                 430 aar gar wsy tagtgatctc ctaggaagcc cgcctaatga gcgggctttt             1345
Lys Glu Ser
``` ttttctggt 1355

<210> SEQ ID NO 594
<211> LENGTH: 434
<212> TYPE: PRT
<213> ORGANISM: Artificial Sequence
<220> FEATURE:
<223> OTHER INFORMATION: Description of Artificial Sequence: M13-III protein sequence

<400> SEQUENCE: 594

```
Ala Ala Ala His His His His His Gly Ala Ala Glu Gln Lys Leu
  1               5                  10                  15

Ile Ser Glu Glu Asp Leu Asn Gly Ala Ala Ala Ser Asp Ile Asn Asp
             20                  25                  30

Asp Arg Met Ala Ser Thr Ala Glu Thr Val Glu Ser Cys Leu Ala Lys
         35                  40                  45

Pro His Thr Glu Asn Ser Phe Thr Asn Val Trp Lys Asp Asp Lys Thr
     50                  55                  60

Leu Asp Arg Tyr Ala Asn Tyr Glu Gly Cys Leu Trp Asn Ala Thr Gly
 65                  70                  75                  80

Val Val Val Cys Thr Gly Asp Glu Thr Gln Cys Tyr Gly Thr Trp Val
                 85                  90                  95

Pro Ile Gly Leu Ala Ile Pro Glu Asn Glu Gly Gly Gly Ser Glu Gly
            100                 105                 110

Gly Gly Ser Glu Gly Gly Ser Glu Gly Gly Thr Lys Pro Pro
        115                 120                 125

Glu Tyr Gly Asp Thr Pro Ile Pro Gly Tyr Thr Tyr Ile Asn Pro Leu
    130                 135                 140

Asp Gly Thr Tyr Pro Pro Gly Thr Glu Gln Asn Pro Ala Asn Pro Asn
145                 150                 155                 160

Pro Ser Leu Glu Glu Ser Gln Pro Leu Asn Thr Phe Met Phe Gln Asn
                165                 170                 175

Asn Arg Phe Arg Asn Arg Gln Gly Ala Leu Thr Val Tyr Thr Gly Thr
            180                 185                 190

Val Thr Gln Gly Thr Asp Pro Val Lys Thr Tyr Tyr Gln Tyr Thr Pro
        195                 200                 205

Val Ser Ser Lys Ala Met Tyr Asp Ala Tyr Trp Asn Gly Lys Phe Arg
    210                 215                 220

Asp Cys Ala Phe His Ser Gly Phe Asn Glu Asp Pro Phe Val Cys Glu
225                 230                 235                 240

Tyr Gln Gly Gln Ser Ser Asp Leu Pro Gln Pro Val Asn Ala Gly
                245                 250                 255

Gly Gly Ser Gly Gly Ser Gly Gly Ser Glu Gly Gly Ser
            260                 265                 270

Glu Gly Gly Gly Ser Gly Gly Ser Gly Ser Gly Asp Phe Asp Tyr
        275                 280                 285

Glu Lys Met Ala Asn Ala Asn Lys Gly Ala Met Thr Glu Asn Ala Asp
    290                 295                 300

Glu Asn Ala Leu Gln Ser Asp Ala Lys Gly Lys Leu Asp Ser Val Ala
305                 310                 315                 320

Thr Asp Tyr Gly Ala Ala Ile Asp Gly Phe Ile Gly Asp Val Ser Gly
                325                 330                 335

Leu Ala Asn Gly Asn Gly Ala Thr Gly Asp Phe Ala Gly Ser Asn Ser
            340                 345                 350

Gln Met Ala Gln Val Gly Asp Gly Asp Asn Ser Pro Leu Met Asn Asn
```

```
                    355                 360                 365
Phe Arg Gln Tyr Leu Pro Ser Leu Pro Gln Ser Val Glu Cys Arg Pro
    370                 375                 380

Phe Val Phe Ser Ala Gly Lys Pro Tyr Glu Phe Ser Ile Asp Cys Asp
385                 390                 395                 400

Lys Ile Asn Leu Phe Arg Gly Val Phe Ala Phe Leu Leu Tyr Val Ala
                405                 410                 415

Thr Phe Met Tyr Val Phe Ser Thr Phe Ala Asn Ile Leu Arg Asn Lys
                420                 425                 430

Glu Ser

<210> SEQ ID NO 595
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
cgttgatatc gctagcctat gc                                              22

<210> SEQ ID NO 596
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
gataggctta gctagcccgg agaacgaagg                                      30

<210> SEQ ID NO 597
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ctttcacagc ggtttcgcta gcgacccttt tgtctgc                              37

<210> SEQ ID NO 598
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ctttcacagc ggtttcgcta gcgacccttt tgtcagcgag taccagggtc                50

<210> SEQ ID NO 599
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
gactgtctcg gcagcatgcg ccatacgatc atcgttg                              37
```

```
<210> SEQ ID NO 600
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (2)..(25)

<400> SEQUENCE: 600 c aac gat gat cgt atg gcg cat gct gccgagacag tc              37
  Asn Asp Asp Arg Met Ala His Ala
   1               5

<210> SEQ ID NO 601
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Asn Asp Asp Arg Met Ala His Ala
 1               5

<210> SEQ ID NO 602
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
ctttcacagc ggtttgcatg cagacccttt tgtctgc                      37

<210> SEQ ID NO 603
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
ctttcacagc ggtttgcatg cagacccttt tgtcagcgag taccagggtc        50

<210> SEQ ID NO 604
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 604

Tyr Ala Asp Ser Val Lys Gly
 1               5

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 605
cctcgacagc gaagtgcaca g                    21

<210> SEQ ID NO 606
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ggctgagtca agacgctctg tgcacttcgc tgtcgagg                    38

<210> SEQ ID NO 607
<211> LENGTH: 7
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 607

Gln Ser Ala Leu Thr Gln Pro
 1               5

<210> SEQ ID NO 608
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
cctctgtcac agtgcacaag ac                    22

<210> SEQ ID NO 609
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
cctctgtcac agtgcacaag acatccagat gacccagtct cc                    42

<210> SEQ ID NO 610
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
gggaggatgg agactgggtc gtctggatgt cttgtgcact gtgacagagg                    50

<210> SEQ ID NO 611
<211> LENGTH: 11
<212> TYPE: PRT
<213> ORGANISM: Artificial Sequence
<220> FEATURE:
<223> OTHER INFORMATION: Description of Artificial Sequence: Illustrative
      peptide

```
<400> SEQUENCE: 611

Gln Asp Ile Gln Met Thr Gln Ser Pro Ser Ser
  1               5                  10

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 612
gactgggtgt agtgatctag                                              20

<210> SEQ ID NO 613
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ggtgtagtga tcttctagtg acaactct                                     28

<210> SEQ ID NO 614
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Val Ser Ser Arg Asp Asn
  1               5

<210> SEQ ID NO 615
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 615 tac tat tgt gcg aaa                                                15
Tyr Tyr Cys Ala Lys
  1               5

<210> SEQ ID NO 616
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Tyr Tyr Cys Ala Lys
  1               5

<210> SEQ ID NO 617
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ggtgccgata ggcttgcatg caccggagaa cgaagg                              36

<210> SEQ ID NO 618
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
cgcttcacta agtctagaga caactctaag aatactctct acttgcagat gaacagctta   60
agggctgagg acactgcagt ctactattgt acgag                              95

<210> SEQ ID NO 619
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, t, c, g, unknown or other

<400> SEQUENCE: 619 gatnnnnatc                                                           10

<210> SEQ ID NO 620
<211> LENGTH: 10
<212> TYPE: PRT
<213> ORGANISM: Unknown
<220> FEATURE:
<223> OTHER INFORMATION: Description of Unknown: MALIA3-derived
      peptide

<400> SEQUENCE: 620

Met Lys Leu Leu Asn Val Ile Asn Phe Val
1               5                   10

<210> SEQ ID NO 621
<211> LENGTH: 29
<212> TYPE: PRT
<213> ORGANISM: Artificial Sequence
<220> FEATURE:
<223> OTHER INFORMATION: Description of Artificial Sequence: CJRA05-
      derived peptide

<400> SEQUENCE: 621

Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu
            20                  25

<210> SEQ ID NO 622
<211> LENGTH: 15
<212> TYPE: DNA
<213> ORGANISM: Artificial Sequence
<220> FEATURE:
```

-continued

```
<223> OTHER INFORMATION: Description of Artificial Sequence:
      Illustrative nucleotide sequence

<400> SEQUENCE: 622
tttttttttt ttttt                                                    15

<210> SEQ ID NO 623
<211> LENGTH: 87
<212> TYPE: PRT
<213> ORGANISM: Unknown
<220> FEATURE:
<223> OTHER INFORMATION: Description of Unknown: MALIA3-derived
      peptide

<400> SEQUENCE: 623
```

Met Ile Lys Val Glu Ile Lys Pro Ser Gln Ala Gln Phe Thr Thr Arg
 1               5                  10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85

```
<210> SEQ ID NO 624
<211> LENGTH: 29
<212> TYPE: PRT
<213> ORGANISM: Unknown
<220> FEATURE:
<223> OTHER INFORMATION: Description of Unknown: MALIA3-derived
      peptide

<400> SEQUENCE: 624
```

Met Ser Val Leu Val Tyr Ser Phe Ala Ser Phe Val Leu Gly Trp Cys
 1               5                  10                  15

Leu Arg Ser Gly Ile Thr Tyr Phe Thr Arg Leu Met Glu
            20                  25

```
<210> SEQ ID NO 625
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, t, c, g, unknown or other

<400> SEQUENCE: 625 ctcttcnnnn                                                          10

<210> SEQ ID NO 626
<211> LENGTH: 87
<212> TYPE: PRT
<213> ORGANISM: Artificial Sequence
<220> FEATURE:
<223> OTHER INFORMATION: Description of Artificial Sequence: CJRA05-
      derived peptide

<400> SEQUENCE: 626
```

```
Met Ile Lys Val Glu Ile Lys Pro Ser Gln Ala Gln Phe Thr Thr Arg
 1               5                  10                 15

Ser Gly Val Ser Arg Gln Gly Lys Pro Tyr Ser Leu Asn Glu Gln Leu
                20                  25                  30

Cys Tyr Val Asp Leu Gly Asn Glu Tyr Pro Val Leu Val Lys Ile Thr
            35                  40                  45

Leu Asp Glu Gly Gln Pro Ala Tyr Ala Pro Gly Leu Tyr Thr Val His
 50                  55                  60

Leu Ser Ser Phe Lys Val Gly Gln Phe Gly Ser Leu Met Ile Asp Arg
 65              70                  75                  80

Leu Arg Leu Val Pro Ala Lys
                85
```

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: CJRA05-
      derived peptide

<400> SEQUENCE: 627

```
Met Lys Leu Leu Asn Val Ile Asn Phe Val
 1               5                  10
```

<210> SEQ ID NO 628
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gacccagtct ccatcctcc                                                  19

<210> SEQ ID NO 629
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gactcagtct ccactctcc                                                  19

<210> SEQ ID NO 630
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
gacgcagtct ccaggcacc                                                  19

<210> SEQ ID NO 631
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
gacgcagtct ccagccacc                                              19

<210> SEQ ID NO 632
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gtctcctgga cagtcgatc                                              19

<210> SEQ ID NO 633
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
ggccttggga cagacagtc                                              19

<210> SEQ ID NO 634
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
gtctcctgga cagtcagtc                                              19

<210> SEQ ID NO 635
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ggccccaggg cagagggtc                                              19

<210> SEQ ID NO 636
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (3)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (5)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr

```
<400> SEQUENCE: 636

Xaa Tyr Xaa Met Xaa
 1               5

<210> SEQ ID NO 637
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)
<223> OTHER INFORMATION: Tyr, Arg, Trp, Val, Gly or Ser
<220> FEATURE:
<221> NAME/KEY: MOD_RES
<222> LOCATION: (3)
<223> OTHER INFORMATION: Tyr, Arg, Trp, Val, Gly or Ser
<220> FEATURE:
<221> NAME/KEY: MOD_RES
<222> LOCATION: (4)
<223> OTHER INFORMATION: Pro or Ser
<220> FEATURE:
<221> NAME/KEY: MOD_RES
<222> LOCATION: (8)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr
<220> FEATURE:
<221> NAME/KEY: MOD_RES
<222> LOCATION: (10)
<223> OTHER INFORMATION: Ala, Asp, Glu, Phe, Gly, His, Ile, Lys, Leu,
      Met, Asn, Pro, Gln, Arg, Ser, Thr, Val, Trp or Tyr

<400> SEQUENCE: 637

Xaa Ile Xaa Xaa Ser Gly Gly Xaa Thr Xaa Tyr Ala Asp Ser Val Lys
 1               5                  10                  15

Gly
```

We claim:

1. A library comprising a collection of members of a family, the family comprising a diversity of antibodies or functional fragments thereof, wherein the antibodies or functional fragments thereof each comprise a VH CDR1, a VH CDR2, a VH CDR3 and framework regions and the antibodies or functional fragments are encoded by DNA sequences comprising sequences encoding (a) the VH CDR1, wherein the VH CDR1 comprises the amino acid sequence according to the formula $-X_1-Y-X_2-M-X_3-$ (SEQ ID NO:636), wherein $X_1$, $X_2$, and $X_3$ are independently selected from the group consisting of A, D, E, F, G, H, I, K, L, M, N, P, Q, R, S, T, V, W, and Y, (b) the VH CDR2, wherein the VH CDR2 comprises the amino acid sequence according to the formula $X_4-I-X_5-X_6-S-G-G-X_7-T-X_8-Y-A-D-S-V-K-G-$ (SEQ ID NO:637), wherein $X_4$ and $X_5$ are independently selected from the group consisting of Y, R, W, V, G, and S, $X_6$ is selected from the group consisting of P and S, and $X_7$ and $X_8$ are independently selected from the group consisting of A, D, E, F, G, H, I, K, L, M, N, P, Q, R, S, T, V, W, and Y, (c) the VH CDR3, wherein the sequence encoding the VH CDR3 is from the CDR3 region of an immunoglobulin gene of a B cell, and (d) the framework regions, wherein the framework regions comprises VH 3-23 framework regions or VH3-23 related germline framework regions.

2. The library according to claim 1, wherein the antibodies or functional fragments thereof further comprise an immunoglobulin light chain, and said DNA sequences further comprise a sequence encoding the immunoglobin light chain.

3. The library according to claim 2, wherein said sequence encoding an immunoglobin light chain is from a B cell.

4. The library according to claim 3, wherein said B cell is from a blood sample from an autoimmune patient.

5. The library according to claim 4, wherein the autoimmune patient is diagnosed with a disorder selected from the group consisting of systemic lupus erythematosus, systemic sclerosis, rheumatoid arthritis, antiphospholipid syndrome and vasculitis.

6. The library according to claim 1, wherein said antibodies or functional fragments thereof are linked via a short linker to the final portion of M13 gene III.

7. The library according to claim 1, wherein the diversity of antibodies or functional fragments thereof is displayed on genetic packages.

8. The library according to claim 7, wherein said genetic packages are M13 phage.

9. The library according to claim 8, wherein said DNA sequences are in a phage vector.

10. The library according to claim 9, wherein said phage vector comprises a wild-type gene iii and a truncated gene iii for display of the antibody or functional fragment thereof.

11. The library according to claim 8, wherein said DNA sequences are in a phagemid vector.

12. The library according to claim 8, wherein said displayed antibodies or functional fragments thereof are linked via a short linker to the final portion of M13 gene III.

13. The library according to claim 2, wherein the diversity of antibodies or functional fragments thereof is displayed on genetic packages.

14. The library according to claim 13, wherein said genetic packages are M13 phage.

15. The library according to claim 14, wherein said DNA sequences are in a phage vector.

16. The library according to claim 14, wherein said DNA sequences are in a phagemid vector.

17. The library according to claim 14, wherein said displayed antibodies or functional fragments thereof are linked via a short linker to the final portion of M13 gene III.

18. The library of claim 1, wherein the functional fragments are Fab fragments or scFv fragments.

* * * * *